(12) United States Patent
Riguet et al.

(10) Patent No.: US 8,779,129 B2
(45) Date of Patent: *Jul. 15, 2014

(54) TRIAZINEDIONE DERIVATIVES AS GABA$_B$ RECEPTOR MODULATORS

(71) Applicant: Addex Pharma S.A., Geneva (CH)

(72) Inventors: Eric Riguet, Plan-les-Ouates (CH); Brice Campo, Plan-les-Ouates (CH); Antoine Gibelin, Plan-les-Ouates (CH); Karim Mhalla, Plan-les-Ouates (CH)

(73) Assignee: Addex Pharma S.A., Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/716,058

(22) Filed: Dec. 14, 2012

(65) Prior Publication Data

US 2013/0123262 A1 May 16, 2013

Related U.S. Application Data

(63) Continuation of application No. 12/514,241, filed as application No. PCT/IB2007/003660 on Nov. 9, 2007, now Pat. No. 8,344,138.

(30) Foreign Application Priority Data

Nov. 10, 2006 (GB) .................................. 0622472.9

(51) Int. Cl.
| | | |
|---|---|---|
| *C07D 253/075* | (2006.01) | |
| *A61K 31/53* | (2006.01) | |
| *A61P 25/04* | (2006.01) | |
| *A61P 25/18* | (2006.01) | |
| *A61P 25/22* | (2006.01) | |
| *A61P 25/28* | (2006.01) | |
| *A61P 25/30* | (2006.01) | |

(52) U.S. Cl.
USPC .......................................... 544/182; 514/242

(58) Field of Classification Search
USPC .......................................... 544/182; 514/242
See application file for complete search history.

(56) References Cited

U.S. PATENT DOCUMENTS

| | | | |
|---|---|---|---|
| 6,673,796 B2 | 1/2004 | Pontillo et al. | |
| 6,951,858 B2 | 10/2005 | Pontillo et al. | |
| 6,974,812 B2 | 12/2005 | Dombroski et al. | |
| 7,015,230 B1 | 3/2006 | South et al. | |
| 7,176,202 B2 | 2/2007 | Dombroski et al. | |
| 8,344,138 B2 * | 1/2013 | Riguet et al. .................. | 544/182 |
| 2004/0192692 A1 | 9/2004 | Blackaby et al. | |

FOREIGN PATENT DOCUMENTS

| | | |
|---|---|---|
| EP | 1212324 | 6/2002 |
| WO | WO-96/22285 | 7/1996 |
| WO | WO-01/14377 | 3/2001 |
| WO | WO-03/011839 | 2/2003 |
| WO | WO-03/011841 | 2/2003 |
| WO | WO-2004/058270 | 7/2004 |
| WO | WO-2006/003517 | 1/2006 |

OTHER PUBLICATIONS

Gil, M.J. et al., Phosphorus, Sulfur and Silicon and the Related elements, Gordon and Breach Science Publishers, Amsterdam, GB, vol. 128, Jan. 1, 1997; pp. 105-117.
Badawey, El Sayed, et. al., "Synthesis of new benzimidazole derivatives as potential antimicrobial agents," Chemicals Abstract Service XP 002479872, CA 115:71532, 1991.
Chemical Abstract Service, XP 002479873, Sep. 6, 2007.
Chemical Abstract Service, XP 002479874, Jul. 9, 2007.
International Search Report for PCT/IB2007/003660 dated May 27, 2008.
International Preliminary Report on Patentability for International Application No. PCT/IB2007/003660 dated May 12, 2009.
Written Opinion of the International Searching Authority dated May 12, 2009.
West, Solid State Chemistry and its Applications, Wiley, New York, 1988, pp. 358 and 365.

(Continued)

*Primary Examiner* — Venkataraman Balasubramanian
(74) *Attorney, Agent, or Firm* — Edwards Wildman Palmer LLP; Peter F. Corless; Mark D. Russett

(57) ABSTRACT

The present invention provides novel compounds of formula I wherein $W_1$, $W_2$, $W_3$, $W_4$, $W_5$, B, $X_1$, $X_2$, $X_3$, $X_4$, $X_5$, E and L are as defined herein; invention compounds are gamma amino butyrique acid receptor-subtype B ("GABA$_B$") positive allosteric modulators (enhancers), which are useful to provide methods of treating or preventing diseases or disorders, including treatment of anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, panic disorder, posttraumatic stress disorders, urge urinary incontinence, gastroesophageal reflux disease, transient lower oesophageal sphincter relaxations, functional gastrointestinal disorders and irritable bowel syndrome.

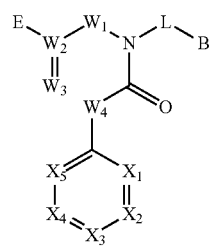

11 Claims, 1 Drawing Sheet

(56) References Cited

OTHER PUBLICATIONS

Vippagunta et al., Advanced Drug Delivery Reviews, 48: 3-26, 2001.
Ulrich et al., Current Opinion in Neurobiology 2007, 17:298-303.
Sperk et al., Adv Exp Med Biol. 2004, 548:92-103, PubMed Abstract provided.
Pontillo et al., Bioorganic Medicinal Chemistry Letters 15(19), 4363-4366, 2005.
South M, CAPLUS Abstract, CA 144: 312107, 2006.

* cited by examiner

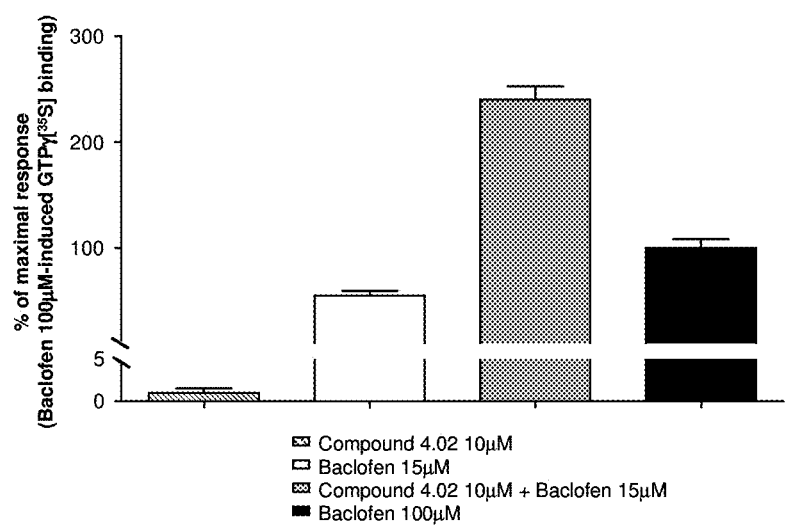

TRIAZINEDIONE DERIVATIVES AS GABA$_B$ RECEPTOR MODULATORS

CROSS-REFERENCE TO RELATED APPLICATIONS

This application is a continuation of U.S. patent application Ser. No. 12/514,241, filed May 8, 2009, pending, which is the U.S. national phase application pursuant to 35 U.S.C. §371 of PCT International Patent Application No. PCT/IB2007/003660, filed Nov. 9, 2007, which claims priority to United Kingdom Patent Application No. 0622472.9, filed Nov. 10, 2006. The entire contents of the aforementioned patent applications are incorporated herein by this reference.

SUMMARY OF THE INVENTION

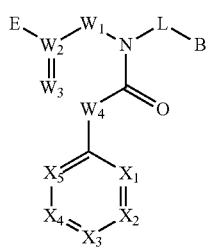

The present invention provides novel compounds of formula I wherein $W_1$, $W_2$, $W_3$, $W_4$, $W_5$, B, $X_1$, $X_2$, $X_3$, $X_4$, $X_5$, E and L are as defined herein; invention compounds are gamma amino butyric acid receptor-subtype B ("GABA$_B$"), positive allosteric modulators (enhancers), which are useful to provide methods of treating or preventing diseases or disorders, including treatment of anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, panic disorder, posttraumatic stress disorders, urge urinary incontinence, gastroesophageal reflux disease, transient lower oesophageal sphincter relaxations, functional gastrointestinal disorders and irritable bowel syndrome.

BACKGROUND OF THE INVENTION

The amino acid GABA (γ-aminobutyric acid) is the main inhibitory neurotransmitter in the adult mammalian brain and regulates many physiological and psychological processes. GABA acts through two major classes of receptors: ionotropic GABA$_A$ (including GABA$_C$) receptors and metabotropic GABA$_B$ receptors (Hill and Bowery, Nature 1981, 290, 149-152; Bormann, J., Trends Pharmacol. Sci. 2000, 21, 16-19). GABA$_B$ receptors are present in most regions of the mammalian brain on presynaptic terminals and postsynaptic neurons, and are involved in the fine-tuning of inhibitory synaptic transmission. Due to their strategic position in neuronal networks to modulate the activity of the various neurotransmitter systems, GABA$_B$ receptors are a target of choice for pharmacological agents intended to treat central and peripheral nervous systems disorders (Bettler et al., Physiol Rev. 2004, 84, 835-867; Cryan and Kaupmann, Trends Pharmacol Sci. 2005, 26, 36-43).

The GABA$_B$ receptor belongs to the Class-III family of G protein-coupled receptors (GPCRs), as are the receptors for glutamate, $Ca^{2+}$, pheromones and putative taste compounds (Pin et al., Pharmaco. Ther. 2003, 98, 325-354). All members of this family share the characteristic of a large extracellular amino-terminal domain that contains a so-called "Venus Flytrap" orthosteric ligand binding site and seven transmembrane (7TM) helical segments plus an intracellular carboxyl-terminal domain that are involved in receptor activation and G-protein coupling (Bockaert and Pin, EMBO J. 1999, 18, 1723; Galvez et al, J. Biol. Chem. 1999, 274, 13362-13369). A distinct feature, however, of the GABA$_B$ receptor is that it operates as a heterodimer of at least two homologous subunits termed GABA$_{B1}$ and GABA$_{B2}$ (Kaupman et al, Nature 1997, 386, 239-246; Gordon et al, J. Biol. Chem. 1999, 12, 7607-7610; Margeta-Mitrovic et al, PNAS 2001, 98, 14649-14654; Bettler et al, Physiol Rev. 2004, 84, 835-867). Orthosteric GABA$_B$ receptor ligands bind only at the N-terminal Venus flytrap region of the GABA$_{B1}$ subunit, which in turn activates the associated GABA$_{B2}$ subunit of the heterodimer. It is this later subunit that is responsible for coupling and activation of G-protein (Galvez et al, EMBO J. 2001, 20, 2152-2159; Duthey et al, J. Biol. Chem. 2002, 277, 3236-3241; Pin et al, Biochem. Pharmacol. 2004, 68, 1565-1572). The resulting effect is an inhibition of the adenylyl cyclase activity and subsequent cyclic AMP formation and the modulation of activity of inwardly rectifying potassium channels and voltage-sensitive calcium channels.

Several studies using knock-out (KO) mice have demonstrated the role of the heterodimeric GABA$_{B1B2}$ receptor in several CNS disorders. Mice lacking the GABA$_{B1}$ subunit exhibit spontaneous seizures and hyperalgesia (Schuler et al, Neuron 2001, 31, 47-58). These behavioral characteristics are paralleled by a loss of all biochemical and electrophysiological GABA$_B$ responses in these KO mice. In these studies, a clear impairment of passive avoidance performance was also observed indicating impaired memory processes. GABA$_{B1}$ deficient mice were also found to be more anxious than their wild-type counterparts (Mombereau et al, Neuropsychopharmacology 2004, 29, 1050-1062). Analogous results were obtained with GABA$_{B2}$ KO mice, which presented all the same behavioural characteristics than the one observed for the GABA$_{B1}$ KO mice (Gassman et al, J. Neurosci. 2004, 24, 6086-6097). Moreover, it has also been shown that a hypoactivity of the GABA system was linked to spasticity, epilepsy, anxiety, stress, sleep disorders, depression, addiction, and pain (Dalvi and Rodgers, Psychopharmacology 1996, 128, 380-397; for a recent review Ong and Kerr, CNS Drug Dev. 2005, 11, 317-334); while on the contrary, a hyperactivity of the GABAergic system was associated with schizophrenia (Blum and Mann, Int. J. Neuropsychopharmacol. 2002, 5, 159-179).

Baclofen is a potent and selective agonist at the GABA$_B$ receptor and is presently a frequently and only used clinical drug in the treatment of spasticity and rigidity (Montane et al, Neurology 2004, 63, 1357-1363). Moreover, all effective pharmacological agents used to treat panic disorder increase GABA synaptic transmission and anxiolytics and antidepressants that lack GABA activity are not effective in panic disorders. Baclofen was shown to be significantly effective in reducing the number of panic attacks and symptoms of anxiety as assessed with the Hamilton anxiety scale, Zung Scale, and Katz-R nervousness subscale (Breslow et al, Am. J. Psychiatry 1989, 146, 353-356). Drake and co-workers, hypothesized that baclofen would be an effective treatment in the symptomatic management of veterans with chronic posttraumatic stress disorder (PTSD). Their results demonstrated that the therapy, well tolerated, resulted in significant improvements of the overall symptoms of PTSD and co-morbid depression and anxiety in patients with chronic PTSD due to combat (Drake et al, *Ann. Pharmacother.* 2003, 37, 1177-1181). More recently, a study looking at the effect of baclofen on the prepulse inhibition (PPI) of the acoustic startle response (ASR), proposed $GABA_B$ receptors as putative new targets in the pharmacological therapy of psychotic disorders (Bortalo et al, *Psychopharmacology* 2004, 171, 322-330). Despite the demonstration of baclofen as being a potential therapeutic tool for the treatment of disorders such as anxiety and spasticity, its use has been limited due to its poor blood-brain-barrier penetration, very short duration of action, muscle relaxing property, hypothermic and sedative side effects, as well as patients' increasing tolerance (Hefferan et al, *Neuroscience Letters* 2006, 403, 195-200).

A new avenue for developing selective compounds acting at GPCRs is to identify molecules that act through allosteric mechanisms, modulating the receptor by binding to a site different from the highly conserved orthosteric binding site. This concept has assumed a greater importance in the pharmacology of family III receptors in general. For example, allosteric modulators have been described for $Ca^{2+}$-sensing receptors (Nemeth et al, U.S. Pat. No. 6,031,003), for metabotropic glutamate receptors (reviewed in Mutel, *Expert Opin. Ther. Patents* 12:1-8, 2002; Ritzen, Mathiesen and Thomsen, *Basic Clin. Pharmacol. Toxicol* 97:202-13, 2005), and most recently for $GABA_B$ receptors (Urwyler et al, *Mol. Pharmacol.* 2001, 60, 963-971; WO 2005/094828; WO 2006/001750; WO 2006/063732; WO 2006/048146; WO 2006/07486; WO 2006/136442; WO 2007/014843; US 2007/027204; WO 2007/073297; WO 2007/073298; WO 2007/073299; WO 2007/073300). These ligands do not activate the receptor by themselves, but, for example in the case of the $GABA_B$ receptor, increase the potency of GABA in the presence of this endogenous agonist (Pin et al, *Mol. Pharmacol.* 2001, 60, 881-884; Urwyler et al, *Neuropharmacol.* 2005, 48, 343-353). Mutational analyses have demonstrated unequivocally that the binding of known $GABA_B$ receptor positive allosteric modulators does not occur at the orthosteric site, but instead at an allosteric site within the seven transmembrane region of the $GABA_{B2}$ subunit at least for CGP7930 (Binet et al, *J. Biol. Chem.* 2004, 279, 29085-29901).

As a therapeutic principle, positive allosteric modulators are expected to have several advantages over compounds acting as orthosteric agonists, because they are only effective in the presence of the endogenous ligand and therefore act in line with physiological neurotransmission in its temporal and spatial organization. Orthosteric agonists, on the other hand, activate receptors independently of synaptic activity, possibly leading to unwanted side effects.

Cryan and co-workers suggested in a recent study, using GS39783 (N,N'-Dicyclopentyl-2-methylsulfanyl-5-nitro-pyrimidine-4,6-diamine), that a positive modulation of $GABA_B$ receptors may serve as a novel therapeutic strategy for the development of anxiolytics with a better side effect profile as compared to baclofen (Cryan et al, *J. Pharm. Exp. Therap.* 2004, 310, 952-963). They showed that GS39783 is active in models of anxiety such as elevated plus maze (rat), elevated zero maze (mice and rats), and the stress-induced hyperthermia (mice) tests. Moreover, as expected for a positive allosteric modulator that do not have any effect on receptor activity in absence of GABA, but do enhance allosterically the affinity of the $GABA_B$ receptor for the endogenous GABA, no side effect on locomotor activity, rotarod, body temperature and traction test was observed for doses ranging from 0.1 to 200 mg/kg, p.o. In comparison baclofen presented those side effects even at efficacious doses in anxiety models. In conclusion, those data suggest that GS39783, and positive allosteric modulators of $GABA_B$ receptors in general, are useful and innovative anxiolytics without side-effects associated with baclofen. An interesting example of the use of such compounds in preclinical studies have been done for CGP7930 and GS39783 for the treatment of Gastro-Esophageal Reflux Disease (GERD) and cocain self-administration in rats, where those compounds were found active (Smith et al, *Psychopharmacology* 2004, 173, 105-111; WO 03/090731).

Recently the 3,3'-diarylpropyl-1-arylethylamines and 3-aryl propyl-1-arylethylamine have been reported as a new class of $GABA_B$ receptor modulators as they potentiate baclofen-induced responses in the brain (Kerr et al, Aust. J. Chem. 2006, 59, 445-456) and they modulate both pre- and postsynaptic $GABA_B$ receptors in rat brain slices (Ong et al, Eur. J. Pharm. 2005, 507, 35-42).

Patent Publications DE10255416 and WO9730980 describe triazinediones derivatives having herbicidal properties. These triazinediones are also described in the field of fungicide (EP0438717), growth of protozoa (EP0232932, WO00006172), binding to PPAR-α and -γ (FR02866339), P2X7 inhibitors (US25288288, WO04058270) and IL-5 production inhibitors (WO09902505).

None of the specifically disclosed compounds are structurally related to the compounds of the present invention. It has now surprisingly been found that the compounds of general Formula I show potent activity and selectivity on $GABA_B$ receptor.

The present invention relates to a method of treating or preventing a condition in a mammal, including a human, the treatment or prevention of which is affected or facilitated by the neuromodulatory effect of $GABA_B$ modulators.

FIGURE

FIG. A represents the ability of 10 μM of the Compound 4.02 to increase the $[GTP\gamma^{35}S]$ binding in rat brain membranes induced by 15 μM of Baclofen, a $GABA_B$ receptor agonist, without having an effect on its own.

DETAILED DESCRIPTION OF THE INVENTION

According to the present invention, there are provided new compounds of the general Formula I:

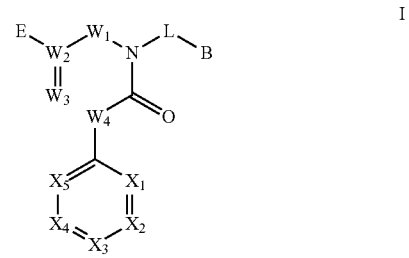

and stereoisomeric forms, mixtures of stereoisomeric forms or pharmaceutically acceptable salts, hydrates or solvates of such compounds, wherein:

B is selected from $C_6$-$C_{10}$ aryl optionally substituted with one to 5 Y, $C_5$-$C_{10}$ cycloalkenyl optionally substituted with one to 7 Y, 5 to 14 membered heteroaryl group optionally substituted by one to 8 Y, wherein said heteroaryl group comprises one, two or three heteroatoms selected from N, O, S;

Y is 1 to 5 substituents independently selected from the group consisting of hydrogen, halogen, —OCF$_3$, —NO$_2$, —CN, —CF$_3$, an optionally substituted —(C$_1$-C$_6$)alkyl, —(C$_3$-C$_6$)cycloalkyl, —(C$_2$-C$_6$)alkenyl, —(C$_2$-C$_6$)alkynyl, halo-(C$_1$-C$_6$)alkyl, —(C$_0$-C$_6$)alkylOR$^1$, —(C$_0$-C$_6$)alkylNR$^2$R$^3$, —(C$_0$-C$_6$)alkyl-C(=NR$^4$)NR$^2$R$^3$, —(C$_0$-C$_6$)alkylSR$^2$, —(C$_0$-C$_6$)alkylNR$^2$C(=O)R$^3$, —(C$_0$-C$_6$)alkylNR$^2$C(=O)$_2$R$^3$, —(C$_0$-C$_6$)alkylNR$^2$S(=O)$_2$R$^3$, —(C$_0$-C$_6$)alkylNR$^4$C(=O)NR$^2$R$^3$, —(C$_0$-C$_6$)alkylS(=O)R$^2$, —(C$_0$-C$_6$)alkylS(=O)$_2$R$^2$, —(C$_0$-C$_6$)alkylS(=O)$_2$NR$^2$R$^3$, —(C$_0$-C$_6$)alkylC(=O)R$^2$, —(C$_0$-C$_6$)alkylC(=O)OR$^1$, —(C$_0$-C$_6$)alkylC(=O)NR$^2$R$^3$, —(C$_0$-C$_6$)alkylC(=NR$^2$)R$^3$, or —(C$_0$-C$_6$)alkylC(=NOR$^1$)R$^3$, heteroaryl, heteroarylalkyl, arylalkyl, aryl alkylaryl, alkylheteroaryl, heterocycloalkyl; wherein optionally two substituents are combined to the intervening atoms to form a bicyclic heterocycloalkyl, aryl or heteroaryl ring; wherein each ring is optionally further substituted with 1-5 independent halogen, —CN, —(C$_1$-C$_6$)alkyl, —O(C$_0$-C$_6$)alkyl, —O(C$_3$-C$_7$)cyclo alkyl, —O(aryl), —O(aryl)-(C$_0$-C$_3$)alkyl, —O(heteroaryl), (heteroaryl)-(C$_0$-C$_3$)alkyl, —O(C$_1$-C$_3$)alkylaryl, —O(C$_1$-C$_3$)alkylheteroaryl, —N((C$_0$-C$_6$)alkyl)$_2$, —N((C$_0$-C$_6$)alkyl))((C$_0$-C$_3$)alkylaryl)) or —N((C$_0$-C$_6$)alkyl)((C$_0$-C$_3$)alkylheteroaryl)) groups;

R$^1$ at each occurrence is selected from hydrogen, —(C$_1$-C$_6$)alkyl, —(C$_2$-C$_6$)alkenyl, —(C$_3$-C$_7$)cycloalkyl, 3 to 7 membered heterocycloalkyl, —(C$_6$-C$_{10}$)aryl, 5 or 6 membered heteroaryl, —(C$_7$-C$_{10}$)arylalkyl, —C(=O)R$^5$;

R$^5$ are selected from —(C$_1$-C$_6$)alkyl, and —(C$_6$-C$_{10}$)aryl;

R$^2$, R$^3$ and R$^4$ each independently is hydrogen, —(C$_1$-C$_6$)alkyl, —(C$_3$-C$_6$)cycloalkyl, —(C$_2$-C$_6$)alkenyl, —(C$_2$-C$_6$)alkynyl, —(C$_1$-C$_6$)alkylhalo, heterocycloalkyl, heteroaryl, heteroarylalkyl, arylalkyl or aryl; any of which is optionally substituted with 1 to 5 independent halogen, —CN, —(C$_1$-C$_6$)alkyl, —O(C$_0$-C$_6$)alkyl, —O(C$_3$-C$_7$)cycloalkylalkyl, —O(aryl), —O(heteroaryl), —N((C$_0$-C$_6$)alkyl)$_2$, —N((C$_0$-C$_6$)alkyl)((C$_3$-C$_7$)cycloalkyl) or —N((C$_0$-C$_6$)alkyl)(aryl) substituents; wherein optionally R$^2$, R$^3$, R$^4$ substituents are combined to the intervening atoms to form a bicyclic heterocycloalkyl;

X$_1$, X$_2$, X$_3$, X$_4$ and X$_5$ are each independently selected from the group consisting of —CR$^6$=, —N=;

R$^6$ is 1 to 5 substituents independently selected from the group consisting of hydrogen, halogen, —OCF$_3$, —CN, —CF$_3$, —NO$_2$, an optionally substituted —(C$_1$-C$_6$)alkyl, —(C$_3$-C$_6$)cycloalkyl, —(C$_2$-C$_6$)alkenyl, —(C$_2$-C$_6$)alkynyl, halo-(C$_1$-C$_6$)alkyl, —(C$_0$-C$_6$)alkylOR$^7$, —(C$_0$-C$_6$)alkylNR$^8$R$^9$, —(C$_0$-C$_6$)alkyl-C(=NR$^{10}$)NR$^8$R$^9$, —(C$_0$-C$_6$)alkylSR$^8$, —(C$_0$-C$_6$)alkylNR$^8$C(=O)R$^9$, —(C$_0$-C$_6$)alkylNR$^8$C(=O)$_2$R$^9$, —(C$_0$-C$_6$)alkylNR$^8$S(=O)$_2$R$^9$, —(C$_0$-C$_6$)alkylNR$^{10}$C(=O)NR$^8$R$^9$, —(C$_0$-C$_6$)alkylS(=O)R$^8$, —(C$_0$-C$_6$)alkylS(=O)$_2$R$^8$, —(C$_0$-C$_6$)alkylS(=O)$_2$NR$^8$R$^9$, —(C$_0$-C$_6$)alkylC(=O)R$^8$, —(C$_0$-C$_6$)alkylC(=O)OR$^7$, —(C$_1$-C$_6$)alkylC(=O)NR$^8$R$^9$, —(C$_0$-C$_6$)alkylC(=NR$^8$)R$^9$, or —(C$_0$-C$_6$)alkylC(=NOR$^7$)R$^9$, heteroaryl, heteroarylalkyl, arylalkyl, aryl, a 3 to 6 heterocycloalkyl; wherein optionally two substituents are combined to the intervening atoms to form a bicyclic heterocycloalkyl, aryl or heteroaryl ring; wherein each ring is optionally further substituted with 1 to 5 independent halogen, —CN, —(C$_1$-C$_6$)alkyl, —O(C$_0$-C$_6$)alkyl, —O(C$_3$-C$_7$)cycloalkyl, —O(aryl), —O(aryl)-(C$_0$-C$_3$)alkyl, —O(heteroaryl), —O(heteroaryl)-(C$_0$-C$_3$)alkyl, —O(C$_1$-C$_3$)alkylaryl, —O(C$_1$-C$_3$)alkylheteroaryl, —N((C$_0$-C$_6$)alkyl)$_2$, —N((C$_0$-C$_6$)alkyl))((C$_0$-C$_3$)alkylaryl)) or —N((C$_0$-C$_6$)alkyl)((C$_0$-C$_3$)alkylheteroaryl)) groups;

R$^7$ at each occurrence is selected from hydrogen, —(C$_1$-C$_6$)alkyl, —(C$_2$-C$_6$)alkenyl, —(C$_3$-C$_7$)cycloalkyl, 3 to 7 membered heterocycloalkyl, —(C$_6$-C$_{10}$)aryl, 5 or 6 membered heteroaryl, —(C$_7$-C$_{10}$)arylalkyl, —C(=O)R$^{11}$;

R$^{11}$ are selected from —(C$_1$-C$_6$)alkyl, —(C$_3$-C$_7$)cycloalkyl and —(C$_6$-C$_{10}$)aryl;

R$^8$, R$^9$ and R$^{10}$ each independently is hydrogen, —(C$_1$-C$_6$)alkyl, —(C$_3$-C$_6$)cycloalkyl, —(C$_2$-C$_6$)alkenyl, —(C$_2$-C$_6$)alkynyl, —(C$_1$-C$_6$)alkylhalo, heterocycloalkyl, heteroaryl, heteroarylalkyl, arylalkyl or aryl; any of which is optionally substituted with 1 to 5 independent halogen, —CN, —(C$_1$-C$_6$)alkyl, —O(C$_0$-C$_6$)alkyl, —O(C$_3$-C$_7$)cycloalkylalkyl, —O(aryl), —O(aryl)-(C$_0$-C$_3$)alkyl, —O(heteroaryl), —O(heteroaryl)-(C$_0$-C$_3$)alkyl, —N((C$_0$-C$_6$)alkyl)$_2$, —N((C$_0$-C$_6$)alkyl)((C$_3$-C$_7$)cycloalkyl) or —N((C$_0$-C$_6$)alkyl)(aryl) substituents;

E is selected from the group consisting of hydrogen, halogen, —OCF$_3$, —NO$_2$, —CN, —CF$_3$, —(C$_1$-C$_6$)alkyl, —(C$_3$-C$_6$)cycloalkyl, —(C$_2$-C$_6$)alkenyl, —(C$_2$-C$_6$)alkynyl, halo-(C$_1$-C$_6$)alkyl, —(C$_0$-C$_6$)alkylOR$^{12}$, —(C$_0$-C$_6$)alkylNR$^{13}$R$^{14}$, —(C$_0$-C$_6$)alkyl-C(=NR$^{15}$)NR$^{13}$R$^{14}$, —(C$_0$-C$_6$)alkylSR$^{12}$, —(C$_0$-C$_6$)alkylNR$^{13}$C(=O)R$^{14}$, —(C$_0$-C$_6$)alkylNR$^{13}$C(=O)$_2$R$^{14}$, —(C$_0$-C$_6$)alkylNR$^{13}$S(=O)$_2$R$^{14}$, —(C$_0$-C$_6$)alkylNR$^{15}$C(=O)NR$^{13}$R$^{14}$, —(C$_0$-C$_6$)alkylS(=O)R$^{13}$, —(C$_0$-C$_6$)alkylS(=O)$_2$R$^{13}$, —(C$_0$-C$_6$)alkylS(=O)$_2$NR$^{13}$R$^{14}$, —(C$_0$-C$_6$)alkylC(=O)R$^{13}$, —(C$_0$-C$_6$)alkylC(=O)OR$^{13}$, —(C$_0$-C$_6$)alkylC(=O)NR$^{13}$R$^{14}$, —(C$_0$-C$_6$)alkylC(=NR$^{13}$)R$^{14}$, or —(C$_0$-C$_6$)alkylC(=NOR$^{13}$)R$^{14}$; wherein optionally two substituents are combined to the intervening atoms to form a bicyclic heterocycloalkyl, aryl or heteroaryl ring; wherein each ring is optionally further substituted with 1 to 5 independent halogen, —CN, an optionally substituted —(C$_1$-C$_6$)alkyl, —O(C$_0$-C$_6$)alkyl, —O(C$_3$-C$_7$)cyclo alkyl, —O(aryl), —O(aryl)-(C$_0$-C$_3$)alkyl, —O(heteroaryl), —O(heteroaryl)-(C$_0$-C$_3$)alkyl, —O(C$_1$-C$_3$)alkylaryl, —O(C$_1$-C$_3$)alkylheteroaryl, —N((C$_0$-C$_6$)alkyl)$_2$, —N((C$_0$-C$_6$)alkyl))((C$_0$-C$_3$)alkylaryl)) or N((C$_0$-C$_6$)alkyl)((C$_0$-C$_3$)alkylheteroaryl)) groups;

R$^{12}$ at each occurrence is selected from hydrogen, —(C$_1$-C$_6$)alkyl, —(C$_2$-C$_6$)alkenyl, —(C$_3$-C$_7$)cycloalkyl, —C(=O)R$^{16}$;

R$^{16}$ are selected from hydrogen, —(C$_1$-C$_6$)alkyl, —(C$_3$-C$_7$)cycloalkyl and —(C$_6$-C$_{10}$)aryl;

R$^{13}$, R$^{14}$ and R$^{15}$ each independently is hydrogen, —(C$_1$-C$_6$)alkyl, —(C$_3$-C$_6$)cycloalkyl, —(C$_2$-C$_6$)alkenyl, —(C$_2$-C$_6$)alkynyl, —(C$_1$-C$_6$)alkylhalo, heterocycloalkyl, heteroaryl, heteroarylalkyl, alkylheteroaryl, arylalkyl, alkylaryl or aryl; any of which is optionally substituted with 1 to 5 independent halogen, —CN, —(C$_1$-C$_6$)alkyl, —O(C$_0$-C$_6$)alkyl, —O(C$_3$-C$_7$)cycloalkylalkyl, —O(aryl), —O(aryl)-(C$_0$-C$_3$)alkyl, —O(heteroaryl), —O(heteroaryl)-(C$_0$-C$_3$)alkyl, —N((C$_0$-C$_6$)alkyl)$_2$, —N((C$_0$-C$_6$)alkyl)((C$_3$-C$_7$)cycloalkyl) or —N((C$_0$-C$_6$)alkyl)(aryl) substituents;

When E is —H the compounds for which X$_3$ is not CH= or —CF= are excluded from the invention;

When E is —CN the compounds of the following list are excluded from the invention:

4-(4-(trifluoromethyl)benzyl)-2-(4-fluorophenyl)-3,5-dioxo-2,3,4,5-tetrahydro-1,2,4-triazine-6-carbonitrile,
4-(4-nitrobenzyl)-2-(4-fluorophenyl)-3,5-dioxo-2,3,4,5-tetrahydro-1,2,4-triazine-6-carbonitrile,
4-(4-chlorobenzyl)-2-(4-fluorophenyl)-3,5-dioxo-2,3,4,5-tetrahydro-1,2,4-triazine-6-carbonitrile,
4-(4-chlorobenzyl)-2-(2,6-difluorophenyl)-3,5-dioxo-2,3,4,5-tetrahydro-1,2,4-triazine-6-carbonitrile,
4-(4-chlorobenzyl)-3,5-dioxo-2-phenyl-2,3,4,5-tetrahydro-1,2,4-triazine-6-carbonitrile,
4-(3-cyanobenzyl)-3,5-dioxo-2-phenyl-2,3,4,5-tetrahydro-1,2,4-triazine-6-carbonitrile,
4-benzyl-3,5-dioxo-2-phenyl-2,3,4,5-tetrahydro-1,2,4-triazine-6-carbonitrile,
4-(2,4-dichlorobenzyl)-3,5-dioxo-2-phenyl-2,3,4,5-tetrahydro-1,2,4-triazine-6-carbonitrile,
4-((3-chloro-5-(trifluoromethyl)pyridin-2-yl)methyl)-2-(4-fluorophenyl)-3,5-dioxo-2,3,4,5-tetrahydro-1,2,4-triazine-6-carbonitrile;

$W_1$ and $W_3$ are each independently selected from —N= or —C(=O);

$W_2$ and $W_4$ are each independently selected from —C= or —N—;

L is independently selected from a —(($C_1$-$C_5$)alkyl-$Q_m$)- substituted with 1-6 T;

m is 0 or 1;

T is 1 to 6 substituents independently selected from the group consisting of hydrogen, fluorine, —$OCF_3$, —$NO_2$, —CN, —$CF_3$, —($C_1$-$C_6$)alkyl, —($C_3$-$C_6$)cycloalkyl, —($C_2$-$C_6$)alkenyl, —($C_2$-$C_6$)alkynyl, halo-($C_1$-$C_6$)alkyl, —($C_0$-$C_6$)alkylOR$^{17}$—($C_0$-$C_6$)alkylNR$^{18}$R$^{19}$, —($C_0$-$C_6$)alkyl-C(=NR$^{20}$)NR$^{18}$R$^{19}$, —($C_0$-$C_6$)alkylSR$^{18}$, —($C_0$-$C_6$)alkylNR$^{18}$C(=O)R$^{19}$, —($C_0$-$C_6$)alkylNR$^{18}$C(=O)$_2$R$^{19}$, —($C_0$-$C_6$)alkylNR$^{18}$S(=O)$_2$R$^{19}$, —($C_0$-$C_6$)alkylNR$^{20}$C(=O)NR$^{18}$R$^{19}$, —($C_0$-$C_6$)alkylS(=O)R$^{18}$, —($C_0$-$C_6$)alkylS(=O)$_2$R$^{18}$—($C_0$-$C_6$)alkylS(=O)$_2$NR$^{18}$R$^{19}$, —($C_0$-$C_6$)alkylC(=O)R$^{18}$, —($C_0$-$C_6$)alkylC(=O)OR$^{17}$, —($C_0$-$C_6$)alkylC(=O)NR$^{18}$R$^{19}$, —($C_0$-$C_6$)alkylC(=NR$^{18}$)R$^{19}$, or —($C_0$-$C_6$)alkylC(=NOR$^{17}$)R$^{19}$, heteroaryl, heteroarylalkyl, arylalkyl, alkylaryl, alkylheteroaryl, aryl; wherein optionally two substituents are combined to the intervening atoms to form a bicyclic heterocycloalkyl, aryl or heteroaryl ring; wherein each ring is optionally further substituted with 1 to 5 independent halogen, —CN, —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkylaryl, —O($C_1$-$C_3$)alkylheteroaryl, —N(($C_0$-$C_6$)alkyl))(($C_0$-$C_3$)alkylaryl)) or —N(($C_0$-$C_6$)alkyl)(($C_0$-$C_3$)alkylheteroaryl)) groups;

R$^{17}$ at each occurrence is selected from hydrogen, —($C_1$-$C_6$)alkyl, —($C_2$-$C_6$)alkenyl, —($C_3$-$C_7$)cycloalkyl, 3 to 7 membered heterocycloalkyl, —($C_6$-$C_{10}$)aryl, 5 or 6 membered heteroaryl, —($C_7$-$C_{10}$)arylalkyl, —C(=O)R$^{21}$;

R$^{21}$ is selected from hydrogen, —($C_1$-$C_6$)alkyl, —($C_3$-$C_7$)cycloalkyl, and —($C_6$-$C_{10}$)aryl;

R$^{18}$, R$^{19}$ and R$^{20}$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, arylalkyl alkylaryl, alkylheteroaryl, aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O(heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

Q is —C(=O)—, —C(=O)O—, —C(=O)NR$^{22}$—, —OC(=O)—, —OC(=O)NR$^{22}$—, —NR$^{22}$—, —NR$^{22}$C(=O)—, —NR$^{22}$C(=O)$_2$—, —NR$^{22}$C(=S)—, —S—, —S(=O)—, or S(=O)$_2$—;

R$^{22}$ is selected from —($C_1$-$C_6$)alkyl, and —($C_6$-$C_{10}$)aryl;

Any N may be an N-oxide.

Restricted compounds of the present invention from Formula I are compounds of Formula II depicted below

II

[Chemical structure of Formula II]

and stereoisomeric forms, mixtures of stereoisomeric forms or pharmaceutically acceptable salts, hydrates or solvates of such compounds, wherein:

B is selected from $C_6$-$C_{10}$ aryl optionally substituted with one to 5 Y, $C_5$-$C_{10}$ cycloalkenyl optionally substituted with one to 7 Y, 5 to 14 membered heteroaryl group optionally substituted by one to 8 Y, wherein said heteroaryl group comprises one, two or three heteroatoms selected from N, O, S;

Y is 1 to 5 substituents independently selected from the group consisting of hydrogen, halogen, —$OCF_3$, —$NO_2$, —CN, —$CF_3$, an optionally substituted —($C_1$-$C_6$)alkyl, —($C_3$-$C_6$)cycloalkyl, —($C_2$-$C_6$)alkenyl, —($C_2$-$C_6$)alkynyl, halo —($C_1$-$C_6$)alkyl, —($C_0$-$C_6$)alkylOR$^1$, —($C_0$-$C_6$)alkylNR$^2$R$^3$, —($C_0$-$C_6$)alkyl-C(=NR$^4$)NR$^2$R$^3$, —($C_0$-$C_6$)alkylSR$^2$, —($C_0$-$C_6$)alkylNR$^2$C(=O)R$^3$, —($C_0$-$C_6$)alkylNR$^2$C(=O)$_2$R$^3$, —($C_0$-$C_6$)alkylNR$^2$S(=O)$_2$R$^3$, —($C_0$-$C_6$)alkylNR$^4$C(=O)NR$^2$R$^3$, —($C_0$-$C_6$)alkylS(=O)R$^2$, —($C_0$-$C_6$)alkylS(=O)$_2$R$^2$, —($C_0$-$C_6$)alkylS(=O)$_2$NR$^2$R$^3$, —($C_0$-$C_6$)alkylC(=O)R$^2$, —($C_0$-$C_6$)alkylC(=O)OR$^1$, —($C_0$-$C_6$)alkylC(=O)NR$^2$R$^3$, —($C_0$-$C_6$)alkylC(=NR$^2$)R$^3$, or —($C_0$-$C_6$)alkylC(=NOR$^1$)R$^3$, heteroaryl, heteroarylalkyl, arylalkyl, aryl alkylaryl, alkylheteroaryl; wherein optionally two substituents are combined to the intervening atoms to form a bicyclic heterocycloalkyl, aryl or heteroaryl ring; wherein each ring is optionally further substituted with 1 to 5 independent halogen, —CN, —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkylaryl, —O($C_1$-$C_3$)alkylheteroaryl, —N(($C_0$-$C_6$)alkyl)$_2$, N(($C_0$-$C_6$)alkyl))(($C_0$-$C_3$)alkylaryl)) or —N(($C_0$-$C_6$)alkyl)(($C_0$-$C_3$)alkylheteroaryl)) groups;

R$^1$ at each occurrence is selected from hydrogen, —($C_1$-$C_6$)alkyl, —($C_2$-$C_6$)alkenyl, —($C_3$-$C_7$)cycloalkyl, 3 to 7 membered heterocycloalkyl, —($C_6$-$C_{10}$)aryl, 5 or 6 membered heteroaryl, —($C_7$-$C_{10}$)arylalkyl, —C(=O)$R^5$;

$R^5$ are selected from hydrogen, —($C_1$-$C_6$)alkyl, and —($C_6$-$C_{10}$)aryl;

$R^2$, $R^3$ and $R^4$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, arylalkyl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(heteroaryl), —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents; wherein optionally $R^2$, $R^3$, $R^4$ substituents are combined to the intervening atoms to form a bicyclic heterocycloalkyl;

$X_1$, $X_2$, $X_3$, $X_4$ and $X_5$ are each independently selected from the group consisting of —$CR^6$=, —N=;

$R^6$ is 1 to 5 substituents independently selected from the group consisting of hydrogen, halogen, —$OCF_3$, —CN, —$CF_3$, —$NO_2$, an optionally substituted —($C_1$-$C_6$)alkyl, —($C_3$-$C_6$)cycloalkyl, —($C_2$-$C_6$)alkenyl, —($C_2$-$C_6$)alkynyl, halo-($C_1$-$C_6$)alkyl, —($C_0$-$C_6$)alkyl$OR^7$, —($C_0$-$C_6$)alkyl$NR^8R^9$, —($C_0$-$C_6$)alkyl-C(=$NR^{10}$)$NR^8R^9$, —($C_0$-$C_6$)alkyl$SR^8$, —($C_0$-$C_6$)alkyl$NR^8$C(=O)$R^9$, —($C_0$-$C_6$)alkyl$NR^8$C(=O)$_2R^9$, —($C_0$-$C_6$)alkyl$NR^8$S(=O)$_2R^9$, —($C_0$-$C_6$)alkyl$NR^{10}$C(=O)$NR^8R^9$, —($C_0$-$C_6$)alkylS(=O)$R^8$, —($C_0$-$C_6$)alkylS(=O)$_2R^8$, —($C_0$-$C_6$)alkylS(=O)$_2NR^8R^9$, —($C_0$-$C_6$)alkylC(=O)$R^8$, —($C_0$-$C_6$)alkylC(=O)$OR^7$, —($C_1$-$C_6$)alkylC(=O)$NR^8R^9$, —($C_0$-$C_6$)alkylC(=$NR^8$)$R^9$, or —($C_0$-$C_6$)alkylC(=$NOR^7$)$R^9$, heteroaryl, heteroarylalkyl, arylalkyl, aryl, a 3 to 6 heterocycloalkyl; wherein optionally two substituents are combined to the intervening atoms to form a bicyclic heterocycloalkyl, aryl or heteroaryl ring; wherein each ring is optionally further substituted with 1 to 5 independent halogen, —CN, —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkyl aryl, —O($C_1$-$C_3$)alkylheteroaryl, —N(($C_0$-$C_6$)alkyl)$_2$, —N(($C_0$-$C_6$)alkyl)(($C_0$-$C_3$)alkylaryl)) or —N(($C_0$-$C_6$)alkyl)(($C_0$-$C_3$)alkylheteroaryl)) groups;

$R^7$ at each occurrence is selected from hydrogen, —($C_1$-$C_6$)alkyl, —($C_2$-$C_6$)alkenyl, —($C_3$-$C_7$)cycloalkyl, 3 to 7 membered heterocycloalkyl, —($C_6$-$C_{10}$)aryl, 5 or 6 membered heteroaryl, —($C_7$-$C_{10}$)aryl alkyl, —C(=O)$R^{11}$;

$R^{11}$ are selected from —($C_1$-$C_6$)alkyl, —($C_3$-$C_7$)cycloalkyl and —($C_6$-$C_{10}$)aryl;

$R^8$, $R^9$ and $R^{10}$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, arylalkyl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O (heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

E is selected from the group consisting of hydrogen, halogen, —$OCF_3$, —$NO_2$, —CN, —$CF_3$, —($C_1$-$C_6$)alkyl, —($C_3$-$C_6$)cycloalkyl, —($C_2$-$C_6$)alkenyl, —($C_2$-$C_6$)alkynyl, halo-($C_1$-$C_6$)alkyl, —($C_0$-$C_6$)alkyl$OR^{12}$, —($C_0$-$C_6$)alkyl$NR^{13}R^{14}$, —($C_0$-$C_6$)alkyl-C(=$NR^{15}$)$NR^{13}R^{14}$, —($C_0$-$C_6$)alkyl$SR^{12}$, —($C_0$-$C_6$)alkyl$NR^{13}$C(=O)$R^{14}$, —($C_0$-$C_6$)alkyl$NR^{13}$C(=O)$_2R^{14}$, —($C_0$-$C_6$)alkyl$NR^{13}$S(=O)$_2R^{14}$, —($C_0$-$C_6$)alkyl$NR^{15}$C(=O)$NR^{13}R^{14}$, —($C_0$-$C_6$)alkylS(=O)$R^{13}$, —($C_0$-$C_6$)alkylS(=O)$_2R^{13}$, —($C_0$-$C_6$)alkylS(=O)$_2NR^{13}R^{14}$, —($C_0$-$C_6$)alkylC(=O)$R^{13}$, —($C_0$-$C_6$)alkylC(=O)$OR^{13}$, —($C_0$-$C_6$)alkylC(=O)$NR^{13}R^{14}$, —($C_0$-$C_6$)alkylC(=$NR^{13}$)$R^{14}$, or —($C_0$-$C_6$)alkylC(=$NOR^{13}$)$R^{14}$; wherein optionally two substituents are combined to the intervening atoms to form a bicyclic heterocycloalkyl, aryl or heteroaryl ring; wherein each ring is optionally further substituted with 1 to 5 independent halogen, —CN, an optionally substituted —($C_1$-$C_6$)alkyl, —O($C_0$-$C_6$)alkyl, —O($C_3$-$C_7$)cyclo alkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkylaryl, —O($C_1$-$C_3$)alkylheteroaryl, —N(($C_0$-$C_6$)alkyl)$_2$, —N(($C_0$-$C_6$)alkyl))(($C_0$-$C_3$)alkylaryl)) or —N(($C_0$-$C_6$)alkyl)(($C_0$-$C_3$)alkylheteroaryl)) groups;

$R^{12}$ at each occurrence is selected from hydrogen, —($C_1$-$C_6$)alkyl, —($C_2$-$C_6$)alkenyl, —($C_3$-$C_7$)cycloalkyl, —C(=O)$R^{16}$;

$R^{16}$ are selected from hydrogen, —($C_1$-$C_6$)alkyl, —($C_3$-$C_7$)cycloalkyl and —($C_6$-$C_{10}$)aryl;

$R^{13}$, $R^{14}$ and $R^{15}$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, alkylheteroaryl, arylalkyl, alkylaryl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O(heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

When E is —H the compounds for which $X_3$ is not CH= or —CF= are excluded from the invention;

When E is —CN the compounds of the following list are excluded from the invention:

4-(4-(trifluoromethyl)benzyl)-2-(4-fluorophenyl)-3,5-dioxo-2,3,4,5-tetrahydro-1,2,4-triazine-6-carbonitrile, 4-(4-nitrobenzyl)-2-(4-fluorophenyl)-3,5-dioxo-2,3,4,5-tetrahydro-1,2,4-triazine-6-carbonitrile, 4-(4-chlorobenzyl)-2-(4-fluorophenyl)-3,5-dioxo-2,3,4,5-tetrahydro-1,2,4-triazine-6-carbonitrile, 4-(4-chlorobenzyl)-2-(2,6-difluorophenyl)-3,5-dioxo-2,3,4,5-tetrahydro-1,2,4-triazine-6-carbonitrile, 4-(4-chlorobenzyl)-3,5-dioxo-2-phenyl-2,3,4,5-tetrahydro-1,2,4-triazine-6-carbonitrile, 4-(3-cyanobenzyl)-3,5-dioxo-2-phenyl-2,3,4,5-tetrahydro-1,2,4-triazine-6-carbonitrile, 4-benzyl-3,5-dioxo-2-phenyl-2,3,4,5-tetrahydro-1,2,4-triazine-6-carbonitrile, 4-(2,4-dichlorobenzyl)-3,5-dioxo-2-phenyl-2,3,4,5-tetrahydro-1,2,4-triazine-6-carbonitrile, 4-((3-chloro-5-(trifluoromethyl)pyridin-2-yl)methyl)-2-(4-fluorophenyl)-3,5-dioxo-2,3,4,5-tetrahydro-1,2,4-triazine-6-carbonitrile;

$W_3$ is selected from —N= or —C(=O);

$W_2$ and $W_4$ are each independently selected from —C= or —N=;

L is independently selected from a —(($C_1$-$C_5$)alkyl-$Q_m$)- substituted with 1-6 T;

m is 0 or 1;

T is 1 to 6 substituents independently selected from the group consisting of hydrogen, fluorine, —$OCF_3$, —$NO_2$, —CN, —$CF_3$, —($C_1$-$C_6$)alkyl, —($C_3$-$C_6$)cycloalkyl, —(C$_2$-C$_6$)alkenyl, —(C$_2$-C$_6$)alkynyl, halo-(C$_1$-C$_6$)alkyl, —(C$_0$-C$_6$)alkylO$^{17}$, —(C$_0$-C$_6$)alkylNR$^{18}$R$^{19}$, —(C$_0$-C$_6$)alkyl-C(=NR$^{20}$)NR$^{18}$R$^{19}$, —(C$_0$-C$_6$)alkylSR$^{18}$, —(C$_0$-C$_6$)alkylNR$^{18}$C(=O)R$^{19}$, —(C$_0$-C$_6$)alkylNR$^{18}$C(=O)$_2$R$^{19}$, —(C$_0$-C$_6$)alkylNR$^{18}$S(=O)$_2$R$^{19}$, —(C$_0$-C$_6$)alkylNR$^{20}$C(=O)NR$^{18}$R$^{19}$, —(C$_0$-C$_6$)alkylS(=O)R$^{18}$, —(C$_0$-C$_6$)alkylS(=O)$_2$R$^{18}$—(C$_0$-C$_6$)alkylS(=O)$_2$NR$^{18}$R$^{19}$, —(C$_0$-C$_6$)alkylC(=O)R$^{18}$, —(C$_0$-C$_6$)alkylC(=O)OR$^{17}$, —(C$_0$-C$_6$)alkylC(=O)NR$^{18}$R$^{19}$, —(C$_0$-C$_6$)alkylC(=NR$^{18}$)R$^{19}$, or —(C$_0$-C$_6$)alkylC(=NOR$^{17}$)R$^{19}$, heteroaryl, heteroarylalkyl, arylalkyl, alkylaryl, alkylheteroaryl, aryl; wherein optionally two substituents are combined to the intervening atoms to form a bicyclic heterocycloalkyl, aryl or heteroaryl ring; wherein each ring is optionally further substituted with 1 to 5 independent halogen, —CN, —(C$_1$-C$_6$)alkyl, —O (C$_0$-C$_6$)alkyl, —O(C$_3$-C$_7$)cycloalkyl, —O(aryl), —O(aryl)-(C$_0$-C$_3$)alkyl, —O (heteroaryl), —O(heteroaryl)-(C$_0$-C$_3$)alkyl, —O(C$_1$-C$_3$)alkylaryl, —O(C$_1$-C$_3$)alkylheteroaryl, —N((C$_0$-C$_6$)alkyl))((C$_0$-C$_3$)alkylaryl)) or —N((C$_0$-C$_6$)alkyl)((C$_0$-C$_3$)alkylheteroaryl)) groups;

R$^{17}$ at each occurrence is selected from hydrogen, —(C$_1$-C$_6$)alkyl, —(C$_2$-C$_6$)alkenyl, —(C$_3$-C$_7$)cycloalkyl, 3 to 7 membered heterocycloalkyl, —(C$_6$-C$_{10}$)aryl, 5 or 6 membered heteroaryl, —(C$_7$-C$_{10}$)arylalkyl, —C(=O)R$^{21}$;

R$^{21}$ is selected from hydrogen, —(C$_1$-C$_6$)alkyl, —(C$_3$-C$_7$)cycloalkyl, and —(C$_6$-C$_{10}$)aryl;

R$^{18}$, R$^{19}$ and R$^{20}$ each independently is hydrogen, —(C$_1$-C$_6$)alkyl, —(C$_3$-C$_6$)cycloalkyl, —(C$_2$-C$_6$)alkenyl, —(C$_2$-C$_6$)alkynyl, —(C$_1$-C$_6$)alkylhalo, heterocycloalkyl, heteroaryl, heteroarylalkyl, arylalkyl alkylaryl, alkylheteroaryl, aryl; any of which is optionally substituted with 1 to 5 independent halogen, —CN, —(C$_1$-C$_6$)alkyl, —O(C$_0$-C$_6$)alkyl, —O(C$_3$-C$_7$)cycloalkylalkyl, —O(aryl), —O(aryl)-(C$_0$-C$_3$)alkyl, —O(heteroaryl), —O(heteroaryl)-(C$_0$-C$_3$)alkyl, —N((C$_0$-C$_6$)alkyl)$_2$, —N((C$_0$-C$_6$)alkyl)((C$_3$-C$_7$)cycloalkyl) or —N((C$_0$-C$_6$)alkyl)(aryl) substituents;

Q is —C(=O)—, —C(=O)O—, —C(=O)NR$^{22}$—, —OC(=O)—, —OC(=O)NR$^{22}$—, —NR$^{22}$—, —NR$^{22}$C(=O)—, —NR$^{22}$C(=O)$_2$—, —NR$^{22}$C(=S)—, —S—, —S(=O)—, or —S(=O)$_2$—;

R$^{22}$ is selected from —(C$_1$-C$_6$)alkyl, and —(C$_6$-C$_{10}$)aryl;

Any N may be an N-oxide.

Restricted compounds of the present invention from Formula II are compounds of Formula III depicted below

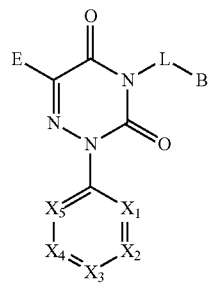

III and stereoisomeric forms, mixtures of stereoisomeric forms or pharmaceutically acceptable salts, hydrates or solvates of such compound, wherein:

B is selected from C$_6$-C$_{10}$ aryl optionally substituted with one to 5 Y, C$_5$-C$_{10}$ cycloalkenyl optionally substituted with one to 7 Y, 5 to 14 membered heteroaryl group optionally substituted by one to 8 Y, wherein said heteroaryl group comprises one, two or three heteroatoms selected from N, O, S;

Y is 1 to 5 substituents independently selected from the group consisting of hydrogen, halogen, —OCF$_3$, —NO$_2$, —CN, —CF$_3$, an optionally substituted —(C$_1$-C$_6$)alkyl, —(C$_3$-C$_6$)cycloalkyl, —(C$_2$-C$_6$)alkenyl, —(C$_2$-C$_6$)alkynyl, halo-(C$_1$-C$_6$)alkyl, —(C$_0$-C$_6$)alkylOR$^1$, —(C$_0$-C$_6$)alkylNR$^2$R$^3$, —(C$_0$-C$_6$)alkyl-C(=NR$^4$)NR$^2$R$^3$, —(C$_0$-C$_6$)alkylSR$^2$, —(C$_0$-C$_6$)alkylNR$^2$C(=O)R$^3$, —(C$_0$-C$_6$)alkylNR$^2$C(=O)$_2$R$^3$, —(C$_0$-C$_6$)alkylNR$^2$S(=O)$_2$R$^3$, —(C$_0$-C$_6$)alkylNR$^4$C(=O)NR$^2$R$^3$, —(C$_0$-C$_6$)alkylS(=O)R$^2$, —(C$_0$-C$_6$)alkylS(=O)$_2$R$^2$, —(C$_0$-C$_6$)alkylS(=O)$_2$NR$^2$R$^3$, —(C$_0$-C$_6$)alkylC(=O)R$^2$, —(C$_0$-C$_6$)alkylC(=O)OR$^1$, —(C$_0$-C$_6$)alkylC(=O)NR$^2$R$^3$, —(C$_0$-C$_6$)alkylC(=NR$^2$)R$^3$, or —(C$_0$-C$_6$)alkylC(=NOR$^1$)R$^3$, heteroaryl, heteroarylalkyl, arylalkyl, aryl alkylaryl, alkylheteroaryl; wherein optionally two substituents are combined to the intervening atoms to form a bicyclic heterocycloalkyl, aryl or heteroaryl ring; wherein each ring is optionally further substituted with 1 to 5 independent halogen, —CN, —(C$_1$-C$_6$)alkyl, —O(C$_0$-C$_6$)alkyl, —O(C$_3$-C$_7$)cycloalkyl, —O(aryl), —O(aryl)-(C$_0$-C$_3$)alkyl, —O(heteroaryl), —O(heteroaryl)-(C$_0$-C$_3$)alkyl, —O(C$_1$-C$_3$)alkylaryl, —O(C$_1$-C$_3$)alkylheteroaryl, —N((C$_0$-C$_6$)alkyl)$_2$, N((C$_0$-C$_6$)alkyl))((C$_0$-C$_3$)alkylaryl)) or —N((C$_0$-C$_6$)alkyl)((C$_0$-C$_3$)alkylheteroaryl)) groups;

R$^1$ at each occurrence is selected from hydrogen, —(C$_1$-C$_6$)alkyl, —(C$_2$-C$_6$)alkenyl, —(C$_3$-C$_7$)cycloalkyl, 3 to 7 membered heterocycloalkyl, —(C$_6$-C$_{10}$)aryl, 5 or 6 membered heteroaryl, —(C$_7$-C$_{10}$)arylalkyl, —C(=O)R$^5$;

R$^5$ are selected from hydrogen, —(C$_1$-C$_6$)alkyl, and —(C$_6$-C$_{10}$)aryl;

R$^2$, R$^3$ and R$^4$ each independently is hydrogen, —(C$_1$-C$_6$)alkyl, —(C$_3$-C$_6$)cycloalkyl, —(C$_2$-C$_6$)alkenyl, —(C$_2$-C$_6$)alkynyl, —(C$_1$-C$_6$)alkylhalo, heterocycloalkyl, heteroaryl, heteroarylalkyl, arylalkyl or aryl; any of which is optionally substituted with 1 to 5 independent halogen, —CN, —(C$_1$-C$_6$)alkyl, —O(C$_0$-C$_6$)alkyl, —O(C$_3$-C$_7$)cycloalkylalkyl, —O(aryl), —O(heteroaryl), —N((C$_0$-C$_6$)alkyl)$_2$, —N((C$_0$-C$_6$)alkyl)((C$_3$-C$_7$)cycloalkyl) or —N((C$_0$-C$_6$)alkyl)(aryl) substituents; wherein optionally R$^2$, R$^3$, R$^4$ substituents are combined to the intervening atoms to form a bicyclic heterocycloalkyl;

X$_1$, X$_2$, X$_3$, X$_4$ and X$_5$ are each independently selected from the group consisting of —CR$^6$=, —N=;

R$^6$ is 1 to 5 substituents independently selected from the group consisting of hydrogen, halogen, —OCF$_3$, —CN, —CF$_3$, —NO$_2$, an optionally substituted —(C$_1$-C$_6$)alkyl, —(C$_3$-C$_6$)cycloalkyl, —(C$_2$-C$_6$)alkenyl, —(C$_2$-C$_6$)alkynyl, halo-(C$_1$-C$_6$)alkyl, —(C$_0$-C$_6$)alkylOR$^7$, —(C$_0$-C$_6$)alkylNR$^8$R$^9$, —(C$_0$-C$_6$)alkyl-C(=NR$^{10}$)NR$^8$R$^9$, —(C$_0$-C$_6$)alkylSR$^8$, —(C$_0$-C$_6$)alkylNR$^8$C(=O)R$^9$, —(C$_0$-C$_6$)alkylNR$^8$C(=O)$_2$R$^9$, —(C$_0$-C$_6$)alkylNR$^8$S(=O)$_2$R$^9$, —(C$_0$-C$_6$)alkylNR$^{10}$C(=O)NR$^8$R$^9$, —(C$_0$-C$_6$)alkylS(=O)R$^8$, —(C$_0$-C$_6$)

alkylS(=O)$_2$R$^8$, —(C$_0$-C$_6$)alkylS(=O)$_2$NR$^8$R$^9$, —(C$_0$-C$_6$)alkylC(=O)R$^8$, —(C$_0$-C$_6$)alkylC(=O)OR$^7$, —(C$_1$-C$_6$)alkylC(=O)NR$^8$R$^9$, —(C$_0$-C$_6$)alkylC(=NR$^8$)R$^9$, or —(C$_0$-C$_6$)alkylC(=NOR$^7$)R$^9$, heteroaryl, heteroarylalkyl, arylalkyl, aryl, a 3 to 6 heterocycloalkyl; wherein optionally two substituents are combined to the intervening atoms to form a bicyclic heterocycloalkyl, aryl or heteroaryl ring; wherein each ring is optionally further substituted with 1 to 5 independent halogen, —CN, —(C$_1$-C$_6$)alkyl, —O(C$_0$-C$_6$)alkyl, —O(C$_3$-C$_7$)cycloalkyl, —O(aryl), —O (aryl)-(C$_0$-C$_3$)alkyl, —O(heteroaryl), —O(heteroaryl)-(C$_0$-C$_3$)alkyl, —O(C$_1$-C$_3$)alkyl aryl, —O(C$_1$-C$_3$)alkylheteroaryl, —N((C$_0$-C$_6$)alkyl)$_2$, —N((C$_0$-C$_6$)alkyl)((C$_0$-C$_3$)alkylaryl)) or —N((C$_0$-C$_6$)alkyl)((C$_0$-C$_3$)alkylheteroaryl)) groups;

R$^7$ at each occurrence is selected from hydrogen, —(C$_1$-C$_6$)alkyl, —(C$_2$-C$_6$)alkenyl, —(C$_3$-C$_7$)cycloalkyl, 3 to 7 membered heterocycloalkyl, —(C$_6$-C$_{10}$)aryl, 5 or 6 membered heteroaryl, —(C$_7$-C$_{10}$)arylalkyl, —C(=O)R$^{11}$;

R$^{11}$ are selected from —(C$_1$-C$_6$)alkyl, —(C$_3$-C$_7$)cycloalkyl and —(C$_6$-C$_{10}$)aryl;

R$^8$, R$^9$ and R$^{10}$ each independently is hydrogen, —(C$_1$-C$_6$)alkyl, —(C$_3$-C$_6$)cycloalkyl, —(C$_2$-C$_6$)alkenyl, —(C$_2$-C$_6$)alkynyl, —(C$_1$-C$_6$)alkylhalo, heterocycloalkyl, heteroaryl, heteroarylalkyl, arylalkyl or aryl; any of which is optionally substituted with 1 to 5 independent halogen, —CN, —(C$_1$-C$_6$)alkyl, —O(C$_0$-C$_6$)alkyl, —O(C$_3$-C$_7$)cycloalkylalkyl, —O(aryl), —O(aryl)-(C$_0$-C$_3$)alkyl, —O (heteroaryl), —O(heteroaryl)-(C$_0$-C$_3$)alkyl, —N((C$_0$-C$_6$)alkyl)$_2$, —N((C$_0$-C$_6$)alkyl)((C$_3$-C$_7$)cycloalkyl) or —N((C$_0$-C$_6$)alkyl)(aryl) substituents;

E is selected from the group consisting of hydrogen, halogen, —OCF$_3$, —NO$_2$, —CN, —CF$_3$, (C$_1$-C$_6$)alkyl, —(C$_3$-C$_6$)cycloalkyl, —(C$_2$-C$_6$)alkenyl, —(C$_2$-C$_6$)alkynyl, halo-(C$_1$-C$_6$)alkyl, —(C$_0$-C$_6$)alkylOR$^{12}$, —(C$_0$-C$_6$)alkylNR$^{13}$R$^{14}$, —(C$_0$-C$_6$)alkyl-C(=NR$^{15}$)NR$^{13}$R$^{14}$, —(C$_0$-C$_6$)alkylSR$^{12}$, —(C$_0$-C$_6$)alkylNR$^{13}$C(=O)R$^{14}$, —(C$_0$-C$_6$)alkylNR$^{13}$C(=O)$_2$R$^{14}$, —(C$_0$-C$_6$)alkylNR$^{13}$S(=O)$_2$R$^{14}$, —(C$_0$-C$_6$)alkylNR$^{15}$C(=O)NR$^{13}$R$^{14}$, —(C$_0$-C$_6$)alkylS(=O)R$^{13}$, —(C$_0$-C$_6$)alkylS(=O)$_2$R$^{13}$, —(C$_0$-C$_6$)alkylS(=O)$_2$NR$^{13}$R$^{14}$, —(C$_0$-C$_6$)alkylC(=O)R$^{13}$, —(C$_0$-C$_6$)alkylC(=O)OR$^{13}$, —(C$_0$-C$_6$)alkylC(=O)NR$^{13}$R$^{14}$, —(C$_0$-C$_6$)alkylC(=NR$^{13}$)R$^{14}$, or —(C$_0$-C$_6$)alkylC(=NOR$^{13}$)R$^{14}$; wherein optionally two substituents are combined to the intervening atoms to form a bicyclic heterocycloalkyl, aryl or heteroaryl ring; wherein each ring is optionally further substituted with 1 to 5 independent halogen, —CN, an optionally substituted —(C$_1$-C$_6$)alkyl, —O(C$_0$-C$_6$)alkyl, —O(C$_3$-C$_7$)cyclo alkyl, —O(aryl), —O(aryl)-(C$_0$-C$_3$)alkyl, —O(heteroaryl), —O(heteroaryl)-(C$_0$-C$_3$)alkyl, —O(C$_1$-C$_3$)alkylaryl, —O(C$_1$-C$_3$)alkylheteroaryl, —N((C$_0$-C$_6$)alkyl)$_2$, N((C$_0$-C$_6$)alkyl))((C$_0$-C$_3$)alkylaryl)) or N((C$_0$-C$_6$)alkyl)((C$_0$-C$_3$)alkylheteroaryl)) groups;

R$^{12}$ at each occurrence is selected from hydrogen, —(C$_1$-C$_6$)alkyl, —(C$_2$-C$_6$)alkenyl, —(C$_3$-C$_7$)cycloalkyl, —C(=O)R$^{16}$;

R$^{16}$ are selected from hydrogen, —(C$_1$-C$_6$)alkyl, —(C$_3$-C$_7$)cycloalkyl and —(C$_6$-C$_{10}$)aryl;

R$^{13}$, R$^{14}$ and R$^{15}$ each independently is hydrogen, —(C$_1$-C$_6$)alkyl, —(C$_3$-C$_6$)cycloalkyl, —(C$_2$-C$_6$)alkenyl, —(C$_2$-C$_6$)alkynyl, —(C$_1$-C$_6$)alkylhalo, heterocycloalkyl, heteroaryl, heteroarylalkyl, alkylheteroaryl, arylalkyl, alkylaryl or aryl; any of which is optionally substituted with 1 to 5 independent halogen, —CN, —(C$_1$-C$_6$)alkyl, —O(C$_0$-C$_6$)alkyl, —O(C$_3$-C$_7$)cycloalkylalkyl, —O(aryl), —O(aryl)-(C$_0$-C$_3$)alkyl, —O(heteroaryl), —O(heteroaryl)-(C$_0$-C$_3$)alkyl, —N((C$_0$-C$_6$)alkyl)$_2$, —N((C$_0$-C$_6$)alkyl)((C$_3$-C$_7$)cycloalkyl) or —N((C$_0$-C$_6$)alkyl)(aryl) substituents;

When E is —H the compounds for which X$_3$ is not CH= or —CF= are excluded from the invention;

When E is —CN the compounds of the following list are excluded from the invention:

4-(4-(trifluoromethyl)benzyl)-2-(4-fluorophenyl)-3,5-dioxo-2,3,4,5-tetrahydro-1,2,4-triazine-6-carbonitrile, 4-(4-nitrobenzyl)-2-(4-fluorophenyl)-3,5-dioxo-2,3,4,5-tetrahydro-1,2,4-triazine-6-carbonitrile, 4-(4-chlorobenzyl)-2-(4-fluorophenyl)-3,5-dioxo-2,3,4,5-tetrahydro-1,2,4-triazine-6-carbonitrile, 4-(4-chlorobenzyl)-2-(2,6-difluorophenyl)-3,5-dioxo-2,3,4,5-tetrahydro-1,2,4-triazine-6-carbonitrile, 4-(4-chlorobenzyl)-3,5-dioxo-2-phenyl-2,3,4,5-tetrahydro-1,2,4-triazine-6-carbonitrile, 4-(3-cyanobenzyl)-3,5-dioxo-2-phenyl-2,3,4,5-tetrahydro-1,2,4-triazine-6-carbonitrile, 4-benzyl-3,5-dioxo-2-phenyl-2,3,4,5-tetrahydro-1,2,4-triazine-6-carbonitrile, 4-(2,4-dichlorobenzyl)-3,5-dioxo-2-phenyl-2,3,4,5-tetrahydro-1,2,4-triazine-6-carbonitrile, 4-((3-chloro-5-(trifluoromethyl)pyridin-2-yl)methyl)-2-(4-fluorophenyl)-3,5-dioxo-2,3,4,5-tetrahydro-1,2,4-triazine-6-carbonitrile;

L is independently selected from a —((C$_1$-C$_5$)alkyl-Q$_m$)-substituted with 1-6 T;

m is 0 or 1;

T is 1 to 6 substituents independently selected from the group consisting of hydrogen, fluorine, —OCF$_3$, —NO$_2$, —CN, —CF$_3$, —(C$_1$-C$_6$)alkyl, —(C$_3$-C$_6$)cycloalkyl, —(C$_2$-C$_6$)alkenyl, —(C$_2$-C$_6$)alkynyl, halo-(C$_1$-C$_6$)alkyl, —(C$_0$-C$_6$)alkylOR$^{17}$, —(C$_0$-C$_6$)alkylNR$^{18}$R$^{19}$, —(C$_0$-C$_6$)alkyl-C(=NR$^{20}$)NR$^{18}$R$^{19}$, —(C$_0$-C$_6$)alkylSR$^{18}$, —(C$_0$-C$_6$)alkylNR$^{18}$C(=O)R$^{19}$, —(C$_0$-C$_6$)alkylNR$^{18}$C(=O)$_2$R$^{19}$, —(C$_0$-C$_6$)alkylNR$^{18}$S(=O)$_2$R$^{19}$, —(C$_0$-C$_6$)alkylNR$^{20}$C(=O)NR$^{18}$R$^{19}$, —(C$_0$-C$_6$)alkylS(=O)R$^{18}$, —(C$_0$-C$_6$)alkylS(=O)$_2$R$^{18}$, —(C$_0$-C$_6$)alkylS(=O)$_2$NR$^{18}$R$^{19}$, —(C$_0$-C$_6$)alkylC(=O)R$^{18}$, —(C$_0$-C$_6$)alkylC(=O)OR$^{17}$, —(C$_0$-C$_6$)alkylC(=O)NR$^{18}$R$^{19}$, —(C$_0$-C$_6$)alkylC(=NR$^{18}$)R$^{19}$, or —(C$_0$-C$_6$)alkylC(=NOR$^{17}$)R$^{19}$, heteroaryl, heteroarylalkyl, arylalkyl, alkylaryl, alkylheteroaryl, aryl; wherein optionally two substituents are combined to the intervening atoms to form a bicyclic heterocycloalkyl, aryl or heteroaryl ring; wherein each ring is optionally further substituted with 1 to 5 independent halogen, —CN, —(C$_1$-C$_6$)alkyl, —O(C$_0$-C$_6$)alkyl, —O(C$_3$-C$_7$)cycloalkyl, —O(aryl), —O(aryl)-(C$_0$-C$_3$) alkyl, —O(heteroaryl), —O(heteroaryl)-(C$_0$-C$_3$)alkyl, —O(C$_1$-C$_3$)alkylaryl, —O(C$_1$-C$_3$)alkylheteroaryl, —N((C$_0$-C$_6$)alkyl))((C$_0$-C$_3$)alkylaryl)) or —N((C$_0$-C$_6$)alkyl)((C$_0$-C$_3$)alkylheteroaryl)) groups;

R$^{17}$ at each occurrence is selected from hydrogen, —(C$_1$-C$_6$)alkyl, —(C$_2$-C$_6$)alkenyl, —(C$_3$-C$_7$)cycloalkyl, 3 to 7 membered heterocycloalkyl, —(C$_6$-C$_{10}$)aryl, 5 or 6 membered heteroaryl, —(C$_7$-C$_{10}$)arylalkyl, —C(=O)R$^{21}$;

R$^{21}$ is selected from hydrogen, —(C$_1$-C$_6$)alkyl, —(C$_3$-C$_7$)cycloalkyl, and —(C$_6$-C$_{10}$)aryl;

R$^{18}$, R$^{19}$ and R$^{20}$ each independently is hydrogen, —(C$_1$-C$_6$)alkyl, —(C$_3$-C$_6$)cycloalkyl, —(C$_2$-C$_6$)alkenyl, —(C$_2$-C$_6$)alkynyl, —(C$_1$-C$_6$)alkylhalo, heterocycloalkyl, heteroaryl, heteroarylalkyl, arylalkyl alkylaryl, alkylheteroaryl, aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O(heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

Q is —C(=O)—, —C(=O)O—, —C(=O)NR$^{22}$—, —OC(=O)—, —OC(=O)NR$^{22}$—, —NR$^{22}$—, —NR$^{22}$C(=O)—, —NR$^{22}$C(=O)$_2$—, —NR$^{22}$C(=S)—, —S—, —S(=O)—, or S(=O)$_2$—;

R$^{22}$ is selected from —($C_1$-$C_6$)alkyl, and —($C_6$-$C_{10}$)aryl;

Any N may be an N-oxide.

More preferred compounds of the present invention from Formula III are compounds of Formula III.A

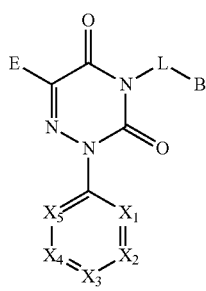

III.A and stereoisomeric forms, mixtures of stereoisomeric forms or pharmaceutically acceptable salts, hydrates or solvates of such compounds, wherein:

B is selected from $C_6$-$C_{10}$ aryl optionally substituted with one to 5 Y, $C_5$-$C_{10}$ cycloalkenyl optionally substituted with one to 7 Y, 5 to 14 membered heteroaryl group optionally substituted by one to 8 Y, wherein said heteroaryl group comprises one, two or three heteroatoms selected from N, O, S;

Y is 1 to 5 substituents independently selected from the group consisting of hydrogen, halogen, —OCF$_3$, —NO$_2$, —CN, —CF$_3$, an optionally substituted —($C_1$-$C_6$)alkyl, —($C_3$-$C_6$)cycloalkyl, —($C_2$-$C_6$)alkenyl, —($C_2$-$C_6$)alkynyl, halo—($C_1$-$C_6$)alkyl, —($C_0$-$C_6$)alkylOR$^1$, —($C_0$-$C_6$)alkylNR$^2$R$^3$, —($C_0$-$C_6$)alkyl-C(=NR$^4$)NR$^2$R$^3$, —($C_0$-$C_6$)alkylSR$^2$, —($C_0$-$C_6$)alkylNR$^2$C(=O)R$^3$, —($C_0$-$C_6$)alkylNR$^2$C(=O)$_2$R$^3$, —($C_0$-$C_6$)alkylNR$^2$S(=O)$_2$R$^3$, —($C_0$-$C_6$)alkylNR$^4$C(=O)NR$^2$R$^3$, —($C_0$-$C_6$)alkylS(=O)R$^2$, —($C_0$-$C_6$)alkylS(=O)$_2$R$^2$, —($C_0$-$C_6$)alkylS(=O)$_2$NR$^2$R$^3$, —($C_0$-$C_6$)alkylC(=O)R$^2$, —($C_0$-$C_6$)alkylC(=O)OR$^1$, —($C_0$-$C_6$)alkylC(=O)NR$^2$R$^3$, —($C_0$-$C_6$)alkylC(=NR$^2$)R$^3$, or —($C_0$-$C_6$)alkylC(=NOR$^1$)R$^3$, heteroaryl, heteroarylalkyl, arylalkyl, aryl alkylaryl, alkylheteroaryl; wherein optionally two substituents are combined to the intervening atoms to form a bicyclic heterocycloalkyl, aryl or heteroaryl ring; wherein each ring is optionally further substituted with 1 to 5 independent halogen, —CN, —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkylaryl, —O($C_1$-$C_3$)alkylheteroaryl, —N(($C_0$-$C_6$)alkyl)$_2$, N(($C_0$-$C_6$)alkyl))(($C_0$-$C_3$)alkylaryl)) or —N(($C_0$-$C_6$)alkyl)(($C_0$-$C_3$)alkylheteroaryl)) groups;

R$^1$ at each occurrence is selected from hydrogen, —($C_1$-$C_6$)alkyl, —($C_2$-$C_6$)alkenyl, —($C_3$-$C_7$)cycloalkyl, 3 to 7 membered heterocycloalkyl, —($C_6$-$C_{10}$)aryl, 5 or 6 membered heteroaryl, —($C_7$-$C_{10}$)arylalkyl, —C(=O)R$^5$;

R$^5$ are selected from hydrogen, —($C_1$-$C_6$)alkyl, and —($C_6$-$C_{10}$)aryl;

R$^2$, R$^3$ and R$^4$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, arylalkyl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(heteroaryl), —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents; wherein optionally R$^2$, R$^3$, R$^4$ substituents are combined to the intervening atoms to form a bicyclic heterocycloalkyl;

$X_1$, $X_2$, $X_3$, $X_4$ and $X_5$ are each independently selected from the group consisting of —CR$^6$=, —N=;

R$^6$ is 1 to 5 substituents independently selected from the group consisting of hydrogen, halogen, —OCF$_3$, —CN, —CF$_3$, —NO$_2$, an optionally substituted —($C_1$-$C_6$)alkyl, —($C_3$-$C_6$)cycloalkyl, —($C_2$-$C_6$)alkenyl, —($C_2$-$C_6$)alkynyl, halo-($C_1$-$C_6$)alkyl, —($C_0$-$C_6$)alkylOR$^7$, —($C_0$-$C_6$)alkylNR$^8$R$^9$, —($C_0$-$C_6$)alkyl-C(=NR$^{10}$)NR$^8$R$^9$, —($C_0$-$C_6$)alkylSR$^8$, —($C_0$-$C_6$)alkylNR$^8$C(=O)R$^9$, —($C_0$-$C_6$)alkylNR$^8$C(=O)$_2$R$^9$, —($C_0$-$C_6$)alkylNR$^8$S(=O)$_2$R$^9$, —($C_0$-$C_6$)alkylNR$^{10}$C(=O)NR$^8$R$^9$, —($C_0$-$C_6$)alkylS(=O)R$^8$, —($C_0$-$C_6$)alkylS(=O)$_2$R$^8$, —($C_0$-$C_6$)alkylS(=O)$_2$NR$^8$R$^9$, —($C_0$-$C_6$)alkylC(=O)R$^8$, —($C_0$-$C_6$)alkylC(=O)OR$^7$, —($C_1$-$C_6$)alkylC(=O)NR$^8$R$^9$, —($C_0$-$C_6$)alkylC(=NR$^8$)R$^9$, or —($C_0$-$C_6$)alkylC(=NOR$^7$)R$^9$, heteroaryl, heteroarylalkyl, arylalkyl, aryl, a 3 to 6 heterocycloalkyl; wherein optionally two substituents are combined to the intervening atoms to form a bicyclic heterocycloalkyl, aryl or heteroaryl ring; wherein each ring is optionally further substituted with 1 to 5 independent halogen, —CN, —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkyl aryl, —O($C_1$-$C_3$)alkylheteroaryl, —N(($C_0$-$C_6$)alkyl)$_2$, —N(($C_0$-$C_6$)alkyl))(($C_0$-$C_3$)alkylaryl)) or —N(($C_0$-$C_6$)alkyl)(($C_0$-$C_3$)alkylheteroaryl)) groups;

R$^7$ at each occurrence is selected from hydrogen, —($C_1$-$C_6$)alkyl, —($C_2$-$C_6$)alkenyl, —($C_3$-$C_7$)cycloalkyl, 3 to 7 membered heterocycloalkyl, —($C_6$-$C_{10}$)aryl, 5 or 6 membered heteroaryl, —($C_7$-$C_{10}$)arylalkyl, —C(=O)R$^{11}$;

R$^{11}$ are selected from —($C_1$-$C_6$)alkyl, —($C_3$-$C_7$)cycloalkyl and —($C_6$-$C_{10}$)aryl;

R$^8$, R$^9$ and R$^{10}$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, arylalkyl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O(heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

E is selected from the group consisting of hydrogen, halogen, —OCF$_3$, —NO$_2$, —CN, —CF$_3$, —($C_1$-$C_6$)alkyl, —($C_3$-$C_6$)cyclo alkyl, halo-($C_1$-$C_6$)alkyl, —($C_0$-$C_6$)alkylOR$^{12}$, —($C_0$-$C_6$)alkylNR$^{13}$R$^{14}$, —($C_0$-$C_6$)alkylSR$^{12}$, —($C_0$-$C_6$)alkylNR$^{13}$C(=O)R$^{14}$, —($C_0$-$C_6$)alkylNR$^{13}$C(=O)$_2$R$^{14}$, —($C_0$-$C_6$)alkylNR$^{13}$S(=O)$_2$R$^{14}$, —($C_0$-$C_6$)alkylNR$^{15}$C(=O)NR$^{13}$R$^{14}$, —($C_0$-$C_6$)alkylS(=O)R$^{13}$, —($C_0$-$C_6$)alkylS(=O)$_2$R$^{13}$, —($C_0$-$C_6$)alkylS(=O)$_2$NR$^{13}$R$^{14}$, —($C_0$-$C_6$)alkylC(=O)R$^{13}$, —($C_0$-$C_6$)alkylC(=O)OR$^{13}$, —($C_0$-$C_6$)alkylC(=O)NR$^{13}$R$^{14}$; wherein optionally two substituents are combined to the intervening atoms to form a bicyclic heterocycloalkyl, aryl or heteroaryl ring; wherein each ring is optionally further substituted with 1 to 5 independent halogen, —CN, an optionally substituted —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkylaryl, —O($C_1$-$C_3$)alkylheteroaryl, —N(($C_0$-$C_6$)alkyl)$_2$, —N(($C_0$-$C_6$)alkyl))(($C_0$-$C_3$)alkylaryl)) or —N(($C_0$-$C_6$)alkyl)(($C_0$-$C_3$)alkylheteroaryl)) groups;

R$^{12}$ at each occurrence is selected from hydrogen, —($C_1$-$C_6$)alkyl, —($C_2$-$C_6$)alkenyl, —($C_3$-$C_7$)cycloalkyl, —C(=O)R$^{16}$;

R$^{16}$ are selected from hydrogen, —($C_1$-$C_6$)alkyl, —($C_3$-$C_7$)cycloalkyl and —($C_6$-$C_{10}$)aryl;

R$^{13}$, R$^{14}$ and R$^{15}$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, alkylheteroaryl, arylalkyl, alkylaryl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O(heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

When E is —H the compounds for which X$_3$ is not CH= or —CF= are excluded from the invention;

When E is —CN the compounds of the following list are excluded from the invention:
4-(4-(trifluoromethyl)benzyl)-2-(4-fluorophenyl)-3,5-dioxo-2,3,4,5-tetrahydro-1,2,4-triazine-6-carbonitrile,
4-(4-nitrobenzyl)-2-(4-fluorophenyl)-3,5-dioxo-2,3,4,5-tetrahydro-1,2,4-triazine-6-carbonitrile,
4-(4-chlorobenzyl)-2-(4-fluorophenyl)-3,5-dioxo-2,3,4,5-tetrahydro-1,2,4-triazine-6-carbonitrile,
4-(4-chlorobenzyl)-2-(2,6-difluorophenyl)-3,5-dioxo-2,3,4,5-tetrahydro-1,2,4-triazine-6-carbonitrile,
4-(4-chlorobenzyl)-3,5-dioxo-2-phenyl-2,3,4,5-tetrahydro-1,2,4-triazine-6-carbonitrile,
4-(3-cyanobenzyl)-3,5-dioxo-2-phenyl-2,3,4,5-tetrahydro-1,2,4-triazine-6-carbonitrile,
4-benzyl-3,5-dioxo-2-phenyl-2,3,4,5-tetrahydro-1,2,4-triazine-6-carbonitrile,
4-(2,4-dichlorobenzyl)-3,5-dioxo-2-phenyl-2,3,4,5-tetrahydro-1,2,4-triazine-6-carbonitrile,
4-((3-chloro-5-(trifluoromethyl)pyridin-2-yl)methyl)-2-(4-fluorophenyl)-3,5-dioxo-2,3,4,5-tetrahydro-1,2,4-triazine-6-carbonitrile;

L is independently selected from a —(($C_1$-$C_5$)alkyl-Q$_m$)- substituted with 1-6 T;

m is 0 or 1;

T is 1 to 6 substituents independently selected from the group consisting of hydrogen, fluorine, —OCF$_3$, —NO$_2$, —CN, —CF$_3$, —($C_1$-$C_6$)alkyl, —($C_3$-$C_6$)cyclo alkyl, —($C_2$-$C_6$)alkenyl, —($C_2$-$C_6$)alkynyl, halo-($C_1$-$C_6$)alkyl, —($C_0$-$C_6$)alkylOR$^{17}$, —($C_0$-$C_6$)alkylNR$^{18}$R$^{19}$, —($C_0$-$C_6$)alkyl-C(=NR$^{20}$)NR$^{18}$R$^{19}$, —($C_0$-$C_6$)alkylSR$^{18}$, —($C_0$-$C_6$)alkylNR$^{18}$C(=O)R$^{19}$, —($C_0$-$C_6$)alkylNR$^{18}$C(=O)$_2$R$^{19}$, —($C_0$-$C_6$)alkylNR$^{18}$S(=O)$_2$R$^{19}$, —($C_0$-$C_6$)alkylNR$^{20}$C(=O)NR$^{18}$R$^{19}$, —($C_0$-$C_6$)alkylS(=O)R$^{18}$, —($C_0$-$C_6$)alkylS(=O)$_2$R$^{18}$—($C_0$-$C_6$)alkylS(=O)$_2$NR$^{18}$R$^{19}$, —($C_0$-$C_6$)alkylC(=O)R$^{18}$, —($C_0$-$C_6$)alkylC(=O)OR$^{17}$, —($C_0$-$C_6$)alkylC(=O)NR$^{18}$R$^{19}$, —($C_0$-$C_6$)alkylC(=NR$^{18}$)R$^{19}$, or —($C_0$-$C_6$)alkylC(=NOR$^{17}$)R$^{19}$, heteroaryl, heteroarylalkyl, arylalkyl, alkylaryl, alkylheteroaryl, aryl; wherein optionally two substituents are combined to the intervening atoms to form a bicyclic heterocycloalkyl, aryl or heteroaryl ring; wherein each ring is optionally further substituted with 1 to 5 independent halogen, —CN, —($C_1$-$C_6$)alkyl, —O($C_0$-$C_6$)alkyl, —O($C_3$-$C_7$)cycloalkyl, —O(aryl), —O(aryl)-($C_0$-$C_3$) alkyl, —O(heteroaryl), —O(heteroaryl)-($C_0$-$C_3$)alkyl, —O($C_1$-$C_3$)alkyl aryl, —O($C_1$-$C_3$)alkylheteroaryl, —N(($C_0$-$C_6$)alkyl))(($C_0$-$C_3$)alkylaryl)) or —N(($C_0$-$C_6$)alkyl)(($C_0$-$C_3$)alkylheteroaryl)) groups;

R$^{17}$ at each occurrence is selected from hydrogen, —($C_1$-$C_6$)alkyl, —($C_2$-$C_6$)alkenyl, —($C_3$-$C_7$)cycloalkyl, 3 to 7 membered heterocycloalkyl, —($C_6$-$C_{10}$)aryl, 5 or 6 membered heteroaryl, —($C_7$-$C_{10}$)arylalkyl, —C(=O)R$^{21}$;

R$^{21}$ is selected from hydrogen, —($C_1$-$C_6$)alkyl, —($C_3$-$C_7$)cycloalkyl, and —($C_6$-$C_{10}$)aryl;

R$^{18}$, R$^{19}$ and R$^{20}$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, arylalkyl alkylaryl, alkylheteroaryl, aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O(heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

Q is —C(=O)—, —C(=O)O—, —C(=O)NR$^{22}$—, —OC(=O)—, —OC(=O)NR$^{22}$—, —NR$^{22}$—, —NR$^{22}$C(=O)—, —NR$^{22}$C(=O)$_2$—, —NR$^{22}$C(=S)—, —S—, —S(=O)—, or —S(=O)$_2$—;

R$^{22}$ is selected from —($C_1$-$C_6$)alkyl, and —($C_6$-$C_{10}$)aryl;

Any N may be an N-oxide.

More preferred compounds of the present invention from Formula III are compounds of Formula III.B

III.B

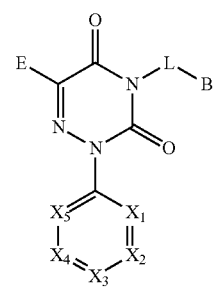

and stereoisomeric forms, mixtures of stereoisomeric forms or pharmaceutically acceptable salts, hydrates or solvates of such compounds,
wherein:
B is selected from $C_6$-$C_{10}$ aryl optionally substituted with one to 5 Y, $C_5$-$C_{10}$ cycloalkenyl optionally substituted with one to 7 Y, 5 to 14 membered heteroaryl group optionally substituted by one to 8 Y, wherein said heteroaryl group comprises one, two or three heteroatoms selected from N, O, S;
- Y is 1 to 5 substituents independently selected from the group consisting of hydrogen, halogen, —$OCF_3$, —$NO_2$, —CN, —$CF_3$, an optionally substituted —($C_1$-$C_6$)alkyl, —($C_3$-$C_6$)cyclo alkyl, —($C_2$-$C_6$)alkenyl, —($C_2$-$C_6$)alkynyl, halo—($C_1$-$C_6$)alkyl, —($C_0$-$C_6$)alkylOR$^1$, —($C_0$-$C_6$)alkylNR$^2$R$^3$, —($C_0$-$C_6$)alkyl-C(=NR$^4$)NR$^2$R$^3$, —($C_0$-$C_6$)alkylSR$^2$, —($C_0$-$C_6$)alkylNR$^2$C(=O)R$^3$, —($C_0$-$C_6$)alkylNR$^2$C(=O)$_2$R$^3$, —($C_0$-$C_6$)alkylNR$^2$S(=O)$_2$R$^3$, —($C_0$-$C_6$)alkylNR$^4$C(=O)NR$^2$R$^3$, —($C_0$-$C_6$)alkylS(=O)R$^2$, —($C_0$-$C_6$)alkylS(=O)$_2$R$^2$, —($C_0$-$C_6$)alkylS(=O)$_2$NR$^2$R$^3$, —($C_0$-$C_6$)alkylC(=O)R$^2$, —($C_0$-$C_6$)alkylC(=O)OR$^1$, —($C_0$-$C_6$)alkylC(=O)NR$^2$R$^3$, —($C_0$-$C_6$)alkylC(=NR$^2$)R$^3$, or —($C_0$-$C_6$)alkylC(=NOR$^1$)R$^3$, heteroaryl, heteroarylalkyl, arylalkyl, aryl alkylaryl, alkylheteroaryl; wherein optionally two substituents are combined to the intervening atoms to form a bicyclic heterocycloalkyl, aryl or heteroaryl ring; wherein each ring is optionally further substituted with 1 to 5 independent halogen, —CN, —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkylaryl, —O($C_1$-$C_3$)alkylheteroaryl, —N(($C_0$-$C_6$)alkyl)$_2$, —N(($C_0$-$C_6$)alkyl))(($C_0$-$C_3$)alkylaryl)) or —N(($C_0$-$C_6$)alkyl)(($C_0$-$C_3$)alkylheteroaryl)) groups;
- R$^1$ at each occurrence is selected from hydrogen, —($C_1$-$C_6$)alkyl, —($C_2$-$C_6$)alkenyl, —($C_3$-$C_7$)cycloalkyl, 3 to 7 membered heterocycloalkyl, —($C_6$-$C_{10}$)aryl, 5 or 6 membered heteroaryl, —($C_7$-$C_{10}$)arylalkyl, —C(=O)R$^5$;
- R$^5$ are selected from hydrogen, —($C_1$-$C_6$)alkyl, and —($C_6$-$C_{10}$)aryl;
- R$^2$, R$^3$ and R$^4$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, arylalkyl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(heteroaryl), —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents; wherein optionally R$^2$, R$^3$, R$^4$ substituents are combined to the intervening atoms to form a bicyclic heterocycloalkyl;

$X_1$, $X_2$, $X_3$, $X_4$ and $X_5$ are each independently selected from the group consisting of —CR$^6$=, —N=;
- R$^6$ is 1 to 5 substituents independently selected from the group consisting of hydrogen, halogen, —$OCF_3$, —CN, —$CF_3$, —$NO_2$, an optionally substituted —($C_1$-$C_6$)alkyl, —($C_3$-$C_6$)cycloalkyl, —($C_2$-$C_6$)alkenyl, —($C_2$-$C_6$)alkynyl, halo-($C_1$-$C_6$)alkyl, —($C_0$-$C_6$)alkylOR$^7$, —($C_0$-$C_6$)alkylNR$^8$R$^9$, —($C_0$-$C_6$)alkylSR$^8$, —($C_0$-$C_6$)alkylNR$^8$C(=O)R$^9$, —($C_0$-$C_6$)alkylNR$^8$C(=O)$_2$R$^9$, —($C_0$-$C_6$)alkylNR$^8$S(=O)$_2$R$^9$, —($C_0$-$C_6$)alkylNR$^{10}$C(=O)NR$^8$R$^9$, —($C_0$-$C_6$)alkylS(=O)R$^8$, —($C_0$-$C_6$)alkylS(=O)$_2$R$^8$, —($C_0$-$C_6$)alkylS(=O)$_2$NR$^8$R$^9$, —($C_0$-$C_6$)alkylC(=O)R$^8$, —($C_0$-$C_6$)alkylC(=O)OR$^7$, —($C_1$-$C_6$)alkylC(=O)NR$^8$R$^9$, heteroaryl, heteroarylalkyl, arylalkyl, aryl, a 3 to 6 heterocycloalkyl; wherein optionally two substituents are combined to the intervening atoms to form a bicyclic heterocycloalkyl, aryl or heteroaryl ring; wherein each ring is optionally further substituted with 1 to 5 independent halogen, —CN, —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkylaryl, —O($C_1$-$C_3$)alkylheteroaryl, —N(($C_0$-$C_6$)alkyl)$_2$, —N(($C_0$-$C_6$)alkyl))(($C_0$-$C_3$)alkylaryl)) or —N(($C_0$-$C_6$)alkyl)(($C_0$-$C_3$)alkylheteroaryl)) groups;
- R$^7$ at each occurrence is selected from hydrogen, —($C_1$-$C_6$)alkyl, —($C_2$-$C_6$)alkenyl, —($C_3$-$C_7$)cycloalkyl, 3 to 7 membered heterocycloalkyl, —($C_6$-$C_{10}$)aryl, 5 or 6 membered heteroaryl, —($C_7$-$C_{10}$)arylalkyl, —C(=O)R$^{11}$;
- R$^{11}$ are selected from —($C_1$-$C_6$)alkyl, —($C_3$-$C_7$)cycloalkyl and —($C_6$-$C_{10}$)aryl;
- R$^8$, R$^9$ and R$^{10}$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, arylalkyl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O(heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

E is selected from the group consisting of hydrogen, halogen, —$OCF_3$, —CN, —$CF_3$, —($C_1$-$C_6$)alkyl, —($C_3$-$C_6$)cycloalkyl, —($C_0$-$C_6$)alkylOR$^{12}$, —($C_0$-$C_6$)alkylNR$^{13}$R$^{14}$, —($C_0$-$C_6$)alkylS(=O)R$^{13}$, —($C_0$-$C_6$)alkylS(=O)$_2$R$^{13}$, ($C_0$-$C_6$)alkylC(=O)R$^{13}$, —($C_0$-$C_6$)alkylC(=O)OR$^{13}$, —($C_0$-$C_6$)alkylC(=O)NR$^{13}$R$^{14}$; wherein optionally two substituents are combined to the intervening atoms to form a bicyclic heterocycloalkyl, aryl or heteroaryl ring; wherein each ring is optionally further substituted with 1 to 5 independent halogen, —CN, an optionally substituted —($C_1$-$C_6$)alkyl, —O($C_0$-$C_6$)alkyl, —O($C_3$-$C_7$)cycloalkyl, —O(aryl), —O(aryl)-($C_0$-$C_3$)alkyl, —O(heteroaryl), —O(heteroaryl)-($C_0$-$C_3$)alkyl, —O($C_1$-$C_3$)alkyl aryl, —O($C_1$-$C_3$)alkylheteroaryl, —N(($C_0$-$C_6$)alkyl)$_2$, —N(($C_0$-$C_6$)alkyl))(($C_0$-$C_3$)alkylaryl)) or —N(($C_0$-$C_6$)alkyl)(($C_0$-$C_3$)alkylheteroaryl)) groups;
- R$^{12}$ at each occurrence is selected from hydrogen, —($C_1$-$C_6$)alkyl, —($C_2$-$C_6$)alkenyl, —($C_3$-$C_7$)cycloalkyl, —C(=O)R$^{16}$;
- R$^{16}$ are selected from hydrogen, —($C_1$-$C_6$)alkyl, —($C_3$-$C_7$)cycloalkyl and —($C_6$-$C_{10}$)aryl;
- R$^{13}$ and R$^{14}$ each independently is hydrogen, —($C_1$-$C_6$)alkyl, —($C_3$-$C_6$)cycloalkyl, —($C_2$-$C_6$)alkenyl, —($C_2$-$C_6$)alkynyl, —($C_1$-$C_6$)alkylhalo, heterocycloalkyl, heteroaryl, heteroarylalkyl, alkylheteroaryl, arylalkyl, alkylaryl or aryl; any of which is optionally substituted with 1 to 5 independent halogen, —CN, —($C_1$-$C_6$)alkyl, —O($C_0$-$C_6$)alkyl, —O($C_3$-$C_7$)cycloalkylalkyl, —O(aryl), —O(aryl)-($C_0$-$C_3$)alkyl, —O(heteroaryl), —O(heteroaryl)-($C_0$-$C_3$)alkyl, —N(($C_0$-$C_6$)alkyl)$_2$, —N(($C_0$-$C_6$)alkyl)(($C_3$-$C_7$)cycloalkyl) or —N(($C_0$-$C_6$)alkyl)(aryl) substituents;

When E is —H the compounds for which $X_3$ is not CH= or —CF= are excluded from the invention;

When E is —H the compounds for which $X_3$ is not —CH= or —CF= are excluded from the invention;

When E is —CN the compounds of the following list are excluded from the invention:

4-(4-(trifluoromethyl)benzyl)-2-(4-fluorophenyl)-3,5-dioxo-2,3,4,5-tetrahydro-1,2,4-triazine-6-carbonitrile,
4-(4-nitrobenzyl)-2-(4-fluorophenyl)-3,5-dioxo-2,3,4,5-tetrahydro-1,2,4-triazine-6-carbonitrile,
4-(4-chlorobenzyl)-2-(4-fluorophenyl)-3,5-dioxo-2,3,4,5-tetrahydro-1,2,4-triazine-6-carbonitrile,
4-(4-chlorobenzyl)-2-(2,6-difluorophenyl)-3,5-dioxo-2,3,4,5-tetrahydro-1,2,4-triazine-6-carbonitrile,
4-(4-chlorobenzyl)-3,5-dioxo-2-phenyl-2,3,4,5-tetrahydro-1,2,4-triazine-6-carbonitrile,
4-(3-cyanobenzyl)-3,5-dioxo-2-phenyl-2,3,4,5-tetrahydro-1,2,4-triazine-6-carbonitrile,
4-benzyl-3,5-dioxo-2-phenyl-2,3,4,5-tetrahydro-1,2,4-triazine-6-carbonitrile,
4-(2,4-dichlorobenzyl)-3,5-dioxo-2-phenyl-2,3,4,5-tetrahydro-1,2,4-triazine-6-carbonitrile,
4-((3-chloro-5-(trifluoromethyl)pyridin-2-yl)methyl)-2-(4-fluorophenyl)-3,5-dioxo-2,3,4,5-tetrahydro-1,2,4-triazine-6-carbonitrile;

L is independently selected from a —(($C_1$-$C_5$)alkyl-$Q_m$)- substituted with 1-6 T;
m is 0 or 1;
T is 1 to 6 substituents independently selected from the group consisting of hydrogen, —($C_1$-$C_6$)alkyl;
Q is —C(=O)—, —C(=O)O—, —C(=O)NR$^{22}$—, —OC(=O)—, —OC(=O)NR$^{22}$—, —NR$^{22}$—, —NR$^{22}$C(=O)—, —NR$^{22}$C(=O)$_2$—, —NR$^{22}$C(=S)—, —S—, —S(=O)—, or S(=O)$_2$—;
R$^{22}$ is selected from —($C_1$-$C_6$)alkyl, and —($C_6$-$C_{10}$) aryl;
Any N may be an N-oxide.

Further preferred compounds of the present invention are compounds of Formula I selected from the following examples:

N-(3-(4-(4-chlorobenzyl)-6-cyano-3,5-dioxo-4,5-dihydro-1,2,4-triazin-2(3H)-yl)phenyl)acetamide, N-(5-(4-(4-chlorobenzyl)-6-cyano-3,5-dioxo-4,5-dihydro-1,2,4-triazin-2(3H)-yl)-2-fluorophenyl)acetamide, N-(3-(4-benzhydryl-6-cyano-3,5-dioxo-4,5-dihydro-1,2,4-triazin-2(3H)-yl)phenyl)acetamide, N-(5-(4-(4-nitrobenzyl)-6-cyano-3,5-dioxo-4,5-dihydro-1,2,4-triazin-2(3H)-yl)-2-fluorophenyl)acetamide, N-(5-(4-(3,4-dichlorobenzyl)-6-cyano-3,5-dioxo-4,5-dihydro-1,2,4-triazin-2(3H)-yl)-2-fluorophenyl)acetamide, N-(5-(4-(4-chloro-2-fluorobenzyl)-6-cyano-3,5-dioxo-4,5-dihydro-1,2,4-triazin-2(3H)-yl)-2-fluorophenyl)acetamide, 4-((2,3-dihydrobenzofuran-5-yl)methyl)-2-(4-fluorophenyl)-3,5-dioxo-2,3,4,5-tetrahydro-1,2,4-triazine-6-carbonitrile, N-(3-(4-(4-chlorobenzyl)-3,5-dioxo-4,5-dihydro-1,2,4-triazin-2(3H)-yl)phenyl)acetamide, N-(3-(4-(4-chlorobenzyl)-3,5-dioxo-4,5-dihydro-1,2,4-triazin-2(3H)-yl)phenyl)methanesulfonamide, 4-(4-chlorobenzyl)-2-(2-methoxyphenyl)-1,2,4-triazine-3,5(2H,4H)-dione, N-(3-(4-(4-nitrobenzyl)-3,5-dioxo-4,5-dihydro-1,2,4-triazin-2(3H)-yl)phenyl)acetamide, N-(3-(4-(4-cyanobenzyl)-3,5-dioxo-4,5-dihydro-1,2,4-triazin-2(3H)-yl)phenyl)acetamide, N-(3-(4-(naphthalen-2-ylmethyl)-3,5-dioxo-4,5-dihydro-1,2,4-triazin-2(3H)-yl)phenyl)acetamide, N-(3-(4-(benzo[c][1,2,5]oxadiazol-5-ylmethyl)-3,5-dioxo-4,5-dihydro-1,2,4-triazin-2(3H)-yl)phenyl)acetamide, N-(3-(4-(4-fluorobenzyl)-3,5-dioxo-4,5-dihydro-1,2,4-triazin-2(3H)-yl)phenyl)acetamide, N-(3-(4-benzyl-3,5-dioxo-4,5-dihydro-1,2,4-triazin-2(3H)-yl)phenyl)acetamide, N-(3-(3,5-dioxo-4-(4-(trifluoromethyl)benzyl)-4,5-dihydro-1,2,4-triazin-2(3H)-yl)phenyl)acetamide, methyl 4-((2-(3-acetamidophenyl)-3,5-dioxo-2,3-dihydro-1,2,4-triazin-4(5H)-yl)methyl)benzoate, N-(3-(4-(naphthalen-1-ylmethyl)-3,5-dioxo-4,5-dihydro-1,2,4-triazin-2(3H)-yl)phenyl)acetamide, N-(3-(4-(4-methoxybenzyl)-3,5-dioxo-4,5-dihydro-1,2,4-triazin-2(3H)-yl)phenyl)acetamide, N-(3-(4-(4-bromobenzyl)-3,5-dioxo-4,5-dihydro-1,2,4-triazin-2(3H)-yl)phenyl)acetamide, N-(3-(4-(3-chlorobenzyl)-3,5-dioxo-4,5-dihydro-1,2,4-triazin-2(3H)-yl)phenyl)acetamide, N-(3-(4-(4-methylbenzyl)-3,5-dioxo-4,5-dihydro-1,2,4-triazin-2(3H)-yl)phenyl)acetamide, N-(3-(4-(4-isopropylbenzyl)-3,5-dioxo-4,5-dihydro-1,2,4-triazin-2(3H)-yl)phenyl)acetamide, N-(3-(4-(3,4-dimethylbenzyl)-3,5-dioxo-4,5-dihydro-1,2,4-triazin-2(3H)-yl)phenyl)acetamide, N-(3-(4-((6-chloropyridin-3-yl)methyl)-3,5-dioxo-4,5-dihydro-1,2,4-triazin-2(3H)-yl)phenyl)acetamide, N-(3-(4-(4-chloro-2-fluorobenzyl)-3,5-dioxo-4,5-dihydro-1,2,4-triazin-2(3H)-yl)phenyl)acetamide, N-(3-(4-(4-chlorobenzyl)-6-methyl-3,5-dioxo-4,5-dihydro-1,2,4-triazin-2(3H)-yl)phenyl)acetamide, N-(3-(4-benzyl-6-methyl-3,5-dioxo-4,5-dihydro-1,2,4-triazin-2(3H)-yl)phenyl)acetamide, N-(3-(4-(4-chloro-3-fluorobenzyl)-6-methyl-3,5-dioxo-4,5-dihydro-1,2,4-triazin-2(3H)-yl)phenyl)acetamide, N-(3-(4-((6-fluoropyridin-3-yl)methyl)-6-methyl-3,5-dioxo-4,5-dihydro-1,2,4-triazin-2(3H)-yl)phenyl)acetamide, N-(3-(4-((6-isopropylpyridin-3-yl)methyl)-6-methyl-3,5-dioxo-4,5-dihydro-1,2,4-triazin-2(3H)-yl)phenyl)acetamide, N-(3-(4-(4-fluorobenzyl)-6-methyl-3,5-dioxo-4,5-dihydro-1,2,4-triazin-2(3H)-yl)phenyl)acetamide, N-(2-fluoro-5-(4-(4-fluorobenzyl)-6-methyl-3,5-dioxo-4,5-dihydro-1,2,4-triazin-2(3H)-yl)phenyl)acetamide, N-(3-(4-(4-methoxybenzyl)-6-methyl-3,5-dioxo-4,5-dihydro-1,2,4-triazin-2(3H)-yl)phenyl)acetamide, N-(3-(4-(4-isopropylbenzyl)-6-methyl-3,5-dioxo-4,5-dihydro-1,2,4-triazin-2(3H)-yl)phenyl)acetamide, 4-(4-chlorobenzyl)-6-methyl-2-phenyl-1,2,4-triazine-3,5(2H,4H)-dione, N-(3-(6-methyl-4-(naphthalen-2-ylmethyl)-3,5-dioxo-4,5-dihydro-1,2,4-triazin-2(3H)-yl)phenyl)acetamide, N-(3-(4-((6-cyclopentylpyridin-3-yl)methyl)-6-methyl-3,5-dioxo-4,5-dihydro-1,2,4-triazin-2(3H)-yl)phenyl)acetamide, N-(3-(4-(3,4-difluorobenzyl)-6-methyl-3,5-dioxo-4,5-dihydro-1,2,4-triazin-2(3H)-yl)phenyl)acetamide, N-(3-(4-(3,4-dimethoxybenzyl)-6-methyl-3,5-dioxo-4,5-dihydro-1,2,4-triazin-2(3H)-yl)phenyl)acetamide, N-(3-(4-(2,4-difluorobenzyl)-6-methyl-3,5-dioxo-4,5-dihydro-1,2,4-triazin-2(3H)-yl)phenyl)acetamide, N-(3-(4-(4-isopropoxybenzyl)-6-methyl-3,5-dioxo-4,5-dihydro-1,2,4-triazin-2(3H)-yl)phenyl)acetamide, N-(3-(6-methyl-4-(naphthalen-1-ylmethyl)-3,5-dioxo-4,5-dihydro-1,2,4-triazin-2(3H)-yl)phenyl)acetamide, N-(3-(6-methyl-4-(4-methylbenzyl)-3,5-dioxo-4,5-dihydro-1,2,4-triazin-2(3H)-yl)phenyl)acetamide, N-(2-fluoro-5-(6-methyl-4-(4-methylbenzyl)-3,5-dioxo-4,5-dihydro-1,2,4-triazin-2(3H)-yl)phenyl)acetamide, N-(2-fluoro-5-(4-(3-methoxybenzyl)-6-methyl-3,5-dioxo-4,5-dihydro-1,2,4-triazin-2(3H)-yl)phenyl)acetamide, 3-(4-(4-fluorobenzyl)-6-methyl-3,5-dioxo-4,5-dihydro-1,2,4-triazin-2(3H)-yl)-N-methylbenzamide, N-(3-(4-(4-fluorobenzyl)-6-methoxy-3,5-dioxo-4,5-dihydro-1,2,4-triazin-2(3H)-yl)phenyl)acetamide, N-(3-(6-methoxy-4-(4-nitrobenzyl)-3,5-dioxo-4,5-dihydro-1,2,4-triazin-2(3H)-yl)phenyl)acetamide, N-(3-(6-methoxy-4-(4-methylbenzyl)-3,5-dioxo-4,5-dihydro-1,2,4-triazin-2(3H)-yl)phenyl)acetamide, N-(3-(6-methoxy-3,5-dioxo-4-(4-

(trifluoromethyl)benzyl)-4,5-dihydro-1,2,4-triazin-2(3H)-yl)phenyl)acetamide, N-(3-(4-(4-chloro-3-fluorobenzyl)-6-methoxy-3,5-dioxo-4,5-dihydro-1,2,4-triazin-2(3H)-yl)phenyl)acetamide, 4-(4-chloro-3-fluorobenzyl)-6-methoxy-2-(2-methoxyphenyl)-1,2,4-triazine-3,5(2H,4H)-dione, N-(3-(4-(4-chlorobenzyl)-6-methoxy-3,5-dioxo-4,5-dihydro-1,2,4-triazin-2(3H)-yl)phenyl)methanesulfonamide, 4-(4-chlorobenzyl)-6-methoxy-2-(2-methoxyphenyl)-1,2,4-triazine-3,5(2H,4H)-dione, 1-(3-(4-(4-chlorobenzyl)-6-methoxy-3,5-dioxo-4,5-dihydro-1,2,4-triazin-2(3H)-yl)phenyl)-3-methylurea, N-(3-(4-(((6-chloropyridin-3-yl)methyl)-6-methoxy-3,5-dioxo-4,5-dihydro-1,2,4-triazin-2(3H)-yl)phenyl)acetamide, N-(2-fluoro-5-(6-methoxy-4-(4-methylbenzyl)-3,5-dioxo-4,5-dihydro-1,2,4-triazin-2(3H)-yl)phenyl)acetamide, N-(5-(4-(4-chlorobenzyl)-6-methoxy-3,5-dioxo-4,5-dihydro-1,2,4-triazin-2(3H)-yl)pyridin-3-yl)acetamide, N-(3-(6-methoxy-4-((6-methylpyridin-3-yl)methyl)-3,5-dioxo-4,5-dihydro-1,2,4-triazin-2(3H)-yl)phenyl)acetamide, N-(5-(4-(4-chloro-3-fluorobenzyl)-6-methoxy-3,5-dioxo-4,5-dihydro-1,2,4-triazin-2(3H)-yl)pyridin-3-yl)acetamide, 4-(4-chlorobenzyl)-2-(4-fluoro-2-methoxyphenyl)-6-methoxy-1,2,4-triazine-3,5(2H,4H)-dione, 4-(4-chlorobenzyl)-6-methoxy-2-(2-(methoxymethyl)phenyl)-1,2,4-triazine-3,5(2H,4H)-dione, 4-(4-chlorobenzyl)-6-methoxy-2-(3-(methoxymethyl)phenyl)-1,2,4-triazine-3,5(2H,4H)-dione, 4-(4-chlorobenzyl)-6-methoxy-2-(3-(2-methoxyethyl)phenyl)-1,2,4-triazine-3,5(2H,4H)-dione, 4-(4-chlorobenzyl)-6-methoxy-2-(2-(trifluoromethoxy)phenyl)-1,2,4-triazine-3,5(2H,4H)-dione, 4-(4-chlorobenzyl)-2-(2,3-dimethoxyphenyl)-6-methoxy-1,2,4-triazine-3,5(2H,4H)-dione, 4-(4-chlorobenzyl)-6-methoxy-2-(2-(morpholinomethyl)phenyl)-1,2,4-triazine-3,5(2H,4H)-dione, 4-(4-chlorobenzyl)-6-methoxy-2-(2-(2-methoxyethyl)phenyl)-1,2,4-triazine-3,5(2H,4H)-dione, 4-(4-chlorobenzyl)-6-methoxy-2-(3-((2-methyl-1,3-dioxolan-2-yl)methyl)phenyl)-1,2,4-triazine-3,5(2H,4H)-dione, 4-(4-chlorobenzyl)-6-methoxy-2-(3-(2-oxopropyl)phenyl)-1,2,4-triazine-3,5(2H,4H)-dione, 4-(4-fluoroobenzyl)-2-(2-((dimethylamino)methyl)phenyl)-6-methoxy-1,2,4-triazine-3,5(2H,4H)-dione, 4-(4-fluorobenzyl)-6-methoxy-2-(2-(pyrrolidin-1-ylmethyl)phenyl)-1,2,4-triazine-3,5(2H,4H)-dione, N-(2-fluoro-5-(6-methoxy-4-(4-methoxybenzyl)-3,5-dioxo-4,5-dihydro-1,2,4-triazin-2(3H)-yl)phenyl)acetamide, 4-(4-fluorobenzyl)-2-(4-fluorophenyl)-6-methoxy-1,2,4-triazine-3,5(2H,4H)-dione, 4-(4-fluorobenzyl)-6-methoxy-2-(2-(piperidin-1-ylmethyl)phenyl)-1,2,4-triazine-3,5(2H,4H)-dione, 4-(4-chlorobenzyl)-6-methoxy-2-(2-(((2-methoxyethyl)(methyl)amino)methyl)phenyl)-1,2,4-triazine-3,5(2H,4H)-dione, N-(2-fluoro-5-(4-(3-fluoro-4-methoxybenzyl)-6-methoxy-3,5-dioxo-4,5-dihydro-1,2,4-triazin-2(3H)-yl)phenyl)acetamide, 2-(4-(4-chlorobenzyl)-6-methoxy-3,5-dioxo-4,5-dihydro-1,2,4-triazin-2(3H)-yl)benzonitrile, 4-(4-chlorobenzyl)-2-(4-fluoro-2-(hydroxymethyl)phenyl)-6-methoxy-1,2,4-triazine-3,5(2H,4H)-dione, 4-(2,4-dichlorobenzyl)-6-methoxy-2-phenyl-1,2,4-triazine-3,5(2H,4H)-dione, 4-benzyl-6-methoxy-2-phenyl-1,2,4-triazine-3,5(2H,4H)-dione, N-(3-(4-(4-isopropylbenzyl)-6-methoxy-3,5-dioxo-4,5-dihydro-1,2,4-triazin-2(3H)-yl)phenyl)acetamide, N-(3-(4-(biphenyl-3-ylmethyl)-6-methoxy-3,5-dioxo-4,5-dihydro-1,2,4-triazin-2(3H)-yl)phenyl)acetamide, N-(3-(6-methoxy-3,5-dioxo-4-(4-(trifluoromethoxy)benzyl)-4,5-dihydro-1,2,4-triazin-2(3H)-yl)phenyl)acetamide, N-(3-(4-(4-(dimethylamino)benzyl)-6-methoxy-3,5-dioxo-4,5-dihydro-1,2,4-triazin-2(3H)-yl)phenyl)acetamide, N-(3-(4-(biphenyl-4-ylmethyl)-6-methoxy-3,5-dioxo-4,5-dihydro-1,2,4-triazin-2(3H)-yl)phenyl)acetamide, N-(3-(4-(4-benzyl-6-methoxy-3,5-dioxo-4,5-dihydro-1,2,4-triazin-2(3H)-yl)phenyl)acetamide, N-(3-(6-methoxy-4-(naphthalen-2-ylmethyl)-3,5-dioxo-4,5-dihydro-1,2,4-triazin-2(3H)-yl)phenyl)acetamide, N-(3-(4-(((6-isopropylpyridin-3-yl)methyl)-6-methoxy-3,5-dioxo-4,5-dihydro-1,2,4-triazin-2(3H)-yl)phenyl)acetamide, N-(3-(4-(4-fluorobenzyl)-6-methoxy-3,5-dioxo-4,5-dihydro-1,2,4-triazin-2(3H)-yl)phenyl)acetamide, N-(3-(6-methoxy-4-(4-methoxybenzyl)-3,5-dioxo-4,5-dihydro-1,2,4-triazin-2(3H)-yl)phenyl)acetamide, N-(3-(6-methoxy-3,5-dioxo-4-(quinolin-6-ylmethyl)-4,5-dihydro-1,2,4-triazin-2(3H)-yl)phenyl)acetamide, N-(3-(4-(4-isopropoxybenzyl)-6-methoxy-3,5-dioxo-4,5-dihydro-1,2,4-triazin-2(3H)-yl)phenyl)acetamide, N-(3-(4-(3,4-dimethoxybenzyl)-6-methoxy-3,5-dioxo-4,5-dihydro-1,2,4-triazin-2(3H)-yl)phenyl)acetamide, N-(3-(4-((6-cyclopentylpyridin-3-yl)methyl)-6-methoxy-3,5-dioxo-4,5-dihydro-1,2,4-triazin-2(3H)-yl)phenyl)acetamide, 4-(4-chlorobenzyl)-6-methoxy-2-phenyl-1,2,4-triazine-3,5(2H,4H)-dione, N-(3-(4-((6-fluoropyridin-3-yl)methyl)-6-methoxy-3,5-dioxo-4,5-dihydro-1,2,4-triazin-2(3H)-yl)phenyl)acetamide, N-(3-(4-((6-chloro-5-fluoropyridin-3-yl)methyl)-6-methoxy-3,5-dioxo-4,5-dihydro-1,2,4-triazin-2(3H)-yl)phenyl)acetamide, N-(3-(4-((6-(dimethylamino)pyridin-3-yl)methyl)-6-methoxy-3,5-dioxo-4,5-dihydro-1,2,4-triazin-2(3H)-yl)phenyl)acetamide, N-(3-(4-((2,3-dihydrobenzofuran-5-yl)methyl)-6-methoxy-3,5-dioxo-4,5-dihydro-1,2,4-triazin-2(3H)-yl)phenyl)acetamide, N-(3-(4-(3,4-difluorobenzyl)-6-methoxy-3,5-dioxo-4,5-dihydro-1,2,4-triazin-2(3H)-yl)phenyl)acetamide, N-(3-(4-(2,4-difluorobenzyl)-6-methoxy-3,5-dioxo-4,5-dihydro-1,2,4-triazin-2(3H)-yl)phenyl)acetamide, N-(3-(6-methoxy-4-((6-methoxypyridin-3-yl)methyl)-3,5-dioxo-4,5-dihydro-1,2,4-triazin-2(3H)-yl)phenyl)acetamide, N-(3-(6-methoxy-3,5-dioxo-4-(pyridin-3-ylmethyl)-4,5-dihydro-1,2,4-triazin-2(3H)-yl)phenyl)acetamide, N-(3-(4-(4-(1H-pyrazol-1-yl)benzyl)-6-methoxy-3,5-dioxo-4,5-dihydro-1,2,4-triazin-2(3H)-yl)phenyl)acetamide, N-(3-(4-(2,6-difluoro-4-methoxybenzyl)-6-methoxy-3,5-dioxo-4,5-dihydro-1,2,4-triazin-2(3H)-yl)phenyl)acetamide, N-(3-(6-methoxy-3,5-dioxo-4-(quinolin-3-ylmethyl)-4,5-dihydro-1,2,4-triazin-2(3H)-yl)phenyl)acetamide, N-(3-(4-(3-fluoro-4-methoxybenzyl)-6-methoxy-3,5-dioxo-4,5-dihydro-1,2,4-triazin-2(3H)-yl)phenyl)acetamide, N-(3-(4-(3,5-difluoro-4-methoxybenzyl)-6-methoxy-3,5-dioxo-4,5-dihydro-1,2,4-triazin-2(3H)-yl)phenyl)acetamide, N-(3-(4-(2,3-difluoro-4-methoxybenzyl)-6-methoxy-3,5-dioxo-4,5-dihydro-1,2,4-triazin-2(3H)-yl)phenyl)acetamide, N-(3-(6-methoxy-4-((1-methyl-1H-indol-5-yl)methyl)-3,5-dioxo-4,5-dihydro-1,2,4-triazin-2(3H)-yl)phenyl)acetamide, N-(3-(4-(2-fluoro-4-methoxybenzyl)-6-methoxy-3,5-dioxo-4,5-dihydro-1,2,4-triazin-2(3H)-yl)phenyl)acetamide, 4-(3,4-difluorobenzyl)-6-methoxy-2-phenyl-1,2,4-triazine-3,5(2H,4H)-dione, 4-(2-chloro-4-fluorobenzyl)-6-methoxy-2-phenyl-1,2,4-triazine-3,5(2H,4H)-dione, 4-(4-chloro-2-fluorobenzyl)-6-methoxy-2-phenyl-1,2,4-triazine-3,5(2H,4H)-dione, N-(3-(6-methoxy-4-(3-methoxybenzyl)-3,5-dioxo-4,5-dihydro-1,2,4-triazin-2(3H)-yl)phenyl)acetamide, 4-((2,3-dihydrobenzo[b][1,4]dioxin-2-yl)methyl)-6-methoxy-2-phenyl-1,2,4-triazine-3,5(2H,4H)-dione, 6-methoxy-2-phenyl-4-((2-phenylthiazol-4-yl)methyl)-1,2,4-triazine-3, 5(2H,4H)-dione, N-(3-(4-(4-chloro-2-fluorobenzyl)-6-methoxy-3,5-dioxo-4,5-dihydro-1,2,4-triazin-2(3H)-yl)phenyl)acetamide, 6-methoxy-2-phenyl-4-(3-(trifluoromethoxy)benzyl)-1,2,4-triazine-3,5(2H,4H)-dione, 4-(2,5-difluorobenzyl)-6-methoxy-2-phenyl-1,2,4-triazine-3,5(2H,4H)-dione, 4-(4-chloro-3-(trifluoromethoxy)benzyl)-6-methoxy-2-phenyl-1,2,4-triazine-3,5(2H,4H)-dione, N-(3-(4-(2,4-difluoro-3-methoxybenzyl)-6-methoxy-3,5-dioxo-4,5-dihydro-1,2,4-triazin-2(3H)-yl)phenyl)acetamide, N-(3-(4-((6-fluoro-2,3-dihydrobenzofuran-5-yl)methyl)-6-methoxy-3,5-dioxo-4,5-dihydro-1,2,4-triazin-2(3H)-yl)phenyl)acetamide, 4-(4-fluoro-3-(trifluoromethyl)benzyl)-6-methoxy-2-phenyl-1,2,4-triazine-3,5(2H,4H)-dione, 4-(4-benzoylbenzyl)-6-methoxy-2-phenyl-1,2,4-triazine-3,5(2H,4H)-dione, N-(4-((6-methoxy-3,5-dioxo-2-phenyl-2,3-dihydro-1,2,4-triazin-4(5H)-yl)methyl)thiazol-2-yl)acetamide, N-(3-(4-(furo[2,3-b]pyridin-5-ylmethyl)-6-methoxy-3,5-dioxo-4,5-dihydro-1,2,4-triazin-2(3H)-yl)phenyl)acetamide, N-(3-(4-(benzo[d]oxazol-6-ylmethyl)-6-methoxy-3,5-dioxo-4,5-dihydro-1,2,4-triazin-2(3H)-yl)phenyl)acetamide, N-(3-(4-(4-fluoro-3-methoxybenzyl)-6-methoxy-3,5-dioxo-4,5-dihydro-1,2,4-triazin-2(3H)-yl)phenyl)acetamide, 3-((6-methoxy-3,5-dioxo-2-phenyl-2,3-dihydro-1,2,4-triazin-4(5H)-yl)methyl)benzonitrile, 4-((6-methoxy-3,5-dioxo-2-phenyl-2,3-dihydro-1,2,4-triazin-4(5H)-yl)methyl)benzonitrile, N-(3-(4-((7-fluoro-2,3-dihydrobenzofuran-5-yl)methyl)-6-methoxy-3,5-dioxo-4,5-dihydro-1,2,4-triazin-2(3H)-yl)phenyl)acetamide, 4-(4-(hydroxymethyl)benzyl)-6-methoxy-2-phenyl-1,2,4-triazine-3,5 (2H,4H)-dione, 4-((6-chloro-4H-benzo[d][1,3]dioxin-8-yl)methyl)-6-methoxy-2-phenyl-1,2,4-triazine-3,5(2H,4H)-dione, 6-methoxy-2-phenyl-4-((5-(trifluoromethyl)furan-2-yl)methyl)-1,2,4-triazine-3,5(2H,4H)-dione, 6-methoxy-4-((1-methyl-1H-imidazol-2-yl)methyl)-2-phenyl-1,2,4-triazine-3,5(2H,4H)-dione, N-(3-(4-(2,4-dichlorobenzyl)-6-methoxy-3,5-dioxo-4,5-dihydro-1,2,4-triazin-2(3H)-yl)phenyl)acetamide, N-(3-(4-((6-(diethylamino)pyridin-3-yl)methyl)-6-methoxy-3,5-dioxo-4,5-dihydro-1,2,4-triazin-2(3H)-yl)phenyl)acetamide, 4-((5-chlorothiophen-2-yl)methyl)-6-methoxy-2-phenyl-1,2,4-triazine-3,5 (2H,4H)-dione, 4-((5-chlorobenzo[b]thiophen-3-yl)methyl)-6-methoxy-2-phenyl-1,2,4-triazine-3,5(2H,4H)-dione, 4-(2,4-difluorobenzyl)-6-methoxy-2-phenyl-1,2,4-triazine-3,5 (2H,4H)-dione, N-(3-(4-((2,3-dihydrofuro[2,3-b]pyridin-5-yl)methyl)-6-methoxy-3,5-dioxo-4,5-dihydro-1,2,4-triazin-2(3H)-yl)phenyl)acetamide, N-(3-(4-((4-fluoro-2,3-dihydrobenzofuran-5-yl)methyl)-6-methoxy-3,5-dioxo-4,5-dihydro-1,2,4-triazin-2(3H)-yl)phenyl)acetamide, N-(3-(4-(4-fluoro-3-(trifluoromethyl)benzyl)-6-methoxy-3,5-dioxo-4,5-dihydro-1,2,4-triazin-2(3H)-yl)phenyl)acetamide, N-(3-(4-((2-ethylbenzo[d]oxazol-6-yl)methyl)-6-methoxy-3,5-dioxo-4,5-dihydro-1,2,4-triazin-2(3H)-yl)phenyl)acetamide, N-(3-(4-(4-cyanobenzyl)-6-methoxy-3,5-dioxo-4,5-dihydro-1,2,4-triazin-2(3H)-yl)phenyl)acetamide, N-(3-(6-methoxy-4-((2-methylbenzo[d]oxazol-6-yl)methyl)-3,5-dioxo-4,5-dihydro-1,2,4-triazin-2(3H)-yl)phenyl)acetamide, N-(3-(4-((6-(dimethylamino)-5-fluoropyridin-3-yl)methyl)-6-methoxy-3,5-dioxo-4,5-dihydro-1,2,4-triazin-2(3H)-yl)phenyl)acetamide, N-(3-(4-(4-(dimethylamino)-3-fluorobenzyl)-6-methoxy-3,5-dioxo-4,5-dihydro-1,2,4-triazin-2(3H)-yl)phenyl)acetamide, N-(3-(6-methoxy-4-((1-methylindolin-5-yl)methyl)-3,5-dioxo-4,5-dihydro-1,2,4-triazin-2(3H)-yl)phenyl)acetamide, N-(3-(4-(2-fluoro-3-methoxybenzyl)-6-methoxy-3,5-dioxo-4,5-dihydro-1,2,4-triazin-2(3H)-yl)phenyl)acetamide, N-(3-(4-((4-fluoro-2,3-dihydrobenzofuran-7-yl)methyl)-6-methoxy-3,5-dioxo-4,5-dihydro-1,2,4-triazin-2(3H)-yl)phenyl)acetamide, N-(3-(4-((2,2-difluorobenzo[d][1,3]dioxol-5-yl)methyl)-6-methoxy-3,5-dioxo-4,5-dihydro-1,2,4-triazin-2(3H)-yl)phenyl)acetamide, N-(3-(4-((5-chloropyridin-2-yl)methyl)-6-methoxy-3,5-dioxo-4,5-dihydro-1,2,4-triazin-2(3H)-yl)phenyl)acetamide, N-(3-(4-((5-isopropylpyridin-2-yl)methyl)-6-methoxy-3,5-dioxo-4,5-dihydro-1,2,4-triazin-2(3H)-yl)phenyl)acetamide, N-(5-(4-(3,5-difluoro-4-methoxybenzyl)-6-methoxy-3,5-dioxo-4,5-dihydro-1,2,4-triazin-2(3H)-yl)-2-fluorophenyl)acetamide, N-(2-fluoro-5-(4-(4-fluoro-3-(trifluoromethoxy)benzyl)-6-methoxy-3,5-dioxo-4,5-dihydro-1,2,4-triazin-2(3H)-yl)phenyl)acetamide, N-(2-fluoro-5-(4-(3-fluoro-4-(trifluoromethoxy)benzyl)-6-methoxy-3,5-dioxo-4,5-dihydro-1,2,4-triazin-2(3H)-yl)phenyl)acetamide, N-(3-(4-(4-chlorobenzyl)-6-methoxy-3,5-dioxo-4,5-dihydro-1,2,4-triazin-2(3H)-yl)phenyl)-N-methylacetamide, N-(3-(6-methoxy-4-(4-nitrobenzyl)-3,5-dioxo-4,5-dihydro-1,2,4-triazin-2(3H)-yl)phenyl)-N-methylacetamide, N-(5-(4-((2,3-dihydrobenzofuran-5-yl)methyl)-6-methoxy-3,5-dioxo-4,5-dihydro-1,2,4-triazin-2(3H)-yl)-2-fluorophenyl)acetamide, N-(3-(6-methoxy-4-(4-methoxybenzyl)-3,5-dioxo-4,5-dihydro-1,2,4-triazin-2(3H)-yl)phenyl)-N-methylacetamide, N-(3-(4-((2,3-dihydrobenzofuran-5-yl)methyl)-6-methoxy-3,5-dioxo-4,5-dihydro-1,2,4-triazin-2(3H)-yl)phenyl)-N-methylacetamide, N-(3-(4-(4-fluoro-3-methoxybenzyl)-6-methoxy-3,5-dioxo-4,5-dihydro-1,2,4-triazin-2(3H)-yl)phenyl)-N-methylacetamide, N-(3-(4-(2,4-difluoro-3-methoxybenzyl)-6-methoxy-3,5-dioxo-4,5-dihydro-1,2,4-triazin-2(3H)-yl)phenyl)-N-methylacetamide, 6-methoxy-4-phenethyl-2-phenyl-1,2,4-triazine-3,5(2H,4H)-dione, N-(3-(4-(4-chlorobenzyl)-6-methoxy-3,5-dioxo-4,5-dihydro-1,2,4-triazin-2(3H)-yl)phenyl)-2-methoxyacetamide, N-(3-(4-(4-chlorobenzyl)-6-methoxy-3,5-dioxo-4,5-dihydro-1,2,4-triazin-2(3H)-yl)phenyl)-3-methoxypropanamide, 4-(4-chlorobenzyl)-2-(2-hydroxyphenyl)-6-methoxy-1,2,4-triazine-3,5(2H,4H)-dione, 4-(4-chlorobenzyl)-6-methoxy-2-(3-(thiazol-2-ylamino)phenyl)-1,2,4-triazine-3,5(2H,4H)-dione, 4-(4-chlorobenzyl)-6-methoxy-2-(3-(2-oxopyrrolidin-1-yl)phenyl)-1,2,4-triazine-3,5(2H,4H)-dione, 4-(4-chlorobenzyl)-6-methoxy-2-(3-(5-methyl-1,2,4-oxadiazol-3-yl)phenyl)-1,2,4-triazine-3,5(2H,4H)-dione, 6-methoxy-4-(4-methoxyphenethyl)-2-phenyl-1,2,4-triazine-3,5(2H,4H)-dione, 4-(4-fluorophenethyl)-6-methoxy-2-phenyl-1,2,4-triazine-3,5(2H,4H)-dione, 4-(3,4-dimethoxyphenethyl)-6-methoxy-2-phenyl-1,2,4-triazine-3,5(2H,4H)-dione, 6-methoxy-4-(3-methoxyphenethyl)-2-phenyl-1,2,4-triazine-3,5(2H,4H)-dione, 6-methoxy-4-(4-methoxyphenethyl)-2-phenyl-1,2,4-triazine-3,5(2H,4H)-dione, 4-(4-fluorophenethyl)-6-methoxy-2-phenyl-1,2,4-triazine-3,5(2H,4H)-dione N-(3-(6-methoxy-4-(3-methoxyphenethyl)-3,5-dioxo-4,5-dihydro-1,2,4-triazin-2(3H)-yl)phenyl)acetamide, N-(5-(4-benzyl-6-methoxy-3,5-dioxo-4,5-dihydro-1,2,4-triazin-2(3H)-yl)-2-fluorophenyl)acetamide, N-(2-fluoro-5-(4-(4-fluoro-3-methoxybenzyl)-6-methoxy-3,5-dioxo-4,5-dihydro-1,2,4-triazin-2(3H)-yl)phenyl)acetamide, N-(5-(4-(2,4-difluoro-3-methoxybenzyl)-6-methoxy-3,5-dioxo-4,5-dihydro-1,2,4-triazin-2(3H)-yl)-2-fluorophenyl)acetamide, N-(5-(4-(4,5-difluoro-2-methoxybenzyl)-6-methoxy-3,5-dioxo-4,5-dihydro-1,2,4-triazin-2(3H)-yl)-2-fluorophenyl)acetamide N-(2-fluoro-5-(6-methoxy- 3,5-dioxo-4-phenethyl-4,5-dihydro-1,2,4-triazin-2(3H)-yl)phenyl)acetamide, N-(5-(4-((6-chloro-5-fluoropyridin-3-yl)methyl)-6-methoxy-3,5-dioxo-4,5-dihydro-1,2,4-triazin-2(3H)-yl)-2-fluorophenyl)acetamide, N-(2-fluoro-5-(6-methoxy-4-(3-methoxybenzyl)-3,5-dioxo-4,5-dihydro-1,2,4-triazin-2(3H)-yl)phenyl)acetamide, N-(3-(4-(2,4-difluoro-3-methoxybenzyl)-6-methoxy-3,5-dioxo-4,5-dihydro-1,2,4-triazin-2(3H)-yl)-4-fluorophenyl)acetamide, N-(2-fluoro-5-(6-methoxy-4-((1-methylindolin-5-yl)methyl)-3,5-dioxo-4,5-dihydro-1,2,4-triazin-2(3H)-yl)phenyl)acetamide, N-(2-fluoro-5-(4-((6-fluoro-2,3-dihydrobenzofuran-5-yl)methyl)-6-methoxy-3,5-dioxo-4,5-dihydro-1,2,4-triazin-2(3H)-yl)phenyl)acetamide, N-(5-(4-(4-(dimethylamino)-3-fluorobenzyl)-6-methoxy-3,5-dioxo-4,5-dihydro-1,2,4-triazin-2(3H)-yl)-2-fluorophenyl)acetamide, N-(5-(4-(3,4-difluoro-2-methoxybenzyl)-6-methoxy-3,5-dioxo-4,5-dihydro-1,2,4-triazin-2(3H)-yl)-2-fluorophenyl)acetamide, 6-methoxy-2-phenyl-4-(3-phenylpropyl)-1,2,4-triazine-3,5(2H,4H)-dione, 2-(2-(4-(4-chlorobenzyl)-6-methoxy-3,5-dioxo-4,5-dihydro-1,2,4-triazin-2(3H)-yl)phenyl)acetonitrile, N-(5-(4-(4-cyanobenzyl)-6-methoxy-3,5-dioxo-4,5-dihydro-1,2,4-triazin-2(3H)-yl)-2-fluorophenyl)acetamide, N-(2-fluoro-5-(6-methoxy-4-(2-methoxybenzyl)-3,5-dioxo-4,5-dihydro-1,2,4-triazin-2(3H)-yl)phenyl)acetamide, N-(5-(4-(4-cyano-3-fluorobenzyl)-6-methoxy-3,5-dioxo-4,5-dihydro-1,2,4-triazin-2(3H)-yl)-2-fluorophenyl)acetamide, N-(5-(4-((6-cyanopyridin-3-yl)methyl)-6-methoxy-3,5-dioxo-4,5-dihydro-1,2,4-triazin-2(3H)-yl)-2-fluorophenyl)acetamide, N-(2-fluoro-5-(4-((6-isopropylpyridin-3-yl)methyl)-6-methoxy-3,5-dioxo-4,5-dihydro-1,2,4-triazin-2(3H)-yl)phenyl)acetamide, N-(2-fluoro-5-(6-methoxy-4-((6-methoxypyridin-3-yl)methyl)-3,5-dioxo-4,5-dihydro-1,2,4-triazin-2(3H)-yl)phenyl)acetamide, N-(2-fluoro-5-(6-methoxy-3,5-dioxo-4-(quinolin-6-ylmethyl)-4,5-dihydro-1,2,4-triazin-2(3H)-yl)phenyl)acetamide, N-(5-(4-(benzofuran-5-ylmethyl)-6-methoxy-3,5-dioxo-4,5-dihydro-1,2,4-triazin-2(3H)-yl)-2-fluorophenyl)acetamide, N-(2-fluoro-5-(4-(4-fluorophenethyl)-6-methoxy-3,5-dioxo-4,5-dihydro-1,2,4-triazin-2(3H)-yl)phenyl)acetamide, N-(5-(4-(3-chloro-4-methoxybenzyl)-6-methoxy-3,5-dioxo-4,5-dihydro-1,2,4-triazin-2(3H)-yl)-2-fluorophenyl)acetamide, N-(2-fluoro-5-(4-(3-fluoro-4-(pyrrolidin-1-yl)benzyl)-6-methoxy-3,5-dioxo-4,5-dihydro-1,2,4-triazin-2(3H)-yl)phenyl)acetamide, N-(3-(4-(3-fluoro-4-morpholinobenzyl)-6-methoxy-3,5-dioxo-4,5-dihydro-1,2,4-triazin-2(3H)-yl)phenyl)acetamide, N-(5-(4-(2,6-difluoro-3-methoxybenzyl)-6-methoxy-3,5-dioxo-4,5-dihydro-1,2,4-triazin-2(3H)-yl)-2-fluorophenyl)acetamide, N-(2-fluoro-5-(6-methoxy-3,5-dioxo-4-(4-(trifluoromethyl)benz yl)-4,5-dihydro-1,2,4-triazin-2(3H)-yl)phenyl)acetamide, N-(2-fluoro-5-(6-methoxy-4-(3-(methoxymethyl)benzyl)-3,5-dioxo-4,5-dihydro-1,2,4-triazin-2(3H)-yl)phenyl)acetamide, N-(2-fluoro-5-(4-(furo[2,3-b]pyridin-5-ylmethyl)-6-methoxy-3,5-dioxo-4,5-dihydro-1,2,4-triazin-2(3H)-yl)phenyl)acetamide, N-(2-fluoro-5-(4-(2-fluoro-5-(methoxymethyl)benzyl)-6-methoxy-3,5-dioxo-4,5-dihydro-1,2,4-triazin-2(3H)-yl)phenyl)acetamide, N-(2-fluoro-5-(4-(4-fluorobenzyl)-6-methoxy-3,5-dioxo-4,5-dihydro-1,2,4-triazin-2(3H)-yl)phenyl)acetamide, N-(2-fluoro-5-(6-methoxy-4-(4-nitrobenzyl)-3,5-dioxo-4,5-dihydro-1,2,4-triazin-2(3H)-yl)phenyl)acetamide, N-(5-(4-(4-(1H-pyrazol-1-yl)benzyl)-6-methoxy-3,5-dioxo-4,5-dihydro-1,2,4-triazin-2(3H)-yl)-2-fluorophenyl)acetamide, N-(2-fluoro-5-(4-(3-fluoro-5-methoxybenzyl)-6-methoxy-3,5-dioxo-4,5-dihydro-1,2,4-triazin-2(3H)-yl)phenyl)acetamide, N-(5-(4-(3-(dimethylamino)benzyl)-6-methoxy-3,5-dioxo-4,5-dihydro-1,2,4-triazin-2(3H)-yl)-2-fluorophenyl)acetamide, N-(3-(6-methoxy-4-((1-methyl-1H-indazol-6-yl)methyl)-3,5-dioxo-4,5-dihydro-1,2,4-triazin-2(3H)-yl)phenyl)acetamide, N-(3-(6-methoxy-4-((4-methyl-3,4-dihydro-2H-benzo[b][1,4]oxazin-7-yl)methyl)-3,5-dioxo-4,5-dihydro-1,2,4-triazin-2(3H)-yl)phenyl)acetamide, N-(5-(4-((2,3-dihydrobenzo[b][1,4]dioxin-6-yl)methyl)-6-methoxy-3,5-dioxo-4,5-dihydro-1,2,4-triazin-2(3H)-yl)-2-fluorophenyl)acetamide, N-(3-(6-methoxy-4-((1-methyl-1H-indazol-5-yl)methyl)-3,5-dioxo-4,5-dihydro-1,2,4-triazin-2(3H)-yl)phenyl)acetamide, N-(3-(6-methoxy-4-((2-methyl-2H-indazol-5-yl)methyl)-3,5-dioxo-4,5-dihydro-1,2,4-triazin-2(3H)-yl)phenyl)acetamide, N-(5-(4-((2,3-dihydrobenzofuran-6-yl)methyl)-6-methoxy-3,5-dioxo-4,5-dihydro-1,2,4-triazin-2(3H)-yl)-2-fluorophenyl)acetamide, N-(5-(4-((2,3-dihydrobenzofuran-4-yl)methyl)-6-methoxy-3,5-dioxo-4,5-dihydro-1,2,4-triazin-2(3H)-yl)-2-fluorophenyl)acetamide, N-(3-(6-methoxy-4-((5-methoxypyridin-3-yl)methyl)-3,5-dioxo-4,5-dihydro-1,2,4-triazin-2(3H)-yl)phenyl)acetamide, N-(3-(4-(4-cyano-3-methoxybenzyl)-6-methoxy-3,5-dioxo-4,5-dihydro-1,2,4-triazin-2(3H)-yl)phenyl)acetamide, N-(3-(6-methoxy-3,5-dioxo-4-phenethyl-4,5-dihydro-1,2,4-triazin-2(3H)-yl)phenyl)acetamide, N-(2-fluoro-5-(4-(4-fluoro-2-methoxybenzyl)-6-methoxy-3,5-dioxo-4,5-dihydro-1,2,4-triazin-2(3H)-yl)phenyl)acetamide, N-(5-(4-(4-(1H-pyrazol-1-yl)benzyl)-6-methoxy-3,5-dioxo-4,5-dihydro-1,2,4-triazin-2(3H)-yl)-2-fluorophenyl)acetamide, N-(5-(4-(3,4-difluorobenzyl)-6-methoxy-3,5-dioxo-4,5-dihydro-1,2,4-triazin-2(3H)-yl)-2-fluorophenyl)acetamide, N-(2-fluoro-5-(6-methoxy-4-((1-methyl-1H-indazol-6-yl)methyl)-3,5-dioxo-4,5-dihydro-1,2,4-triazin-2(3H)-yl)phenyl)acetamide, N-(5-(4-(3,4-dichlorobenzyl)-6-methoxy-3,5-dioxo-4,5-dihydro-1,2,4-triazin-2(3H)-yl)-2-fluorophenyl)acetamide, N-(5-(4-(3-(dimethylamino)-4-fluorobenzyl)-6-methoxy-3,5-dioxo-4,5-dihydro-1,2,4-triazin-2(3H)-yl)-2-fluorophenyl)acetamide, N-(2-chloro-5-(4-(4-fluorobenzyl)-6-methoxy-3,5-dioxo-4,5-dihydro-1,2,4-triazin-2(3H)-yl)phenyl)acetamide, N-(5-(4-((2,2-dimethyl-2,3-dihydrobenzofuran-5-yl)methyl)-6-methoxy-3,5-dioxo-4,5-dihydro-1,2,4-triazin-2(3H)-yl)-2-fluorophenyl)acetamide, 4-(4-chlorobenzyl)-2-(4-fluorophenyl)-6-methoxy-1,2,4-triazine-3,5(2H,4H)-dione, N-(5-(4-(4-chlorobenzyl)-6-methoxy-3,5-dioxo-4,5-dihydro-1,2,4-triazin-2(3H)-yl)-2-fluorophenyl)acetamide, N-(3-(4-(benzo[d] isoxazol-6-ylmethyl)-6-methoxy-3,5-dioxo-4,5-dihydro-1,2,4-triazin-2(3H)-yl)phenyl)acetamide, N-(5-(4-(4-chloro-3-fluorobenzyl)-6-methoxy-3,5-dioxo-4,5-dihydro-1,2,4-triazin-2(3H)-yl)-2-fluorophenyl)acetamide, N-(2-chloro-5-(4-(4-chloro-3-fluorobenzyl)-6-methoxy-3,5-dioxo-4,5-dihydro-1,2,4-triazin-2(3H)-yl)phenyl)acetamide, N-(2-chloro-5-(4-(4-fluoro-2-methoxybenzyl)-6-methoxy-3,5-dioxo-4,5-dihydro-1,2,4-triazin-2(3H)-yl)phenyl)acetamide, N-(5-(4-(2,4-difluorobenzyl)-6-methoxy-3,5-dioxo-4,5-dihydro-1,2,4-triazin-2(3H)-yl)-2-fluorophenyl)acetamide, N-(5-(4-(4-chloro-2-methoxybenzyl)-6-methoxy-3,5-dioxo-4,5-dihydro-1,2,4-triazin-2(3H)-yl)-2-fluorophenyl)acetamide, N-(5-(4-(4-chloro-5-methoxybenzyl)-6-methoxy-3,5-dioxo-4,5-dihydro-1,2,4-triazin-2(3H)-yl)-2-fluorophenyl)acetamide, N-(5-(4-

(2,4-difluorophenethyl)-6-methoxy-3,5-dioxo-4,5-dihydro-1,2,4-triazin-2(3H)-yl)-2-fluorophenyl)acetamide, N-(3-(4-((5-fluoro-6-methoxypyridin-3-yl)methyl)-6-methoxy-3,5-dioxo-4,5-dihydro-1,2,4-triazin-2(3H)-yl)phenyl)acetamide, N-(2-chloro-5-(4-(4-chloro-2-methoxybenzyl)-6-methoxy-3,5-dioxo-4,5-dihydro-1,2,4-triazin-2(3H)-yl)phenyl)acetamide, N-(2-chloro-5-(4-(4-chloro-3-methoxybenzyl)-6-methoxy-3,5-dioxo-4,5-dihydro-1,2,4-triazin-2(3H)-yl)phenyl)acetamide, N-(5-(4-(3,4-difluoro-5-methoxybenzyl)-6-methoxy-3,5-dioxo-4,5-dihydro-1,2,4-triazin-2(3H)-yl)-2-fluorophenyl)acetamide, N-(2-chloro-5-(4-(4-chloro-2-fluorobenzyl)-6-methoxy-3,5-dioxo-4,5-dihydro-1,2,4-triazin-2(3H)-yl)phenyl)acetamide, N-(2-chloro-5-(4-(2,4-difluorobenzyl)-6-methoxy-3,5-dioxo-4,5-dihydro-1,2,4-triazin-2(3H)-yl)phenyl)acetamide, N-(2-chloro-5-(4-(4-chlorobenzyl)-6-methoxy-3,5-dioxo-4,5-dihydro-1,2,4-triazin-2(3H)-yl)phenyl)acetamide, N-(5-(4-(4-chloro-2-(dimethylamino)benzyl)-6-methoxy-3,5-dioxo-4,5-dihydro-1,2,4-triazin-2(3H)-yl)-2-fluorophenyl)acetamide, N-(2-chloro-5-(4-(4-chloro-2-(dimethylamino)benzyl)-6-methoxy-3,5-dioxo-4,5-dihydro-1,2,4-triazin-2(3H)-yl)phenyl)acetamide, N-(2-chloro-5-(4-(3-(dimethylamino)-4-fluorobenzyl)-6-methoxy-3,5-dioxo-4,5-dihydro-1,2,4-triazin-2(3H)-yl)phenyl)acetamide, N-(5-(4-benzyl-6-methoxy-3,5-dioxo-4,5-dihydro-1,2,4-triazin-2(3H)-yl)-2-chlorophenyl)acetamide, N-(5-(4-(2-(dimethylamino)-4-fluorobenzyl)-6-methoxy-3,5-dioxo-4,5-dihydro-1,2,4-triazin-2(3H)-yl)-2-fluorophenyl)acetamide, N-(2-chloro-5-(4-(4-fluoro-3-methoxybenzyl)-6-methoxy-3,5-dioxo-4,5-dihydro-1,2,4-triazin-2(3H)-yl)phenyl)acetamide, N-(2-fluoro-5-(4-(3-fluoro-4-(trifluoromethyl)benzyl)-6-methoxy-3,5-dioxo-4,5-dihydro-1,2,4-triazin-2(3H)-yl)phenyl)acetamide, N-(5-(4-(4-chloro-3-(dimethylamino)benzyl)-6-methoxy-3,5-dioxo-4,5-dihydro-1,2,4-triazin-2(3H)-yl)-2-fluorophenyl)acetamide, N-(2-chloro-5-(4-(4-chloro-3-(dimethylamino)benzyl)-6-methoxy-3,5-dioxo-4,5-dihydro-1,2,4-triazin-2(3H)-yl)phenyl)acetamide, N-(5-(4-(3,4-dichlorobenzyl)-6-methoxy-3,5-dioxo-4,5-dihydro-1,2,4-triazin-2(3H)-yl)-2-fluorophenyl)acetamide, N-(2-chloro-5-(4-((6-(dimethylamino)pyridin-3-yl)methyl)-6-methoxy-3,5-dioxo-4,5-dihydro-1,2,4-triazin-2(3H)-yl)phenyl)acetamide, N-(5-(4-(4-chloro-3-(trifluoromethoxy)benzyl)-6-methoxy-3,5-dioxo-4,5-dihydro-1,2,4-triazin-2(3H)-yl)-2-fluorophenyl)acetamide, N-(2-chloro-5-(6-methoxy-4-(3-methoxybenzyl)-3,5-dioxo-4,5-dihydro-1,2,4-triazin-2(3H)-yl)phenyl)acetamide, N-(2-chloro-5-(4-((2,3-dihydrobenzofuran-5-yl)methyl)-6-methoxy-3,5-dioxo-4,5-dihydro-1,2,4-triazin-2(3H)-yl)phenyl)acetamide, N-(2-chloro-5-(4-(3,4-difluoro-2-methoxybenzyl)-6-methoxy-3,5-dioxo-4,5-dihydro-1,2,4-triazin-2(3H)-yl)phenyl)acetamide, 4-(4-chlorobenzyl)-2-(4-fluorophenyl)-6-methoxy-1,2,4-triazine-3,5(2H,4H)-dione, N-(2-chloro-5-(4-(4-chloro-3-(trifluoromethyl)benzyl)-6-methoxy-3,5-dioxo-4,5-dihydro-1,2,4-triazin-2(3H)-yl)phenyl)acetamide, N-(5-(4-(4-chloro-3-isopropoxybenzyl)-6-methoxy-3,5-dioxo-4,5-dihydro-1,2,4-triazin-2(3H)-yl)-2-fluorophenyl)acetamide, N-(2-chloro-5-(6-methoxy-4-((1-methyl-1H-indazol-6-yl)methyl)-3,5-dioxo-4,5-dihydro-1,2,4-triazin-2(3H)-yl)phenyl)acetamide, N-(5-(4-(4-chloro-3-isopropylbenzyl)-6-methoxy-3,5-dioxo-4,5-dihydro-1,2,4-triazin-2(3H)-yl)-2-fluorophenyl)acetamide, N-(2-fluoro-5-(4-(3-fluoro-4-morpholinobenzyl)-6-methoxy-3,5-dioxo-4,5-dihydro-1,2,4-triazin-2(3H)-yl)phenyl)acetamide, N-(5-(4-(4-chloro-3-hydroxybenzyl)-6-methoxy-3,5-dioxo-4,5-dihydro-1,2,4-triazin-2(3H)-yl)-2-fluorophenyl)acetamide, N-(5-(4-((3,3-dimethyl-2,3-dihydrobenzofuran-5-yl)methyl)-6-methoxy-3,5-dioxo-4,5-dihydro-1,2,4-triazin-2(3H)-yl)-2-fluorophenyl)acetamide, N-(5-(4-((3,3-dimethyl-2,3-dihydrobenzofuran-6-yl)methyl)-6-methoxy-3,5-dioxo-4,5-dihydro-1,2,4-triazin-2(3H)-yl)-2-fluorophenyl)acetamide, N-(2-fluoro-5-(4-(3-fluoro-4-isopropylbenzyl)-6-methoxy-3,5-dioxo-4,5-dihydro-1,2,4-triazin-2(3H)-yl)phenyl)acetamide, N-(3-(4-(4-chloro-3-(dimethylamino)benzyl)-6-methoxy-3,5-dioxo-4,5-dihydro-1,2,4-triazin-2(3H)-yl)-4-fluorophenyl)acetamide, N-(5-(4-(4-cyano-3-methoxybenzyl)-6-methoxy-3,5-dioxo-4,5-dihydro-1,2,4-triazin-2(3H)-yl)-2-fluorophenyl)acetamide, 4-(3,4-dichlorobenzyl)-2-(4-fluorophenyl)-6-methoxy-1,2,4-triazine-3,5(2H,4H)-dione, N-(5-(4-(4-chloro-2-fluoro-3-methoxybenzyl)-6-methoxy-3,5-dioxo-4,5-dihydro-1,2,4-triazin-2(3H)-yl)-2-fluorophenyl)acetamide, 4-(4-chloro-2-fluoro-3-methoxybenzyl)-2-(4-fluorophenyl)-6-methoxy-1,2,4-triazine-3,5(2H,4H)-dione, N-(5-(4-(4-bromo-3-methoxybenzyl)-6-methoxy-3,5-dioxo-4,5-dihydro-1,2,4-triazin-2(3H)-yl)-2-fluorophenyl)acetamide, N-(2-fluoro-5-(4-(4-isopropyl-3-methoxybenzyl)-6-methoxy-3,5-dioxo-4,5-dihydro-1,2,4-triazin-2(3H)-yl)phenyl)acetamide, 2-(4-fluorophenyl)-4-(4-isopropyl-3-methoxybenzyl)-6-methoxy-1,2,4-triazine-3,5(2H,4H)-dione, N-(5-(4-(4-chloro-3-(pyrrolidin-1-yl)benzyl)-6-methoxy-3,5-dioxo-4,5-dihydro-1,2,4-triazin-2(3H)-yl)-2-fluorophenyl)acetamide, N-(2-fluoro-5-(4-(4-fluoro-3-(trifluoromethyl)benzyl)-6-methoxy-3,5-dioxo-4,5-dihydro-1,2,4-triazin-2(3H)-yl)phenyl)acetamide, N-(5-(4-(2,4-difluoro-3-isopropoxybenzyl)-6-methoxy-3,5-dioxo-4,5-dihydro-1,2,4-triazin-2(3H)-yl)-2-fluorophenyl)acetamide, N-(5-(4-((5,6-dichloropyridin-3-yl)methyl)-6-methoxy-3,5-dioxo-4,5-dihydro-1,2,4-triazin-2(3H)-yl)-2-fluorophenyl)acetamide, N-(5-(4-(4-cyano-2-fluoro-3-methoxybenzyl)-6-methoxy-3,5-dioxo-4,5-dihydro-1,2,4-triazin-2(3H)-yl)-2-fluorophenyl)acetamide, 4-((5,6-dichloropyridin-3-yl)methyl)-2-(4-fluorophenyl)-6-methoxy-1,2,4-triazine-3,5(2H,4H)-dione, N-(5-(4-(4-chloro-3-morpholinobenzyl)-6-methoxy-3,5-dioxo-4,5-dihydro-1,2,4-triazin-2(3H)-yl)-2-fluorophenyl)acetamide, N-(5-(4-(3-(dimethylamino)-4-(trifluoromethyl)benzyl)-6-methoxy-3,5-dioxo-4,5-dihydro-1,2,4-triazin-2(3H)-yl)-2-fluorophenyl)acetamide, 4-(4-chloro-3-methoxybenzyl)-2-(4-fluorophenyl)-6-methoxy-1,2,4-triazine-3,5(2H,4H)-dione, N-(2-fluoro-5-(4-(3-fluoro-4-(trifluoromethyl)benzyl)-6-methoxy-3,5-dioxo-4,5-dihydro-1,2,4-triazin-2(3H)-yl)phenyl)-N-methylacetamide, N-(5-(4-(4-chloro-3-(methoxymethyl)benzyl)-6-methoxy-3,5-dioxo-4,5-dihydro-1,2,4-triazin-2(3H)-yl)-2-fluorophenyl)acetamide, N-(2-fluoro-5-(4-(4-fluoro-3-morpholinobenzyl)-6-methoxy-3,5-dioxo-4,5-dihydro-1,2,4-triazin-2(3H)-yl)phenyl)acetamide, N-(5-(4-((6-chloro-5-isopropylpyridin-3-yl)methyl)-6-methoxy-3,5-dioxo-4,5-dihydro-1,2,4-triazin-2(3H)-yl)-2-fluorophenyl)acetamide, N-(3-(4-(4-chlorobenzyl)-6-isopropyl-3,5-dioxo-4,5-dihydro-1,2,4-triazin-2(3H)-yl)phenyl)acetamide, N-(3-(4-(4-chlorobenzyl)-6-ethyl-3,5-dioxo-4,5-dihydro-1,2,4-triazin-2(3H)-yl)phenyl)acetamide, N-(3-(6-butyl-4-(4-chlorobenzyl)-3,5-dioxo-4,5-dihydro-1,2,4-triazin-2(3H)-yl)phenyl)acetamide, 2-(6-bromo-4-(4-fluorobenzyl)-3,5-dioxo-4,5-dihydro-1,2,4-triazin-2(3H)-yl)benzonitrile, N-(3-(4-(4-chlorobenzyl)-6-(2-(dimethylamino)ethoxy)-3,5-dioxo-4,5-dihydro-1,2,4-triazin-2(3H)-yl)phenyl)acetamide, N-(3-(6-(2-methoxyethoxy)-4-(4-nitrobenzyl)-3,5-dioxo-4,5-dihydro-1,2,4-triazin-2(3H)-yl)phenyl)acetamide, N-(3-(4-(4-chlorobenzyl)-6-(2-methoxyethoxy)-3,5-dioxo-4,5-dihydro-1,2,4-triazin-2(3H)-yl)phenyl)acetamide, N-(3-(4-(4-chlorobenzyl)-6-(methylamino)-3,5-dioxo-4,5-dihydro-1,2,4-triazin-2(3H)-yl)phenyl)acetamide, N-(3-(4-(4-chlorobenzyl)-6-ethoxy-3,5-dioxo-4,5-dihydro-1,2,4-triazin-2(3H)-yl)phenyl)acetamide, N-(3-(6-bromo-4-(4-methylbenzyl)-3,5-dioxo-4,5-dihydro-1,2,4-triazin-2(3H)-yl)phenyl)acetamide, N-(3-(4-(4-chlorobenzyl)-6-isopropoxy-3,5-dioxo-4,5-dihydro-1,2,4-triazin-2(3H)-yl)phenyl)acetamide, N-(3-(6-bromo-4-(4-chlorobenzyl)-3,5-dioxo-4,5-dihydro-1,2,4-triazin-2(3H)-yl)phenyl)acetamide, N-(3-(4-(4-chlorobenzyl)-6-(dimethylamino)-3,5-dioxo-4,5-dihydro-1,2,4-triazin-2(3H)-yl)phenyl)acetamide, N-(3-(4-(4-chlorobenzyl)-6-(hydroxymethyl)-3,5-dioxo-4,5-dihydro-1,2,4-triazin-2(3H)-yl)phenyl)acetamide, N-(3-(4-(4-chlorobenzyl)-6-((dimethylamino)methyl)-3,5-dioxo-4,5-dihydro-1,2,4-triazin-2(3H)-yl)phenyl)acetamide, N-(3-(6-((1H-pyrazol-1-yl)methyl)-4-(4-chlorobenzyl)-3,5-dioxo-4,5-dihydro-1,2,4-triazin-2(3H)-yl)phenyl)acetamide, N-(3-(4-(4-chlorobenzyl)-6-(methoxymethyl)-3,5-dioxo-4,5-dihydro-1,2,4-triazin-2(3H)-yl)phenyl)acetamide, methyl 2-(3-acetamidophenyl)-4-(4-chlorobenzyl)-3,5-dioxo-2,3,4,5-tetrahydro-1,2,4-triazine-6-carboxylate, isopropyl 2-(3-acetamidophenyl)-4-(4-chlorobenzyl)-3,5-dioxo-2,3,4,5-tetrahydro-1,2,4-triazine-6-carboxylate, N-(3-(4-(4-chlorobenzyl)-6-(3-methyl-1,2,4-oxadiazol-5-yl)-3,5-dioxo-4,5-dihydro-1,2,4-triazin-2(3H)-yl)phenyl)acetamide, N-(3-(4-(4-chlorobenzyl)-6-(5-methyl-1,2,4-oxadiazol-3-yl)-3,5-dioxo-4,5-dihydro-1,2,4-triazin-2(3H)-yl)phenyl)acetamide, N-(3-(4-(4-chlorobenzyl)-6-(1,2,4-oxadiazol-5-yl)-3,5-dioxo-4,5-dihydro-1,2,4-triazin-2(3H)-yl)phenyl)acetamide, N-(2-fluoro-5-(4-(4-fluorobenzyl)-6-(2-methoxyethoxy)-3,5-dioxo-4,5-dihydro-1,2,4-triazin-2(3H)-yl)phenyl)acetamide.

The present invention relates to the pharmaceutically acceptable acid addition salts of compounds of the Formula I and compositions of the compounds with pharmaceutically acceptable carriers or excipients.

The present invention relates to a method of treating or preventing a condition in a mammal, including a human, the treatment or prevention of which is affected or facilitated by the neuromodulatory effect of $GABA_B$ positive allosteric modulators.

The present invention relates to a method useful for treating or preventing peripheral and central nervous system disorders selected from the group consisting of: anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, panic disorder, posttraumatic stress disorders, urge urinary incontinence or gastro-intestinal disorders.

The present invention relates to pharmaceutical compositions which provide from about 0.01 to 1000 mg of the active ingredient per unit dose. The compositions may be administered by any suitable route. For example orally in the form of capsules, etc., parenterally in the form of solutions for injection, topically in the form of onguents or lotions, ocularly in the form of eye-drops, rectally in the form of suppositories, intranasally or transcutaneously in the form of delivery system like patches.

The pharmaceutical formulations of the invention may be prepared by conventional methods in the art; the nature of the pharmaceutical composition employed will depend on the desired route of administration. The total daily dose usually ranges from about 0.05-2000 mg.

DEFINITIONS

The following terms and expressions contained herein are defined as follows:

As used herein, the term "about" refers to a range of value from ±10% of a specified value. For example, the phrase "about 30 mg" include ±10% of 30, or form 27 to 33 mg.

As used herein, a range of values in the form "x-y" or "x to y" or "x through y", include integers x, y and the integers there between. For example, the phrase "1-6" or "1 to 6" or "1 through 6" are intended to include the integers 1, 2, 3, 4, 5 and 6.

Preferred structures include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5 or 2-6, etc.

As used herein, "stable compound" or "stable structure" refers to a compound that is sufficiently robust to survive isolation to a useful degree of purity from a reaction mixture and preferably capable of formulation into an efficacious therapeutic agent.

As used herein, the specification "C" means 1 carbon atom.

As used herein, in the case where a subscript is the integer "0" (zero), the group to which the subscript refers to indicates that the group is absent, i.e. there is a direct bond between the groups.

"Halogen" includes atoms such as fluorine, bromine, chlorine and iodine.

As used herein, the term "alkyl" refers to a straight-chain or branched alkyl group having 1 to 6 carbon atoms, such as methyl, ethyl, propyl, isopropyl, butyl, isobutyl, sec-butyl, tert-butyl, pentyl, isopentyl, neopentyl, 1-ethylpropyl, 3-methylpenthyl, 2,2-dimethylbutyl, 2,3-dimethylbutyl, hexyl, etc. The alkyl moiety of alkyl-containing groups, such as alkoxy, alkoxycarbonyl and alkylaminocarbonyl groups, has the same meaning as alkyl defined above.

As used herein, the term "alkenyl" refers to a straight-chain or branched hydrocarbon group of 2 to 6 carbon atoms having at least one carbon-carbon double bond. A designation "$C_2$-$C_6$ alkenyl" refers to an alkenyl radical containing from 2 to 6 carbon atoms. Examples of alkenyl groups include, but are not limited to, ethenyl, propenyl, isopropenyl, allyl, butenyl, pentenyl, 2,4-pentanedienyl, etc.

As used herein, the term "alkynyl" refers to a straight-chain or branched hydrocarbon group of 2 to 6 carbon atoms having at least one carbon-carbon triple bond. A designation "$C_2$-$C_6$ alkynyl" refers to an alkenyl radical containing from 2 to 6 carbon atoms. Examples include, but are not limited to, ethynyl, propynyl, butynyl, pentynyl, etc.

The term "Aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl, indenyl and the like.

"Arylalkyl" includes ($C_6$-$C_{10}$)aryl-($C_1$-$C_3$)alkyl group such as 2-ethyl-phenyl group, 3-ethyl-phenyl group, 4-propyl-phenyl group, 2-propyl-phenyl group, 3-propyl-phenyl group, 2-methyl-naphtyl group, 4-methyl-naphtyl group or the like.

"Alkylaryl" includes $(C_1-C_3)$alkyl-$(C_6-C_{10})$aryl group such as benzyl group, as phenyl-ethyl group, phenyl-propyl, naphtyl-2-methyl group or the like.

In this specification, unless stated otherwise, the term "alkylhalo" means an alkyl group as defined above, substituted with one or more halogen. The term "$C_1$-$C_6$-alkylhalo" may include, but not limited to fluoroethyl, difluoromethyl, trifluoromethyl, fluoroethyl, difluoroethyl, bromoethyl and the like. The term "O—$C_1$-$C_6$-alkylhalo" may include, but is not limited to fluoromethoxy, difluoromethoxy, trifluoromethoxy, fluoroethoxy and the like.

"Heteroatom" includes atoms such as nitrogen, oxygen and sulphur.

In the specification, unless stated otherwise, the term "Heteroaryl" refer to an optionally substituted monocyclic or bicyclic unsaturated, aromatic ring system containing at least one heteroatom selected independently from O, N or S to form a ring such as furyl (furan ring), benzofuranyl (benzofuran ring), thienyl (thiophene ring), benzothiophenyl (benzothiophene ring), pyrrolyl (pyrrole ring), imidazolyl (imidazole ring), pyrazolyl (pyrazole ring), thiazolyl (thiazole ring), isothiazolyl (isothiazole ring), triazolyl (triazole ring), tetrazolyl (tetrazole ring), pyridil (pyridine ring), pyrazynyl (pyrazine ring), pyrimidinyl (pyrimidine ring), pyridazinyl (pyridazine ring), indolyl (indole ring), isoindolyl (isoindole ring), benzoimidazolyl (benzimidazole ring), purinyl group (purine ring), quinolyl (quinoline ring), phtalazinyl (phtalazine ring), naphtyridinyl (naphtyridine ring), quinoxalinyl (quinoxaline ring), cinnolyl (cinnoline ring), pteridinyl (pteridine ring), oxazolyl (oxazole ring), isoxazolyl (isoxazole ring), benzoxazolyl (benzoxazole ring), benzothiazoly (benzothiaziole ring), furazanyl (furazan ring), benzotriazolyl (benzotriazol ring), imidazopyridinyl (imidazopyridine ring), pyrazolopyridinyl (pyrazolopyridine ring), 2,3-dihydrobenzofuranyl (2,3-dihydrobenzofuran ring) and the like.

"Heteroarylalkyl" includes heteroaryl-$(C_1-C_3)$alkyl group, wherein examples of heteroaryl are the same as those illustrated in the above definition, such as 2-methyl-furyl group, 3-methyl-furyl group, 2-methyl-thienyl group, 3-methyl-thienyl group, 1-methyl-imidazolyl group, 2-methyl-imidazolyl group, 2-methyl-thiazolyl group, 2-methyl-pyridyl group, 3-methyl-pyridyl group, 1-methyl-quinolyl group or the like.

"Alkylheteroaryl" includes $(C_1-C_3)$alkyl-heteroaryl group, wherein examples of heteroaryl are the same as those illustrated in the above definition, such as 2-furylmethyl group, 3-furylmethyl group, 2-thienylmethyl group, 3-thienylmethyl group, 1-imidazolylmethyl group, 2-imidazolylmethyl group, 2-thiazolylmethyl group, 2-pyridylmethyl group, 3-pyridylmethyl group, 1-quinolylmethyl group or the like.

In this specification, unless stated otherwise, the term "heterocyclic" (or "heterocyclo") means a 5- or 6-membered ring containing one or more atoms independently selected from N, O, or S, includes monocyclic or bicyclic rings as well which may be saturated or unsaturated.

"Heterocycloalkyl" includes heterocycloalkyl-$C_1$-$C_3$-alkyl group, wherein examples of heterocyclo are the same as those illustrated in the above definition such as morpholine, piperazine, methylpiperazine, piperidine, dioxane and the like.

The term "cycloalkyl" means carbocycles containing no heteroatoms, includes mono-, bi-, and tricyclic saturated carbocycles, as well as fused ring systems. Such fused ring systems can include on ring that is partially or fully unsaturated such as a benzene ring to form fused ring systems such as benzo fused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, fluorenyl, 1,2,3,4-tetrahydronaphthalene and the like.

The term "cycloalkenyl" refers to a carbocycles includes mono- and bi-carbocycles, as well as fused ring, having at least one carbon-carbon double bond. Examples of cycloalkenyl includes 1,2,3,4,4a,5,6,7-octahydronaphthalene, 2,3,5, 6,7,7a-hexahydro-1H-indene, 2,3,4,5,6,7-hexahydro-1H-indene and the like.

"Solvate" refers to a complex of variable stoichiometry formed by a solute (e.g. a compound of formula I) and a solvent. The solvent is a pharmaceutically acceptable solvent as water preferably; such solvent may not interfere with the biological activity of the solute.

"Optionally" means that the subsequently described event(s) may or may not occur, and includes both event(s), which occur, and events that do not occur.

The term "substituted" refers to substitution with the named substituent or substituents, multiple degrees of substitution being allowed unless otherwise stated.

Synthesis

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley et Sons). These groups are removed at a convenient stage of the compound synthesis using methods that are readily apparent to those skilled in the art. The selection of process as well as the reaction conditions and order of their execution shall be consistent with the preparation of compounds of formula I.

The compound of formula I may be represented as a mixture of enantiomers, which may be resolved into the individual pure R- or S-enantiomers. If for instance, a particular enantiomer of the compound of formula I is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group such as amino, or an acidic functional group such as carboxyl, this resolution may be conveniently performed by fractional crystallization from various solvents, of the salts of the compounds of formula I with optical active acid or by other methods known in the literature, e.g. chiral column chromatography.

Resolution of the final product, an intermediate or a starting material may be performed by any suitable method known in the art as described by E. L. Eliel, S. H. Wilen and L. N. Mander (1984) *Stereochemistry of Organic Compounds*, Wiley-Interscience.

All the products generated from the following reactions can be isolated and purified employing standard techniques, such as extraction, chromatography, crystallization, distillation, and the like.

General routes to prepare the Examples of the present invention are shown in the Schemes and Examples that follow.

All substituents in the synthetic Schemes unless otherwise indicated, are as previously defined.

The compounds of Formula I may be prepared by general route of synthesis as disclosed in the following methods.

The compounds of Formula III wherein B, L, $X_1$, $X_2$, $X_3$, $X_4$, $X_5$ and -E are as described above may be prepared following a cyclisation reaction key step presented in Scheme 1. The amine 1.1 react with the corresponding carboxylic 1.2 acid in a classic peptidic coupling condition (Piskunova, I. P. & al. *Tetrahedron* 1993, 49(21), 4671-4676) where E can be different electroattractive substituents, i.e —CN to generate 1.3. Then 1.3 can react with the diazonium salt already obtained by mixing the aniline 1.4 with $NaNO_2$ to generate 1.5 (Bilek, P.; Slouka, J. *Heterocycl. Commun.* 2004, 10(1), 67-70). The final compound 1.6 is obtained by reaction of the intermediate 1.5 with ethylchloroformiate in a presence of pyridine.

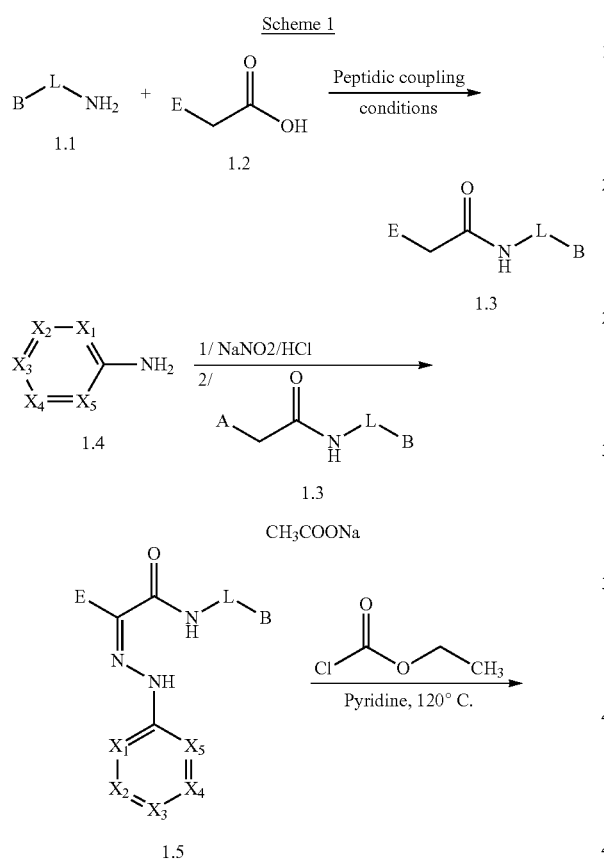

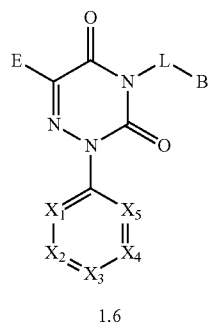

1.6

Alternatively the E substituent can be introduced at a late stage in the synthesis, to provide the compounds of Formula III (Scheme 2). Thus the uracyl derivative is brominated to lead to the intermediates 2.1 (Dudfield, P. J. & al. *J. Chem. Soc. Perkin Trans.* 1, 1999, 20, 2929-2936). The introduction of the L-B group can be achieved through alkylation of 2.2 with Z-L-B (Z=Br, Cl, I, Mesylate, Tosylate, Triflate, OH) in presence of a suitable base such as $K_2CO_3$, NaH or using a Mitsonobu condition (Z=OH) (Pontillo, J. & al. *Bioorg. Med. Chem. Lett.* 2005, 15(19), 4363-4366) to afford the intermediate 2.3. Introduction of the suitable substituted aryl/heteroaryl boronic acid is achieved in a presence of copper salt (Lam, P. Y. S. & al. *Tetrahedron Lett.* 2001, 42, 3415-3418) to afford the compound 2.4. Displacement of the bromoderivative 2.4 by suitable nucleophiles such as amine alcohol in conditions known to the skilled in the art and exemplified in this document lead to compound of formula 2.5 where E=($OR^{12}$, $NR^{13}R^{14}$), G=(H or a counterion). Additionally reaction of 2.4 with organometallics such as organozinc organoboron, organotin reagent in a presence of palladium catalyst and a co-solvent (M is a metal, zinc or boron or tin or silicon) afford 2.5 whereas E=(alkylaryl, alkyl, heteroaryl, aryl and the like).

Scheme 2

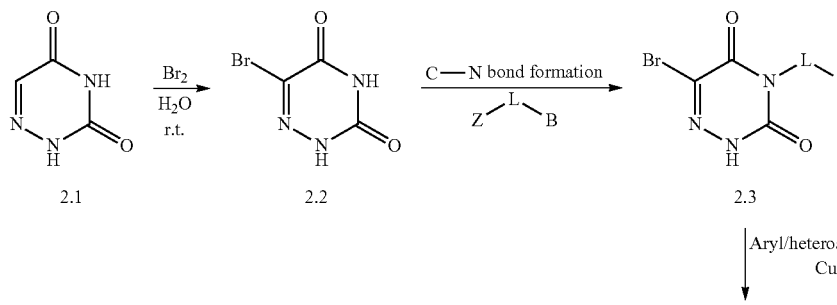

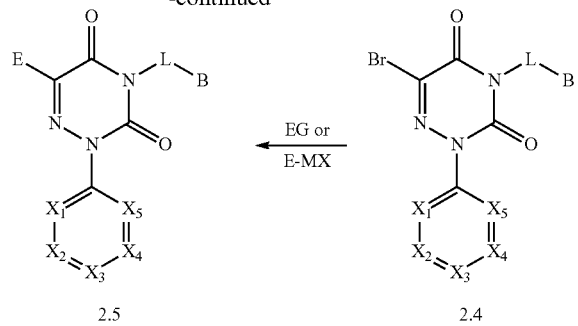

Yet another approach to the cpds of Formula III can be represented with the introduction of the L-B group at the final stage of the synthesis (Scheme 3). To achieve such procedure bromouracyl is protected using a suitable protecting group (P.G.) such as benzyl or allyl by reaction of 2.2 with benzyl bromide to afford the intermediate 3.1. The introduction of the suitable substituted aryl/heteroaryl boronic acid is the same as reported in previous scheme to afford 3.2. The displacement of the bromoderivative was done as reported in Scheme 2 to afford 3.3. Deprotection of the amide moiety can be achieved with palladium or ruthenium catalyst in presence of nucleophile such as acetate in a manner well known to those skilled in the art. The introduction of the L-B group proceeds in a similar manner described in Scheme 2 to afford the compound of Formula III (ie 3.5).

A similar procedure as those described in Scheme 2 and 3 can be used starting from commercially available uracyl 4.1 (E=H or $CH_3$). The introduction of the L-B group can be achieved through alkylation of 4.1 with Z-L-B (Z=Br, Cl, I, Mesylate, Tosylate, Triflate, OH) in presence of a suitable base such as $K_2CO_3$, NaH or using a Mitsonobu condition (Z=OH) (Pontillo, J. & al. *Bioorg. Med. Chem. Lett.* 2005, 15(19), 4363-4366) to afford the intermediate 4.2. The introduction of the suitable substituted aryl/heteroaryl boronic acid is the same as reported in a Scheme 2 to afford compound of Formula III (i.e 4.3).

Scheme 3

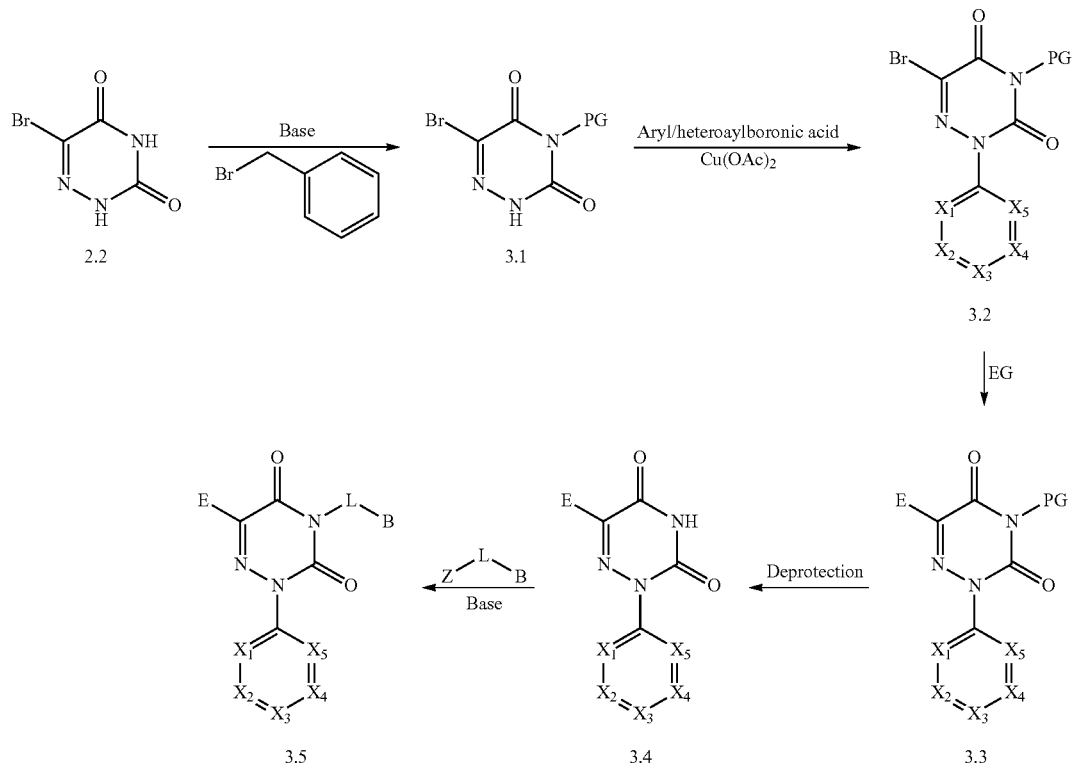

Scheme 4

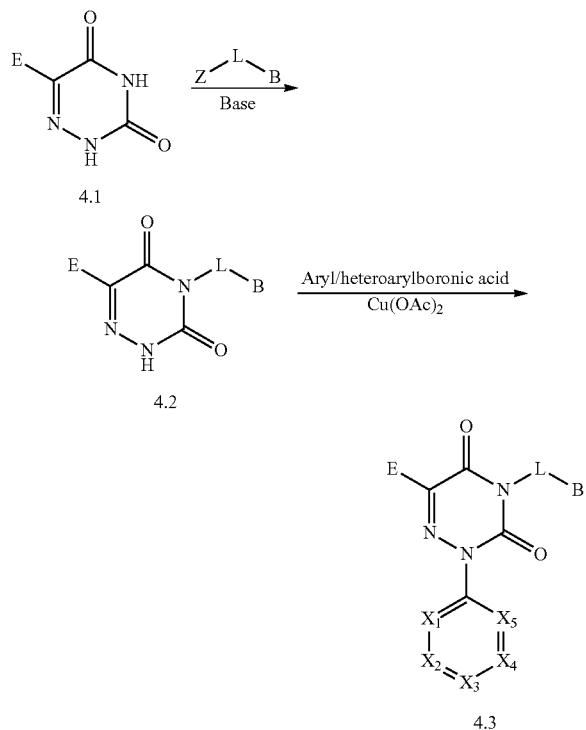

E = H, CH3

Yet another approach to the compound of Formula III is described in Scheme 5 in particular for those compounds of Formula III for which the introduction of the aryl or heteroaryl through Cham Lam coupling is difficult. In those cases the azalactam ring already was bearing the aryl substituent. 5.4 is built from the open intermediate 5.3 which is cyclised in basic medium. The intermediate 5.3 was obtained by condensation of a diazonium salt of suitably substituted aniline (in this case $R^6=NO_2$) with ethyl 2-cyanoacetylcarbamate Further transformation of the E substituent when E=CN in compound of Formula III can be performed (see also Scheme 7 & 8). Thus decyanation was achieved via a two step procedure known in the art such as hydrolysis to the acid and decarboxylation of the acid bearing intermediate (Falco & al. *J. Am. Chem. Soc.* 1956, 78, 1938-1939). By extension further transformation of the $R^5$ group can be also performed such as transformation of the nitro group to an acetamido group. The target compound is then obtained by introduction of the L-B group in a manner similar as that reported in previous to afford the compound 5.7.

Scheme 5

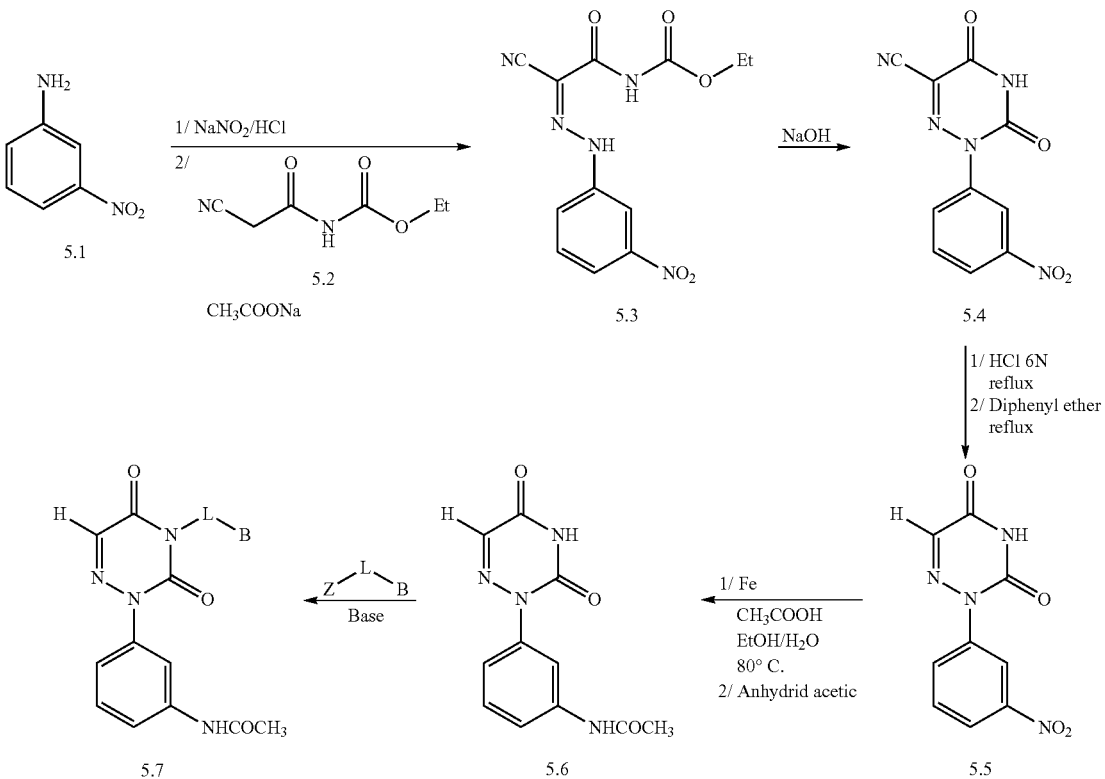

Additional possibility of introducing the L-B group at a final stage of the synthesis of compound of Formula III, proceed through clivative alkylation procedure (Scheme 6). Thus 6.1 (described in *Collect. Czechoslov. Chem. Commun.* 1961, 26, 986-997; *Collect. Czechoslov. Chem. Commun.* 1975, 40, 2326-2339) is subjected to the Cham Lam coupling in order to introduce the aryl or heteroaylboronic acid in a manner similar to that described in previous schemes to afford 6.2. The clivative alkylation procedure can be performed with a Z-L-B (Z=Br, Cl, I, Mesylate, Tosylate, Triflate) in presence of sodium iodide (NaI) under microwave irradiation to afford compounds of Formula III (i.e 6.3).

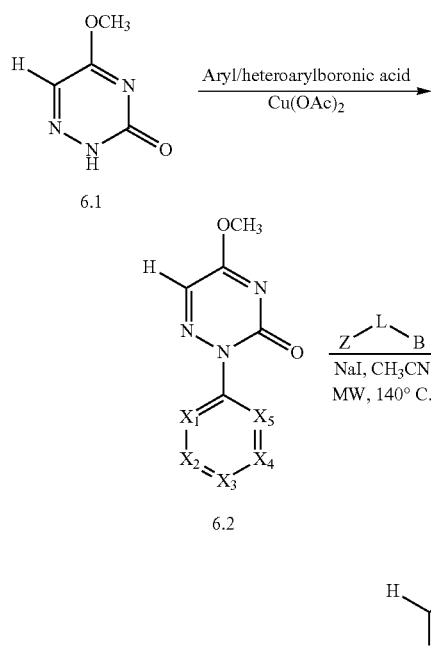

The compounds of Formula III wherein B, L, $X_1$, $X_2$, $X_3$, $X_4$, $X_5$ are as described above and E=COOH is an important intermediate may be prepared following one variation presented Scheme 7. The commercially available aniline 7.1 is able to react with sodium nitrite in acidic media to generate a diazo intermediate which is able to react with the commercially available compound 7.2 to form the compound 7.3. In a basic condition, the cyclisation of 7.3 can occur to form the disubstituted azauracil 7.4. This intermediate can react with different halogenalkylaryl (Z=Br, Cl, I, Mesylate, Tosylate, Triflate) in a presence of base to obtain the compound 7.5. After refluxing the compound 7.5 in a presence of HCl 6N the nitrile function is transformed into a carboxylic acid function and in a same time the deacetylation of the acetamido is realised. The compound 7.6 can be obtained after acetylation of the aniline. The carboxylic acid function can be transformed in ester function (Colletti, S. L. & al. *Tetrahedron Lett.* 2000, 41(41), 7825-7830) and can be reduce in a presence of sodium borohydride to get the alcohol. This alcohol can then react with the phosphorus(III)bromide (Rastelli, G. *Bioorg. Med. Chem. Lett.* 1997, 7(14), 1897-1902) or with sodium iodide (Baldwin, J. E. *Tetrahedron* 1991, 47(24), 4089-4100) to afford the bromo or iodo derivative. These halo derivatives could then react with different nucleophile (Nu-H) to obtain the compound 7.12.

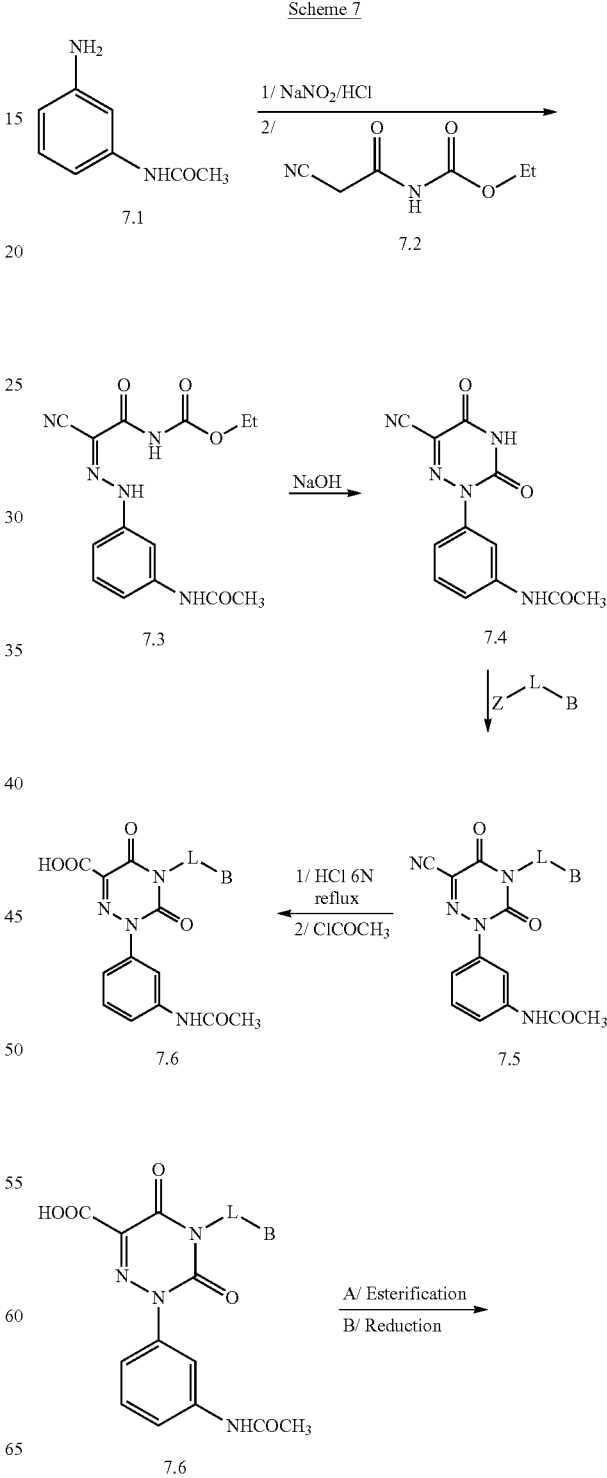

-continued

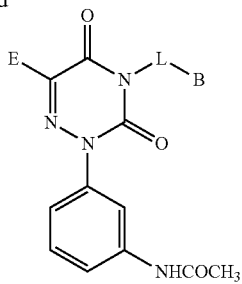

E = COOMe 7.7
E = COOiPr 7.8
E = CH$_2$OH 7.9

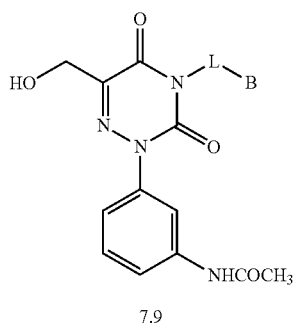

7.9

A/ Bromination
B/ Iodination

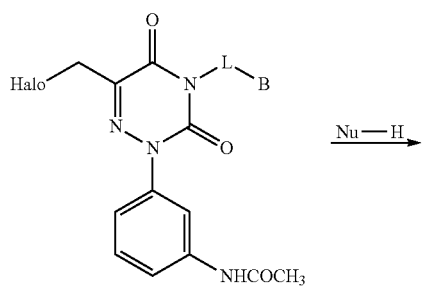

Halo = Br 7.10
Halo = I 7.11

Nu—H

-continued

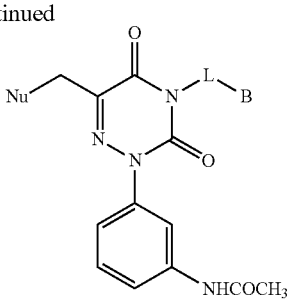

7.12

The compounds of Formula III wherein B, L, $X_1$, $X_2$, $X_3$, $X_4$, $X_5$ are as described above and E=CN is an important intermediate for further reactions. Some transformations of the nitrile organic function are presented in Scheme 8. Thus, derivative 8.1 obtained following the Scheme 1 can be hydrolised into the corresponding carboxylic acid in conditions described in previous schemes. The acid function can itself be the starting for the formation of several heteoaryl groups in manner known to the skilled in the art and are supported in literature in books (Katrizky A. R. and. Rees C. W. (1984) *Comprehensive Heterocyclic Chemistry*, Pergamon Press), but not limited to. In particular treatment of the acid with hydroxyacetamidine followed by cyclisation of the intermediate acylamidoxine will lead to the suitable substituted oxadiazole. Alternatively, the nitrile function can be easily transformed into precursor of heterocycles, i.e N-((dimethylamino)methylene)acetamide (two steps: transformation to acylamide and reaction with DMF-DMA) or N-hydroxyformimidamide (in direct reaction with suitable hydroxylamine).

Scheme 8

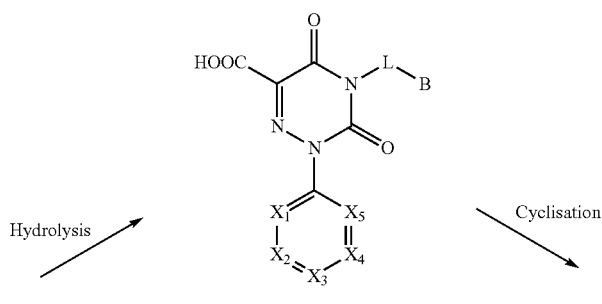

Hydrolysis 8.2

Cyclisation

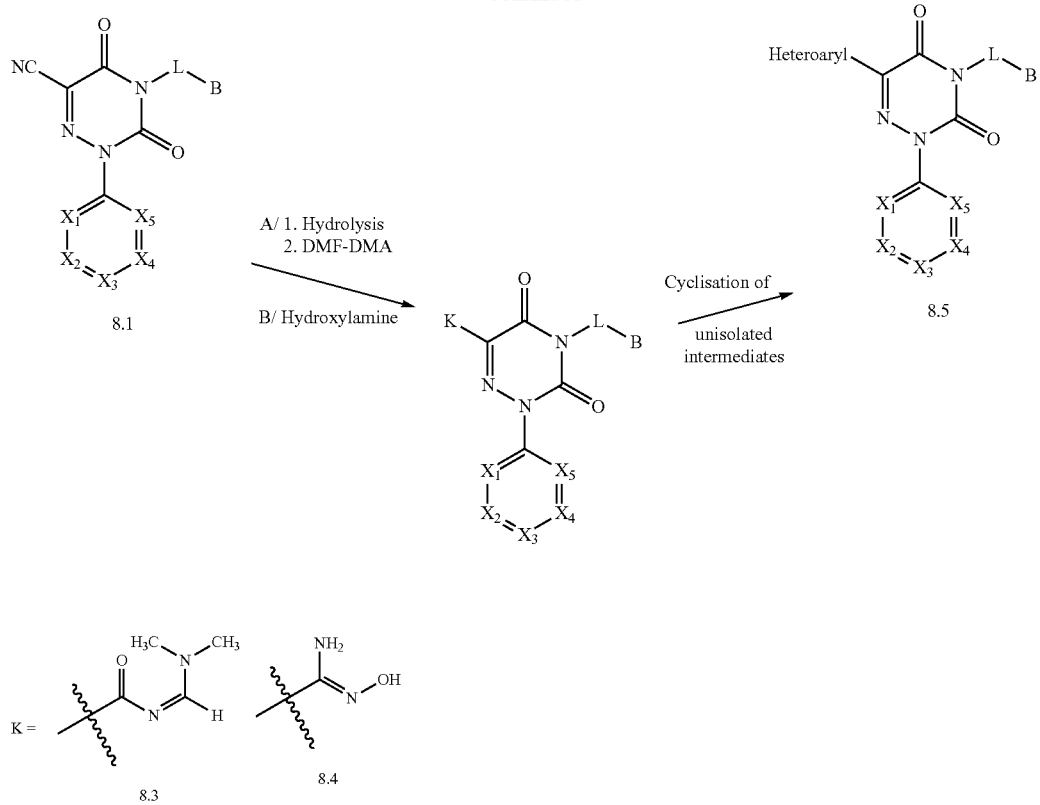

The compounds of Formula III wherein B, L, $X_1$, $X_2$, $X_3$, $X_4$, $X_5$, E are as described above and $R^6$ is $NO_2$, $NR^8R^9$, $OR^7$ or CN could give compounds of Formula III where $R^6$ was transformed into $NR^8R^9$, substituted heteroaryl or substituted heterocycloalkyl are presented in Scheme 9. Thus, derivative 9.1, with $R^6$ is —$NO_2$ can be reduced in primary amine function. The amine function can itself be the starting for the formation of several amide by acylation reaction, secondary or tertiary amine by alkylation reaction and substituted heterocycloalkyl groups in manner known to the skilled in the art and are supported in literature in books (Katrizky A. R. and. Rees C. W. (1984) *Comprehensive Heterocyclic Chemistry*, Pergamon Press), but not limited to. When derivative 9.1, with $R^6$ is $NR^8R^9$ can be reduce or deprotected to give the corresponding primary amine, secondary amine which can react as describe before. With $R^6$ is —$OR^7$, the deprotection reaction can occur, i.e with $BBr_3$ to give the alcohol. Then when $R^6$ is CN the reactions already describe in the Scheme 8 can be realised to finally conduct to heteroaryl.

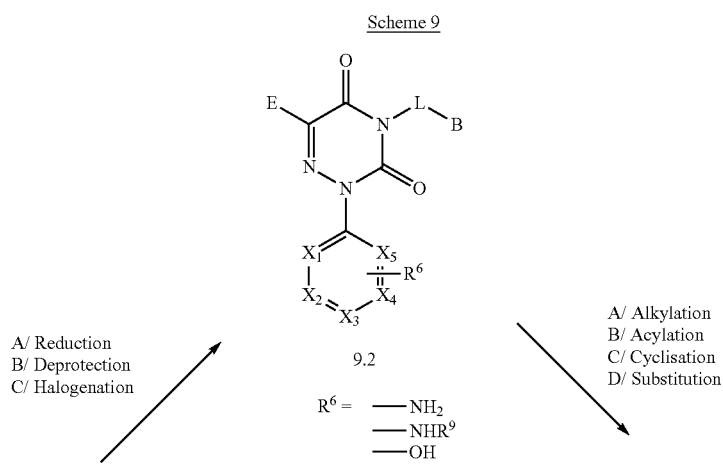

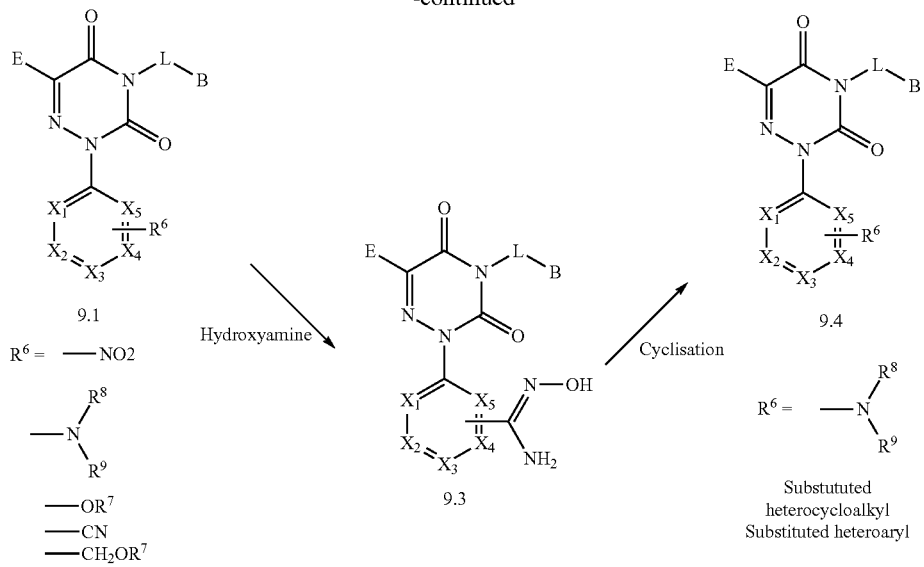

The reagents and starting materials are commercially available and/or, using well-known techniques, can be readily synthesized by one of ordinary skill in the art. Unless otherwise noted, all commercially starting materials were used without further purification.

Specifically, the following abbreviations may be used in the examples and throughout the specification.

| | |
|---|---|
| g (grams) | Rt (retention time) |
| mg (milligrams) | MeOH (methanol) |
| mL (milliliters) | NaCl (Sodium chloride) |
| μL (microliters) | Hz (Hertz) |
| M (molar) | LCMS (Liquid Chromatography Mass Spectrum) |
| MHz (megahertz) | HPLC (High Pressure Liquid Chromatography) |
| mmol (millimoles) | NMR (Nuclear Magnetic Reasonance) |
| min (minutes) | $^1$H (proton) |
| AcOEt (ethyl acetate) | LiAlH$_4$ (lithium aluminium hydride) |
| Pd(PPh$_3$)$_4$ (tetrakis(triphenylphosphine)palladium(0) | MgSO$_4$ (magnesium sulphate) |
| PdCl$_2$(PPh$_3$)$_2$ (Bis(triphenylphosphine) palladium (II) dichloride | TLC (tin layer chromatography) |
| CDCl$_3$ (deutered chloroform) | HOBT (1-hydroxybenzotriazole) |
| EDCI•HCl(1-3(Dimethylaminopropyl)-3-ethylcarbodiimide, hydrochloride) | R.T. (Room Temperature) |
| Et$_2$O (diethyl ether) | NaOH (sodium hydroxide) |
| % (percent) | h (hour) |
| DCM (dichloromethane) | HCl (hydrochloric acid) |
| DIEA (diisopropyl ethyl amine) | n-BuLi (n-butyllithium) |
| Mp (melting point) | THF (tetrahydrofuran) |
| NaHCO$_3$ (sodium hydrogenocarbonate) | NH$_4$Cl (ammonium chloride) |
| H$_2$SO$_4$ (Sulfuric acid) | N$_2$ (nitrogen) |
| DMAP (N,N-dimethylaminopyridine) | DAST (diethylaminosulfur trifluoride) |
| (BOC)$_2$O (Di-tert-butyl dicarbonate) | mm (millimeters) |
| SiO$_2$ (silicon(IV)oxyde) | V (volt) |
| ° C. (Celsius degrees) | MW (Microwave irradiation) |
| s (singulet) | bs (broad singulet) |
| d (doublet) | dd (doublet of doublet) |
| t (triplet) | dt (doublet of triplet) |
| m (multiplet) | td (triplet of doublet) |
| q (quintuplet) | dq (doublet of quintuplet) |
| OTf (triflate) | OMs (mesylate) |
| OTs (tosylate) | |

All references to brine refer to a saturated aqueous solution of NaCl unless otherwise indicated. All temperatures are expressed in ° C. All reactions are not conducted under an inert atmosphere at room temperature unless otherwise noted.

The microwave oven used is an apparatus from Biotage (Optimizer™) equipped with an internal probe that monitors reaction temperature and pressure, and maintains the desired temperature by computer control.

Example 1

N-(3-(4-(4-chlorobenzyl)-6-cyano-3,5-dioxo-4,5-dihydro-1,2,4-triazin-2(3H)-yl)phenyl)acetamide (Final Compound 1.01)

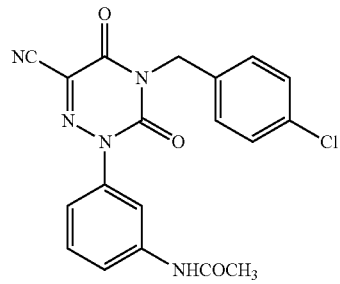

1(A): N-(4-chlorobenzyl)-2-cyanoacetamide

According to the Scheme 1 Step 1: A mixture of 4-chlorobenzylamine (10.0 g, 71 mmol), cyanoacetic acid (6.13 g, 72 mmol), HOBt (11 g, 72 mmol), EDCI.HCl (20 g, 106 mmol) in 100 mL of dioxane was stirred for 3 h at room temperature. The solvent was removed under vacuum and 300 mL of DCM was added. The organic layer was successively washed with 2×100 mL of water, 2×50 mL of a solution 1N of NaOH, 4×100 mL of water until neutral pH. The organic layer was dried over Na$_2$SO$_4$, filtered and concentrated to afford N-(4-chlorobenzyl)-2-cyanoacetamide 1(A) (13.12 g, 89%) as a brown solid.

1(B): (Z)-N-(4-chlorobenzyl)-2-cyano-2-(2-(3-aminophenyl)acetamide)hydrazono)acetamide According to the Scheme 1 Step 2: To a suspension of N-(3-aminophenyl)acetamide (1.5 g, 10 mmol) in concentrated HCl (2.9 mL) at 0° C. was added dropwise a solution of sodium nitrite (661 mg, 10 mmol in 10 mL of water); the obtained diazonium salt solution was added under vigorous stiffing to a suspension of compound 1(A) (1.0 g, 5 mmol) and sodium acetate (3.0 g) in ethanol (25 mL). The reaction mixture was allowed to rest at 0° C. for 2 h. The mixture was filtered, washed with cooled ethanol and dried to afford the hydrazone 1(B) (1.2 g, 68%) as yellow crystals.

1(C): N-(3-(4-(4-chlorobenzyl)-6-cyano-3,5-dioxo-4,5-dihydro-1,2,4-triazin-2(3H)-yl)phenyl)acetamide According to the Scheme 1 Step 3: A mixture of the compound 1(B) (500 mg, 1.4 mmol) and 3 mL of pyridine was cooled at 0° C. Onto this suspension was added dropwise 293 mg (2.7 mmol) of ethylchloroformate, with a syringe. The reaction mixture was heated at 120° C. for 6 h and concentrated under vacuum. The residue was successively dissolved in 3 mL of DCM, washed twice with a solution of 5N HCl (1 mL), dried over sodium sulfate, filtrated and concentrated to dryness. The crude oil was purified by flash chromatography over Silica gel (AIT Flashmart prepacked column 10 g $SiO_2$) using DCM/MeOH 98/2 as eluant to afford a yellow solid. The solid was washed with diethylether, filtered and dried to afford N-(3-(4-(4-chlorobenzyl)-6-cyano-3,5-dioxo-4,5-dihydro-1,2,4-triazin-2(3H)-yl)phenyl)acetamide 1(C) (192 mg, 36%) as a yellow solid.

mp: 196° C.
$LC_1$: Rt=4.35
MS m/z (ES) [M–H]⁻=394
¹H-NMR (DMSO-$d_6$), δ (ppm): 10.21 (1H, bs), 7.89-7.88 (1H, m), 7.60-7.57 (1H, m), 7.47-7.39 (5H, m), 7.16-7.13 (1H, m), 4.99 (2H, m), 2.05 (3H, s).

Example 2

N-(3-(4-(4-chlorobenzyl)-6-(dimethylamino)-3,5-dioxo-4,5-dihydro-1,2,4-triazin-2(3H)-yl)phenyl)acetamide (Final Compound 5.13)

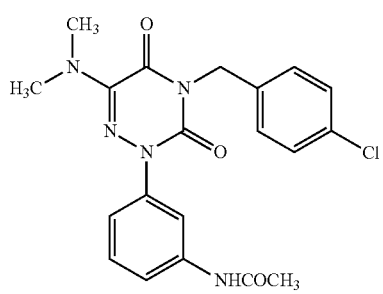

2(A): 6-bromo-1,2,4-triazine-3,5(2H,4H)-dione

According to Scheme 2 Step 1: To a stirred suspension of 2 g of 6-azauracyl (17.7 mmol) and water (15 mL) was added 2 mL of bromine (38.9 mmol) at room temperature. The mixture was stirred for 48 h at room temperature and filtered. The crude solid was washed with water and dried to afford 2(A) as a white powder (2.3 g, 11% yield).

$LC_1$: Rt=0.69-1.53
MS m/z (ES) [M–H]⁻=189.9, 191.9

2(B): 4-(4-chlorobenzyl)-6-bromo-1,2,4-triazine-3,5(2H,4H)-dione

According to Scheme 2 Step 2: to a solution of 4-chlorobenzyl bromide (1 g, 5.2 mmol) and 2(A) (1.1 g, 5.2 mmol) in DMSO (10 mL) was added portionwise NaH (55%) (230 mg, 5.2 mmol). After 15 min at room temperature the reaction mixture was quenched with water and extracted with ethyl acetate (×3). The combined organic layers were successively washed with water (×2), with brine, dried over $MgSO_4$, filtered and concentrated. The crude product was purified by flash chromatography, 50 gr column, (Eluant: DCM/MeOH 98/2) to obtain 0.856 g of 4-(4-chlorobenzyl)-6-bromo-1,2,4-triazine-3,5(2H,4H)-dione 2(B).

$LC_1$: Rt=3.93
MS m/z (ES) [M–H]⁻=315.8

2(C): N-(3-(4-(4-chlorobenzyl)-6-bromo-3,5-dioxo-4,5-dihydro-1,2,4-triazin-2(3H)-yl)phenyl)acetamide According to Scheme 2 Step 3: To a stirred solution of 4-(4-chlorobenzyl)-6-bromo-1,2,4-triazine-3,5(2H,4H)-dione (0.400 g) and 2(B) (411 mg, 1.3 mmol) in DMF (5 mL) were successively added of the 3-acetamidophenylboronic acid (0.34 g, 1.9 mmol), copper(II) acetate (0.23 g, 1.3 mmol) and 0.20 g of pyridine (2.5 mmol). The mixture was stirred overnight at 60° C. The reaction mixture was quenched with a saturated sodium bicarbonate solution and extracted with ethyl acetate (×3). The combined organic layers were washed successively with water, brine, dried over $MgSO_4$, filtered and concentrated. The crude product was purified by $C_{18}$ reverse phase column, 65 g column: 20% $CH_3CN$ gradient 20 to 60% to afford 0.350 g (yield=62%) of N-(3-(4-(4-chlorobenzyl)-6-bromo-3,5-dioxo-4,5-dihydro-1,2,4-triazin-2(3H)-yl)phenyl)acetamide 2(C).

TLC (DCM/MeOH 95/5): rf=0.35
$LC_1$: Rt=4.30
MS m/z (ES) [M+H]⁺=450.7
mp=202° C.
RMN 1H (300 MHz, DMSO-$d_6$), δ (ppm): 10.17 (1H, s), 7.83 (1H, s), 7.60-7.54 (1H, s), 7.46-7.37 (5H, m), 5.0 (2H, s), 2.05 (3H, s).

2(D): N-(3-(4-(4-chlorobenzyl)-6-(dimethylamino)-3,5-dioxo-4,5-dihydro-1,2,4-triazin-2(3H)-yl)phenyl)acetamide According to Scheme 2 Step 4: To a solution of 2(C) (100 mg, 0.22 mmol) in 0.5 mL of DMF was added dimethylamine 2M solution in methanol (0.56 mL, 1.11 mmol). The reaction was heated 5 h at 150° C. under microwave irradiation. The reaction mixture was quenched with water and extracted with ethyl acetate (×3). The combined organic layers were washed successively with water, with brine, dried over $MgSO_4$, filtered and concentrated. The crude product was purified by flash chromatography, 5 g column (Eluant: DCM/MeOH 98/2). 10 mg, (11% yield) of N-(3-(4-(4-chlorobenzyl)-6-(dimethylamino)-3,5-dioxo-4,5-dihydro-1,2,4-triazin-2(3H)-yl)phenyl)acetamide 2(D) were obtained.

TLC (DCM/MeOH 95/5): rf=0.44
$LC_1$: Rt=4.39
MS m/z (ES) [M+H]⁺=414.0
mp=189-190° C.
RMN 1H (300 MHz, DMSO-$d_6$), δ (ppm): 10.07 (1H, s), 7.87 (1H, s), 7.53-7.49 (1H, m), 7.38-7.23 (6H, m), 5 (2H, s), 2.95 (6H, s), 2.04 (3H, s).

Example 3

N-(3-(4-(4-chlorobenzyl)-6-methoxy-3,5-dioxo-4,5-dihydro-1,2,4-triazin-2(3H)-yl)phenyl)acetamide
(Final Compound 4.01)

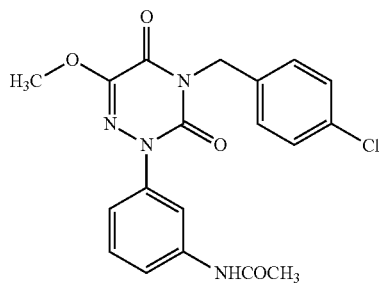

According to Scheme 2 Step 4: To a cooled solution of N-(3-(4-(4-chlorobenzyl)-6-bromo-3,5-dioxo-4,5-dihydro-1,2,4-triazin-2(3H)-yl)phenyl)acetamide 2(C) (80 mg, 0.18 mmol) in 0.5 mL of methanol (0.5 mL) at 0° C., was added a solution of sodium methoxide (2M) in Methanol (85 μL 0.18 mmol). After 1 h at 0° C. the reaction mixture was allowed to reach room temperature. After 1 h the reaction mixture was quenched with water and extracted with ethyl acetate (×3). The combined organic layers were washed successively with water, with brine, dried over MgSO$_4$, filtered and concentrated. The crude product was purified by flash chromatography, 5 g column, (Eluant: DCM/AcOEt/MeOH 80/18/2). 25 mg (35% yield) of N-(3-(4-(4-chlorobenzyl)-6-methoxy-3,5-dioxo-4,5-dihydro-1,2,4-triazin-2(3H)-yl)phenyl)acetamide were recovered.

TLC (DCM/MeOH 95/5): rf=0.36
LC$_1$: Rt=3.98
MS m/z (ES) [M+H]$^+$=400.9
mp=190-191° C.
RMN 1H (300 MHz, DMSO-d$_6$), δ (ppm): 10.11 (1H, s), 7.87 (1H, s), 7.56-7.53 (1H, m), 7.43-7.34 (5H, m), 7.25-7.21 (1H, m), 5 (2H, s), 3.82 (3H, s), 2.05 (3H, s).

Example 4

N-(3-(4-(4-chlorobenzyl)-6-isopropyl-3,5-dioxo-4,5-dihydro-1,2,4-triazin-2(3H)-yl)phenyl)acetamide
(Final Compound 5.01)

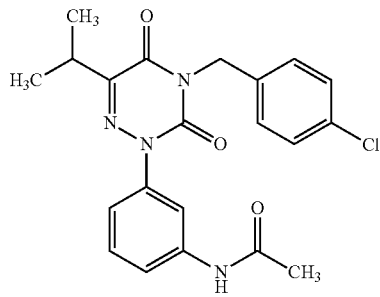 [SMILES: CC(=O)Nc1cccc(-n2nc(C(C)C)c(=O)n(Cc3ccc(Cl)cc3)c2=O)c1]

According to Scheme 2 Step 4: A mixture of N-(3-(4-(4-chlorobenzyl)-6-bromo-3,5-dioxo-4,5-dihydro-1,2,4-triazin-2(3H)-yl)phenyl)acetamide 2(C) (100 mg, 0.22 mmol), THF (2 mL), dimethoxyethane (69 μl, 0.67 mmol) and PdCl$_2$(dppf) (8 mg, 0.011 mmol) was stirred under nitrogen atmosphere at 50° C. Isopropylzinc(II) chloride solution 0.58M (1.15 mL, 0.67 mmol) was added dropwise and the mixture was stirred at 50° C. during 1 hour. The reaction mixture was diluted with 100 mL of water and extracted twice with 100 mL of CH$_2$Cl$_2$. The combined organic layers were dried over MgSO$_4$, filtered and concentrated under reduced pressure to afford a brown solid. The crude solid was purified by flash chromatography with silica gel (Merck Flashmart prepacked column 15 g SiO$_2$) using AcOEt/cyclohexane 4/6 as eluant to afford a brown solid. The solid was washed with diisopropylether and was filtered to afford N-(3-(4-(4-chlorobenzyl)-6-isopropyl-3,5-dioxo-4,5-dihydro-1,2,4-triazin-2(3H)-yl)phenyl)acetamide (53 mg, 58%) as a white solid.

LC$_2$: Rt=2.82
MS m/z (ES) [M+H]$^+$=413.0
mp=178° C.
$^1$H-NMR (DMSO-d$_6$), δ (ppm): 10.2 (1H, bs), 7.93 (1H, s), 7.67 (1H, dt), 7.5 (5H, m), 7.3 (1H, dt), 5.11 (2H, s), 3.26 (1H, m), 2.16 (3H, s), 1.27 (6H, d).

Example 5

N-(3-(4-((2,2-difluorobenzo[d][1,3]dioxol-5-yl)methyl)-6-methoxy-3,5-dioxo-4,5-dihydro-1,2,4-triazin-2(3H)-yl)phenyl)acetamide (Final Compound 4.127)

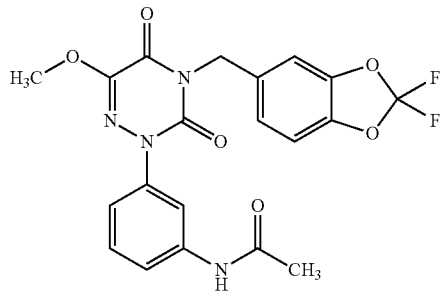 [SMILES: COc1nn(-c2cccc(NC(C)=O)c2)c(=O)n(Cc2ccc3c(c2)OC(F)(F)O3)c1=O]

5(A): 6-Bromo-4-((2,2-difluorobenzo[d][1,3]dioxol-5-yl)methyl)-1,2,4-triazine-3,5(2H,4H)-dione According to Scheme 2 Step 2: A mixture of 6-bromo-1,2,4-triazine-3,5(2H,4H)-dione 2(A) (943 mg, 4.91 mmol), CH$_2$Cl$_2$ (40 mL), triphenylphosphine (1.76 g, 6.69 mmol), (2,2-difluorobenzo[d][1,3]dioxol-5-yl)methanol (840 mg, 4.46 mmol) was stirred at 0° C. under nitrogen atmosphere. Di-tertbutyl azodicarboxylate (2.05 g, 8.93 mmol) was added portionwise and the mixture was stirred for 16 hours at room temperature. 200 mL of water were added and the aqueous layer was extracted thrice with 200 mL of DCM. The organic layers were combined and were successively dried over MgSO$_4$, filtered and concentrated under reduce pressure to afford a brown solid. The crude solid was purified by flash chromatography with silica gel (Merck Flashmart prepacked column SiO$_2$) using AcOEt/cyclohexane 3/7 as eluant to afford 6-bromo-4-((2,2-difluorobenzo[d][1,3]dioxol-5-yl)methyl)-1,2,4-triazine-3,5(2H,4H)-dione 5(A) (330 mg, 20%) as a white solid.

LC$_1$: Rt=2.44
MS m/z (ES) [M−H]$^-$=362

5(B): N-(3-(6-bromo-4-((2,2-difluorobenzo[d][1,3] dioxol-5-yl)methyl)-3,5-dioxo-4,5-dihydro-1,2,4-triazin-2(3H)-yl)phenyl)acetamide According to Scheme 2 Step 3: A mixture of 6-bromo-4-((2,2-difluorobenzo[d][1,3]dioxol-5-yl)methyl)-1,2,4-triazine-3,5(2H,4H)-dione (300 mg, 0.83 mmol), DMF (5 mL), 3-acetamidophenylboronic acid (222 mg, 1.24 mmol), copper acetate (150 mg, 0.83 mmol) and pyridine (135 μl, 1.66 mmol) was stirred at 65° C. for 15 hours under room atmosphere. A saturated solution of $NaHCO_3$ (200 mL) was added and the aqueous layer was extracted thrice with 200 mL of DCM. The organic layers were combined to be dried over $MgSO_4$, filtered and concentrated under reduced pressure to afford a brown solid. The crude solid was purified by flash chromatography with silica gel (AIT Flashmart 25 g prepacked column $C_{18}$) using water/acetonitrile 6/4 as eluant to afford N-(3-(6-bromo-4-((2,2-difluorobenzo[d][1,3]dioxol-5-yl)methyl)-3,5-dioxo-4,5-dihydro-1,2,4-triazin-2(3H)-yl)phenyl)acetamide (250 mg, 61%) as a white solid.

$LC_1$: Rt=2.68
MS m/z (ES) [M−H]⁻=495

5(C): N-(3-(4-((2,2-difluorobenzo[d][1,3]dioxol-5-yl)methyl)-6-methoxy-3,5-dioxo-4,5-dihydro-1,2,4-triazin-2(3H)-yl)phenyl)acetamide According to Scheme 2 Step 4: A mixture of N-(3-(6-bromo-4-((2,2-difluorobenzo[d][1,3]dioxol-5-yl)methyl)-3,5-dioxo-4,5-dihydro-1,2,4-triazin-2(3H)-yl)phenyl)acetamide (250 mg, 0.51 mmol), DMF (6 mL) was stirred at 0° C. under nitrogen atmosphere. A sodium methoxide solution 2M (303 μL, 0.61 mmol) was added dropwise and the mixture was stirred at 0° C. during 15 min. The reaction mixture was diluted with 100 mL of a saturated solution of $NH_4Cl$ and the aqueous layer was extracted twice with 100 mL of $CH_2Cl_2$. The organic layers were combined and successively dried over $MgSO_4$, filtered and concentrated under reduced pressure to afford a brown solid. The crude solid was purified by flash chromatography with silica gel (Merck Flashmart prepacked column 15 g $SiO_2$) using $CH_2Cl_2$/MeOH 98/2 as eluant to afford a beige solid. The solid was washed with diethylether and filtered to afford N-(3-(4-((2,2-difluorobenzo[d][1,3]dioxol-5-yl)methyl)-6-methoxy-3,5-dioxo-4,5-dihydro-1,2,4-triazin-2(3H)-yl)phenyl)acetamide 5(C) (141 mg, 63%) as a white solid.

mp=184° C.
$LC_2$: Rt=2.47
MS m/z (ES) [M+H]⁺=447
RMN 1H (300 MHz, DMSO-$d_6$), δ (ppm): 10.12 (1H, bs), 7.89 (1H, t), 7.54 (1H, d), 7.39 (3H, m), 7.24 (1H, d), 5.03 (2H, s), 3.83 (3H, s), 2.06 (3H, s).

Example 6

N-(3-(4-(4-isopropylbenzyl)-6-methoxy-3,5-dioxo-4,5-dihydro-1,2,4-triazin-2(3H)-yl)phenyl)acetamide (Final Compound 4.36)

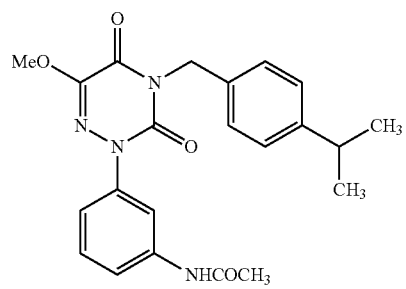

6(A): 4-allyl-6-bromo-1,2,4-triazine-3,5(2H,4H)-dione

According to Scheme 3 Step 1: To a solution of 6-bromoazauracil (2.00 g, 10.4 mmol) and allyl bromide (1.26 g, 10.4 mmol) in DMSO (25 mL) was added portionwise NaH (55%) (0.45 g, 10.4 mmol) at room temperature. The reaction mixture was stirred during 1 h. 100 mL of water were added and the aqueous layer was extracted thrice with ethyl acetate. The combined organic layers were successively washed twice with water, saturated brine, dried over $MgSO_4$, filtered and concentrated under reduce pressure. The crude solid was purified by flash chromatography with silica gel using $CH_2Cl_2$/MeOH 98/2 as eluant to afford 4-allyl-6-bromo-1,2,4-triazine-3,5(2H,4H)-dione 6(A) (1.10 g, 45%) with a purity of 90% (containing 10% of starting material) as a colorless oil.

$LC_2$: Rt=1.40
MS m/z (ES) [M−H]⁻=230

6(B): N-(3-(4-allyl-6-bromo-3,5-dioxo-4,5-dihydro-1,2,4-triazin-2(3H)-yl)phenyl)acetamide According to Scheme 3 Step 2: A mixture of compound 6(A) (1.10 g, 4.74 mmol), 3-acetamidophenylboronic acid (1.20 g, 6.64 mmol), copper acetate (258 mg, 1.42 mmol) and pyridine (229 μL, 2.84 mmol) in DMF (30 mL) was stirred at 65° C. during 15 h under room atmosphere. The mixture was diluted with 50 mL of a saturated solution of $NaHCO_3$ and the aqueous layer was extracted twice with 60 mL of DCM. The organic layers were combined dried over $MgSO_4$, filtered filtrated and concentrated under reduce pressure to afford a brown solid. The crude solid was purified by flash chromatography with silica gel (Merck Flashmart prepacked column 10 g $SiO_2$) (Eluant: $CH_2Cl_2$/MeOH 98/2) to afford N-(3-(4-allyl-6-bromo-3,5-dioxo-4,5-dihydro-1,2,4-triazin-2(3H)-yl)phenyl)acetamide 6(B) (800 mg, 46%) as a colorless oil.

$LC_2$: Rt=2.01
MS m/z (ES) [M−H]⁻=363.

6(C): N-(3-(4-allyl-6-methoxy-3,5-dioxo-4,5-dihydro-1,2,4-triazin-2(3H)-yl)phenyl)acetamide According to Scheme 3 Step 3: To a solution of compound 6(B) (800 mg, 2.19 mmol) in MeOH (10 mL) was added. a solution of sodium methoxyde 2M in methanol (1.1 mL, 2.19 mol). After 1 h of stirring at room temperature, the mixture was quenched with water and extracted with ethyl acetate (×3). The combined organic layers were successively washed with water, brine, dried over $MgSO_4$, filtered and concentrated under reduced pressure. The crude solid was purified by flash chromatography with silica gel (Merck Flashmart prepacked column 10 g $SiO_2$) using $CH_2Cl_2$/MeOH 98/2 as eluant to afford N-(3-(4-allyl-6-methoxy-3,5-dioxo-4,5-dihydro-1,2,4-triazin-2(3H)-yl)phenyl)acetamide 6(C) (600 mg, 86%) as a white solid.

mp=72-73° C.
$LC_2$: Rt=1.71
MS m/z (ES) [M+H]⁺=317 and (ES) [M−H]⁻=315.
RMN 1H (DMSO-$d_6$), δ (ppm): 10.12 (1H, s), 7.88-7.87 (1H, m), 7.56-7.36 (1H, m), 7.40-7.35 (1H, t), 7.25-7.22 (1H, m), 5.89-5.80 (1H, m), 5.26-5.14 (2H, m), 4.45-4.43 (2H, m), 3.82 (3H, s), 2.09 (3H, s), 2.05 (3H, s).

6(D): N-(3-(4-allyl-6-methoxy-3,5-dioxo-4,5-dihydro-1,2,4-triazin-2(3H)-yl)phenyl)acetamide According to Scheme 3 Step 4: To a solution of compound 6(C) (600 mg, 1.90 mmol) in dioxane (5 mL) was added dichlorotris(triphenylphospine)ruthenium (91 mg, 0.10 mmol) and formic acid (87 mg, 1.90 mmol). The reaction mixture was heated at 200° C. under microwave irradiation for 30 min and filtered over celite. The filtrate was concentrated under reduced pressure. The crude product was then dissolved with AcOEt, washed twice with water and once with brine. The organic layer was dried, concentrated until dryness and the crude was then purified by flash chromatography with silica gel (Merck Flashmart prepacked column 10 g $SiO_2$) using $CH_2Cl_2$/MeOH 98/2 as eluant to afford N-(3-(4-allyl-6-methoxy-3,5-dioxo-4,5-dihydro-1,2,4-triazin-2(3H)-yl)phenyl)acetamide 6(D) (250 mg, 50%) as a purple solid.

$LC_2$: Rt=1.19
MS m/z (ES) $[M+H]^+$=277 and (ES) $[M-H]^-$=275.

6(E): N-(3-(4-(4-isopropylbenzyl)-6-methoxy-3,5-dioxo-4,5-dihydro-1,2,4-triazin-2(3H)-yl)phenyl)acetamide According to Scheme 3 Step 5: A suspension of compound 6(D) (60 mg, 0.22 mmol), 4-isopropylbenzyl bromide (41 µL, 0.24 mmol) and potassium carbonate (90 mg, 0.65 mmol) was stirred at 60° C. for 15 h in acetonitrile (2 mL). The mixture was diluted with AcOEt and water. The organic layer was washed twice with water and once with brine. The resulting organic layer was dried over $MgSO_4$ and concentrated under reduced pressure. The crude product was purified by flash chromatography over silica gel (Merck Flashmart prepacked column 10 g $SiO_2$) using $CH_2Cl_2$/MeOH 98/2 as eluant to afford N-(3-(4-(4-isopropylbenzyl)-6-methoxy-3,5-dioxo-4,5-dihydro-1,2,4-triazin-2(3H)-yl)phenyl)acetamide 6(E) (10 mg, 11%) as a yellow solid.

$LC_2$: Rt=2.62
MS m/z (ES) $[M+H]^+$=409.0 and (ES) $[M-H]^-$=407.0.
$^1$H-NMR (DMSO-$d_6$), δ (ppm): 10.12 (1H, bs), 7.87 (1H, s), 7.57-7.54 (1H, m), 7.40-7.34 (1H, t), 7.30-7.18 (5H, m), 4.98 (2H, s), 3.81 (3H, s), 2.9-2.81 (1H, q), 2.05 (3H, s), 1.18-1.16 (6H, m).

Example 7

N-(3-(4-(4-chlorobenzyl)-3,5-dioxo-4,5-dihydro-1,2,4-triazin-2(3H)-yl)phenyl)acetamide (Final Compound 2.01)

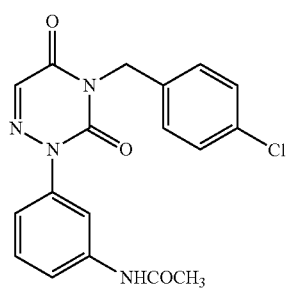

7(A): 4-(4-Chlorobenzyl)-1,2,4-triazine-3,5(2H,4H)-dione

According to Scheme 4 Step 1: To a solution of 6-Azauracyl (5 g, 44.2 mmol) and 4-chlorobenzyl bromide (9.09 g, 44.2 mmol) in DMSO (190 mL) under nitrogen atmosphere was added portionwise NaH (55%) (1.93 g, 44.2 mmol) at room temperature. The reaction mixture was stirred during 15 min. 300 mL of water was added and the aqueous layer was extracted thrice with ethyl acetate (300 mL). The combined organic layers were washed twice with water (200 mL), dried over $MgSO_4$, filtered and concentrated under reduce pressure to afford a yellow solid. The crude solid was purified by flash chromatography with silica gel using $CH_2Cl_2$/MeOH 98/2 as eluant to afford 4-(4-chlorobenzyl)-1,2,4-triazine-3,5(2H,4H)-dione 7(A) (6.4 g, 61%) as a white solid.

$LC_1$: Rt=3.48
MS m/z (ES) $[M-H]^-$=236

7(B): N-(3-(4-(4-chlorobenzyl)-3,5-dioxo-4,5-dihydro-1,2,4-triazin-2(3H)-yl)phenyl)acetamide According to Scheme 4 Step 2: To a stirred solution of 4-(4-chlorobenzyl)-1,2,4-triazine-3,5(2H,4H)-dione (0.250 g, 1.1 mmol) in DMF (5 mL) were added 3-acetamidophenylboronic acid (0.28 g, 1.6 mmol), copper(II) acetate (0.19 g, 1 mmol) and pyridine (0.17 g, 2.1 mmol) and the mixture was stirred overnight at 60° C. The reaction was quenched with a saturated sodium bicarbonate solution and extracted with ethyl acetate (×3). The combined organic layers were successively washed with water then with brine, dried over $MgSO_4$, filtered and concentrated. The crude product was purified by $C_{18}$ reverse phase column, 15 g column: starting from 20% $CH_3CN$ and gradually increasing the percentage of $CH_3CN$ (10% each 300 ml) the product came out at 60% of $CH_3CN$. 0.160 g (39%) of N-(3-(4-(4-chlorobenzyl)-3,5-dioxo-4,5-dihydro-1,2,4-triazin-2(3H)-yl)phenyl)acetamide 7(B) were obtained.

$LC_1$: Rt=3.92
MS m/z (ES) $[M+H]^+$=371.0
$^1$H-NMR (CDCl$_3$), δ (ppm): 7.81 (1H, bs), 7.57-7.54 (1H, m), 7.49-7.18 (9H, m), 5.1 (2H, s).

Example 8

N-(3-(4-(4-chlorobenzyl)-6-methyl-3,5-dioxo-4,5-dihydro-1,2,4-triazin-2(3H)-yl)phenyl)acetamide (Final Compound 3.01)

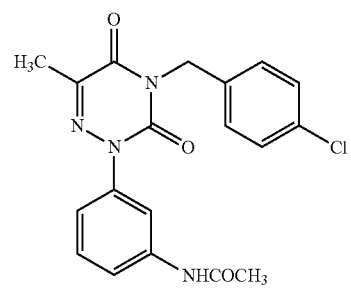

8(A): 4-(4-chlorobenzyl)-6-methyl-1,2,4-triazine-3,5(2H,4H)-dione

According to Scheme 4 Step 1: To a solution of Azathymine (300 mg, 2.36 mmol) and 4-chlorobenzyl bromide (485 mg, 2.36 mmol) in DMSO (10 mL) was added portionwise NaH (55%) (103 mg, 2.36 mmol) at room temperature under nitrogen atmosphere. The mixture was stirred for 15 min at room temperature. Ethyl Acetate was then added (150 mL) and the organic layer was extracted thrice with water (100 mL). The organic layer was dried over MgSO$_4$, filtered and concentrated under reduced pressure to afford a yellow solid. The crude solid was purified by flash chromatography with silica gel using CH$_2$Cl$_2$/MeOH 98/2 as eluant to afford 4-(4-chlorobenzyl)-6-methyl-1,2,4-triazine-3,5(2H,4H)-dione 8(A) (500 mg, 84%) as a white solid.

LC$_1$: Rt=3.66
MS m/z (ES) [M−H]$^−$=249

8(B): N-(3-(4-(4-chlorobenzyl)-6-methyl-3,5-dioxo-4,5-dihydro-1,2,4-triazin-2(3H)-yl)phenyl)acetamide According to Scheme 4 Step 2: A mixture of compound 8(A) (100 mg, 0.39 mmol), 3-acetamidophenylboronic acid (107 mg, 0.59 mmol), copper acetate (79 mg, 0.44 mmol) and pyridine (65 µl, 0.79 mmol) in DMF (3 mL) was stirred at 65° C. during 15 hours. The reaction mixture was diluted with 100 mL of a saturated solution of NaHCO$_3$ and the aqueous layer was extracted twice with DCM (100 mL). The organic layers were combined and successively dried over MgSO$_4$, filtered and concentrated under reduce pressure to afford a brown solid. The crude solid was purified by flash chromatography with silica gel (Merck Flashmart prepacked column 20 g, C18) using Water/CH$_3$CN 6/4 as eluant to afford N-(3-(4-(4-chlorobenzyl)-6-methyl-3,5-dioxo-4,5-dihydro-1,2,4-triazin-2(3H)-yl)phenyl)acetamide 8(B) (97 mg, 63%) as a white solid.

LC$_1$: Rt=4.08
MS m/z (ES) [M+H]$^+$=384
$^1$H-NMR (DMSO-d$_6$), δ (ppm): 10.12 (1H, bs), 7.8 (1H, t), 7.55 (1H, d), 7.37 (5H, m), 7.15 (1H, dd), 5 (2H, s), 2.19 (3H, s), 2.05 (3H, s).

Example 9

N-(3-(4-(4-cyanobenzyl)-3,5-dioxo-4,5-dihydro-1,2,4-triazin-2(3H)-yl)phenyl)acetamide (Final Compound 2.05)

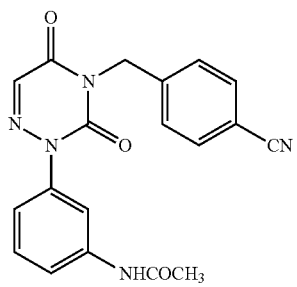

9(A): Ethyl(Z)-2-cyano-2-(2-(3-nitrophenyl)hydrazono)acetylcarbamate

According to Scheme 5 Step 1: To a suspension of nitoaniline (5 g, 36.2 mmol) in concentrated HCl (9 mL) and water (50 mL) at 0° C. was added dropwise over 30 minutes a solution of sodium nitrite (5 g, 72.4 mmol in 200 mL water) the crude orange suspension was filtered at 0° C. and the obtained diazonium salt was added portionwise over 1 hour under vigorous stiffing to a suspension of ethyl 2-cyanoacetate (6.22 g, 39.8 mmol) and sodium acetate (21.0 g, 257 mmol) in ethanol (200 mL). The reaction mixture was allowed to rest at 0° C. for 1 h. The mixture was filtered, washed with water then cooled ethanol and dried to afford (Z)-2-cyano-2-(2-(3-nitrophenyl)hydrazono)acetylcarbamate 9(A) (11.0 g, 100%, 75% of purity) as an orange solid. The crude solid was used in the next step without further purification.

Rf=0.32 CH$_2$Cl$_2$/MeOH (95/5)
LC$_1$: Rt=3.65
MS m/z (ES) [M+H]$^+$=306

9(B): 2-(3-nitrophenyl)-3,5-dioxo-2,3,4,5-tetrahydro-1,2,4-triazine-6-carbonitrile According to Scheme 5 Step 2: The crude compound 9(A) (11.0 g, 75% of purity) was stirred with NaOH 1M (65 mL) and 200 mL of water. The corresponding heterogeneous mixture was stirred at room temperature. After 1 h, two additional set of NaOH 1M (20 mL+20 mL) was added. After complete conversion, the mixture was diluted with EtOAc and the aqueous layers were successively decanted and acidified. The acidified aqueous layers were extracted with EtOAc and the organic layers were combined and successively washed with brine, dried over MgSO$_4$ filtered and concentrated to afford the 9(B) (8 g, 47%) as a crude yellow solid. 9B was used in the next step without further purification.

LC$_1$: Rt=3.46
MS m/z (ES) [M−H]$^−$=258

9(C): 2-(3-nitrophenyl)-1,2,4-triazine-3,5(2H,4H)-dione 5.5

According to Scheme 5 Step 3: 2-(3-nitrophenyl)-3,5-dioxo-2,3,4,5-tetrahydro-1,2,4-triazine-6-carbonitrile (3.8 g) was successively splitted over 8 microwave flasks, diluted with an aqueous solution of HCl (6N, 10 mL) and were irradiated under Microwave at 150° C. for 1 hour. The clear brown solids were combined filtered and dried to afford the corresponding acid (6.5 g, 76% yield).

LC$_1$: Rt=2.08
A solution of 2-(3-nitrophenyl)-3,5-dioxo-2,3,4,5-tetrahydro-1,2,4-triazine-6-carboxylic acid (3 g) in diphenylether (30 mL) was refluxed for 1 hour and cooled to room temperature. The mixture was quenched with 1M NaOH solution. The basic aqueous layer was then acidified and extracted with ethyl acetate (×3). The organic layers were successively washed with brine, dried over MgSO$_4$, filtered and concentrated. 1 g (40% yield) of 2-(3-nitrophenyl)-1,2,4-triazine-3,5(2H,4H)-dione 9(C) was recovered and used in next step without any further purification.

LC$_1$: Rt=2.95

9(D): N-(3-(3,5-dioxo-4,5-dihydro-1,2,4-triazin-2(3H)-yl)phenyl)acetamide 5.6

According to Scheme 5 Step 4: To a mixture of compound 9(C) (2 g, 8.54 mmol) and 60 mL of H$_2$O/EtOH 50/50 and acetic acid (0.488 mL, 8.54 mmol) was added iron (2.24 g, 40.1 mmol). The reaction mixture was heated at 80° C. A solution of NaOH 1M was added until neutral pH. The mixture was filtered over celite. The aqueous layers where diluted with EtOAc and decanted. The combined organic layers were acidified till pH=2 and extracted with EtOAc The combined organic layers were successively washed with brine, dried over MgSO$_4$, filtered and concentrated to afford 1.2 g (69% yield) of the crude compound 2-(3-aminophenyl)-1,2,4-triazine-3,5(2H,4H)-dione which is used in next step without any further purification LC$_1$: Rt=1.74
MS m/z (ES) [M+H]$^+$=205.2

To a stirred solution of 2-(3-aminophenyl)-1,2,4-triazine-3,5(2H,4H)-dione (1.2 g, 5.88 mmol) in THF (20 mL) was added acetic anhydride (1.2 g, 11.8 mmol) and the mixture was heated at 50° C. After 2 h the mixture was cooled at room temperature, quenched with water and extracted with ethyl acetate (×3). The organic layers were washed with brine, dried over MgSO$_4$, filtered and concentrated to afford the 900 mg, 62% yield, of N-(3-(3,5-dioxo-4,5-dihydro-1,2,4-triazin-2(3H)-yl)phenyl)acetamide 9(D) (900 mg, 62%) which is used in next step without any further purification.

LC$_1$: Rt=2.23
MS m/z (ES) [M+H]$^+$=247.1

9(E): N-(3-(4-(4-cyanobenzyl)-3,5-dioxo-4,5-dihydro-1,2,4-triazin-2(3H)-yl)phenyl)acetamide According to Scheme 5 Step 5: A suspension of N-(3-(3,5-dioxo-4,5-dihydro-1,2,4-triazin-2(3H)-yl)phenyl)acetamide (50 mg, 0.203 mmol), 4-cyanobenzylbromide (40 mg, 0.203 mmol) and potassium carbonate (31 mg, 0.223 mmol) in acetonitrile (2 mL) was stirred at 60° C. for 15 h The reaction mixture was then partitioned between AcOEt and water The organic layer was washed twice with water and once with brine. The organic layer was dried over MgSO$_4$ and evaporated under reduced pressure. The crude product was purified by flash chromatography over silica gel (Merck Flashmart prepacked column 10 g SiO$_2$) using DCM/MeOH 98/2 as eluent to afford N-(3-(4-(4-cyanobenzyl)-3,5-dioxo-4,5-dihydro-1,2,4-triazin-2(3H)-yl)phenyl)acetamide 9(E) (26 mg, 35%) as a white solid.

LC$_1$: Rt=3.47
MS m/z (ES) [M+H]$^+$=362 and (ES) [M−H]$^-$=360.
$^1$H-NMR (DMSO-d$_6$), δ (ppm): 10.14 (1H, bs), 7.85-7.80 (4H, m), 7.60-7.55 (3H, m), 7.41-7.36 (1H, t), 7.18-7.16 (1H, m), 5.07 (2H, s), 2.05 (3H, s).

Example 10

N-(3-(4-(4-chloro-2-fluorobenzyl)-3,5-dioxo-4,5-dihydro-1,2,4-triazin-2(3H)-yl)phenyl)acetamide (Final Compound 2.20)

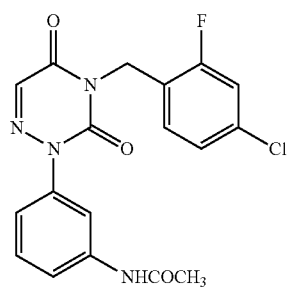

10(A): N-(3-(5-methoxy-3-oxo-1,2,4-triazin-2(3H)-yl)phenyl)acetamide

According to Scheme 6 Step 1: To a stirred solution of 5-methoxy-1,2,4-triazin-3(2H)-one (1 g, 7.9 mmol) in DMF (5 mL) were successively added the 3-acetamidophenylboronic acid (1.4 g, 7.9 mmol), copper(II) acetate (1.4 g, 7.9 mmol) and pyridine (1.2 g, 7.9 mmol). The mixture was stirred overnight at 60° C. The reaction mixture was quenched with a saturated sodium bicarbonate solution and extracted with ethyl acetate (×3). The combined organic layers were washed successively with water, brine, dried over MgSO$_4$, filtered and concentrated. The crude product was purified by flash chromatography, 70 g column, CH$_2$Cl$_2$/MeOH 98/2 to afford (0.493 g, 24%) of N-(3-(5-methoxy-3-oxo-1,2,4-triazin-2(3H)-yl)phenyl)acetamide LC$_1$: Rt=2.46
MS m/z (ES) [M+H]$^+$=261.2

10(B): N-(3-(4-(4-chloro-2-fluorobenzyl)-3,5-dioxo-4,5-dihydro-1,2,4-triazin-2(3H)-yl)phenyl)acetamide According to Scheme 6 Step 2: To a stirred solution of N-(3-(5-methoxy-3-oxo-1,2,4-triazin-2(3H)-yl)phenyl)acetamide (40 mg, 0.15 mmol) in acetonitrile (3 mL) were added 1-(bromomethyl)-4-chloro-2-fluorobenzene (52 mg, 0.23 mmol) and sodium iodide (46 mg, 0.31 mmol). The mixture was heated irradiated at 160° C. under microwave irradiation. The reaction mixture was quenched with water and extracted with ethyl acetate (×3). The combined organic layers were successively washed with water then with brine, dried over MgSO$_4$, filtered and concentrated. The crude product was purified by flash chromatography, 5 g column, CH$_2$Cl$_2$/MeOH 98/2 to afford the N-(3-(4-(4-chloro-2-fluorobenzyl)-3,5-dioxo-4,5-dihydro-1,2,4-triazin-2(3H)-yl)phenyl)acetamide 10(B) as a yellow solid (13 mg, 22%).

LC$_1$: Rt=3.98
MS m/z (ES) [M+H]$^+$=389.2
mp=184° C.
$^1$H-NMR (DMSO-d$_6$), δ (ppm): 10.14 (1H, s), 7.85-7.81 (2H, m), 7.57-7.13 (6H, m), 5 (2H, s), 2.06-2.03 (3H, m).

Example 11

N-(3-(4-(4-chlorobenzyl)-6-(hydroxymethyl)-3,5-dioxo-4,5-dihydro-1,2,4-triazin-2(3H)-yl)phenyl)acetamide (Final Compound 5.14)

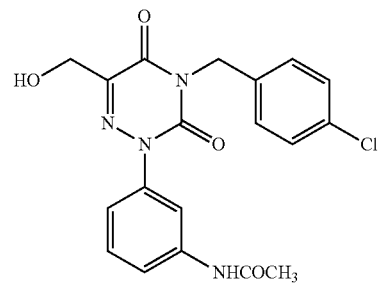

11(A): (Z)-ethyl 2-(2-(3-acetamidophenyl)hydrazono)-2-cyanoacetylcarbamate

According to Scheme 7 Step 1: To a suspension of 3-aminophenylacetamide (1.50 g, 9.9 mmol), in concentrated HCl (2.5 mL) and water (11 mL) at 0° C. was added dropwise over 30 min a solution of sodium nitrite (1.38 g, 19.9 mmol) in water (20 mL). The crude orange suspension was stirred at 0° C. and the obtained diazonium salt was added portionwise over 1 hour under vigorous stirring to a suspension made of compound N-cyanoacetylurethane (1.71 g, 10.9 mmol) and sodium acetate (5.82 g, 70.9 mmol) in ethanol (37 mL). The reaction mixture was stirred at 0° C. for 2 h. The brown resulting mixture was successively filtered, washed with water, cooled ethanol, Et$_2$O and dried to afford the hydrazone Ethyl(Z)-2-cyano-2-(2-(3-acetamidophenyl)hydrazono)acetylcarbamate 11(A) (3.18 g, 99%).

11(B): N-(3-(6-cyano-3,5-dioxo-4,5-dihydro-1,2,4-triazin-2(3H)-yl)phenyl)acetamide According to Scheme 7 Step 2: A mixture of compound 11(A) (3.18 g, 9.9 mmol) in water (10 mL) and sodium hydroxide (0.40 g, 9.9 mmol) was stirred during 30 min at room temperature. The mixture was filtered. The precipitate was dried under vacuum to afford N-(3-(6-cyano-3,5-dioxo-4,5-dihydro-1,2,4-triazin-2(3H)-yl)phenyl)acetamide 11(B) (1.9 g, 69%) as an orange solid.

LC$_1$: Rt=2.75
MS m/z (ES) [M−H]$^-$=270

11(C): N-(3-(4-(4-chlorobenzyl)-6-cyano-3,5-dioxo-4,5-dihydro-1,2,4-triazin-2(3H)-yl)phenyl)acetamide According to Scheme 7 Step 3: A suspension of 11(B) (500 mg, 1.8 mmol), 4-chlorobenzyl bromide (455 mg, 2.2 mmol) and potassium carbonate (510 mg, 3.7 mmol) in CH$_3$CN (10 mL) was stirred 12 h under reflux. The mixture was cooled at room temperature and 100 mL of water were added. The aqueous layer was extracted thrice with DCM (100 mL). The organic layers were mixed, dried over MgSO$_4$, filtered and concentrated under reduced pressure to afford a brown solid. The crude solid was purified by flash chromatography with silica gel (AIT Flashmart prepacked column 50 g SiO$_2$) using CH$_2$Cl$_2$/MeOH (98/2) as eluant to afford N-(3-(4-(4-chlorobenzyl)-6-cyano-3,5-dioxo-4,5-dihydro-1,2,4-triazin-2(3H)-yl)phenyl)acetamide 11(C) (460 mg, 63%) as a beige solid.

11(D): 2-(3-acetamidophenyl)-4-(4-chlorobenzyl)-3,5-dioxo-2,3,4,5-tetrahydro-1,2,4-triazine-6-carboxylic acid According to Scheme 7 Step 4: A mixture of compound 11(C) (2.00 g, 5.1 mmol) and hydrochloric acid 33% (30 mL) was stirred at reflux during 3 h. The solvent was removed concentrated under reduce pressure and then the crude residue was treated with a saturated solution of Na$_2$CO$_3$ (50 ml). The aqueous layer was acidified (pH=4) with acetic acid (pH=4) and the reaction mixture was filtered to afford 4-(4-chlorobenzyl)-2-(3-aminophenyl)-3,5-dioxo-2,3,4,5-tetrahydro-1,2,4-triazine-6-carboxylic acid (1.65 g, 88%) as a beige solid.

To a solution of the crude chlorobenzyl-2-(3-aminophenyl)-3,5-dioxo-2,3,4,5-tetrahydro-1,2,4-triazine-6-carboxylic acid (1.65 g) in THF (50 mL) was added the acetyl chloride (751 µL, 10.4 mmol) dropwise. The mixture was stirred for 1 hour. The reaction mixture was quenched with water (2 mL) and the resulting mixture was concentrated under reduced pressure to afford 4-(4-chlorobenzyl)-2-(3-acetamidophenyl)-3,5-dioxo-2,3,4,5-tetrahydro-1,2,4-triazine-6-carboxylic acid 11(D) (1.70 g, 98%) as a beige solid.

11(E): N-(3-(4-(4-chlorobenzyl)-6-(hydroxymethyl)-3,5-dioxo-4,5-dihydro-1,2,4-triazin-2(3H)-yl)phenyl)acetamide According to Scheme 7 Step 5: To a solution of 11(D) (380 mg, 0.92 mmol)) and diisopropylethylamine (189 µL, 1.1 mmol) in THF (10 mL) at 0° C. under nitrogen atmosphere was added ethyl chloroformate (101 µL, 1.06 mmol) dropwise. The reaction mixture was stirred for 1 h then treated dropwise with a solution of sodium borohydride (90 mg, 2.38 mmol) in water (2 mL). The mixture was stirred overnight at room temperature and quenched slowly with a saturated solution of NaHCO$_3$ (100 mL). The aqueous layer was extracted thrice with CH$_2$Cl$_2$ (100 mL). The organic layers were combined, dried over MgSO$_4$, filtered and concentrated under reduced pressure to afford a yellow solid. The crude solid was purified by flash chromatography with silica gel (Merck Flashmart prepacked column 20 g SiO$_2$) using CH$_2$Cl$_2$/MeOH 97/3 as eluant to afford N-(3-(4-(4-chlorobenzyl)-6-(hydroxymethyl)-3,5-dioxo-4,5-dihydro-1,2,4-triazin-2(3H)-yl)phenyl)acetamide 11(E) (32 mg, 9%) as a white solid.

LC$_2$: Rt=2.07
MS m/z (ES) [M+H]$^+$=400.8
RMN 1H (300 MHz, DMSO-d$_6$), δ (ppm): 10.14 (1H, bs), 7.82 (1H, t), 7.56 (1H, dd), 7.4 (5H, m), 7.17 (1H, dd), 5 (2H, s), 5.31 (1H, t, 6 Hz), 4.4 (2H, d, 6 Hz), 2.05 (3H, s).

Example 12

Methyl 4-(4-chlorobenzyl)-2-(3-acetamidophenyl)-3,5-dioxo-2,3,4,5-tetrahydro-1,2,4-triazine-6-carboxylate (Final Compound 5.17)

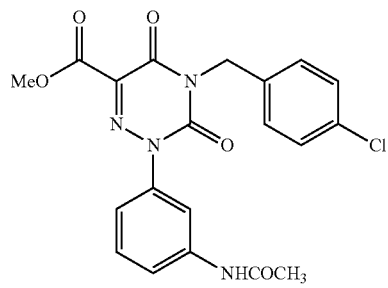

According to Scheme 7 Step 5: To a solution of 2-(3-acetamidophenyl)-4-(4-chlorobenzyl)-3,5-dioxo-2,3,4,5-tetrahydro-1,2,4-triazine-6-carboxylic acid 11(D) (80 mg, 0.19 mmol) in MeOH (3 mL) was added dropwise at 0° C. a solution of trimethylsilyldiazomethane 2M (1.3 mL, 2.70 mmol). The mixture was stirred at room temperature for 18 h. The mixture was diluted with 100 mL of a saturated solution of NaHCO$_3$ and the aqueous layer was extracted twice with 100 mL of DCM. The organic layers were combined, dried over MgSO$_4$, filtered and concentrated under reduced pressure to afford a yellow solid. The crude solid was purified by flash chromatography with silica gel (AIT Flashmart prepacked column 7 g SiO$_2$) using CH$_2$Cl$_2$/MeOH 98/2 as eluant to afford a yellow solid. The solid was further triturated with diisopropylether and filtered to afford methyl 4-(4-chlorobenzyl)-2-(3-acetamidophenyl)-3,5-dioxo-2,3,4,5-tetrahydro-1,2,4-triazine-6-carboxylate (35 mg, 42%) as a beige solid.

LC$_1$: Rt=3.95
MS m/z (ES) [M+H]$^+$=428.0
mp=193° C.

¹H-NMR (DMSO-d₆), δ (ppm): 7.84 (1H, bs), 7.45 (5H, m), 7.3 (3H, m), 5.15 (2H, s), 3.97 (3H, s), 2.2 (3H, s).

Example 13

N-(3-(4-(4-chlorobenzyl)-6-((dimethylamino)methyl)-3,5-dioxo-4,5-dihydro-1,2,4-triazin-2(3H)-yl) phenyl)acetamide hydrochloride (Final Compound 5.15)

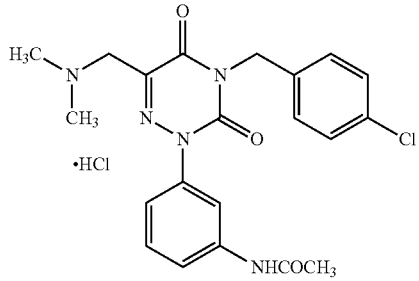

13(A): N-(3-(6-(bromomethyl)-4-(4-chlorobenzyl)-3, 5-dioxo-4,5-dihydro-1,2,4-triazin-2(3H)-yl)phenyl) acetamide According to Scheme 7 Step 6: To a solution of N-(3-(4-(4-chlorobenzyl)-6-(hydroxymethyl)-3,5-dioxo-4,5-dihydro-1,2,4-triazin-2(3H)-yl)phenyl)acetamide (500 mg, 1.25 mmol) in acetonitrile (20 mL) under nitrogen atmosphere was added phosphorus tribromide (176 µL, 1.87 mmol) dropwise and the mixture was refluxed for 90 min. The reaction mixture was diluted with 200 mL a saturated solution of NaHCO₃ (200 mL) and the aqueous layer was extracted twice with DCM (200 mL). The organic layers were combined to be dried over MgSO₄, filtered and concentrated under reduced pressure to afford N-(3-(4-(4-chlorobenzyl)-6-(bromomethyl)-3,5-dioxo-4,5-dihydro-1,2,4-triazin-2(3H)-yl)phenyl) acetamide 13(A) (540 mg, 93%) as a yellow solid.

13(B): N-(3-(4-(4-chlorobenzyl)-6-((dimethylamino) methyl)-3,5-dioxo-4,5-dihydro-1,2,4-triazin-2(3H)-yl)phenyl)acetamide hydrochloride According to Scheme 7 Step 7: A solution of 13(A) (60 mg, 0.13 mmol), (1 mL), and dimethylamine 2M (in methanol, 23 µL, 0.65 mmol) in DMF (1 ml) was irradiated at 80° C. under microwave irradiation for 5 min. The mixture was diluted with 50 mL of a saturated solution of NaHCO₃, and the aqueous layer was extracted twice with 50 mL of DCM. The organic layers were combined and successively dried over MgSO₄, filtered and concentrated under reduced pressure to afford a brown solid. The crude solid was purified by flash chromatography with silica gel (Merck Flashmart prepacked column 5 g SiO₂) using CH₂Cl₂/MeOH 95/5 as eluant to afford a white solid. The solid was dissolved in DCM (3 mL) and hydrogen chloride 1N (2 mL) was added. The solution was concentrated under reduced pressure to afford the HCl salt N-(3-(4-(4-chlorobenzyl)-6-((dimethylamino)methyl)-3,5-dioxo-4,5-dihydro-1,2,4-triazin-2(3H)-yl)phenyl)acetamide hydrochloride 13(B) (17 mg, 28%) as a beige solid.
LC₂: Rt=1.74
MS m/z (ES) [M+H]⁺=427.9
mp=143° C.

¹H-NMR (DMSO-d₆), δ (ppm): 10.27 (1H, bs), 10.09 (1H, bs), 7.98 (1H, t), 7.47 (6H, m), 7.21 (1H, dq), 5.02 (2H, s), 4.3 (2H, s), 2.87 (6H, s), 2.06 (3H, s).

Example 14

N-(3-(4-(4-chlorobenzyl)-6-(methoxymethyl)-3,5-dioxo-4,5-dihydro-1,2,4-triazin-2(3H)-yl)phenyl) acetamide (Final Compound 5.16)

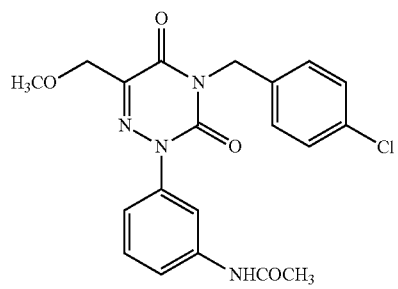

14(A): N-(3-(4-(4-chlorobenzyl)-6-(iodomethyl)-3,5-dioxo-4,5-dihydro-1,2,4-triazin-2(3H)-yl)phenyl) acetamide According to Scheme 7 Step 6: A mixture of N-(3-(4-(4-chlorobenzyl)-6-(bromomethyl)-3,5-dioxo-4,5-dihydro-1,2, 4-triazin-2(3H)-yl)phenyl)acetamide (200 mg, 0.43 mmol) and sodium iodide (97 mg, 0.65 mmol) in acetone (10 mL) was stirred overnight at room temperature. The mixture was diluted with water (100 mL) and the aqueous layer was extracted twice with 100 mL of DCM. The organic layer were combined and successively dried over MgSO₄, filtered and concentrated under reduced pressure to afford N-(3-(4-(4-chlorobenzyl)-6-(iodomethyl)-3,5-dioxo-4,5-dihydro-1,2,4-triazin-2(3H)-yl)phenyl)acetamide 14(A) (220 mg) as a white solid. The tittle product was used in the next reaction without any further purification.
LC₂: Rt=2.69
MS m/z (ES) [M+H]⁺=510.7

14(B): N-(3-(4-(4-chlorobenzyl)-6-(methoxymethyl)-3,5-dioxo-4,5-dihydro-1,2,4-triazin-2(3H)-yl) phenyl)acetamide According to Scheme 7 Step 7: To a cooled solution of 14(A) (220 mg, 0.43 mmol) in DMF (2 mL) under nitrogen atmosphere was added dropwise at 0° C. sodium methoxide 2M (in methanol, 215 µL, 0.43 mmol). The mixture was stirred at 0° C. for 1 h. The reaction mixture was diluted with water (100 mL) and the aqueous layer was extracted twice with DCM (100 mL). The organic layers were combined and successively dried over MgSO₄, filtered and concentrated under reduced pressure to afford a brown solid. The crude solid was purified by flash chromatography with silica gel (Merck Flashmart prepacked column 25 g C₁₈) using water/CH₃CN 6/4 as eluant to afford N-(3-(4-(4-chlorobenzyl)-6-(methoxymethyl)-3,5-dioxo-4,5-dihydro-1,2,4-triazin-2 (3H)-yl)phenyl)acetamide 14(B) (16 mg, 9%) as a yellow solid.
LC₂: Rt=2.36
MS m/z (ES) [M+H]⁺=414.8
mp=97° C.
¹H-NMR (DMSO-d₆), δ (ppm): 10.15 (1H, bs), 7.82 (1H, t), 7.57 (1H, dd), 7.4 (5H, m), 7.17 (1H, dd), 5 (2H, s), 4.34 (2H, s), 2.05 (3H, s).

Example 15

Isopropyl 2-(3-acetamidophenyl)-4-(4-chlorobenzyl)-3,5-dioxo-2,3,4,5-tetrahydro-1,2,4-triazine-6-carboxylate (Final Compound 5.18)

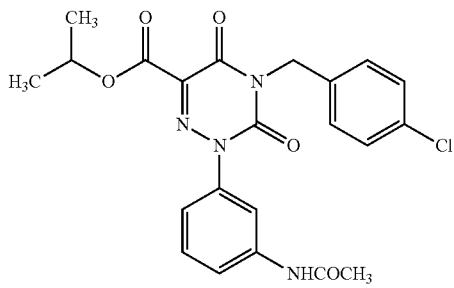

According to Scheme 7 Step 5: A mixture of 4-(4-chlorobenzyl)-2-(3-acetamidophenyl)-3,5-dioxo-2,3,4,5-tetrahydro-1,2,4-triazine-6-carboxylic acid 7.6 (100 mg, 0.24 mmol), isopropylalcohol (3 mL) and sulfuric acid (2 drops) was heated at 80° C. for 20 hours. The reaction mixture was diluted with a saturated solution of NaHCO$_3$ (50 mL) and the aqueous layer was extracted twice with DCM (50 mL). The organic layers were combined and selectively dried over MgSO$_4$, filtered and concentrated under reduced pressure to afford a brown solid. The crude solid was purified by flash chromatography with silica gel (Merck Flashmart prepacked column 7 g SiO$_2$) using CH$_2$Cl$_2$/MeOH 98/2 as eluant to afford isopropyl 4-(4-chlorobenzyl)-2-(3-acetamidophenyl)-3,5-dioxo-2,3,4,5-tetrahydro-1,2,4-triazine-6-carboxylate (33 mg, 30%) as a beige solid.

LC$_2$: Rt=2.65
MS m/z (ES) [M+H]$^+$=457.0
mp=183° C.
$^1$H-NMR (DMSO-d$_6$), δ (ppm): 10.19 (1H, bs), 7.84 (1H, s), 7.59 (1H, d), 7.41 (5H, m), 7.16 (1H, dd), 5.13 (1H, m), 4.97 (2H, s), 2.05 (3H, s), 1.27 (6H, d).

Example 16

N-(3-(4-(4-chlorobenzyl)-6-methoxy-3,5-dioxo-4,5-dihydro-1,2,4-triazin-2(3H)-yl)phenyl)-N-methylacetamide (Final Compound 4.133)

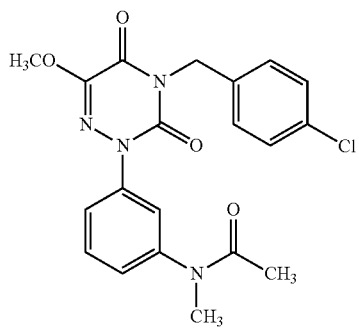 [SMILES: COc1nn(-c2cccc(N(C)C(C)=O)c2)c(=O)n(Cc2ccc(Cl)cc2)c1=O]

According to Scheme 9 Step 1: To a solution of N-(3-(4-(4-chlorobenzyl)-6-methoxy-3,5-dioxo-4,5-dihydro-1,2,4-triazin-2(3H)-yl)phenyl)acetamide (70 mg, 0.17 mmol) in THF (3 mL) was added portionwise at 0° C. sodium hydride (55%) 11 mg, 0.26 mmol). The suspension was stirred 10 minutes at room temperature. Then, methyl iodide (87 µl, 1.40 mmol) was added dropwise and the reaction mixture was stirred at room temperature under nitrogen atmosphere overnight. The mixture was diluted with 100 mL of a saturated solution of ammonium chloride and the aqueous layer was extracted twice with 100 mL of DCM. The organic layers were combined to be successively dried over MgSO$_2$, filtered and concentrated under reduced pressure to afford a brown solid. The crude solid was purified by flash chromatography with silica gel (Merck Flashmart prepacked column 10 g SiO$_2$) using CH$_2$Cl$_2$/MeOH 99/1 as eluant to afford N-(3-(4-(4-chlorobenzyl)-6-methoxy-3,5-dioxo-4,5-dihydro-1,2,4-triazin-2(3H)-yl)phenyl)-N-methylacetamide (54 mg, 75%) as a white solid.

LC$_1$: Rt=4.09
MS m/z (ES) [M+H]$^+$=414.0
mp=157° C.
$^1$H-NMR (DMSO-d$_6$), δ (ppm): 7.5 (8H, m), 5.01 (2H, s), 3.85 (3H, s), 3.18 (3H, s), 2.5 (3H, s).

Example 17

4-(4-chlorobenzyl)-2-(2-hydroxyphenyl)-6-methoxy-1,2,4-triazine-3,5(2H,4H)-dione (Final Compound 4.143)

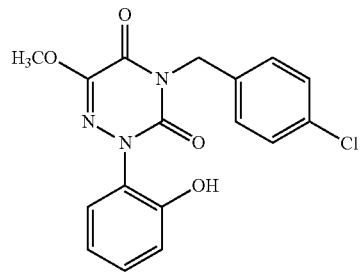 [SMILES: COc1nn(-c2ccccc2O)c(=O)n(Cc2ccc(Cl)cc2)c1=O]

17(A): 4-(4-chlorobenzyl)-6-bromo-2-(2-hydroxyphenyl)-1,2,4-triazine-3,5(2H,4H)-dione According to Scheme 9 Step 1: To a solution of 4-(4-chlorobenzyl)-6-bromo-2-(2-methoxyphenyl)-1,2,4-triazine-3,5(2H,4H)-dione (150 mg, 0.35 mmol) in DCM (2 ml) cooled at −78° C. was added dropwise BBr$_3$ (0.710 mL, 0.710 mmol). The reaction mixture was stirred 1 h at −78° C. and was quenched with MeOH. The mixture was allowed to reach room temperature. Water was added and the aqueous layer was extracted with DCM (×3). The combined organic layers were successively washed with water, brine, dried over MgSO4, filtered and concentrated. 131 mg (yield=90%) of 4-(4-chlorobenzyl)-6-bromo-2-(2-hydroxyphenyl)-1,2,4-triazine-3,5(2H,4H)-dione were recovered as a beige solid which was used in the next step without any purification.

17(B): 4-(4-chlorobenzyl)-2-(2-hydroxyphenyl)-6-methoxy-1,2,4-triazine-3,5(2H,4H)-dione According to Scheme 9 Step 2: To a solution of 4-(4-chlorobenzyl)-6-bromo-2-(2-hydroxyphenyl)-1,2,4-triazine-3,5(2H,4H)-dione (0.130 g, 0.32 mmol) in DMF (3 ml) was added, dropwise, at 0° C. a solution 2M of sodium methoxide (0.32 mmol, 0.160 ml). The mixture was stirred 1 h at 0° C. 1 more equivalent of a solution 2M of sodium methoxide was necessary to complete the conversion. Then the reaction mixture was quenched with water. The aqueous layers was neutralised till pH=7 and extracted with ethyl acetate (×3). The organic layer were combined and successively washed with water then, brine, dried over MgSO4, filtered and concentrated. The crude product was purified by flash chromatography, 10 g prepacked column, DCM/MeOH 98/2 to afford (30 mg, Yield=26%) 30 mg (Yield=26%) of 4-(4-chlorobenzyl)-2-(2-hydroxyphenyl)-6-methoxy-1,2,4-triazine-3,5(2H,4H)-dione 4.143 were recovered as a white solid.

LC$_2$: Rt=2.45
mp=164-165° C.
$^1$H-NMR (DMSO-d$_6$), δ (ppm): 7.4 (4H, s), 7.30-7.23 (2H, m), 6.95-6.82 (2H, m), 5 (2H, s), 3.74 (3H, s).

Example 18

4-(4-chlorobenzyl)-6-methoxy-2-(3-(thiazol-2-ylamino)phenyl)-1,2,4-triazine-3,5(2H,4H)-dione (Final Compound 4.144)

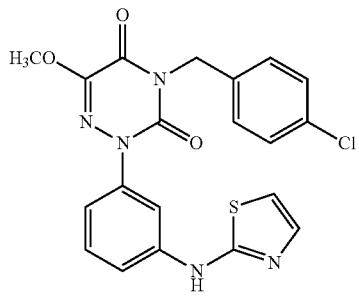 [SMILES: COc1nn(-c2cccc(Nc3nccs3)c2)c(=O)n(Cc2ccc(Cl)cc2)c1=O]

18(A): 2-(3-aminophenyl)-4-(4-chlorobenzyl)-6-methoxy-1,2,4-triazine-3,5(2H,4H)-dione According to Scheme 9 Step 1: A mixture of N-(3-(4-(4-chlorobenzyl)-6-methoxy-3,5-dioxo-4,5-dihydro-1,2,4-triazin-2(3H) yl)phenyl)acetamide (500 mg, 1.24 mmol) in a solution 6N of HCl (10 mL) and THF (10 mL) was stirred at reflux for 3 hours. The THF was evaporated and the aqueous layer was basified with saturated solution of NaHCO$_3$ until neutral pH. The aqueous layer was then extracted with ethyl acetate (×3). The organic layers were combined to be successively washed with water then with brine, dried over MgSO$_4$, filtered and concentrated. The crude product was azeotroped with acetonitrile to afford 2-(3-aminophenyl)-4-(4-chlorobenzyl)-6-methoxy-1,2,4-triazine-3,5(2H,4H)-dione as a beige solid (423 mg, 94.5%).

18(B): 4-(4-chlorobenzyl)-6-methoxy-2-(3-(thiazol-2-ylamino)phenyl)-1,2,4-triazine-3,5(2H,4H)-dione According to Scheme 9 Step 2: To a Solution of 2-(3-Aminophenyl)-4-(4-chlorobenzyl)-6-methoxy-1,2,4-triazine-3,5(2H,4H)-dione (125 mg, 0.34 mmol) in ethanol (10 ml) was added bromothiazole (124 μL, 1.4 mmol) and 5 mL of concentrated hydrochloric acid. The reaction mixture was heated to 100° C. for 48 hours. The reaction mixture was quenched and neutralised with sat NaHCO$_3$ and extracted in ethyl acetate (×3). The organic layers were combined and successively washed with water, brine, dried over MgSO$_4$, filtered and concentrated. The crude oily solid was purified by flash chromatography, 10 g prepacked column, cyclohexane/ethyl acetate 70/30 to afford 4-(4-chlorobenzyl)-6-methoxy-2-(3-(thiazol-2-ylamino)phenyl)-1,2,4-triazine-3,5(2H,4H)-dione 4.144 (10 mg (Yield=6.5%) as a white solid.

LC$_2$: Rt=2.82
mp=176-178° C.
$^1$H-NMR (CDCl$_3$), δ (ppm): 10.4 (1H, s), 8.0 (1H, s), 7.6-6.9 (9H, m), 5.0 (2H, s), 3.8 (3H, s).

Example 19

4-(4-chlorobenzyl)-6-methoxy-2-(3-(2-oxopyrrolidin-1-yl)phenyl)-1,2,4-triazine-3,5(2H,4H)-dione (Final Compound 4.145)

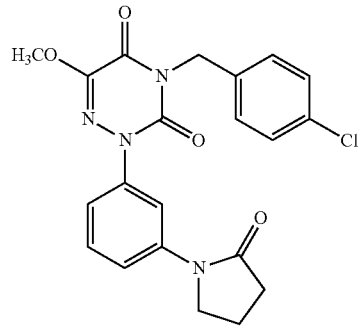 [SMILES: COc1nn(-c2cccc(N3CCCC3=O)c2)c(=O)n(Cc2ccc(Cl)cc2)c1=O]

According to Scheme 9 Step 2: To a solution of 2-(3-aminophenyl)-4-(4-chlorobenzyl)-6-methoxy-1,2,4-triazine-3,5(2H,4H)-dione (100 mg, 0.27 mmol) (1 mL) and NEt$_3$ (78 μL, 0.55 mmol) in DMF was added bromobutyryl chloride (36 μL, 0.30 mmol). The reaction mixture was heated at 80° C. for 4 hours then quenched with water and extracted with ethyl acetate. The organic layers were combined and successively washed with water, brine, dried over MgSO$_4$, filtered and concentrated. The crude product was purified on a prepacked silica column (10 g) 8:2 cyclohexane/Ethyl acetate 80/20 to afford 4-(4-chlorobenzyl)-6-methoxy-2-(3-(2-oxopyrrolidin-1-yl)phenyl)-1,2,4-triazine-3,5(2H,4H)-dione 4.145 as a white solid (6 mg, 5%).

LC$_2$: Rt=2.64
MS m/z (ES) [M+H]$^+$=427.0
mp=91-93° C.
$^1$H-NMR (CDCl$_3$), δ (ppm): 7.9 (1H, s), 7.6-7.3 (7H, m), 5.2 (2H, s), 3.9 (3H, s), 1.5-0.9 (6H, m).

Example 20

N-(3-(4-(4-chlorobenzyl)-6-methoxy-3,5-dioxo-4,5-dihydro-1,2,4-triazin-2(3H)-yl)phenyl)-2-methoxyacetamide (Final Compound 4.141)

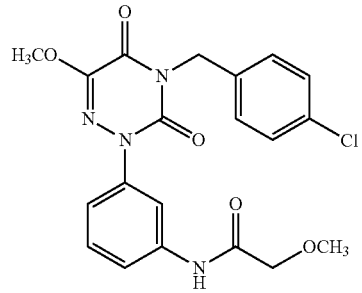 [SMILES: COCC(=O)Nc1cccc(-n2nc(OC)c(=O)n(Cc3ccc(Cl)cc3)c2=O)c1]

According to Scheme 9 Step 2: A mixture of 2-(3-aminophenyl)-4-(4-chlorobenzyl)-6-methoxy-1,2,4-triazine-3,5 (2H,4H)-dione (100 mg, 0.28 mmol), DMF (4 mL), diisopropylethylamine (95 µl, 0.56 mmol) and methoxyacetyl chloride (30 µl, 0.33 mmol) was stirred under nitrogen at room temperature during 1 hour. The mixture was diluted with 50 mL of a saturated solution of sodium carbonate and the aqueous layer was extracted twice with 50 mL of DCM. The organic layers were combined to be dried over MgSO$_4$, filtered and concentrated under reduced pressure to afford a brown solid. The crude solid was purified by flash chromatography with silica gel (Merck Flashmart prepacked column 15 g SiO$_2$) using AcOEt/cyclohexane 4/6 as eluant to afford a beige solid. The solid was washed with diethylether to afford N-(3-(4-(4-chlorobenzyl)-6-methoxy-3,5-dioxo-4,5-dihydro-1,2,4-triazin-2(3H)-yl)phenyl)-2-methoxyacetamide 4.141 (84 mg, 70%) as a white solid.

LC$_2$: Rt=2.48
MS m/z (ES) [M+H]$^+$=431.0
mp=143° C.
$^1$H-NMR (CDCl$_3$), δ (ppm): 10.1 (1H, bs), 8.01 (1H, t), 7.65 (1H, d), 7.4 (5H, m), 7.33 (1H, dd), 5.01 (2H, s), 4.02 (2H, s), 3.81 (3H, s), 3.38 (3H, s)

Example 21

4-(4-chlorobenzyl)-6-methoxy-2-(3-(5-methyl-1,2,4-oxadiazol-3-yl)phenyl)-1,2,4-triazine-3,5(2H,4H)-dione (Final Compound 4.146)

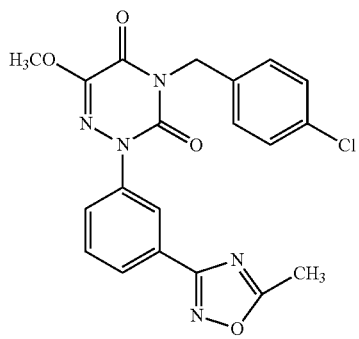 [SMILES: COc1nn(-c2cccc(-c3noc(C)n3)c2)c(=O)n(Cc2ccc(Cl)cc2)c1=O]

21(A): 3-(4-(4-chlorobenzyl)-6-bromo-3,5-dioxo-4,5-dihydro-1,2,4-triazin-2(3H)-yl)benzonitrile According to Scheme 2 Step 3: To a solution of 6-bromo-4-(4-chlorobenzyl)-1,2,4-triazine-3,5(2H,4H)-dione (0.600 g, 1.9 mmol) in DCM (8 ml) were added 3-cyanophenylboronic acid (0.42 g, 2.8 mmol), copper(II) acetate (0.069 g, 0.38 mmol), pyridine (0.3 g, 3.8 mmol) and pyridine N-oxide (0.2 g, 2.1 mmol) and the mixture was stirred overnight at room temperature. The reaction mixture was quenched with a saturated sodium bicarbonate solution and extracted with ethyl acetate (×3). The combined organic layers were washed with water then with brine, dried over MgSO$_4$, filtered and concentrated. The crude product was purified by flash chromatography, 30 g prepacked column, cyclohexane/ethyl acetate 85/15 to afford 3-(4-(4-chlorobenzyl)-6-bromo-3,5-dioxo-4,5-dihydro-1,2,4-triazin-2(3H)-yl)benzonitrile (300 mg, 38%) which was used in the next step without any purification 21(B): 3-(4-(4-chlorobenzyl)-6-methoxy-3,5-dioxo-4,5-dihydro-1,2,4-triazin-2(3H)-yl)benzonitrile According to Scheme 2 Step 4: To a stirred solution of 3-(4-(4-chlorobenzyl)-6-bromo-3,5-dioxo-4,5-dihydro-1,2,4-triazin-2(3H)-yl)benzonitrile (0.300 g, 0.72 mmol) in DMF (5 ml) was added, dropwise, at 0° C., 2M solution of sodium methoxide (0.72 mmol, 0.359 ml). The mixture was stirred 1 hour at 0° C. then quenched with water and extracted with ethyl acetate (×3). The combined organic layers were successively washed with water then with brine, dried over MgSO$_4$, filtered and concentrated. The crude product was purified by flash chromatography, 10 g prepacked column, DCM 100%. 150 mg (Yield=57%) of 3-(4-(4-chlorobenzyl)-6-methoxy-3,5-dioxo-4,5-dihydro-1,2,4-triazin-2(3H)-yl)benzonitrile were recovered and used for the next step.

21(C): (Z)-3-(4-(4-chlorobenzyl)-6-methoxy-3,5-dioxo-4,5-dihydro-1,2,4-triazin-2(3H)-yl)-N'-hydroxybenz amidine According to Scheme 9 Step 1: To a stirred solution of 3-(4-(4-chlorobenzyl)-6-methoxy-3,5-dioxo-4,5-dihydro-1,2,4-triazin-2(3H)-yl)benzonitrile (150 mg, 0.41 mmol) in ethanol (5 ml) was added hydroxylamine (0.100 ml of a 50% solution in water, 1.2 mmol) and the mixture was heated at 80° C. overnight. The reaction mixture was quenched with a saturated ammonium chloride solution and extracted with ethyl acetate (×3). The combined organic layers were successively washed with water, with brine, dried over MgSO$_4$, filtered and concentrated to afford (Z)-3-(4-(4-chlorobenzyl)-6-methoxy-3,5-dioxo-4,5-dihydro-1,2,4-triazin-2(3H)-yl)-N'-hydroxybenzamidine (150 mg, 99%) which was used in the next step without any further purification.

21(D): 4-(4-chlorobenzyl)-6-methoxy-2-(3-(5-methyl-1,2,4-oxadiazol-3-yl)phenyl)-1,2,4-triazine-3,5 (2H,4H)-dione According to Scheme 9 Step 2: A mixture of (Z)-3-(4-(4-chlorobenzyl)-6-methoxy-3,5-dioxo-4,5-dihydro-1,2,4-triazin-2(3H)-yl)-N'-hydroxybenzamidine (150 mg, 0.4 mmol), triethyl orthoacetate (2 mL) and of sulfuric acid (1 drop) was stirred at 100° C. 4 hours. The reaction mixture was quenched with water and extracted with ethyl acetate (×3). The combined organic layers were successively washed with water, brine, dried over MgSO$_4$, filtered and concentrated. The crude product was purified by flash chromatography, 10 g prepacked column, cyclohexane/ethyl acetate 80/20 to afford 4-(4-chlorobenzyl)-6-methoxy-2-(3-(5-methyl-1,2,4-oxadiazol-3-yl)phenyl)-1,2,4-triazine-3,5(2H,4H)-dione 4.146 (40 mg, Yield=25%) as a white solid.

LC$_2$: Rt=2.88
MS m/z (ES) [M+H]$^+$=426.0
mp=163-165° C.
$^1$H-NMR (CDCl$_3$), δ (ppm): 8.27 (1H, bs), 7.98 (1H, d), 7.82-7.78 (1H, m), 7.68 (1H, t), 7.44-7.36 (4H, m), 5.03 (2H, s), 3.85 (3H, s), 2.68 (3H, s)

Example 22

2-(2-(4-(4-chlorobenzyl)-6-methoxy-3,5-dioxo-4,5-dihydro-1,2,4-triazin-2(3H)-yl)phenyl)acetonitrile (Final Compound 4.167)

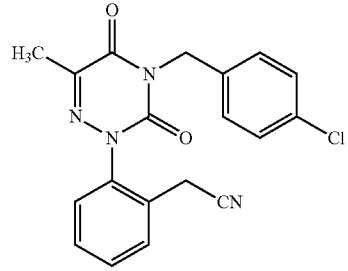 [SMILES: Cc1nn(-c2ccccc2CC#N)c(=O)n(Cc2ccc(Cl)cc2)c1=O]

22(A): 6-bromo-4-(4-chlorobenzyl)-2-(2-(hydroxymethyl)phenyl)-1,2,4-triazine-3,5(2H,4H)-dione According to Scheme 2 Step 3: To a solution of 6-bromo-4-(4-chlorobenzyl)-1,2,4-triazine-3,5(2H,4H)-dione (0.400 g, 1.3 mmol) in DMF (8 mL) were added 2-(hydroxymethyl)phenylboronic acid (0.29 g, 1.9 mmol), copper(II) acetate (0.23 g, 1.3 mmol) and pyridine (0.20 g, 2.5 mmol) and the mixture was left stiffing overnight at 60° C. The reaction mixture was quenched with a saturated sodium bicarbonate solution. The precipitate formed was filtered, washed first with water and then with diethyl ether. 330 mg (Yield=62%) of 6-bromo-4-(4-chlorobenzyl)-2-(2-(hydroxymethyl)phenyl)-1,2,4-triazine-3,5(2H,4H)-dione were recovered. The product was pure enough to be used without any purification.

22(B): 4-(4-chlorobenzyl)-2-(2-(hydroxymethyl)phenyl)-6-methoxy-1,2,4-triazine-3,5(2H,4H)-dione According to Scheme 2 Step 4: To a stirred solution of 6-bromo-4-(4-chlorobenzyl)-2-(2-(hydroxymethyl)phenyl)-1,2,4-triazine-3,5(2H,4H)-dione (0.330 g, 0.79 mmol) in DMF (10 ml) was added, dropwise, at 0° C., 2M solution of sodium methoxide (0.79 mmol, 0.40 ml). The mixture was stirred 1 hour at 0° C. then quenched with water and extracted with ethyl acetate (×3). The combined organic layers were successively washed with water then with brine, dried over MgSO$_4$, filtered and concentrated. 270 mg (Yield=92.5%) of 4-(4-chlorobenzyl)-2-(2-(hydroxymethyl)phenyl)-6-methoxy-1,2,4-triazine-3,5(2H,4H)-dione were recovered. The product was pure enough to be used in the next step without any purification.

22(C): 2-(2-(bromomethyl)phenyl)-4-(4-chlorobenzyl)-6-methoxy-1,2,4-triazine-3,5(2H,4H)-dione According to Scheme 9 Step 1: To a stirred solution of 4-(4-chlorobenzyl)-2-(2-(hydroxymethyl)phenyl)-6-methoxy-1,2,4-triazine-3,5(2H,4H)-dione (70 mg, 0.19 mmol) in CH$_3$CN (10 mL) was added phosphorus tribromide (76 mg, 0.28 mmol) and the mixture was heated at 60° C. during two hours. The reaction mixture was diluted with 100 mL of water and the aqueous layer was extracted with DCM (×2). The combined organic layers were successively washed with water, with brine, dried over MgSO$_4$, filtered and concentrated to afford 70 mg (Yield=86%) of 2-(2-(bromomethyl)phenyl)-4-(4-chlorobenzyl)-6-methoxy-1,2,4-triazine-3,5 (2H,4H)-dione. The product was pure enough to be used in the next step without any purification

22(D): 2-(2-(4-(4-chlorobenzyl)-6-methoxy-3,5-dioxo-4,5-dihydro-1,2,4-triazin-2(3H)-yl)phenyl) acetonitrile According to Scheme 9 Step 2: A mixture of 4-(4-chlorobenzyl)-2-(2-(bromomethyl)phenyl)-6-methoxy-1,2,4-triazine-3,5(2H,4H)-dione (70 mg, 0.16 mmol) in DMF (2 mL) and potassium cyanide (31 mg, 0.13 mmol) was stirred at 20° C. 12 hours. The reaction mixture was quenched with water and extracted with ethyl acetate (×3). The combined organic layers were successively washed with water, brine, dried over MgSO$_4$, filtered and concentrated. The crude product was purified by flash chromatography, 10 g prepacked column, DCM/MeOH 99/1 to afford 2-(2-(4-(4-chlorobenzyl)-6-methoxy-3,5-dioxo-4,5-dihydro-1,2,4-triazin-2(3H)-yl)phenyl)acetonitrile 4.167 (50 mg, Yield=81%) as a white oil.

LC$_2$: Rt=2.63

MS m/z (ES) [M+H]$^+$=383.0

$^1$H-NMR (DMSO-d$_6$), δ (ppm): 7.58-7.36 (4H, m), 7.44-7.36 (4H, m), 5 (2H, s), 4.02 (2H, s), 3.8 (3H, s)

The compounds in the following Tables have been synthesized according to the previous examples, as denoted in the column as "Exp. Nr". The compounds denoted with the asterisk have been exemplified in the Examples.

TABLE 1

| Compound Nr | Exp. Nr. | L-B | D |
|---|---|---|---|
| 1.01* | 1.01 | | |

TABLE 1-continued
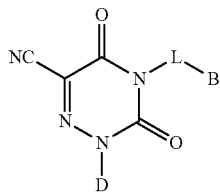
| Compound Nr | Exp. Nr. |  | 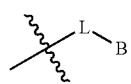 |
|---|---|---|---|
| 1.02 | 1.01 |  | 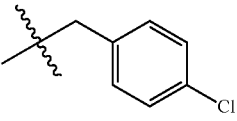 [SMILES: *Cc1ccc(Cl)cc1] |
| 1.03 | 1.01 | 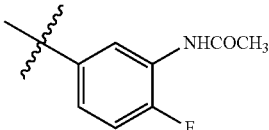 | 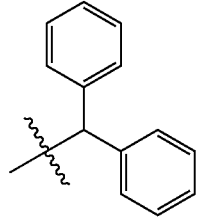 [SMILES: *C(c1ccccc1)c1ccccc1] |
| 1.04 | 1.01 | 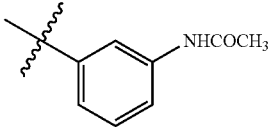 | 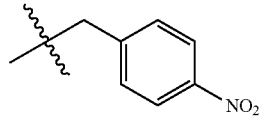 [SMILES: *Cc1ccc([N+](=O)[O-])cc1] |
| 1.05 | 1.01 | 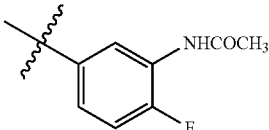 | 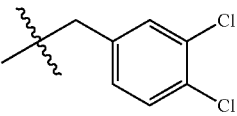 [SMILES: *Cc1ccc(Cl)c(Cl)c1] |
| 1.06 | 1.01 | 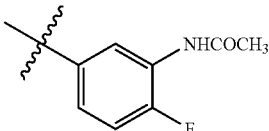 | 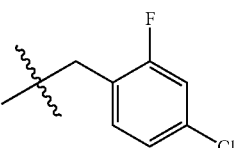 |
| 1.07 | 1.01 | 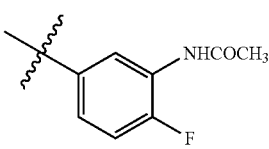 | 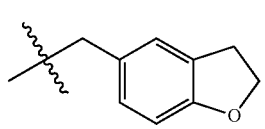 [SMILES: *Cc1ccc2c(c1)CCO2] |

TABLE 2
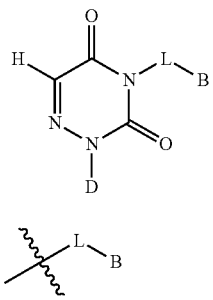
| Compound Nr | Exp. Nr. | L–B | D |
|---|---|---|---|
| 2.01* | 2.01 |  4-Cl-benzyl | 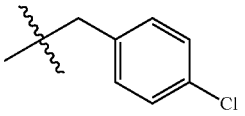 [SMILES: *Cc1ccc(Cl)cc1] 3-NHCOCH₃-phenyl |
| 2.02 | 2.01 | 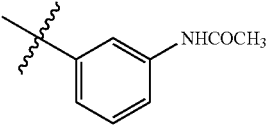 4-Cl-benzyl | 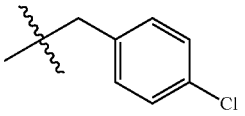 [SMILES: *Cc1ccc(Cl)cc1] 3-NHSO₂CH₃-phenyl |
| 2.03 | 2.01 | 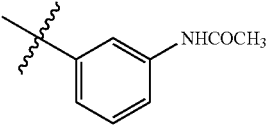 4-Cl-benzyl | 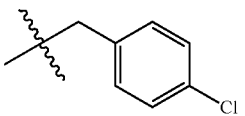 [SMILES: *Cc1ccc(Cl)cc1] 2-OCH₃-phenyl |
| 2.04 | 2.01 | 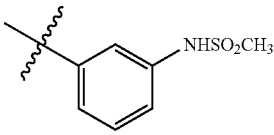 4-NO₂-benzyl | 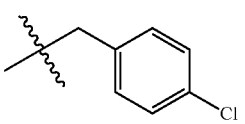 [SMILES: *Cc1ccc(Cl)cc1] 3-NHCOCH₃-phenyl |
| 2.05* | 2.05 | 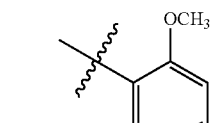 4-CN-benzyl | 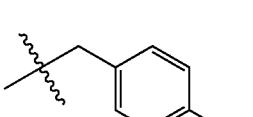 3-NHCOCH₃-phenyl |
| 2.06 | 2.05 | 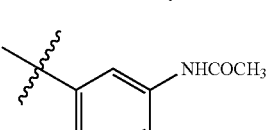 naphthyl-methyl | 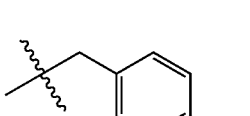 3-NHCOCH₃-phenyl |
| 2.07 | 2.05 | 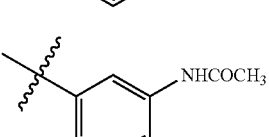 benzofurazan-methyl | 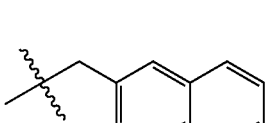 3-NHCOCH₃-phenyl |
| 2.08 | 2.05 | 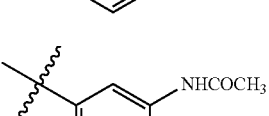 4-F-benzyl | 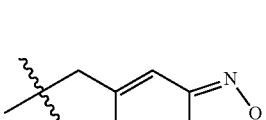 3-NHCOCH₃-phenyl |
| 2.09 | 2.05 | 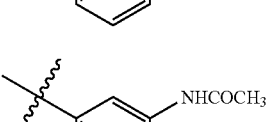 benzyl | 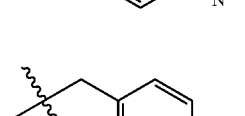 3-NHCOCH₃-phenyl |

TABLE 2-continued
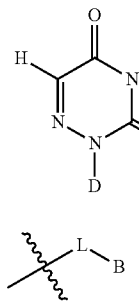
| Compound Nr | Exp. Nr | L–B | D |
|---|---|---|---|
| 2.10 | 2.05 |  | 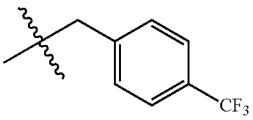 |
| 2.11 | 2.05 | 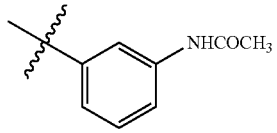 | 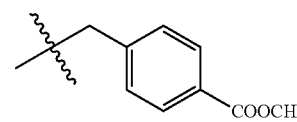 |
| 2.12 | 2.05 | 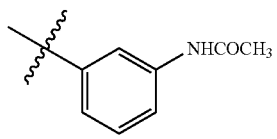 | 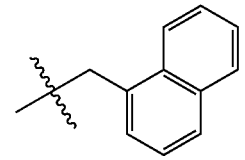 [SMILES: *Cc1cccc2ccccc12] |
| 2.13 | 2.05 | 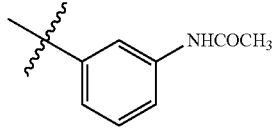 | 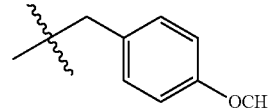 |
| 2.14 | 2.05 | 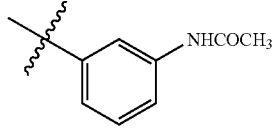 | 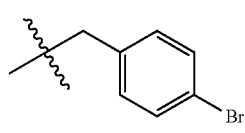 [SMILES: *Cc1ccc(Br)cc1] |
| 2.15 | 2.05 | 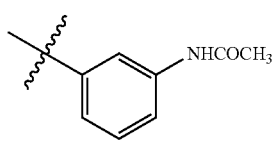 | 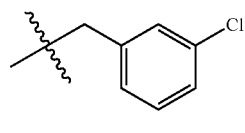 [SMILES: *Cc1cccc(Cl)c1] |
| 2.16 | 2.05 | 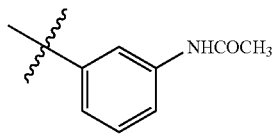 | 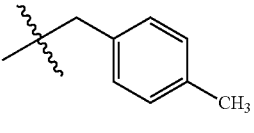 [SMILES: *Cc1ccc(C)cc1] |
| 2.17 | 2.05 | 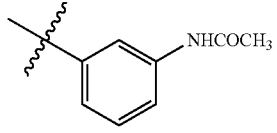 | 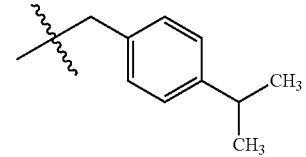 [SMILES: *Cc1ccc(C(C)C)cc1] |

TABLE 2-continued
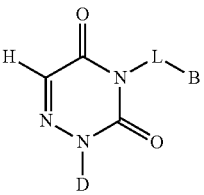
| Compound Nr | Exp. Nr. | 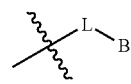 L–B |  D |
|---|---|---|---|
| 2.18 | 2.05 | 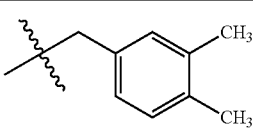 | 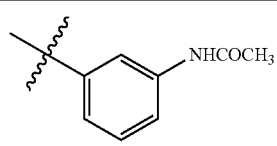 |
| 2.19 | 2.05 | 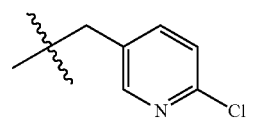 [SMILES: *Cc1ccc(Cl)nc1] | 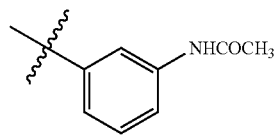 |
| 2.20* | 2.20 |  | 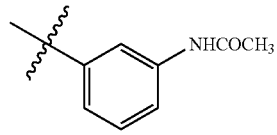 |
TABLE 3
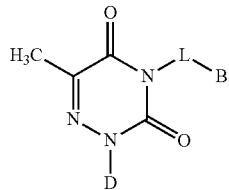
| Compound Nr | Exp. Nr. | 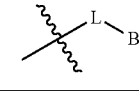 L–B |  D |
|---|---|---|---|
| 3.01* | 3.01 | 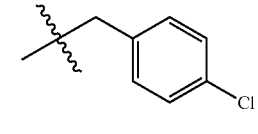 [SMILES: *Cc1ccc(Cl)cc1] | 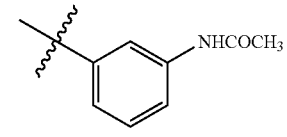 |
| 3.02 | 3.01 | 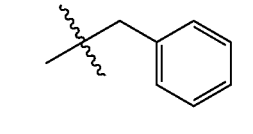 [SMILES: *Cc1ccccc1] | 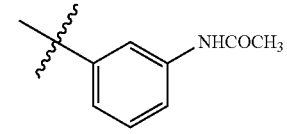 |
| 3.03 | 3.01 | 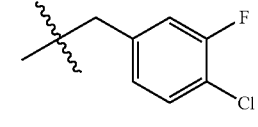 | 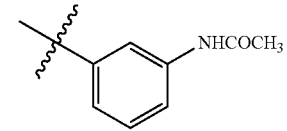 |

TABLE 3-continued
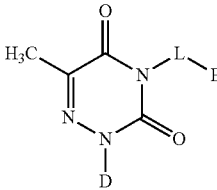
| Compound Nr | Exp. Nr. | ⁓L–B | ⁓D |
|---|---|---|---|
| 3.04 | 3.01 | 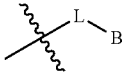 |  |
| 3.05 | 3.01 | 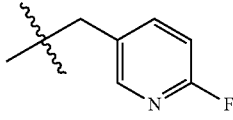 [SMILES: *Cc1ccc(F)nc1] | 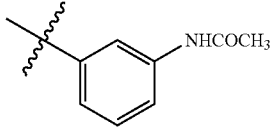 |
| 3.06 | 3.01 | 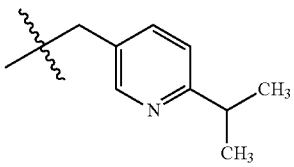 | 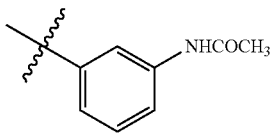 |
| 3.07 | 3.01 | 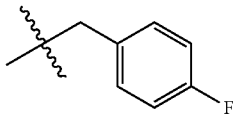 [SMILES: *Cc1ccc(F)cc1] | 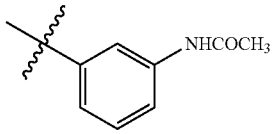 |
| 3.08 | 3.01 | 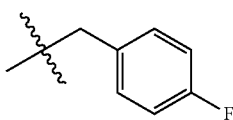 [SMILES: *Cc1ccc(F)cc1] | 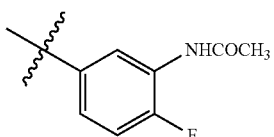 |
| 3.09 | 3.01 | 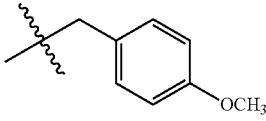 | 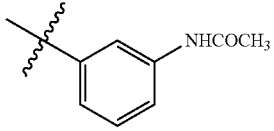 |
| 3.10 | 3.01 | 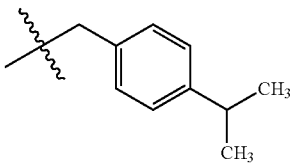 | 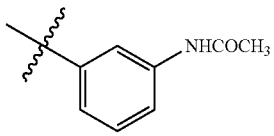 |
| 3.11 | 3.01 | 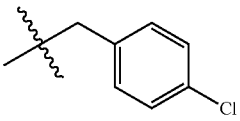 [SMILES: *Cc1ccc(Cl)cc1] | 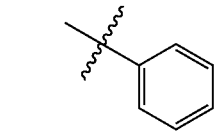 [SMILES: *c1ccccc1] |

TABLE 3-continued
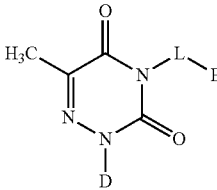
| Compound Nr | Exp. Nr. | ⸺L⸺B | ⸺D |
|---|---|---|---|
| 3.12 | 3.01 | 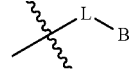 |  |
| 3.13 | 3.01 | 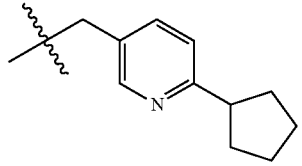 [SMILES: *Cc1ccc(C2CCCC2)nc1] | 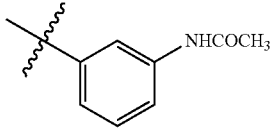 |
| 3.14 | 3.01 | 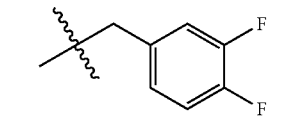 [SMILES: *Cc1ccc(F)c(F)c1] | 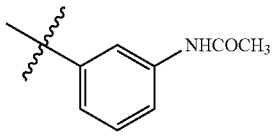 |
| 3.15 | 3.01 | 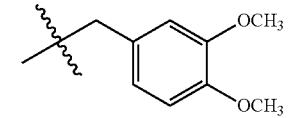 | 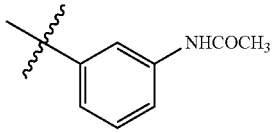 |
| 3.16 | 3.01 | 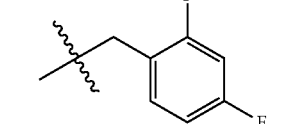 | 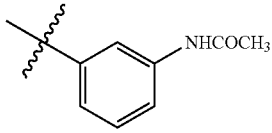 |
| 3.17 | 3.01 | 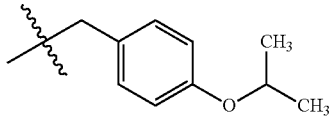 | 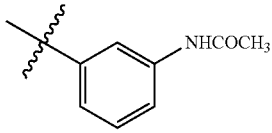 |
| 3.18 | 3.01 | 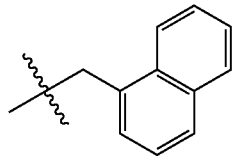 [SMILES: *Cc1cccc2ccccc12] | 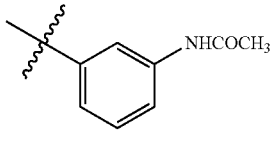 |
| 3.19 | 3.01 | 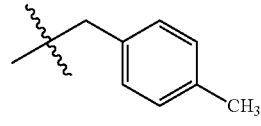 [SMILES: *Cc1ccc(C)cc1] | 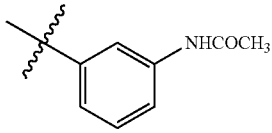 |

TABLE 3-continued
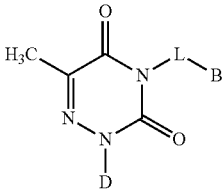
| Compound Nr | Exp. Nr. | L—B | D |
|---|---|---|---|
| 3.20 | 3.01 |  3-OCH₃ benzyl | 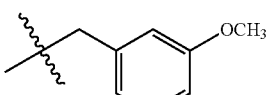 5-NHCOCH₃, 2-F phenyl |
TABLE 4
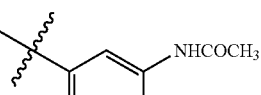
| Compound Nr | Exp. Nr. | L—B | D |
|---|---|---|---|
| 4.01* | 4.01 | 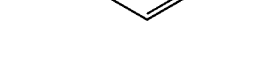 4-Cl benzyl | 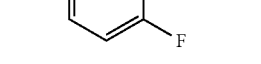 3-NHCOCH₃ phenyl |
| 4.02 | 4.01 | 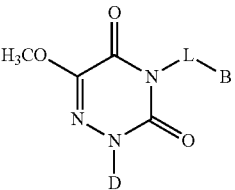 4-NO₂ benzyl |  3-NHCOCH₃ phenyl |
| 4.03 | 4.01 | 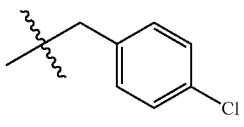 [SMILES: *Cc1ccc(Cl)cc1] 4-CH₃ benzyl | 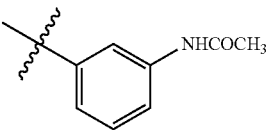 3-NHCOCH₃ phenyl |
| 4.04 | 4.01 | 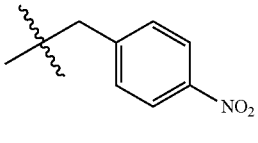 [SMILES: *Cc1ccc([N+](=O)[O-])cc1] 4-CF₃ benzyl | 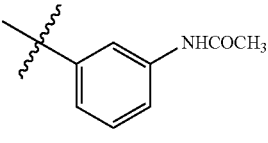 3-NHCOCH₃ phenyl |
| 4.05 | 4.01 | 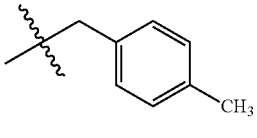 3-F, 4-Cl benzyl | 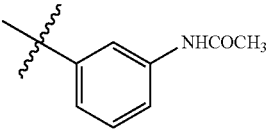 3-NHCOCH₃ phenyl |

TABLE 4-continued
| Compound Nr | Exp. Nr. | L—B | D |
|---|---|---|---|
| 4.06 | 4.01 | 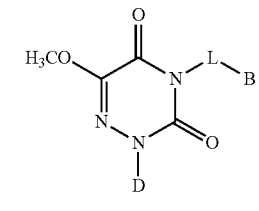 | 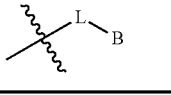 |
| 4.07 | 4.01 | 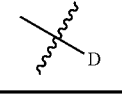 | 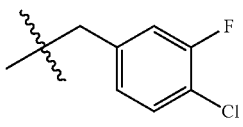 [SMILES: *Cc1ccc(Cl)c(F)c1] |
| 4.08 | 4.01 | 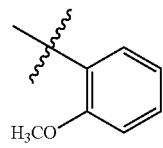 | 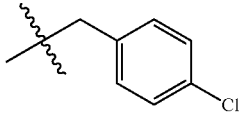 [SMILES: *Cc1ccc(Cl)cc1] |
| 4.09 | 4.01 | 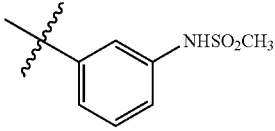 | 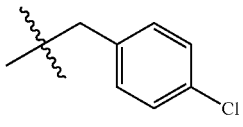 [SMILES: *Cc1ccc(Cl)cc1] |
| 4.10 | 4.01 | 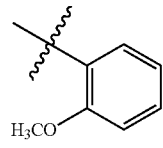 | 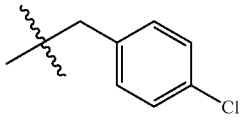 [SMILES: *Cc1ccc(Cl)cc1] |
| 4.11 | 4.01 | 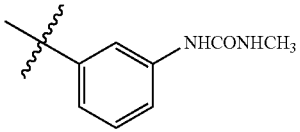 | 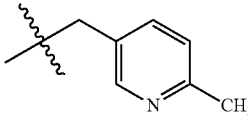 |
| 4.12 | 4.01 | 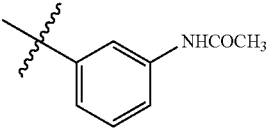 | 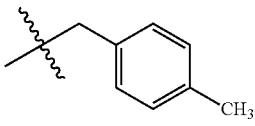 |
| 4.13 | 4.01 | 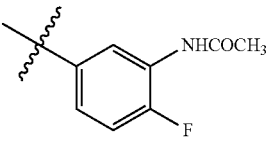 | 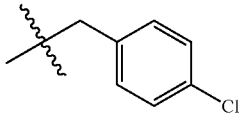 [SMILES: *Cc1ccc(Cl)cc1] |
| 4.14 | 4.01 | 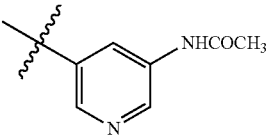 | 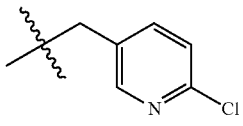 [SMILES: *Cc1ccc(Cl)nc1] |

TABLE 4-continued
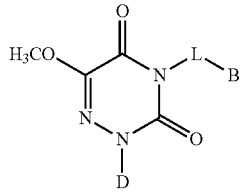
| Compound Nr | Exp. Nr. | ⸎—L—B | ⸎—D |
|---|---|---|---|
| 4.15 | 4.01 | 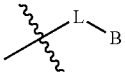 |  |
| 4.16 | 4.01 | 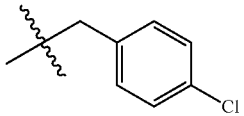 [SMILES: *Cc1ccc(Cl)cc1] | 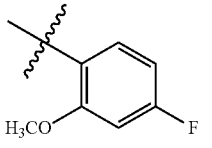 |
| 4.17 | 4.01 | 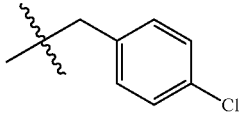 [SMILES: *Cc1ccc(Cl)cc1] | 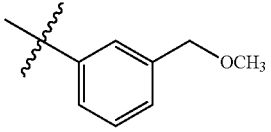 [SMILES: *c1cccc(COC)c1] |
| 4.18 | 4.01 | 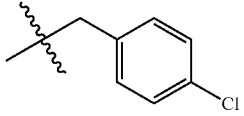 [SMILES: *Cc1ccc(Cl)cc1] | 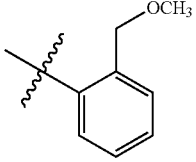 [SMILES: *c1ccccc1COC] |
| 4.19 | 4.01 | 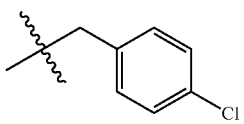 | 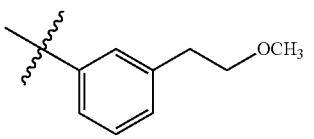 [SMILES: *c1cccc(CCOC)c1] |
| 4.20 | 4.01 | 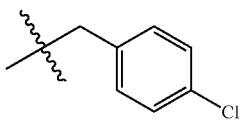 [SMILES: *Cc1ccc(Cl)cc1] | 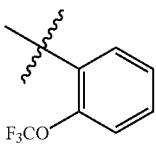 |
| 4.21 | 4.01 | 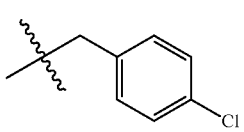 [SMILES: *Cc1ccc(Cl)cc1] | 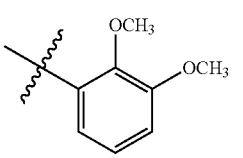 [SMILES: *c1cccc(OC)c1OC] |

TABLE 4-continued
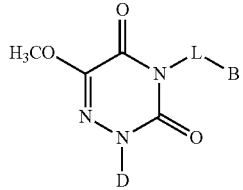
| Compound Nr | Exp. Nr. | ⸺L—B | ⸺D |
|---|---|---|---|
| 4.22 | 4.01 | 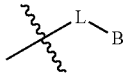 |  |
| 4.23 | 4.01 | 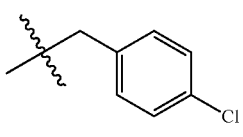 | 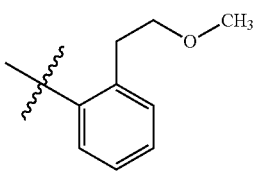 [SMILES: *c1ccccc1CCOC] |
| 4.24 | 4.01 | 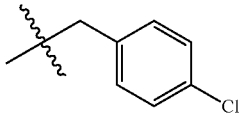 | 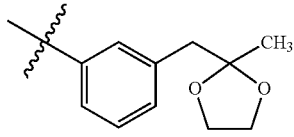 [SMILES: *c1cccc(CC2(C)OCCO2)c1] |
| 4.25 | 4.01 | 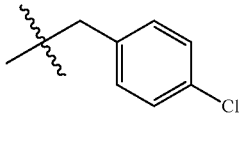 [SMILES: *Cc1ccc(Cl)cc1] | 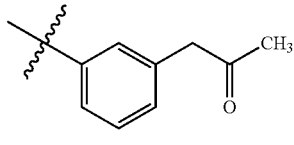 [SMILES: *c1cccc(CC(C)=O)c1] |
| 4.26 | 4.01 | 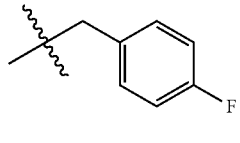 | 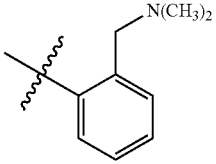 |
| 4.27 | 4.01 | 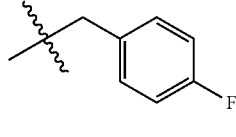 [SMILES: *Cc1ccc(F)cc1] | 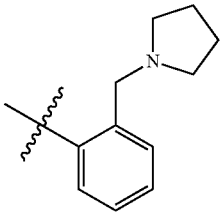 [SMILES: *c1ccccc1CN1CCCC1] |
| 4.28 | 4.01 | 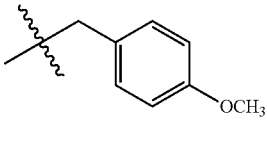 [SMILES: *Cc1ccc(OC)cc1] | 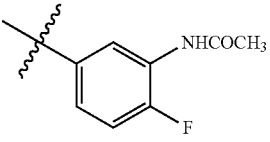 |

TABLE 4-continued
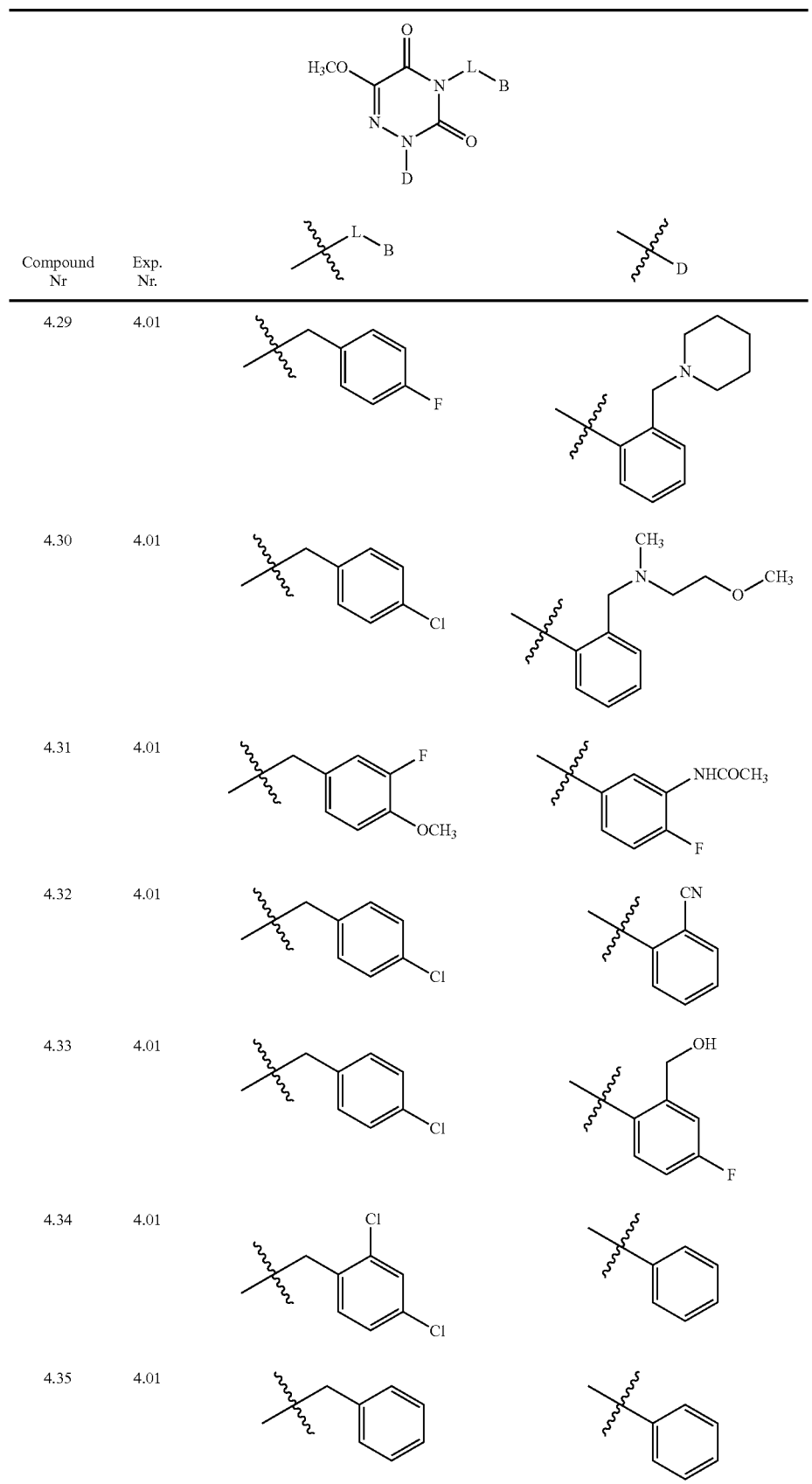

TABLE 4-continued
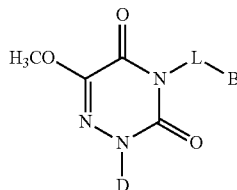
| Compound Nr | Exp. Nr. | 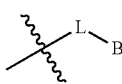 |  |
|---|---|---|---|
| 4.36* | 4.36 | 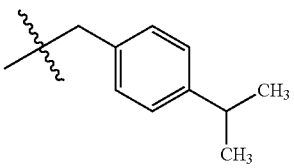 | 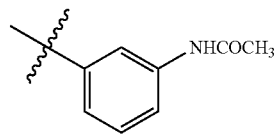 |
| 4.37 | 4.36 | 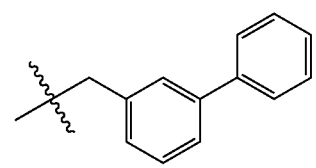 [SMILES: *Cc1cccc(-c2ccccc2)c1] | 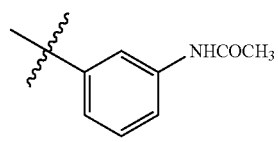 |
| 4.38 | 4.36 | 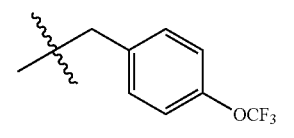 | 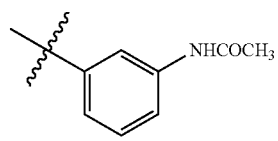 |
| 4.39 | 4.36 | 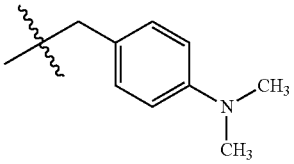 | 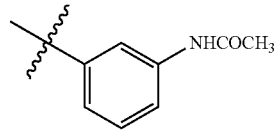 |
| 4.40 | 4.36 | 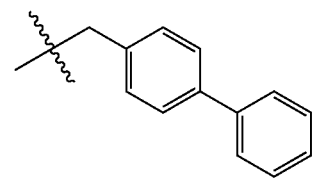 [SMILES: *Cc1ccc(-c2ccccc2)cc1] | 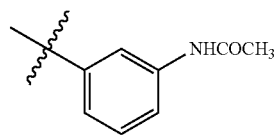 |
| 4.41 | 4.36 | 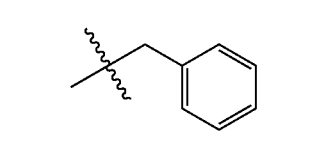 [SMILES: *Cc1ccccc1] | 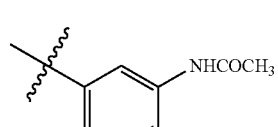 |
| 4.42 | 4.36 | 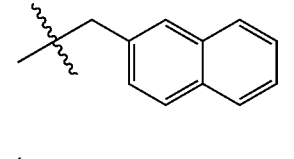 | 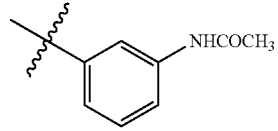 |
| 4.43 | 4.36 | 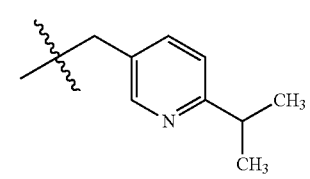 | 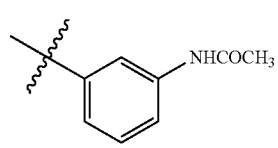 |

TABLE 4-continued
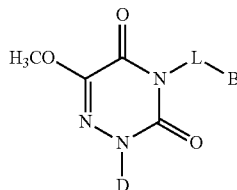
| Compound Nr | Exp. Nr. | ⸺L—B | ⸺D |
|---|---|---|---|
| 4.44 | 4.36 | 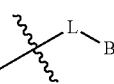 |  |
| 4.45 | 4.36 | 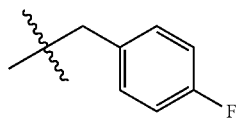 | 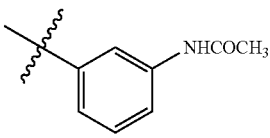 |
| 4.46 | 4.36 | 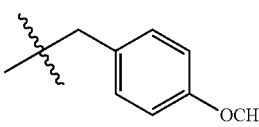 | 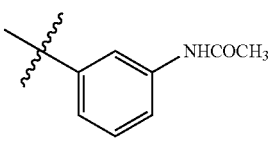 |
| 4.47 | 4.36 | 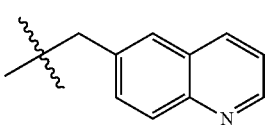 [SMILES: *Cc1ccc2ncccc2c1] | 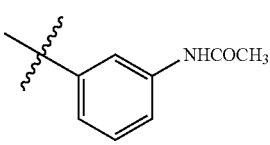 |
| 4.48 | 4.36 | 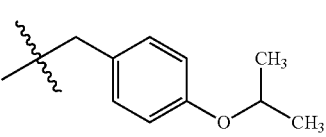 | 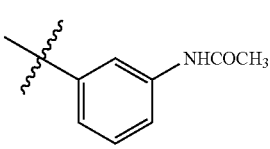 |
| 4.49 | 4.36 | 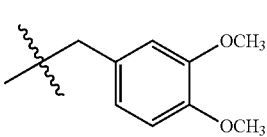 | 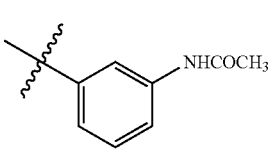 |
| 4.50 | 4.36 | 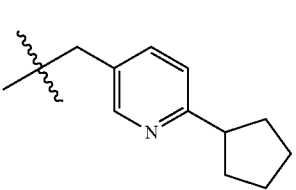 [SMILES: *Cc1ccc(C2CCCC2)nc1] | 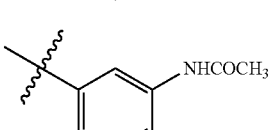 |
| 4.51 | 4.36 | 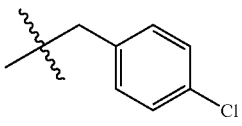 | 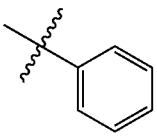 [SMILES: *c1ccccc1] |
| 4.52 | 4.36 | 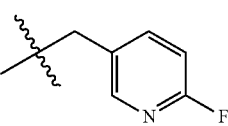 [SMILES: *Cc1ccc(F)nc1] | 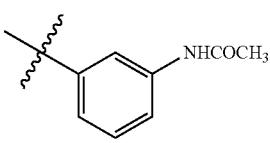 |

TABLE 4-continued

| Compound Nr | Exp. Nr. | ⸺L—B | ⸺D |
|---|---|---|---|
| 4.53 | 4.36 | 5-(dimethylamino)pyridin-2-yl-methyl | 3-NHCOCH₃-phenyl |
| 4.54 | 4.36 | (2,3-dihydrobenzofuran-5-yl)methyl | 3-NHCOCH₃-phenyl |
| 4.55 | 4.36 | (3,4-difluorophenyl)methyl | 3-NHCOCH₃-phenyl |
| 4.56 | 4.36 | (2,4-difluorophenyl)methyl | 3-NHCOCH₃-phenyl |
| 4.57 | 4.36 | (6-methoxypyridin-3-yl)methyl | 3-NHCOCH₃-phenyl |
| 4.58 | 4.36 | pyridazin-3-ylmethyl | 3-NHCOCH₃-phenyl |
| 4.59 | 4.36 | (4-(1H-pyrazol-1-yl)phenyl)methyl | 3-NHCOCH₃-phenyl |
| 4.60 | 4.36 | (2,6-difluoro-4-methoxyphenyl)methyl | 3-NHCOCH₃-phenyl |

TABLE 4-continued
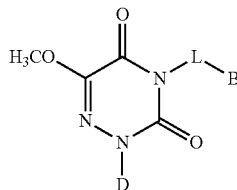
| Compound Nr | Exp. Nr. | L—B | D |
|---|---|---|---|
| 4.61 | 4.36 | 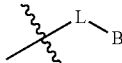 |  |
| 4.62 | 4.36 | 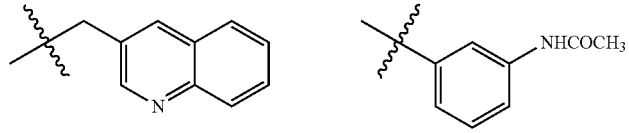 |  |
| 4.63 | 4.36 | 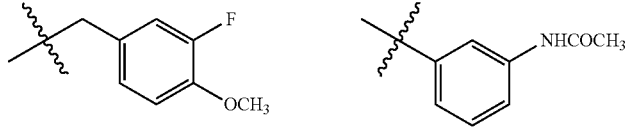 |  |
| 4.64 | 4.36 | 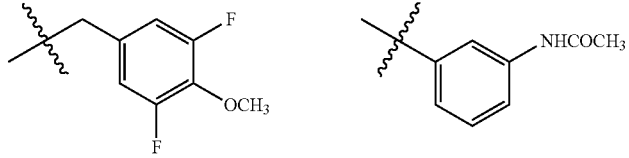 |  |
| 4.65 | 4.36 | 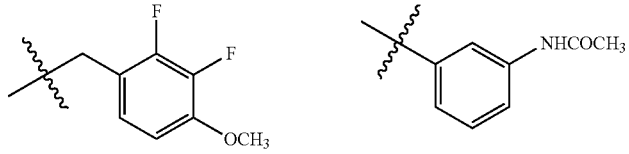 |  |
| 4.66 | 4.36 | 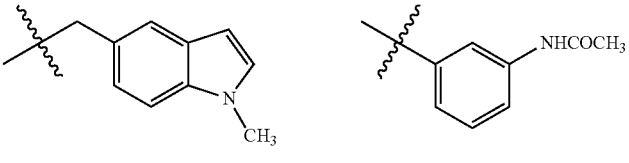 |  |
| 4.67 | 4.36 | 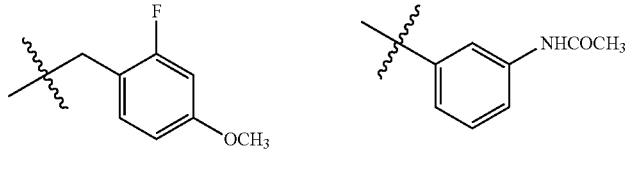 |  |
| 4.68 | 4.36 |  |  |

TABLE 4-continued

| Compound Nr | Exp. Nr. | L—B | D |
|---|---|---|---|
| 4.69 | 4.36 | 2-F, 4-Cl benzyl | phenyl |
| 4.80 | 4.36 | 3-OCH₃ benzyl | 3-NHCOCH₃ phenyl |
| 4.90 | 4.36 | 2,3-dihydro-1,4-benzodioxin-2-ylmethyl | phenyl |
| 4.91 | 4.36 | (2-phenylthiazol-4-yl)methyl | phenyl |
| 4.92 | 4.36 | 2-F, 4-Cl benzyl | 3-NHCOCH₃ phenyl |
| 4.93 | 4.36 | 3-OCF₃ benzyl | phenyl |
| 4.94 | 4.36 | 2,5-diF benzyl | phenyl |

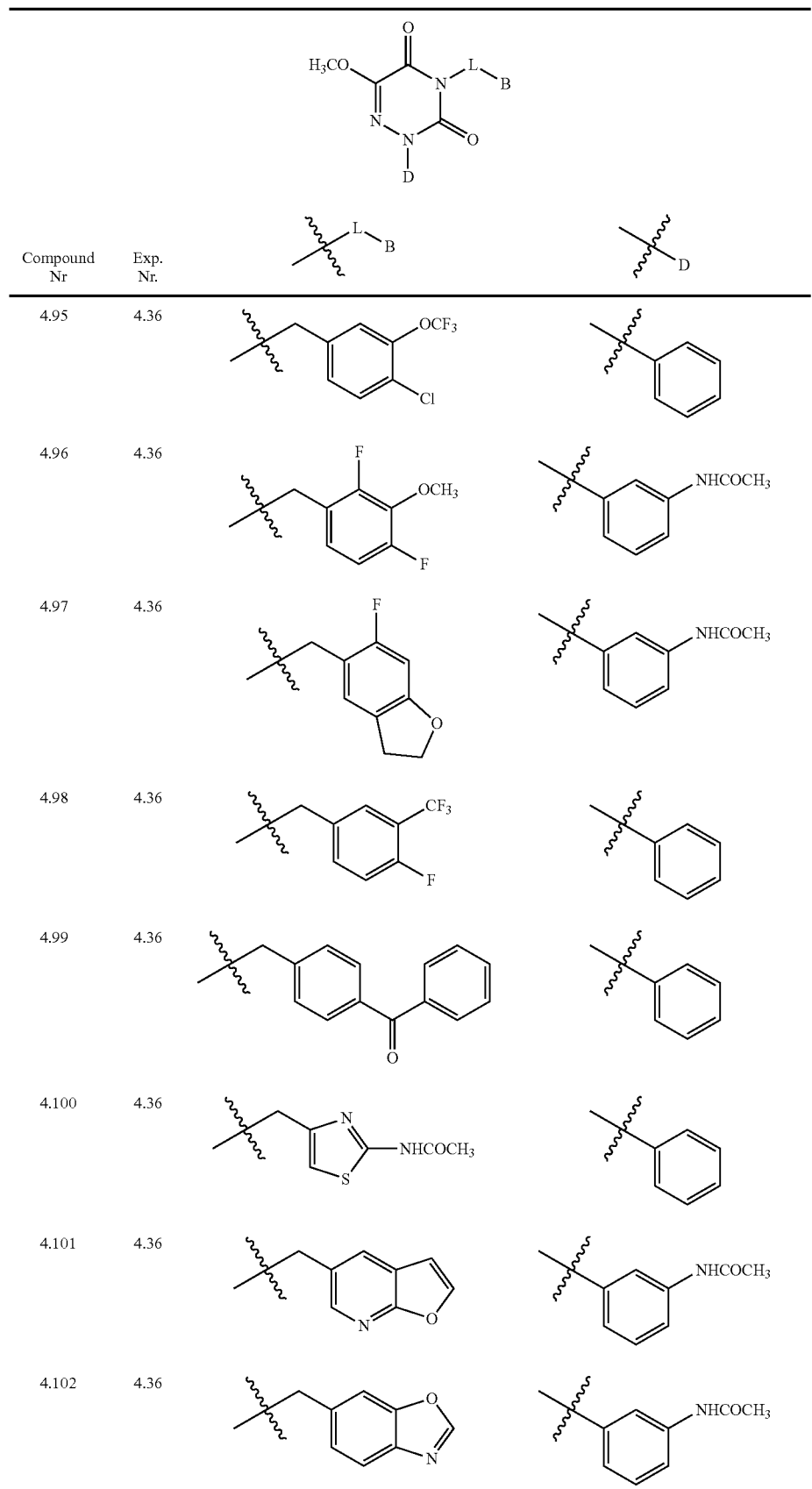

TABLE 4-continued
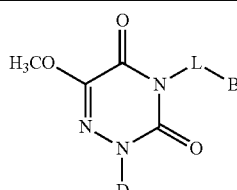
| Compound Nr | Exp. Nr. | L-B | D |
|---|---|---|---|
| 4.103 | 4.36 | 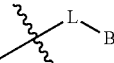 |  |
| 4.104 | 4.36 | 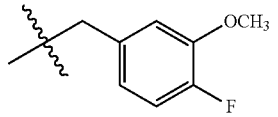 [SMILES: *Cc1ccc(F)c(OC)c1] | 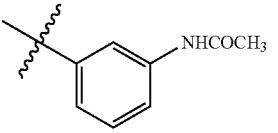 |
| 4.105 | 4.36 | 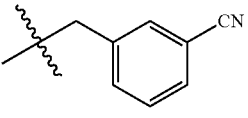 [SMILES: *Cc1cccc(C#N)c1] | 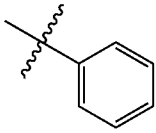 [SMILES: *c1ccccc1] |
| 4.106 | 4.36 | 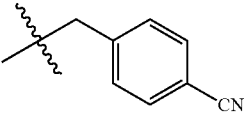 [SMILES: *Cc1ccc(C#N)cc1] | 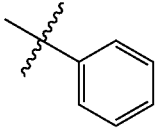 [SMILES: *c1ccccc1] |
| 4.107 | 4.36 | 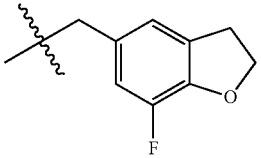 [SMILES: *Cc1cc(F)c2c(c1)CCO2] | 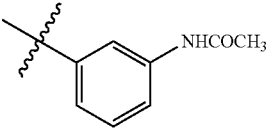 |
| 4.108 | 4.36 | 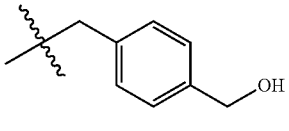 [SMILES: *Cc1ccc(CO)cc1] | 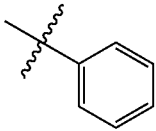 [SMILES: *c1ccccc1] |
| 4.109 | 4.36 | 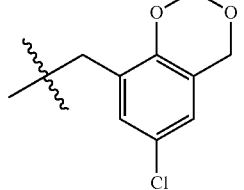 | 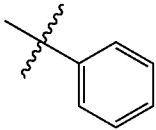 [SMILES: *c1ccccc1] |
| 4.110 | 4.36 | 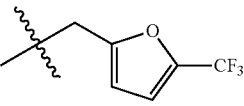 [SMILES: *Cc1ccc(C(F)(F)F)o1] | 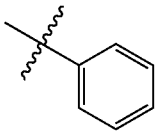 [SMILES: *c1ccccc1] |

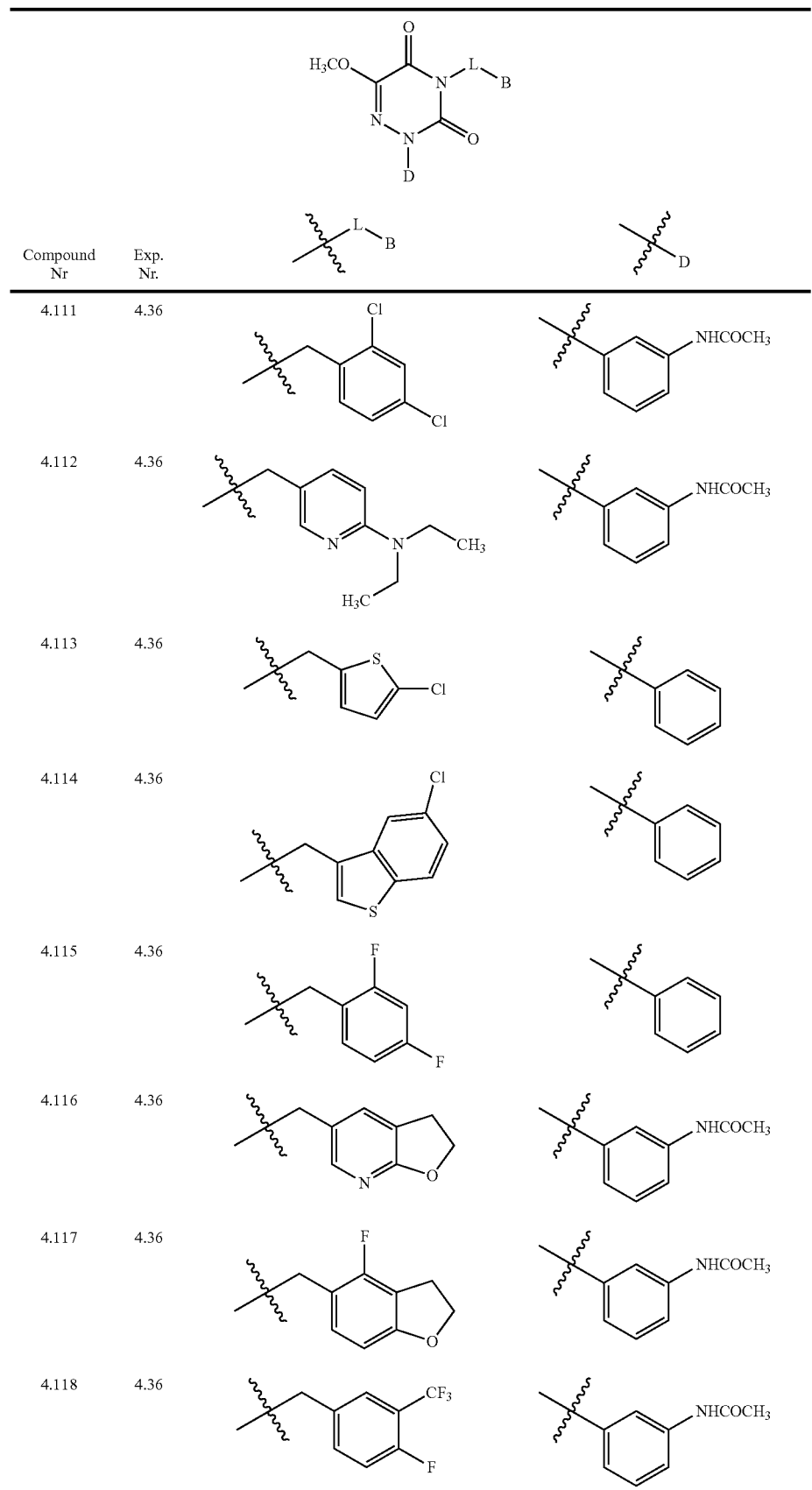

TABLE 4-continued
| Compound Nr | Exp. Nr. | L—B | D |
|---|---|---|---|
| 4.119 | 4.36 | 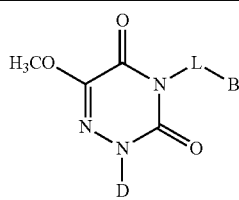 |  |
| 4.120 | 4.36 |  | 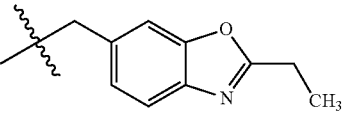 |
| 4.121 | 4.36 | 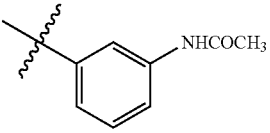 | 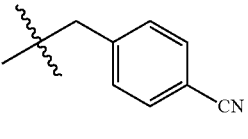 |
| 4.122 | 4.36 | 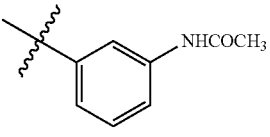 | 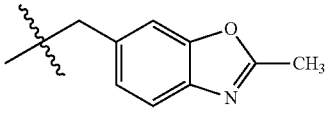 [SMILES: *Cc1ccc2nc(C)oc2c1] |
| 4.123 | 4.36 | 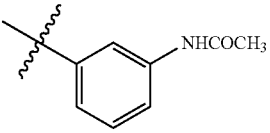 | 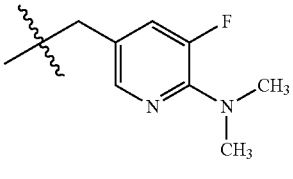 |
| 4.124 | 4.36 | 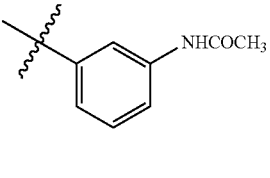 | 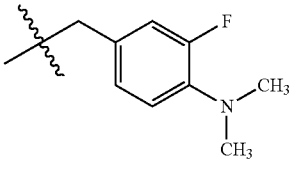 |
| 4.125 | 4.36 | 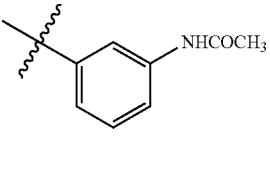 | 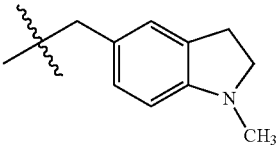 |
| 4.126 | 4.36 | 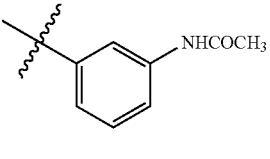 | 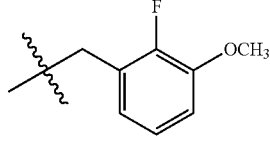 [SMILES: *Cc1cccc(OC)c1F] |

TABLE 4-continued
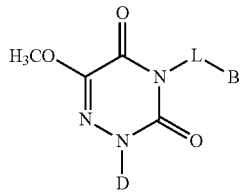
| Compound Nr | Exp. Nr. | ⁂–L–B | ⁂–D |
|---|---|---|---|
| 4.127* | 4.127 | 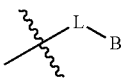 |  |
| 4.128 | 4.127 | 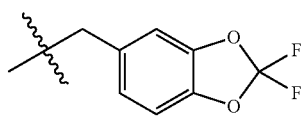 [SMILES: *Cc1ccc2c(c1)OC(F)(F)O2] | 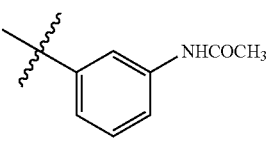 |
| 4.129 | 4.127 | 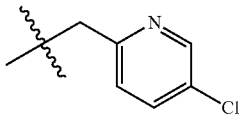 [SMILES: *Cc1ccc(Cl)cn1] | 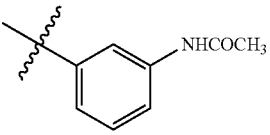 |
| 4.130 | 4.36 | 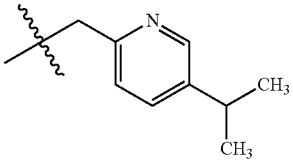 | 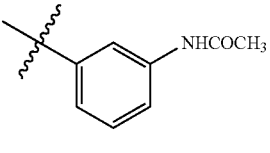 |
| 4.131 | 4.36 | 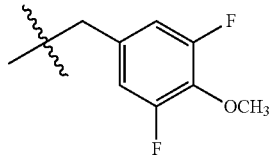 [SMILES: *Cc1cc(F)c(OC)c(F)c1] | 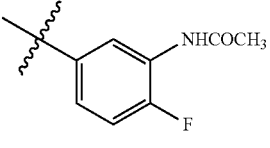 |
| 4.132 | 4.36 | 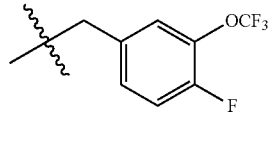 [SMILES: *Cc1ccc(F)c(OC(F)(F)F)c1] | 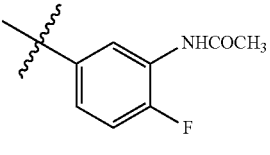 |
| 4.133* | 4.133 | 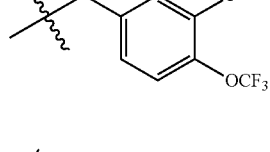 | 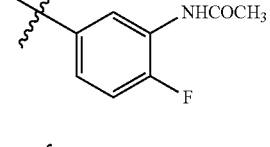 |
| 4.134 | 4.133 | 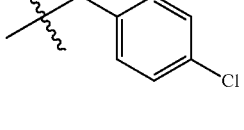 | 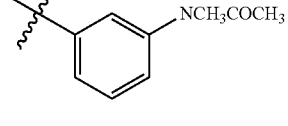 |

TABLE 4-continued
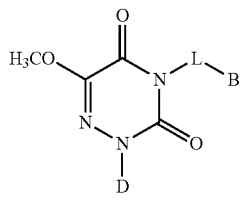
| Compound Nr | Exp. Nr. | ⁓L⁓B | ⁓D |
|---|---|---|---|
| 4.135 | 4.36 |  |  |
| 4.136 | 4.133 | 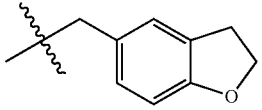 | 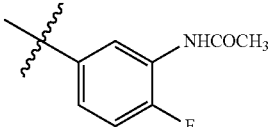 |
| 4.137 | 4.133 | 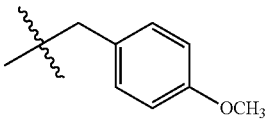 | 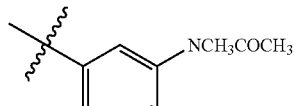 |
| 4.138 | 4.133 | 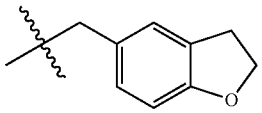 [SMILES: *Cc1ccc2c(c1)CCO2] | 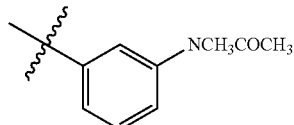 |
| 4.139 | 4.133 | 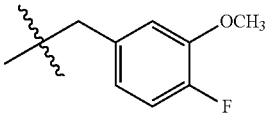 [SMILES: *Cc1ccc(F)c(OC)c1] | 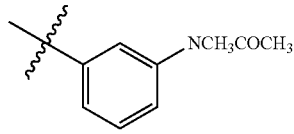 |
| 4.140 | 4.36 | 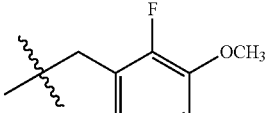 | 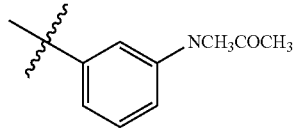 |
| 4.141* | 4.141 | 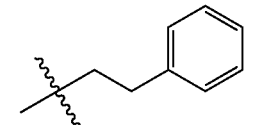 [SMILES: *CCc1ccccc1] | 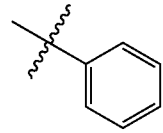 [SMILES: *c1ccccc1] |
| 4.142 | 4.141 | 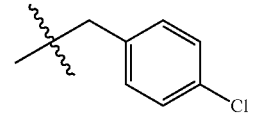 [SMILES: *Cc1ccc(Cl)cc1] | 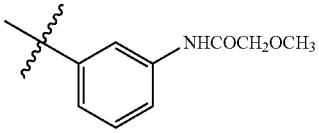 |

TABLE 4-continued
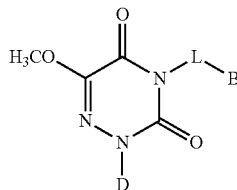
| Compound Nr | Exp. Nr. | 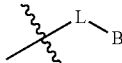 |  |
|---|---|---|---|
| 4.143* | 4.143 | 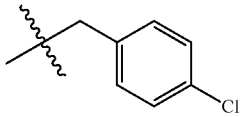 [SMILES: *Cc1ccc(Cl)cc1] | 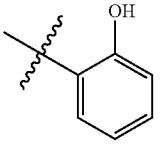 [SMILES: *c1ccccc1O] |
| 4.144* | 4.144 | 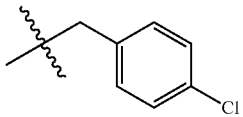 [SMILES: *Cc1ccc(Cl)cc1] | 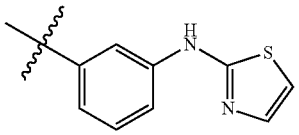 [SMILES: *c1cccc(Nc2nccs2)c1] |
| 4.145* | 4.145 | 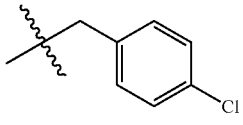 [SMILES: *Cc1ccc(Cl)cc1] | 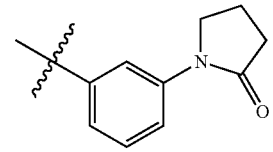 [SMILES: *c1cccc(N2CCCC2=O)c1] |
| 4.146* | 4.146 | 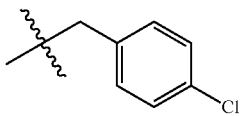 [SMILES: *Cc1ccc(Cl)cc1] | 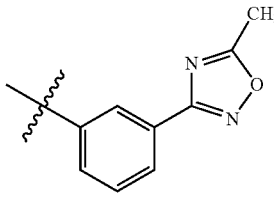 |
| 4.147 | 4.36 | 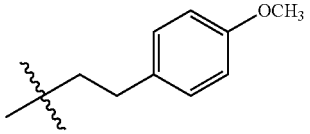 [SMILES: *CCc1ccc(OC)cc1] | 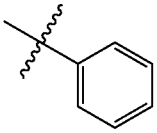 [SMILES: *c1ccccc1] |
| 4.148 | 4.36 | 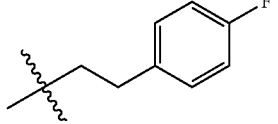 | 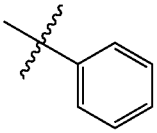 [SMILES: *c1ccccc1] |
| 4.149 | 4.36 | 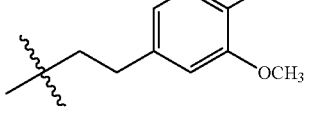 | 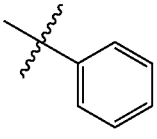 [SMILES: *c1ccccc1] |
| 4.150 | 4.36 | 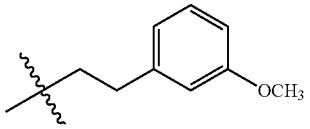 [SMILES: *CCc1cccc(OC)c1] | 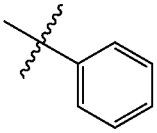 [SMILES: *c1ccccc1] |

TABLE 4-continued
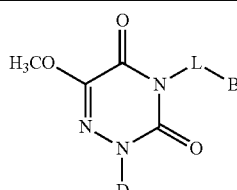
| Compound Nr | Exp. Nr. | ⸺L―B | ⸺D |
|---|---|---|---|
| 4.151 | 4.36 | 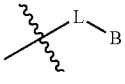 |  |
| 4.152 | 4.36 | 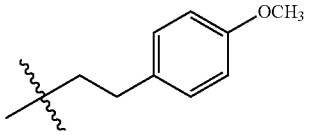 [SMILES: *CCc1ccc(OC)cc1] | 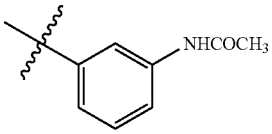 |
| 4.153 | 4.36 | 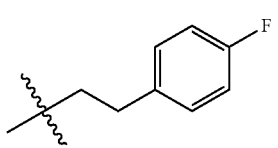 [SMILES: *CCc1ccc(F)cc1] | 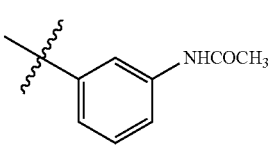 |
| 4.154 | 4.36 | 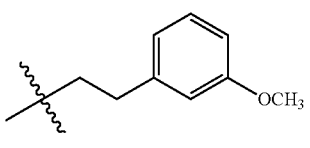 [SMILES: *CCc1cccc(OC)c1] | 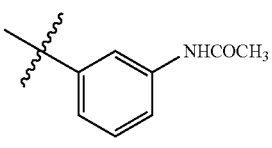 |
| 4.155 | 4.36 | 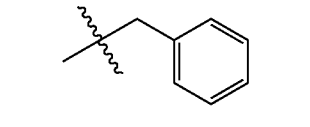 [SMILES: *Cc1ccccc1] | 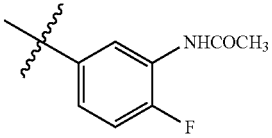 |
| 4.156 | 4.36 | 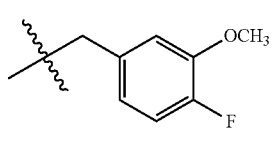 [SMILES: *Cc1ccc(F)c(OC)c1] | 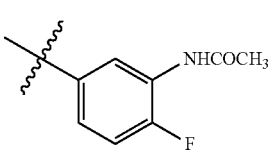 |
| 4.157 | 4.36 | 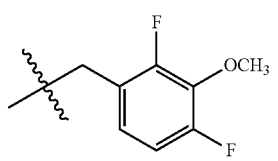 | 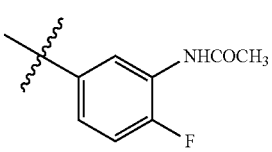 |
| 4.158 | 4.36 | 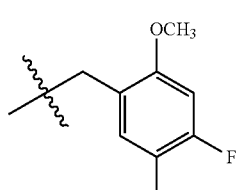 | 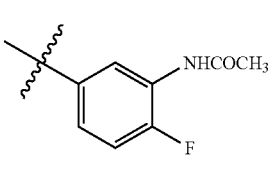 |

TABLE 4-continued
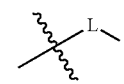
| Compound Nr | Exp. Nr. | 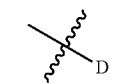 | 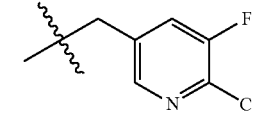 |
|---|---|---|---|
| 4.159 | 4.36 | 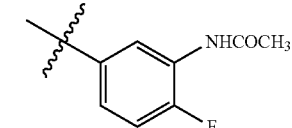 | 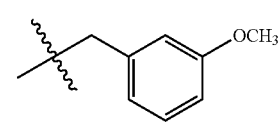 [SMILES: *Cc1cccc(OC)c1] |
| 4.160 | 4.36 | 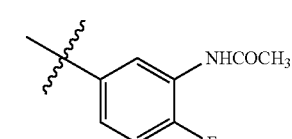 | 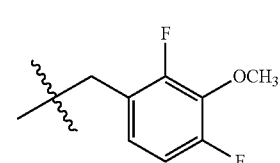 |
| 4.161 | 4.36 | 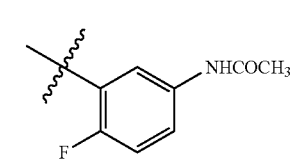 | 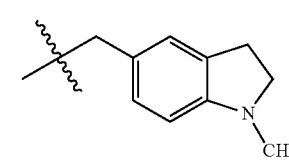 |
| 4.162 | 4.36 | 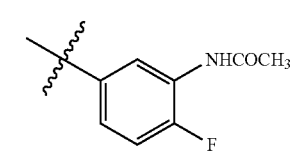 | 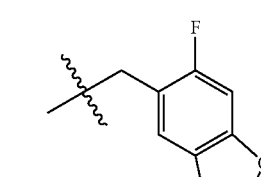 |
| 4.163 | 4.36 | 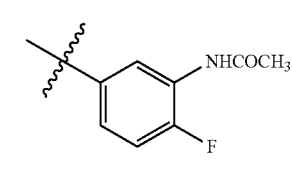 | 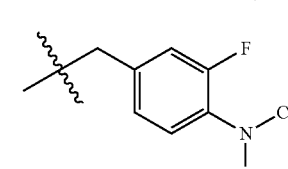 |
| 4.164 | 4.36 | 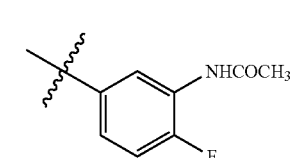 | 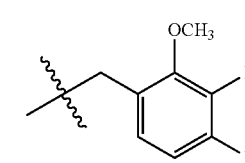 |
| 4.165 | 4.36 | 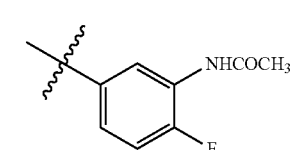 | 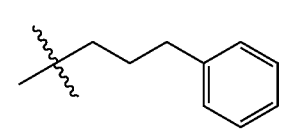 [SMILES: *CCCc1ccccc1] |
| 4.166 | 4.36 | 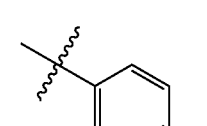 |  |

TABLE 4-continued
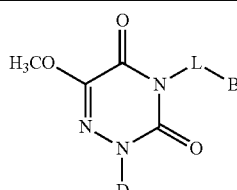
| Compound Nr | Exp. Nr. | L–B | D |
|---|---|---|---|
| 4.167* | 4.167 | 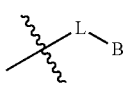 |  |
| 4.168 | 4.36 | 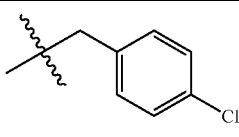 | 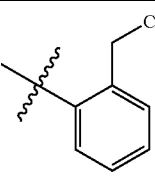 |
| 4.169 | 4.36 | 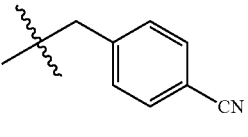 [SMILES: *Cc1ccc(C#N)cc1] | 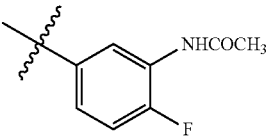 |
| 4.170 | 4.36 | 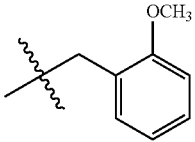 [SMILES: *Cc1ccccc1OC] |  |
| 4.171 | 4.36 | 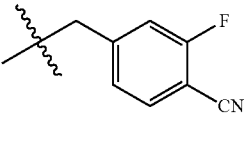 [SMILES: *Cc1ccc(C#N)c(F)c1] | 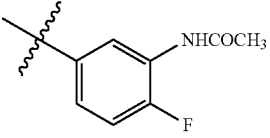 |
| 4.172 | 4.36 | 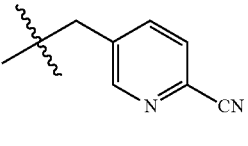 [SMILES: *Cc1ccc(C#N)nc1] | 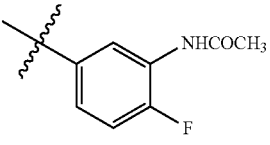 |
| 4.173 | 4.36 | 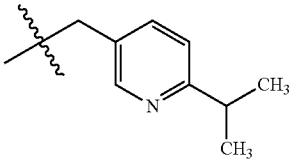 [SMILES: *Cc1ccc(C(C)C)nc1] | 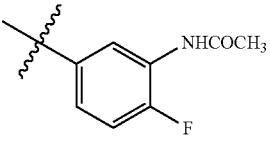 |
| 4.174 | 4.36 | 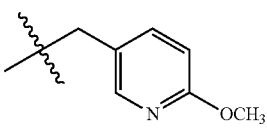 [SMILES: *Cc1ccc(OC)nc1] | 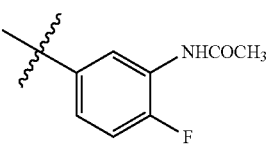 |

TABLE 4-continued
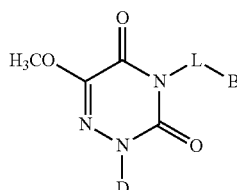
| Compound Nr | Exp. Nr. | ⸺L—B | ⸺D |
|---|---|---|---|
| 4.175 | 4.36 |  |  |
| 4.176 | 4.36 | 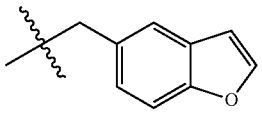 [SMILES: *Cc1ccc2occc2c1] | 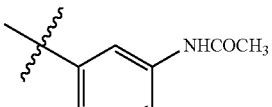 |
| 4.177 | 4.36 | 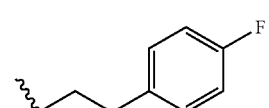 | 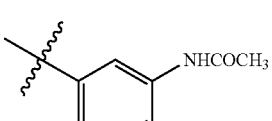 |
| 4.178 | 4.36 | 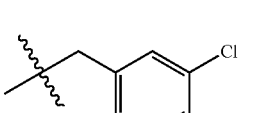 | 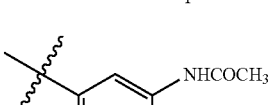 |
| 4.179 | 4.36 | 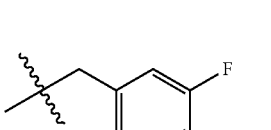 | 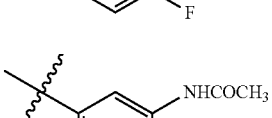 |
| 4.180 | 4.36 |  | 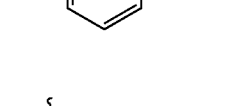 |
| 4.181 | 4.36 | 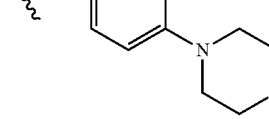 | 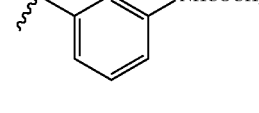 |
| 4.182 | 4.36 | 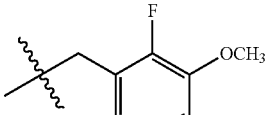 | 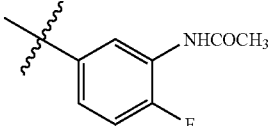 |

TABLE 4-continued
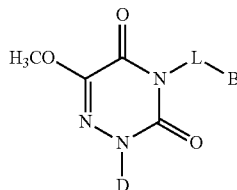
| Compound Nr | Exp. Nr. | ⌇L-B | ⌇D |
|---|---|---|---|
| 4.183 | 4.36 | 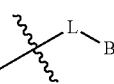 |  |
| 4.184 | 4.36 | 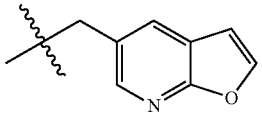 [SMILES: *Cc1cnc2occc2c1] | 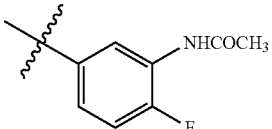 |
| 4.185 | 4.36 | 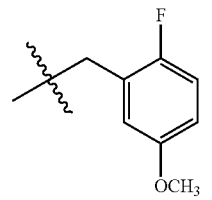 [SMILES: *Cc1cc(OC)ccc1F] | 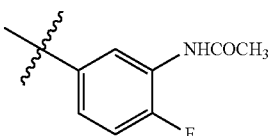 |
| 4.186 | 4.36 | 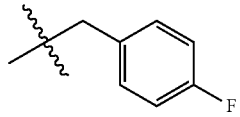 [SMILES: *Cc1ccc(F)cc1] |  |
| 4.187 | 4.36 | 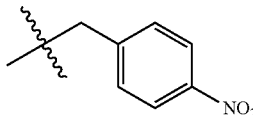 | 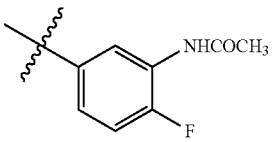 |
| 4.188 | 4.36 | 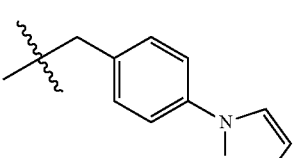 | 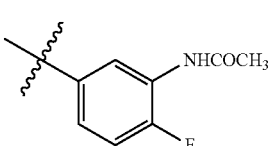 |
| 4.189 | 4.36 | 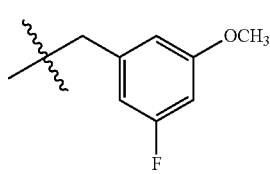 [SMILES: *Cc1cc(F)cc(OC)c1] | 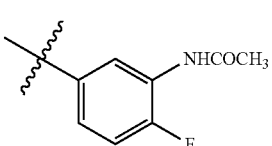 |
| 4.190 | 4.36 | 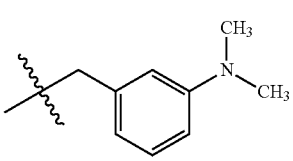 [SMILES: *Cc1cccc(N(C)C)c1] | 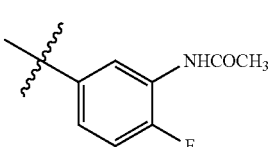 |

TABLE 4-continued
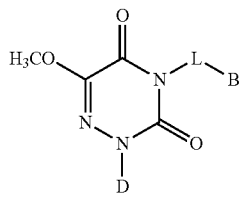
| Compound Nr | Exp. Nr. | 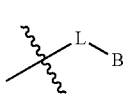 |  |
|---|---|---|---|
| 4.191 | 4.36 | 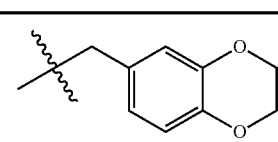 | 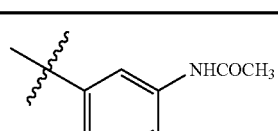 |
| 4.192 | 4.36 | 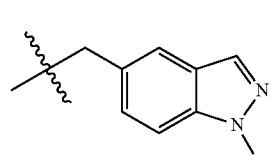 | 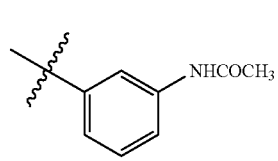 |
| 4.193 | 4.36 | 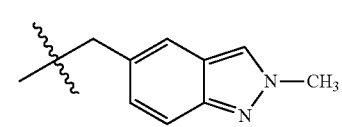 [SMILES: *Cc1ccc2nn(C)cc2c1] | 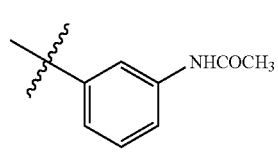 |
| 4.194 | 4.36 | 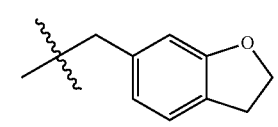 [SMILES: *Cc1ccc2c(c1)OCC2] | 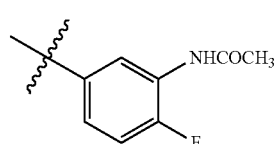 |
| 4.195 | 4.36 | 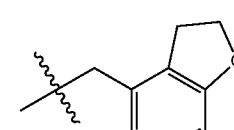 | 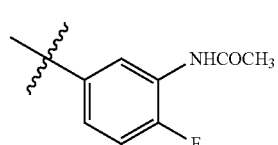 |
| 4.196 | 4.36 | 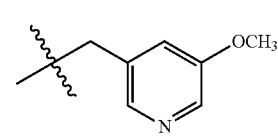 [SMILES: *Cc1cncc(OC)c1] | 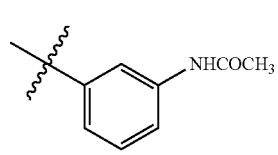 |
| 4.197 | 4.36 | 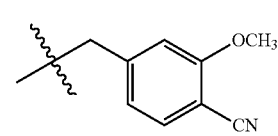 [SMILES: *Cc1ccc(C#N)c(OC)c1] | 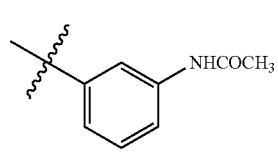 |
| 4.198 | 4.36 | 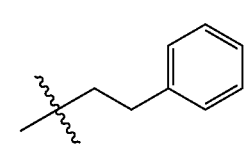 [SMILES: *CCc1ccccc1] | 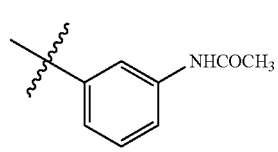 |

TABLE 4-continued
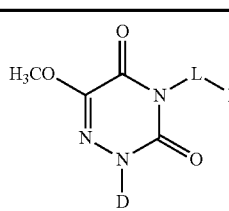
| Compound Nr | Exp. Nr. | ⸹–L–B | ⸹–D |
|---|---|---|---|
| 4.199 | 4.36 | 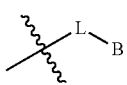 |  |
| 4.200 | 4.36 | 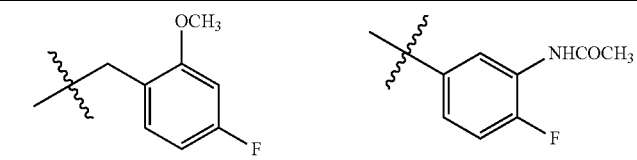 | 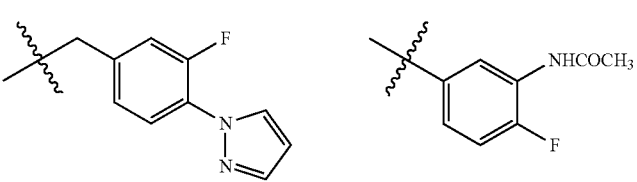 |
| 4.201 | 4.36 |  |  |
| 4.202 | 4.36 |  |  |
| 4.203 | 4.127 |  |  |
| 4.204 | 4.36 |  |  |
| 4.205 | 4.36 |  |  |
| 4.206 | 4.36 | 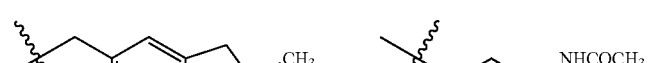 | 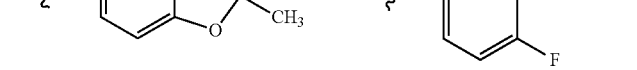 |

TABLE 4-continued
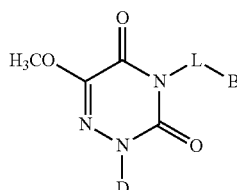
| Compound Nr | Exp. Nr. | L—B | D |
|---|---|---|---|
| 4.207 | 4.167 | 4-Cl-phenyl-CH2 | 2-(CH2CN)-5-F-phenyl |
| 4.208 | 4.36 | 4-Cl-phenyl-CH2 | 5-NHCOCH3-2-F-phenyl |
| 4.209 | 4.36 | benzo[d]isoxazol-6-yl-CH2 | 3-NHCOCH3-phenyl |
| 4.210 | 4.127 | 3-F-4-Cl-phenyl-CH2 | 5-NHCOCH3-2-F-phenyl |
| 4.211 | 4.36 | 3-F-4-Cl-phenyl-CH2 | 5-NHCOCH3-2-Cl-phenyl |
| 4.212 | 4.36 | 2-OCH3-4-F-phenyl-CH2 | 5-NHCOCH3-2-Cl-phenyl |
| 4.213 | 4.36 | 2,4-diF-phenyl-CH2 | 5-NHCOCH3-2-F-phenyl |
| 4.214 | 4.36 | 2-OCH3-4-Cl-phenyl-CH2 | 5-NHCOCH3-2-F-phenyl |

TABLE 4-continued
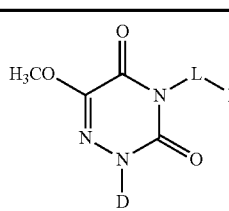
| Compound Nr | Exp. Nr. | L—B | D |
|---|---|---|---|
| 4.215 | 4.36 | 3-OCH₃, 4-Cl benzyl | 5-NHCOCH₃, 2-F phenyl |
| 4.216 | 4.36 | 2,4-diF phenethyl | 5-NHCOCH₃, 2-F phenyl |
| 4.217 | 4.36 | 3-F, 2-OCH₃-pyridin-5-yl methyl | 3-NHCOCH₃ phenyl |
| 4.219 | 4.36 | 2-OCH₃, 4-Cl benzyl | 3-NHCOCH₃, 4-Cl phenyl |
| 4.219 | 4.36 | 3-OCH₃, 4-Cl benzyl | 3-NHCOCH₃, 4-Cl phenyl |
| 4.220 | 4.36 | 3-OCH₃, 4,5-diF benzyl | 3-NHCOCH₃, 4-F phenyl |
| 4.221 | 4.36 | 2-F, 4-Cl benzyl | 3-NHCOCH₃, 4-Cl phenyl |
| 4.222 | 4.36 | 2,4-diF benzyl | 3-NHCOCH₃, 4-Cl phenyl |

TABLE 4-continued
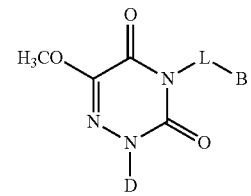
| Compound Nr | Exp. Nr. | 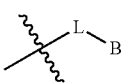 L—B |  D |
|---|---|---|---|
| 4.223 | 4.36 | 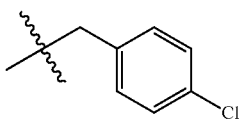 | 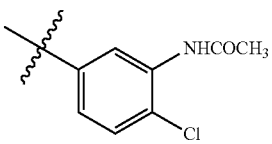 |
| 4.224 | 4.36 | 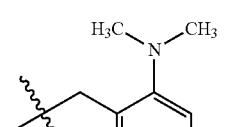 | 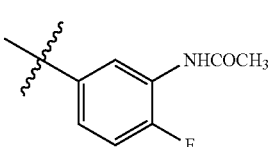 |
| 4.225 | 4.36 | 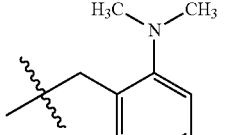 | 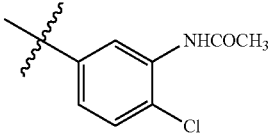 |
| 4.226 | 4.36 | 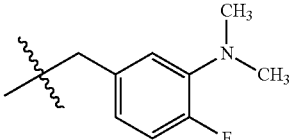 | 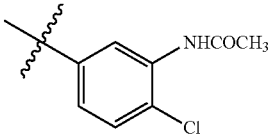 |
| 4.227 | 4.36 | 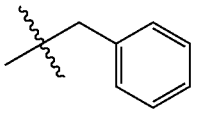 [SMILES: *Cc1ccccc1] | 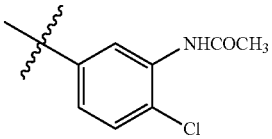 |
| 4.228 | 4.36 | 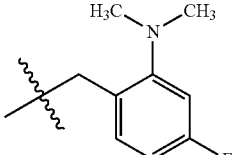 | 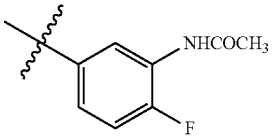 |
| 4.229 | 4.36 | 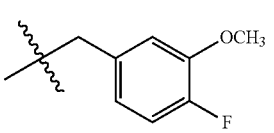 [SMILES: *Cc1ccc(F)c(OC)c1] | 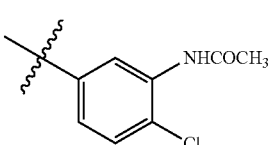 |
| 4.230 | 4.211 | 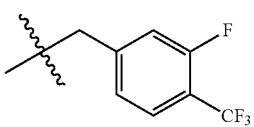 | 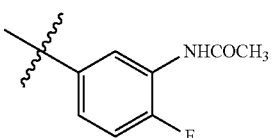 |

TABLE 4-continued
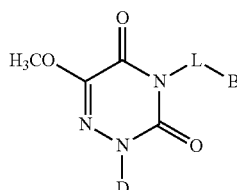
| Compound Nr | Exp. Nr. | L—B | D |
|---|---|---|---|
| 4.231 | 4.127 | 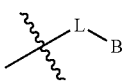 |  |
| 4.232 | 4.36 | 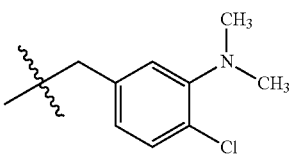 [SMILES: *Cc1ccc(Cl)c(N(C)C)c1] | 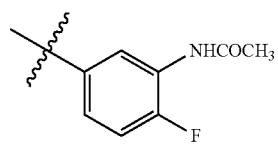 |
| 4.233 | 4.36 | 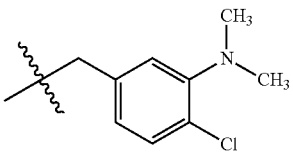 [SMILES: *Cc1ccc(Cl)c(N(C)C)c1] | 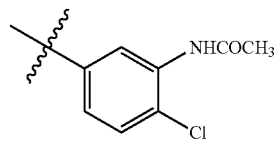 |
| 4.234 | 4.36 | 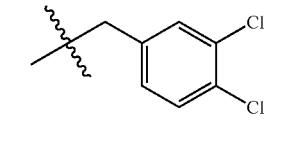 [SMILES: *Cc1ccc(Cl)c(Cl)c1] | 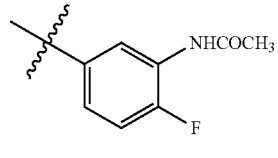 |
| 4.235 | 4.36 | 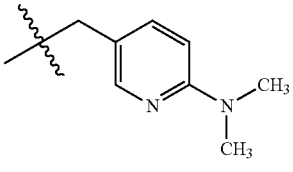 | 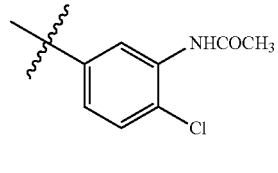 |
| 4.236 | 4.36 | 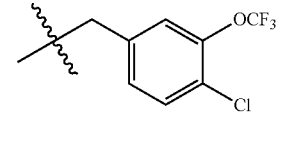 [SMILES: *Cc1ccc(Cl)c(OC(F)(F)F)c1] | 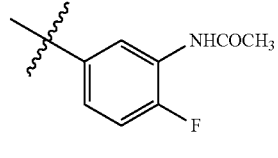 |
| 4.237 | 4.36 | 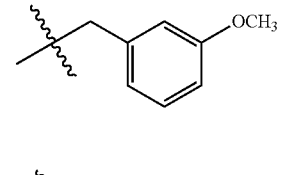 | 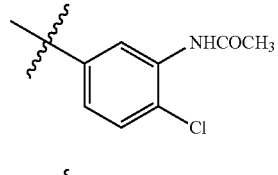 |
| 4.238 | 4.36 | 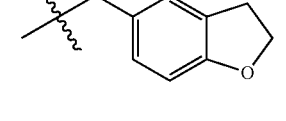 | 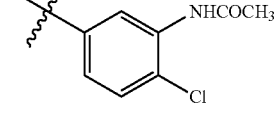 |

TABLE 4-continued
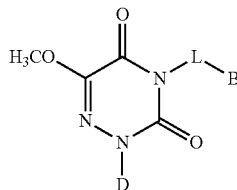
| Compound Nr | Exp. Nr. | ⸺L—B | ⸺D |
|---|---|---|---|
| 4.239 | 4.36 | 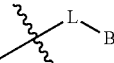 4-Cl-benzyl |  4-F-phenyl |
| 4.240 | 4.36 | 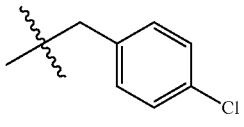 [SMILES: *Cc1ccc(Cl)cc1] 3-CF₃-4-Cl-benzyl | 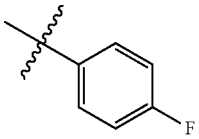 [SMILES: *c1ccc(F)cc1] 3-NHCOCH₃-4-Cl-phenyl |
| 4.241 | 4.36 | 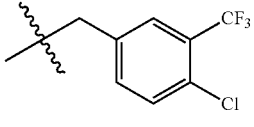 [SMILES: *Cc1ccc(Cl)c(C(F)(F)F)c1] 3-OiPr-4-Cl-benzyl | 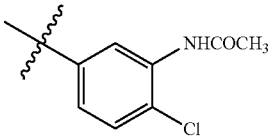 3-NHCOCH₃-4-F-phenyl |
| 4.242 | 4.36 | 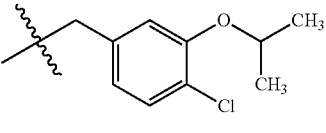 [SMILES: *Cc1ccc(Cl)c(OC(C)C)c1] 1-methylindazol-6-yl-methyl | 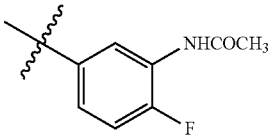 3-NHCOCH₃-4-Cl-phenyl |
| 4.243 | 4.36 | 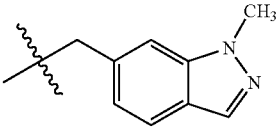 [SMILES: *Cc1ccc2cnn(C)c2c1] 3-iPr-4-Cl-benzyl | 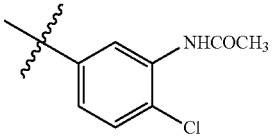 3-NHCOCH₃-4-F-phenyl |
| 4.244 | 4.36 | 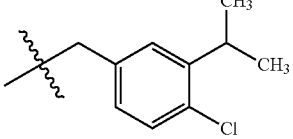 3-F-4-morpholinyl-benzyl | 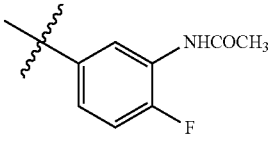 3-NHCOCH₃-4-F-phenyl |
| 4.245 | 4.36 | 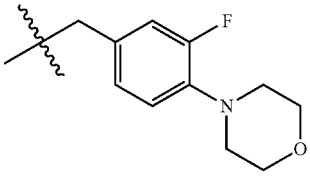 [SMILES: *Cc1ccc(N2CCOCC2)c(F)c1] 3-OH-4-Cl-benzyl | 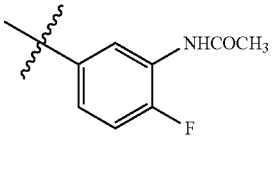 3-NHCOCH₃-4-F-phenyl |
| 4.246 | 4.36 | 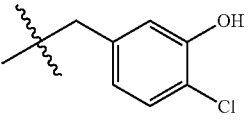 [SMILES: *Cc1ccc(Cl)c(O)c1] 3,3-dimethyl-2,3-dihydrobenzofuran-5-yl-methyl | 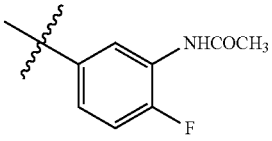 3-NHCOCH₃-4-F-phenyl |

TABLE 4-continued
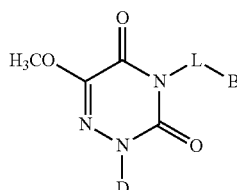
| Compound Nr | Exp. Nr. | ⁂—L—B | ⁂—D |
|---|---|---|---|
| 4.247 | 4.36 | 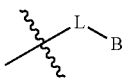 |  |
| 4.248 | 4.36 | 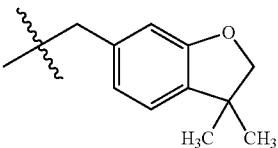 [SMILES: *Cc1ccc2c(c1)OCC2(C)C] | 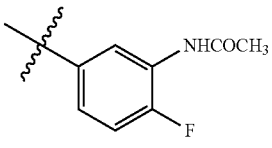 |
| 4.249 | 4.36 | 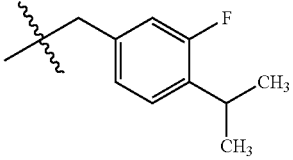 | 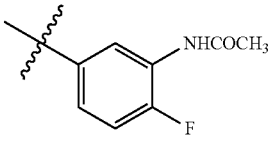 |
| 4.250 | 4.36 | 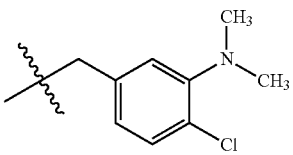 [SMILES: *Cc1ccc(Cl)c(N(C)C)c1] | 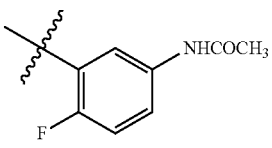 |
| 4.251 | 4.36 | 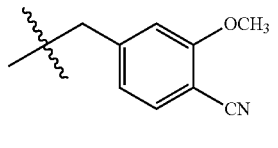 | 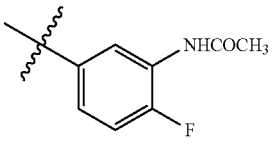 |
| 4.252 | 4.36 | 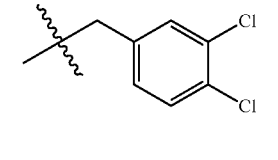 | 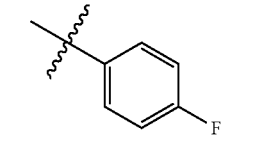 [SMILES: *c1ccc(F)cc1] |
| 4.253 | 4.36 | 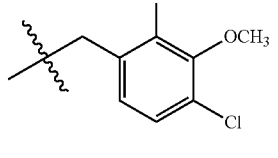 | 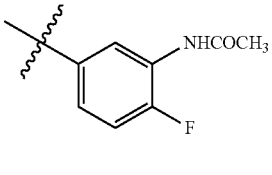 |
| 4.254 | 4.36 | 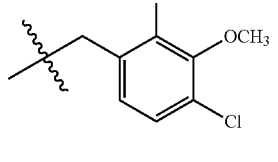 | 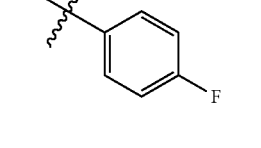 |

TABLE 4-continued
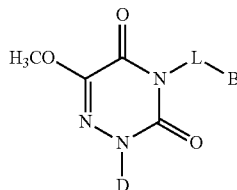
| Compound Nr | Exp. Nr. | 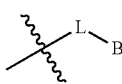 L—B |  D |
|---|---|---|---|
| 4.255 | 4.36 | 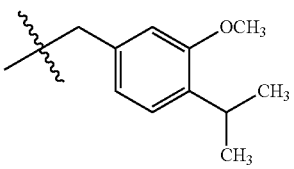 [SMILES: *Cc1ccc(C(C)C)c(OC)c1] | 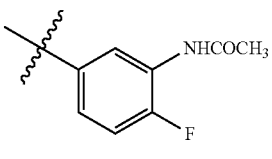 |
| 4.256 | 4.36 | 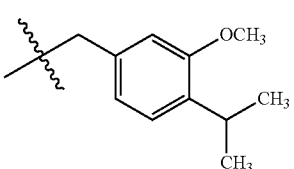 | 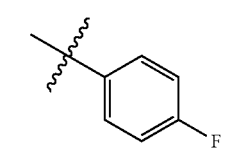 |
| 4.257 | 4.36 | 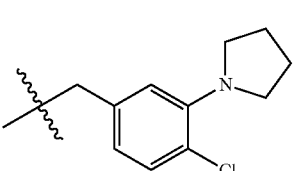 | 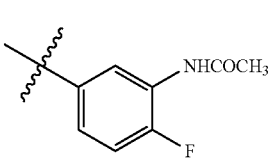 |
| 4.258 | 4.36 | 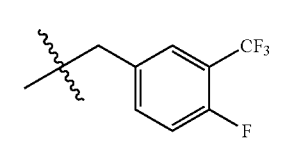 [SMILES: *Cc1ccc(F)c(C(F)(F)F)c1] | 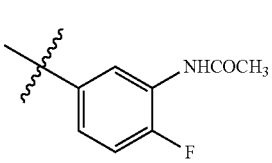 |
| 4.259 | 4.36 | 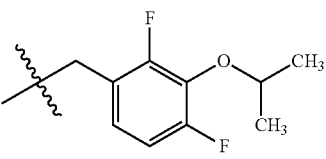 [SMILES: *Cc1ccc(F)c(OC(C)C)c1F] | 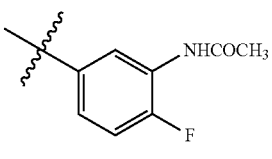 |
| 4.260 | 4.36 | 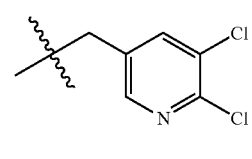 | 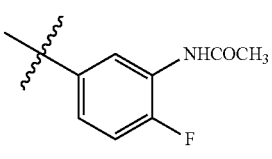 |
| 4.261 | 4.36 | 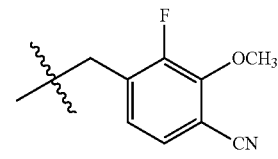 | 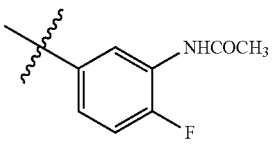 |
| 4.262 | 4.36 | 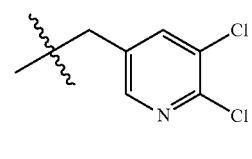 | 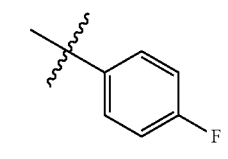 [SMILES: *c1ccc(F)cc1] |

TABLE 4-continued
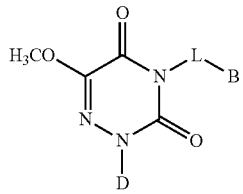
| Compound Nr | Exp. Nr. | ⸻L⸻B | ⸻D |
|---|---|---|---|
| 4.263 | 4.36 | 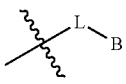 |  |
| 4.264 | 4.36 | 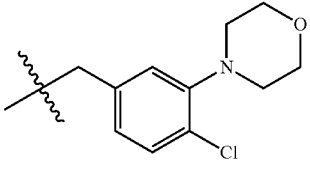 [SMILES: *Cc1ccc(Cl)c(N2CCOCC2)c1] | 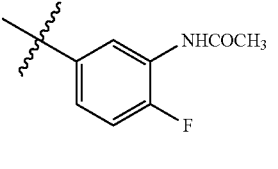 |
| 4.265 | 4.36 | 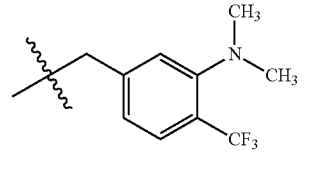 | 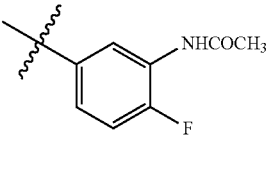 |
| 4.266 | 4.133 | 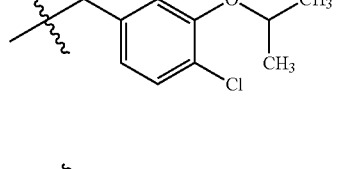 | 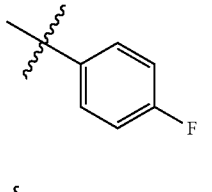 |
| 4.267 | 4.36 | 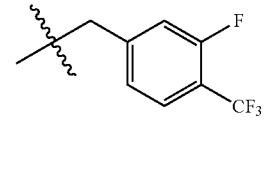 | 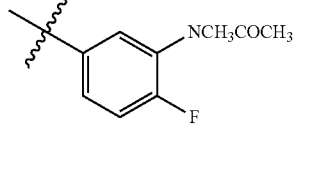 |
| 4.268 | 4.36 | 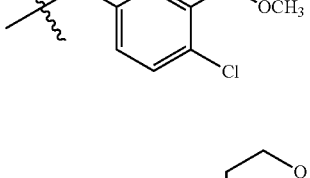 | 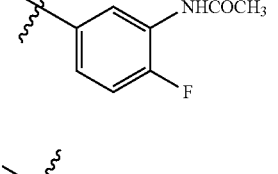 |
| 4.269 | 4.36 | 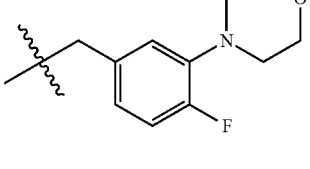 | 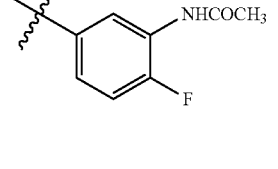 |

TABLE 5
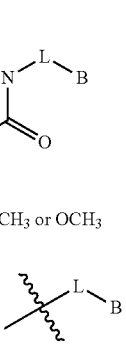
E is not H, CN, CH₃ or OCH₃
| Compound Nr | Exp. Nr. | E |  L–B |  D |
|---|---|---|---|---|
| 5.01* | 5.01 | iPr | 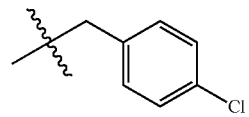 [SMILES: *Cc1ccc(Cl)cc1] 4-Cl-benzyl | 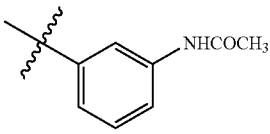 3-NHCOCH₃-phenyl |
| 5.02 | 5.01 | Et | 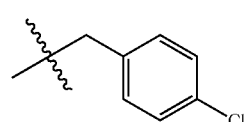 4-Cl-benzyl | 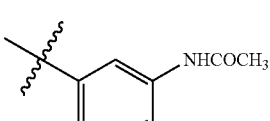 3-NHCOCH₃-phenyl |
| 5.03 | 5.01 | nBu | 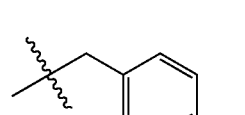 4-Cl-benzyl | 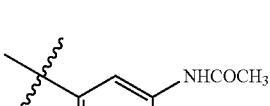 3-NHCOCH₃-phenyl |
| 5.04 | 4.01 | Br— | 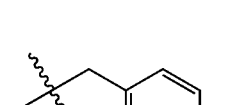 4-F-benzyl | 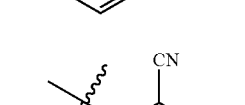 2-CN-phenyl |
| 5.05 | 4.01 | (CH₃)₂N(CH₂)₂O— | 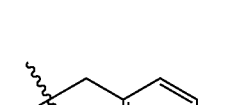 4-Cl-benzyl | 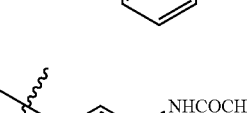 3-NHCOCH₃-phenyl |
| 5.06 | 4.01 | CH₃O(CH₂)₂O— | 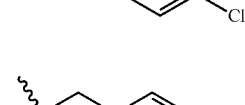 4-NO₂-benzyl | 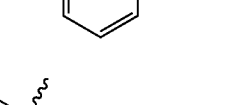 3-NHCOCH₃-phenyl |
| 5.07 | 4.01 | CH₃O(CH₂)₂O— | 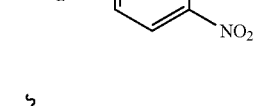 4-Cl-benzyl | 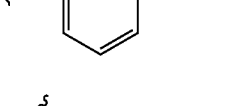 3-NHCOCH₃-phenyl |
| 5.08 | 4.01 | CH₃NH— | 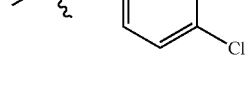 4-Cl-benzyl | 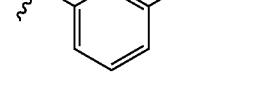 3-NHCOCH₃-phenyl |

TABLE 5-continued
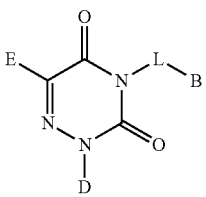
E is not H, CN, CH₃ or OCH₃
| Compound Nr | Exp. Nr. | E | L–B | D |
|---|---|---|---|---|
| 5.09 | 4.01 | CH₃CH₂O— | 4-Cl-benzyl | 3-NHCOCH₃-phenyl |
| 5.10 | 4.01 | Br— | 4-CH₃-benzyl | 3-NHCOCH₃-phenyl |
| 5.11 | 4.01 | (CH₃)₂CHO— | 4-Cl-benzyl | 3-NHCOCH₃-phenyl |
| 5.12 | 4.01 | Br— | 4-Cl-benzyl | 3-NHCOCH₃-phenyl |
| 5.13* | 5.13 | (CH₃)₂N— | 4-Cl-benzyl | 3-NHCOCH₃-phenyl |
| 5.14* | 5.14 | HOCH₂— | 4-Cl-benzyl | 3-NHCOCH₃-phenyl |
| 5.15* | 5.15 | (H₃C)₂NCH₂— | 4-Cl-benzyl | 3-NHCOCH₃-phenyl |
| 5.16* | 5.16 | H₃COCH₂— | 4-Cl-benzyl | 3-NHCOCH₃-phenyl |

TABLE 5-continued

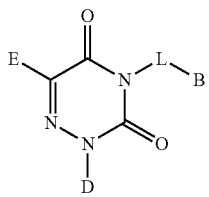

E is not H, CN, $CH_3$ or $OCH_3$

| Compound Nr | Exp. Nr. | E | L-B | D |
|---|---|---|---|---|
| 5.17* | 5.17 | (structure: methyl ester isobutyrate) | 4-Cl-benzyl | 3-NHCOCH$_3$-phenyl |
| 5.18* | 5.18 | (structure: isopropyl ester isobutyrate) | 4-Cl-benzyl | 3-NHCOCH$_3$-phenyl |
| 5.19 | 4.01 | $CH_3O(CH_2)_2O—$ | 4-F-benzyl | 3-NHCOCH$_3$-4-F-phenyl |

Physicochemical Data $^1$H NMR spectra were recorded on a Brucker 500 MHz. Chemical shifts are expressed in parts of million (ppm, δ units). Coupling constants are in units of hertz (Hz) Splitting patterns describe apparent multiplicities and are designated as s (singlet), d (doublet), t (triplet), q (quadruplet), quint (quintuplet), m (multiplet).

LCMS were recorded on a Waters Micromass ZQ 2996 system by the following conditions.

Method $LC_1$:

Column 3.0*50 mm stainless steel packed with 3.5 μm XTerra RP C-18; flow rate 1 mL/min; mobile phase: A phase=0.1% formic acid in water, B phase=0.07% formic acid in acetonitrile. 0-0.5 min (A: 95%, B: 5%), 0.5-6.0 min (A: 0%, B: 100%), 6.0-6.5 min (A: 95%, B: 5%), 6.5-7 min (A: 95%, B: 5%); UV detection Diode Array: 200-400 nm; Injection volume: 10 μL.

Method $LC_2$:

Column 4.6*30 mm stainless steel packed with 1.8 μm Zorbax SB C-18; flow rate 1.5 mL/min; mobile phase: A phase=0.05% formic acid in water, B phase=0.05% formic acid in acetonitrile. 0-3.5 min (A: 0%, B: 10%), 3.5-3.7 min (A: 0%, B: 100%), 3.8-4.5 min (A: 90%, B: 10%); Oven temperature: 30° C.±1° C.; UV detection Diode Array: 200-400 nm; Injection volume: 10 μL.

All mass spectra were taken under electrospray ionisation (ESI) methods.

MS:
Source
  Voltage
    capillarity=3.31 (kV)
    cone=30 (V)
    extraction=6 (V)
    RF lens=0.9 (V)
  Temperature
    source temperature=140° C.
    desolvation temperature=300° C.
Gas flow (N2):
  Desolvation=250 (L/hour)
  Cone=50 (L/hour)

Most of the reactions were monitored by thin-layer chromatography on 0.25 mm Macherey-Nagel silica gel plates (60F-2254), visualized with UV light. Flash column chromatography was performed on silica gel (220-440 mesh, Fluka). Melting point determination was performed on a Buchi B-540 apparatus.

TABLE 6

| Compound Nr | Melting point (° C.) | [MH$^+$] | [MH$^-$] | LC Method | Rt (min) | Appearance |
|---|---|---|---|---|---|---|
| 1.01 | 196 | — | 394.0 | 1 | 4.35 | Yellow solid |
| 1.02 | 127-128 | — | 412.0 | 1 | 4.43 | White solid |
| 1.03 | 118-119 | — | 436.0 | 1 | 4.50 | Yellow solid |
| 1.04 | 228-229 | — | 423.0 | 1 | 4.05 | Yellow solid |

TABLE 6-continued

| Compound Nr | Melting point (° C.) | [MH+] | [MH−] | LC Method | Rt (min) | Appearance |
|---|---|---|---|---|---|---|
| 1.05 | 176-177 | 448.0 | 446.0 | 1 | 4.51 | Yellow solid |
| 1.06 | 135-136 | 432.0 | 430.0 | 1 | 4.31 | Yellow solid |
| 1.07 | 85-91 | — | — | 2 | 2.78 | Yellow solid |
| 2.01 | 171-172 | 371.0 | 369.0 | 1 | 4.02 | Yellow solid |
| 2.02 | — | — | 405.0 | 1 | 4.11 | White solid |
| 2.03 | — | 344.0 | — | 1 | 4.51 | Beige oil |
| 2.04 | 229-230 | 382.0 | 380.0 | 1 | 3.64 | White solid |
| 2.05 | 184-185 | 362.0 | 360.0 | 1 | 3.47 | White solid |
| 2.06 | 189-190 | 387.0 | 385.0 | 1 | 4.08 | White solid |
| 2.07 | 163-164 | 379.0 | 377.0 | 1 | 3.60 | White solid |
| 2.08 | 135-138 | 355.3 | — | 1 | 3.71 | Yellow solid |
| 2.09 | 80-81 | 337.0 | 335.0 | 1 | 3.61 | Yellow solid |
| 2.10 | 80-82 | 405.2 | — | 1 | 4.06 | Yellow solid |
| 2.11 | 92-93 | 395.3 | — | 1 | 3.58 | Yellow solid |
| 2.12 | 96-97 | 387.2 | — | 1 | 4.04 | Yellow solid |
| 2.13 | 85-86 | 367.2 | — | 1 | 3.62 | Yellow solid |
| 2.14 | 168-169 | 415.0 | 413.0 | 1 | 4.0 | Yellow solid |
| 2.15 | 160-161 | 371.0 | 369.0 | 1 | 3.90 | White solid |
| 2.16 | 195-196 | 351.0 | 349.0 | 1 | 3.85 | White solid |
| 2.17 | 135-136 | 379.0 | 377.0 | 1 | 4.32 | White solid |
| 2.18 | — | 365.0 | 363.0 | 1 | 4.05 | Colorless oil |
| 2.19 | — | 372.0 | 370.0 | 1 | 3.29 | White solid |
| 2.20 | 184 | 389.2 | — | 1 | 3.98 | Yellow solid |
| 3.01 | 168 | 384.0 | — | 1 | 4.08 | White solid |
| 3.02 | 204-206 | 351.1 | — | 2 | 2.23 | White solid |
| 3.03 | 147-148 | 402.9 | 400.9 | 2 | 2.49 | White solid |
| 3.04 | 180-181 | 370.0 | 368.0 | 2 | 1.91 | White solid |
| 3.05 | 191-193 | 394.1 | — | 2 | 1.49 | White solid |
| 3.06 | 162 | 369.1 | — | 2 | 2.29 | White solid |
| 3.07 | 128-130 | 387 | — | 2 | 2.31 | White solid |
| 3.08 | 165 | 381.1 | — | 2 | 2.23 | White solid |
| 3.09 | 155 | 393.0 | — | 2 | 2.74 | White solid |
| 3.10 | 98-99 | 328.1 | — | 2 | 2.94 | White solid |
| 3.11 | 182-184 | 401.1 | — | 2 | 2.61 | White solid |
| 3.12 | 169-170 | 420.2 | 418.2 | 2 | 1.65 | White solid |
| 3.13 | 80-84 | 387.1 | 385.1 | 2 | 2.23 | White solid |
| 3.14 | 90-92 | 411.1 | — | 2 | 2.02 | White solid |
| 3.15 | 172-174 | 387.0 | — | 2 | 2.29 | White solid |
| 3.16 | 190-191 | 409.1 | 407.1 | 2 | 2.52 | White solid |
| 3.17 | 150-151 | 401.9 | 399.1 | 2 | 2.50 | White solid |
| 3.18 | 172 | 365.0 | — | 1 | 4.01 | White solid |
| 3.19 | 185-186 | 383.0 | 381.0 | 2 | 2.44 | White solid |
| 3.20 | 134-135 | 399.0 | 397.9 | 2 | 2.26 | White solid |
| 4.01 | 190-191 | 400.9 | — | 1 | 3.98 | White solid |
| 4.02 | 150-151 | 310.0 | — | 1 | 3.67 | White solid |
| 4.03 | 190-191 | 381.0 | — | 1 | 3.89 | White solid |
| 4.04 | 120 | 434.9 | — | 1 | 4.10 | Beige solid |
| 4.05 | 194-196 | 418.9 | — | 1 | 4.03 | White solid |
| 4.06 | 75 | 391.9 | — | 1 | 4.55 | White solid |
| 4.07 | 120 | 434.9 | — | 1 | 4.11 | White solid |
| 4.08 | 150-151 | 373.8 | — | 1 | 4.50 | White solid |
| 4.09 | 234-236 | 429.9 | — | 2 | 2.42 | White solid |
| 4.10 | 110 | 382.0 | — | 2 | 1.14 | Beige solid |
| 4.11 | 159-160 | 399.0 | 397.0 | 2 | 2.35 | White solid |
| 4.12 | — | — | 399.9 | 2 | 2.10 | White solid |
| 4.13 | 215-216 | 402 | 400 | 2 | 1.93 | White solid |
| 4.14 | 120 | 419.8 | — | 2 | 2.15 | Yellow solid |
| 4.15 | 80 | 391.9 | — | 2 | 2.77 | White solid |
| 4.16 | — | 387.9 | — | 2 | 2.82 | Green oil |
| 4.17 | — | 387.9 | — | 2 | 2.77 | Colourless oil |
| 4.18 | — | 401.9 | — | 2 | 2.97 | Yellow oil |
| 4.19 | — | 427.9 | — | 2 | 3.03 | Colourless oil |
| 4.20 | 75 | 404.0 | — | 2 | 2.77 | Yellow solid |
| 4.21 | 80 | 443.0 | — | 2 | 2.45 | White solid |
| 4.22 | — | 402.0 | — | 2 | 2.79 | Yellow oil |
| 4.23 | — | 444.0 | — | 2 | 2.91 | Colourless oil |
| 4.24 | — | 400.0 | — | 2 | 2.67 | Colourless oil |
| 4.25 | — | 401.1 | — | 2 | 1.74 | Colourless oil |
| 4.26 | — | 427.1 | — | 2 | 1.87 | Colourless oil |
| 4.27 | 135 | 415.0 | — | 2 | 2.18 | White solid |
| 4.28 | 153-155 | 346.1 | — | 2 | 2.70 | White solid |
| 4.29 | — | 441.1 | — | 2 | 2.08 | Colourless oil |
| 4.30 | — | 445.2 | — | 2 | 1.97 | Colourless oil |
| 4.31 | 181 | 433.0 | — | 2 | 2.21 | White solid |
| 4.32 | — | 369.0 | — | 2 | 2.64 | Yellow oil |
| 4.33 | — | 391.9 | — | 2 | 2.41 | White oil |
| 4.34 | 192-194 | 377.9 | — | 2 | 3.00 | White solid |

TABLE 6-continued

| Compound Nr | Melting point (° C.) | [MH+] | [MH−] | LC Method | Rt (min) | Appearance |
|---|---|---|---|---|---|---|
| 4.35 | 143-144 | 310.0 | — | 2 | 2.62 | White solid |
| 4.36 | — | 409.0 | 407.0 | 2 | 2.62 | Yellow solid |
| 4.37 | 119 | 443.0 | 441.0 | 2 | 2.64 | Brown solid |
| 4.38 | 131 | 451.0 | 449.0 | 2 | 2.53 | Brown solid |
| 4.39 | 130-131 | 410 | 408 | 2 | 1.70 | Yellow solid |
| 4.40 | >290 | 443 | 441 | 2 | 2.64 | Brown solid |
| 4.41 | 174-175 | — | 365.1 | 2 | 2.15 | White solid |
| 4.42 | — | 415.0 | — | 2 | 2.46 | White solid |
| 4.43 | 158 | 410.0 | — | 2 | 1.59 | White solid |
| 4.44 | 195-196 | 385.1 | 383.1 | 2 | 2.21 | White solid |
| 4.45 | 159-161 | 397.0 | — | 2 | 2.13 | White solid |
| 4.46 | 120 | 418.0 | — | 2 | 1.61 | White solid |
| 4.47 | 177 | 425.0 | — | 2 | 2.44 | White solid |
| 4.48 | 174-175 | 441.1 | — | 2 | 1.94 | White solid |
| 4.49 | 148-150 | 436.1 | — | 2 | 1.61 | White solid |
| 4.50 | 143-144 | 344.0 | — | 2 | 2.83 | White solid |
| 4.51 | 154-156 | 386.1 | 384.1 | 2 | 1.81 | White solid |
| 4.52 | 118-120 | 420.0 | 418.0 | 2 | 2.10 | White solid |
| 4.53 | 110-112 | 411.1 | 409.1 | 2 | 1.20 | White solid |
| 4.54 | 142 | 409.0 | — | 2 | 2.13 | White solid |
| 4.55 | 209-212 | 403.1 | — | 2 | 2.25 | White solid |
| 4.56 | 216-217 | 403.1 | — | 2 | 2.23 | White solid |
| 4.57 | 164 | 398.1 | — | 2 | 1.86 | White solid |
| 4.58 | 168 | — | 366.1 | 2 | 1.13 | White solid |
| 4.59 | 249 | — | 431.1 | 2 | 2.10 | Orange Solid |
| 4.60 | 234 | 433.0 | — | 2 | 2.22 | White solid |
| 4.61 | 214 | 418.1 | — | 2 | 1.70 | White solid |
| 4.62 | 170 | 415.0 | — | 2 | 2.16 | White solid |
| 4.63 | 125 | 433.0 | — | 2 | 2.29 | White solid |
| 4.64 | 168 | 433.0 | — | 2 | 2.23 | White solid |
| 4.65 | 128-130 | 420.1 | 418.1 | 2 | 2.36 | White solid |
| 4.66 | 197 | 415.0 | — | 2 | 2.19 | White solid |
| 4.67 | 110-112 | 346.1 | — | 2 | 2.71 | White solid |
| 4.68 | 172-174 | 346.0 | — | 2 | 2.67 | White solid |
| 4.69 | 143-145 | 362.0 | — | 2 | 2.85 | White solid |
| 4.80 | — | 397.0 | — | 2 | 2.14 | Colourless oil |
| 4.90 | — | 368.0 | — | 2 | 2.69 | White solid |
| 4.91 | 144-145 | 393.0 | — | 2 | 2.83 | White solid |
| 4.92 | 197-198 | 419.0 | 418.0 | 2 | 2.38 | White solid |
| 4.93 | 70-72 | 394.0 | — | 2 | 2.93 | White solid |
| 4.94 | 119-120 | 346.0 | — | 2 | 2.64 | White solid |
| 4.95 | 121-122 | 427.9 | — | 2 | 3.11 | White solid |
| 4.96 | 148 | 433.0 | — | 2 | 2.24 | White solid |
| 4.97 | 181 | 427.0 | — | 2 | 2.16 | White solid |
| 4.98 | 140-142 | 396.0 | — | 2 | 2.88 | White solid |
| 4.99 | 65-67 | 414.0 | — | 2 | 2.83 | White solid |
| 4.100 | 251-253 | 374.1 | — | 2 | 1.92 | White solid |
| 4.101 | 138 | 408.0 | — | 2 | 1.82 | White solid |
| 4.102 | 209 | 408.0 | — | 2 | 1.81 | White solid |
| 4.103 | 109 | 415.0 | — | 2 | 2.16 | White solid |
| 4.104 | 65-66 | 335.1 | — | 2 | 2.45 | White solid |
| 4.105 | 164-166 | 335.1 | — | 2 | 2.43 | White solid |
| 4.106 | 181 | 417 | — | 2 | 2.18 | White solid |
| 4.107 | 166-168 | 340.1 | — | 2 | 2.03 | White solid |
| 4.108 | 78-80 | 402.0 | — | 2 | 2.67 | White solid |
| 4.109 | 112-114 | 368.0 | — | 2 | 2.68 | White solid |
| 4.110 | 158-160 | 314.1 | — | 2 | 1.00 | White solid |
| 4.111 | 196 | 397.0 | — | 2 | 2.14 | White solid |
| 4.112 | 187 | 439.2 | — | 2 | 1.17 | White solid |
| 4.113 | 131-133 | 350.0 | — | 2 | 2.82 | White solid |
| 4.114 | 83-85 | 400.0 | — | 2 | 3.11 | White solid |
| 4.115 | 172-174 | 346 | — | 2 | 2.67 | White solid |
| 4.116 | 204 | 410 | — | 2 | 1.63 | White solid |
| 4.117 | 186-188 | 427 | — | 2 | 2.14 | White solid |
| 4.118 | 170-172 | 453 | 451 | 2 | 2.46 | White solid |
| 4.119 | 105 | 436.1 | — | 2 | 2.06 | Brown solid |
| 4.120 | 186 | 392 | — | 2 | 2.01 | White solid |
| 4.121 | 120 | 422 | — | 2 | 1.88 | Yellow solid |
| 4.122 | 162-163 | 429.0 | 427.0 | 2 | 1.96 | White solid |
| 4.123 | 167-168 | 428 | — | 2 | 2.06 | White solid |
| 4.124 | 137-138 | — | 420.2 | 2 | 2.00 | Yellow foam |
| 4.125 | 137 | 415 | — | 2 | 2.11 | White solid |
| 4.126 | 175 | 427.0 | — | 2 | 2.22 | White solid |
| 4.127 | 184 | 447.0 | — | 2 | 2.47 | White solid |
| 4.128 | 175 | 402.0 | — | 2 | 1.93 | White solid |
| 4.129 | 140 | 410.1 | — | 2 | 1.88 | White solid |
| 4.130 | 174-175 | 451 | 449 | 2 | 2.34 | White solid |

TABLE 6-continued

| Compound Nr | Melting point (° C.) | [MH+] | [MH−] | LC Method | Rt (min) | Appearance |
|---|---|---|---|---|---|---|
| 4.131 | 165-166 | 487 | 485 | 2 | — | White solid |
| 4.132 | 165-167 | 487 | 485 | 2 | — | White solid |
| 4.133 | 157 | 414.0 | — | 1 | 4.09 | White solid |
| 4.134 | 163 | 426.0 | — | 2 | 2.22 | Yellow solid |
| 4.135 | 138 | 427 | 425 | 2 | 2.13 | White solid |
| 4.136 | 60 | 411.1 | — | 2 | 2.19 | White solid |
| 4.137 | — | 423.0 | — | 2 | 2.20 | Colourless oil |
| 4.138 | — | 429 | — | 2 | 2.22 | Colourless oil |
| 4.139 | — | 447 | — | 2 | 2.28 | Colourless oil |
| 4.140 | 141-142 | 324 | — | 2 | 2.70 | White solid |
| 4.141 | 143 | 431.0 | — | 2 | 2.48 | White solid |
| 4.142 | 146 | 443.0 | — | 2 | 2.43 | White solid |
| 4.143 | 164-165 | — | — | 2 | 2.45 | White solid |
| 4.144 | 176-178 | — | — | 2 | 2.82 | White solid |
| 4.145 | 91-93 | 427.0 | — | 2 | 2.64 | White solid |
| 4.146 | 163-165 | 426.0 | — | 2 | 2.88 | White solid |
| 4.147 | 125-127 | 354 | — | 2 | 2.66 | White solid |
| 4.148 | 123-125 | 342 | — | 2 | 2.71 | White solid |
| 4.149 | 142-144 | 384.1 | — | 2 | 2.45 | White solid |
| 4.150 | 138-140 | 354 | — | 2 | 2.67 | White solid |
| 4.151 | 172-174 | 411.1 | — | 2 | 2.18 | White solid |
| 4.152 | 153-155 | 399.1 | — | 2 | 2.25 | White solid |
| 4.153 | 136-138 | 411.1 | — | 2 | 2.20 | White solid |
| 4.154 | 104 | 385.0 | — | 2 | 2.14 | White solid |
| 4.155 | 173 | 432.9 | — | 2 | 2.20 | White solid |
| 4.156 | 156-158 | 451 | — | 2 | 2.25 | Beige solid |
| 4.157 | 196-198 | 451 | — | 2 | 2.34 | Beige solid |
| 4.158 | 155-157 | 399 | — | 2 | 2.30 | White solid |
| 4.159 | 171 | 437.9 | — | 2 | 2.14 | White solid |
| 4.160 | 156-157 | 415.9 | 413.0 | 2 | 2.16 | White solid |
| 4.161 | 110 | 451 | — | 2 | 2.28 | White solid |
| 4.162 | 210-212 | 440 | — | 2 | 2.05 | Yellow foam |
| 4.163 | 207 | 445 | — | 2 | 2.24 | White solid |
| 4.164 | 176-177 | 446.1 | — | 2 | 2.13 | White solid |
| 4.165 | 180-182 | 450.9 | — | 2 | 2.36 | White solid |
| 4.166 | — | 338.1 | — | 2 | 2.83 | Colourless oil |
| 4.167 | — | 383 | — | 2 | 2.63 | White oil |
| 4.168 | 215-217 | 410 | — | 2 | 2.10 | White solid |
| 4.169 | 169-171 | 415 | — | 2 | 2.19 | White solid |
| 4.170 | 134 | 428 | — | 2 | 2.15 | White solid |
| 4.171 | 141 | 411 | — | 2 | 1.83 | White solid |
| 4.172 | 170-171 | 428.1 | — | 2 | 1.43 | White solid |
| 4.173 | 160-161 | 416 | — | 2 | 1.90 | White solid |
| 4.174 | 147-148 | 436 | — | 2 | 1.48 | White solid |
| 4.175 | 122 | 425 | — | 2 | 2.28 | White solid |
| 4.176 | 169-171 | 417 | — | 2 | 2.32 | White solid |
| 4.177 | 116-118 | 416.9 | — | 2 | 2.33 | White solid |
| 4.178 | 193-194 | 454 | — | 2 | 2.60 | Pink solid |
| 4.179 | 198-199 | 469.9 | — | 2 | 2.12 | White solid |
| 4.180 | 194-195 | 450.9 | — | 2 | 2.14 | Yellow solid |
| 4.181 | 86-89 | 452.9 | — | 2 | 2.46 | White solid |
| 4.182 | 138 | 429 | — | 2 | 2.13 | White solid |
| 4.183 | 209 | 425 | — | 2 | 1.88 | White solid |
| 4.184 | 173-176 | 432.9 | — | 2 | 2.20 | Beige solid |
| 4.185 | 108-111 | 403 | — | 2 | 2.22 | White solid |
| 4.186 | 200-202 | 430 | — | 2 | 2.19 | White solid |
| 4.187 | 273-275 | 450.9 | — | 2 | 2.12 | Beige solid |
| 4.188 | 158-159 | 432.9 | — | 2 | 2.28 | Beige solid |
| 4.189 | 161 | 428 | 426.9 | 2 | 1.75 | Yellow solid |
| 4.190 | 191-193 | 420.9 | — | 2 | 1.90 | White solid |
| 4.191 | 168-170 | 443 | — | 2 | 2.12 | Yellow solid |
| 4.192 | 188-190 | 420.9 | — | 2 | 1.90 | Orange solid |
| 4.193 | 188-190 | 420.9 | — | 2 | 1.72 | Yellow solid |
| 4.194 | 169 | 427 | — | 2 | 2.16 | White solid |
| 4.195 | 211 | 427 | — | 2 | 2.15 | White solid |
| 4.196 | 94 | 398 | 396 | 2 | 1.53 | Yellow solid |
| 4.197 | 230-231 | 422 | 420 | 2 | 2.08 | White solid |
| 4.198 | 194-195 | 381 | — | 2 | 2.24 | White solid |
| 4.199 | 219 | 433.9 | 431.9 | 2 | 2.25 | White solid |
| 4.200 | 207-208 | 468.9 | — | 2 | 2.17 | White solid |
| 4.201 | 142-144 | 420.9 | — | 2 | 2.30 | White solid |
| 4.202 | 239-241 | 439 | — | 2 | 1.93 | Pink solid |
| 4.203 | 143-146 | 454.8 | 452.9 | 2 | 2.52 | White solid |
| 4.204 | 136-137 | 446 | 443.9 | 2 | 2.11 | Beige solid |
| 4.205 | 132 | 419.9 | 416.9 | 2 | 2.36 | White solid |
| 4.206 | 184 | 455 | — | 2 | 2.41 | White solid |
| 4.207 | 136-137 | 400.9 | — | 2 | 2.68 | Beige solid |

TABLE 6-continued

| Compound Nr | Melting point (° C.) | [MH+] | [MH−] | LC Method | Rt (min) | Appearance |
|---|---|---|---|---|---|---|
| 4.208 | 120 | 418.9 | — | 2 | 2.36 | White solid |
| 4.209 | 160 | 408.9 | — | 2 | 1.83 | White solid |
| 4.210 | 162-163 | 437 | 435 | 2 | 2.41 | White solid |
| 4.211 | 190-191 | 453 | 452.9 | 2 | 2.56 | White solid |
| 4.212 | 226-227 | 449.9 | 447.9 | 2 | 2.38 | White solid |
| 4.213 | 197 | 454.8 | 452.9 | 2 | 2.52 | Yellow solid |
| 4.214 | 191 | 448.9 | — | 2 | 2.38 | White solid |
| 4.215 | 195-196 | 448.9 | — | 2 | 2.33 | White solid |
| 4.216 | 163-164 | 435 | — | 2 | 2.31 | White solid |
| 4.217 | 166 | 416.0 | 414.0 | 2 | 2.02 | White solid |
| 4.218 | 232-233 | 464.9 | — | 2 | 2.53 | White solid |
| 4.219 | 220-221 | 464.9 | 462.9 | 2 | 2.49 | White solid |
| 4.220 | 177 | 451 | 449 | 2 | 2.32 | Brown solid |
| 4.221 | 197-198 | 454.9 | 452.9 | 2 | 2.55 | White solid |
| 4.222 | 184-185 | 437.0 | 435.9 | 2 | 2.39 | White solid |
| 4.223 | 185-186 | 470.9 | 467.0 | 2 | 2.62 | White solid |
| 4.224 | 147 | 463.9 | 462 | 2 | 2.44 | White solid |
| 4.225 | 154 | 480 | 478 | 2 | 2.6 | White solid |
| 4.226 | 171 | 462 | 460 | 2 | 2.33 | Yellow solid |
| 4.227 | 158-159 | 401.0 | 399.1 | 2 | 2.31 | White solid |
| 4.228 | 108 | 446 | — | 2 | 2.20 | White solid |
| 4.229 | 179 | 449 | — | 2 | 2.35 | Beige solid |
| 4.230 | 180-181 | 471.1 | 469.0 | 2 | 2.51 | White solid |
| 4.231 | 201-202 | 464 | 462 | 2 | 2.22 | White solid |
| 4.232 | 203 | 480 | 478 | 2 | 2.44 | White solid |
| 4.233 | 161 | 487.9 | 485.0 | 2 | 2.62 | Beige solid |
| 4.234 | 160-161 | 444.1 | 442.0 | 2 | 1.56 | White solid |
| 4.235 | 150-151 | 503.0 | 501.9 | 2 | 2.67 | Beige solid |
| 4.236 | 179 | 431 | — | 2 | 2.30 | Beige solid |
| 4.237 | 236-237 | 443 | 441 | 2 | 2.30 | White solid |
| 4.238 | 205-206 | 467 | 465 | 2 | 2.49 | White solid |
| 4.239 | 129-130 | 362.0 | — | 2 | 2.83 | White solid |
| 4.240 | 219 | 503/505/506 | — | 2 | 2.73 | White solid |
| 4.241 | 188 | 477 | — | 2 | 2.65 | White solid |
| 4.242 | 218 | 456.9 | 455 | 2 | 2.06 | White solid |
| 4.243 | 182 | 463 | 461 | 2 | 2.78 | White solid |
| 4.244 | 191 | 488 | — | 2 | 2.09 | White solid |
| 4.245 | 192 | 435 | — | 2 | 2.01 | White solid |
| 4.246 | 119 | 455 | — | 2 | 2.40 | White solid |
| 4.247 | 99 | 455 | — | 2 | 2.46 | White solid |
| 4.248 | 96 | 445 | — | 2 | 2.68 | White solid |
| 4.249 | 113 | 462 | — | 2 | 2.25 | White solid |
| 4.250 | 234.5 | 440 | — | 2 | 2.23 | White solid |
| 4.251 | 161 | — | — | 2 | 3.01 | White solid |
| 4.252 | 180 | 467 | — | 2 | 2.40 | White solid |
| 4.253 | 114-115 | 410/412 | — | 2 | 2.84 | White solid |
| 4.254 | 205-206 | 494.1 | — | 2 | 2.40 | White solid |
| 4.255 | 167-168 | 457.2 | 455.2 | 2 | 2.72 | White solid |
| 4.256 | 87-88 | 400.2 | — | 2 | 3.16 | White solid |
| 4.257 | 120 | 488.1 | — | 2 | 2.69 | White solid |
| 4.258 | 150-151 | 471 | — | 2 | 2.69 | White solid |
| 4.259 | 137 | 479 | — | 2 | 2.55 | Beige solid |
| 4.260 | 100-105 | 455.0 | — | 2 | 2.25 | White solid |
| 4.261 | 158 | 458 | — | 2 | 2.16 | Beige solid |
| 4.262 | 65 | — | — | 2 | 2.69 | White solid |
| 4.263 | 154 | 504 | — | 2 | 2.33 | White solid |
| 4.264 | 184-185 | 496.1 | — | 2 | 2.60 | White solid |
| 4.265 | — | 420 | — | 2 | 3.09 | Beige solid |
| 4.266 | 69 | 485/486 | — | 2 | 2.59 | White solid |
| 4.267 | 155 | 463 | — | 2 | 2.39 | White solid |
| 4.268 | 148 | 488 | — | 2 | 2.14 | Beige solid |
| 4.269 | 179 | 462.1 | 460.0 | 2 | 2.38 | White solid |
| 5.01 | 178 | 413.0 | — | 2 | 2.82 | White solid |
| 5.02 | 184 | 399.0 | — | 2 | 2.63 | White solid |
| 5.03 | 164 | 427.0 | — | 2 | 2.96 | White solid |
| 5.04 | 76-78 | — | — | 2 | 2.71 | White solid |
| 5.05 | 103 | 457.9 | — | 2 | 1.75 | White solid |
| 5.06 | 145 | 453.0 | — | 2 | 2.17 | White solid |
| 5.07 | 148 | 444.8 | — | 2 | 2.36 | White solid |
| 5.08 | 186-187 | 399.9 | — | 1 | 3.99 | Yellow solid |
| 5.09 | 105 | 414.9 | — | 1 | 4.18 | White solid |
| 5.10 | 197-198 | 430.9 | 428.9 | 1 | 4.22 | Beige solid |
| 5.11 | 190-191 | 428.9 | — | 1 | 4.34 | Beige solid |
| 5.12 | 202 | 450.7 | — | 1 | 4.3 | Yellow solid |
| 5.13 | 189-190 | 414.0 | — | 1 | 4.39 | Yellow solid |
| 5.14 | — | 400.8 | — | 2 | 2.07 | White solid |
| 5.15 | 143 | 427.9 | — | 2 | 1.74 | Beige solid |

TABLE 6-continued

| Compound Nr | Melting point (° C.) | [MH+] | [MH−] | LC Method | Rt (min) | Appearance |
|---|---|---|---|---|---|---|
| 5.16 | 97 | 414.8 | — | 2 | 2.36 | Yellow solid |
| 5.17 | 193 | 428 | — | 1 | 3.95 | Beige solid |
| 5.18 | 183 | 457 | — | 2 | 2.65 | Beige solid |
| 5.19 | 184-186 | 447.4 | — | 2 | 2.25 | Pink solid |

TABLE 7

NMR-data

| Compound Nr | NMR-data |
|---|---|
| 1.01 | $^1$H-NMR (DMSO-$d_6$), δ (ppm): 10.21 (1H, bs), 7.89-7.88 (1H, m), 7.60-7.57 (1H, m), 7.47-7.39 (5H, m), 7.16-7.13 (1H, m), 4.99 (2H, m), 2.05 (3H, s) |
| 1.02 | $^1$H-NMR (DMSO-$d_6$), δ (ppm): 9.97 (1H, bs), 8.22-8.19 (1H, m), 7.60-7.57 (1H, m), 7.46-7.39 (5H, m), 7.27-7.21 (1H, m), 4.98 (2H, m), 2.11 (3H, s) |
| 1.03 | $^1$H-NMR (DMSO-$d_6$), δ (ppm): 10.12 (1H, bs), 7.76-7.75 (1H, m), 7.50-7.47 (1H, m), 7.35-7.18 (11H, m), 7.05-7.02 (1H, m), 6.99 (1H, m), 4.95 (2H, s), 1.96 (3H, s) |
| 1.04 | $^1$H-NMR (DMSO-$d_6$), δ (ppm): 9.97 (1H, s), 8.22-8.19 (3H, m), 7.72-7.69 (2H, m), 7.41-7.39 (1H, m), 7.27-7.22 (1H, m), 5.13 (2H, s), 2.11 (3H, s) |
| 1.05 | $^1$H-NMR (DMSO-$d_6$), δ (ppm): 9.97 (1H, s), 8.23-8.20 (1H, dd), 7.69-7.68 (1H, d), 7.63-7.61 (1H, d), 7.46-7.39 (2H, m), 7.27-7.21 (1H, m), 5.00 (2H, s), 2.12 (3H, s) |
| 1.06 | $^1$H-NMR (DMSO-$d_6$), δ (ppm): 9.97 (1H, s), 8.23-8.18 (1H, m), 7.54-7.39 (3H, m), 7.32-7.21 (2H, m), 5.01 (2H, s), 2.11 (3H, s) |
| 1.07 | $^1$H-NMR (DMSO-$d_6$), δ (ppm): 7.56 (2H, m), 7.41 (2H, m), 7.3 (1H, s), 7.17 (1H, dd), 6.72 (1H, d), 4.92 (2H, s), 4.51 (2H, t), 3.15 (2H, t) |
| 2.01 | $^1$H-NMR (CDCl$_3$), δ (ppm): 7.82 (1H, s), 7.54 (2H, s), 7.46-7.44 (2H, m), 7.37-7.35 (2H, m), 7.32-7.29 (2H, m), 7.21-7.18 (1H, m), 5.08 (2H, s), 2.13 (3H, s) |
| 2.02 | $^1$H-NMR (DMSO-$d_6$), δ (ppm): 10.00 (1H, sl), 7.82 (1H, s), 7.40 (6H, m), 7.23 (2H, m), 4.98 (2H, s), 3.02 (3H, s) |
| 2.03 | $^1$H-NMR (CDCl$_3$), δ (ppm): 7.46 (1H, m), 7.42 (1H, m), 7.39 (1H, m), 7.36-7.33 (1H, m), 7.24-7.19 (3H, m), 7.01-6.94 (2H, m), 5.04 (1H, s), 3.75 (3H, s) |
| 2.04 | $^1$H-NMR (DMSO-$d_6$), δ (ppm): 10.14 (1H, bs), 8.21-8.19 (2H, d, 8.7 Hz), 7.86-7.85 (2H, m), 7.68-7.65 (2H, d, 8.7 Hz), 7.55-7.52 (1H, d, 8.2 Hz), 7.42-7.36 (1H, t, 8.1 Hz), 7.19 (1H, d, 8.2 Hz), 5.12 (2H, s), 2.05 (3H, s) |
| 2.05 | $^1$H-NMR (DMSO-$d_6$), δ (ppm): 10.14 (1H, bs), 7.85-7.80 (4H, m), 7.60-7.55 (3H, m), 7.41-7.36 (1H, t, 7.94 Hz), 7.18-7.16 (1H, dm, 7.94 Hz), 5.07 (2H, s), 2.05 (3H, s) |
| 2.06 | $^1$H-NMR (DMSO-$d_6$), δ (ppm): 10.13 (1H, bs), 7.91-7.83 (6H, m), 7.56-7.49 (4H, m), 7.41-7.35 (1H, t), 7.20-7.16 (1H, m), 5.16 (2H, s), 2.03 (3H, s) |
| 2.07 | $^1$H-NMR (DMSO-$d_6$), δ (ppm): 10.14 (1H, bs), 8.07-8.04 (2H, m), 7.89-7.85 (2H, m), 7.66-7.62 (1H, m), 7.55-7.52 (1H, m), 7.42-7.37 (1H, t), 7.21-7.18 (1H, m), 5.11 (2H, s), 2.05 (3H, s) |
| 2.08 | $^1$H-NMR (DMSO-$d_6$), δ (ppm): 10.05 (1H, s), 7.75(1H, s), 7.71 (1H, s), 7.47 (2H, d, J = 7.13 Hz), 7.32 (4H, m), 7.07(1H, t, J = 7.13 Hz), 4.98 (2H, s), 1.98(3H, s) |
| 2.09 | $^1$H-NMR (DMSO-$d_6$), δ (ppm): 10.14 (1H, bs), 7.84-7.81 (2H, m), 7.57-7.54 (1H, dm, 8.19 Hz), 7.41-7.27 (6H, m), 7.19-7.15 (1H, dm, 8.19 Hz), 5 (2H, s), 2.05 (3H, s) |
| 2.10 | $^1$H-NMR (DMSO-$d_6$), δ (ppm): 10.14 (1H, bs), 7.84-7.83 (1H, m), 7.81 (1H, s), 7.56-7.51 (3H, m), 7.41-7.33 (3H, m), 7.18-7.15 (1H, dm), 4.96 (2H, s), 2.05 (3H, s) |
| 2.11 | $^1$H-NMR (DMSO-$d_6$), δ (ppm): 10.13 (1H, s), 7.94-7.82 (4H, m), 7.57-7.47 (3H, m), 7.42-7.35 (1H, m), 7.18-7.15 (1H, m), 5.06 (2H, s), 3.83 (3H, s), 2.04 (3H, s) |
| 2.12 | $^1$H-NMR (DMSO-$d_6$), δ (ppm): 10.15 (1H, s), 8.22-8.19 (1H, m), 8.01-7.96 (1H, m), 7.91-7.83 (2H, m), 7.65-7.52 (3H, m), 7.47-7.36 (2H, m), 7.22-7.18 (1H, m), 5.49 (2H, s), 2.05 (3H, s) |
| 2.13 | $^1$H-NMR (CDCl$_3$), δ (ppm): 7.77 (1H, bs), 7.55-7.34 (6H, m), 7.24-7.18 (1H, m), 6.86-6.81 (2H, m), 5.08 (2H, s), 3.78 (3H, s), 2.15 (3H, s) |

TABLE 7-continued

NMR-data

| Compound Nr | NMR-data |
|---|---|
| 2.14 | $^1$H-NMR (DMSO-$d_6$), δ (ppm): 10.14 (1H, bs), 7.84-7.83 (1H, m), 7.81 (1H, s), 7.56-7.51 (3H, m), 7.41-7.33 (3H, m), 7.18-7.15 (1H, dm), 4.96 (2H, s), 2.05 (3H, s) |
| 2.15 | $^1$H-NMR (DMSO-$d_6$), δ (ppm): 10.14 (1H, bs), 7.85-7.81 (2H, m), 7.56-7.53 (1H, d, 8.7 Hz), 7.46 (1H, s), 7.42-7.35 (4H, m), 7.18-7.16 (1H, d, 8.7 Hz), 4.99 (2H, s), 2.05 (3H, s) |
| 2.16 | $^1$H-NMR (DMSO-$d_6$), δ (ppm): 10.14 (1H, bs), 7.82-7.77 (2H, m), 7.56-7.51 (1H, m), 7.41-7.36 (1H, m), 7.27-7.22 (2H, m), 7.17-7.10 (3H, m), 4.95 (2H, s), 2.27 (3H, s), 2.06 (3H, s) |
| 2.17 | $^1$H-NMR (DMSO-$d_6$), δ (ppm): 10.14 (1H, bs), 7.83-7.79 (2H, m), 7.57-7.54 (1H, m), 7.42-7.36 (1H, m), 7.31-7.29 (2H, m), 7.23-7.14 (3H, m), 4.96 (2H, s), 2.97-2.94 (1H, m), 2.05 (3H, s), 1.19-1.16 (6H, m) |
| 2.18 | $^1$H-NMR (DMSO-$d_6$), δ (ppm): 10.14 (1H, bs), 7.83-7.80 (2H, m), 7.57-7.54 (1H, d, 8.7 Hz), 7.42-7.36 (1H, t, 8.7 Hz), 7.18-7.14 (2H, m), 7.08 (2H, s), 4.92 (2H, s), 2.19-2.18 (6H, m), 2.05 (3H, s) |
| 2.19 | $^1$H-NMR (DMSO-$d_6$), δ (ppm): 10.14 (1H, bs), 8.46-8.45 (1H, s), 7.89-7.81 (3H, m), 7.55-7.48 (2H, m), 7.41-7.36 (1H, t, 8.5 Hz), 7.18-7.15 (1H, d, 8.5 Hz), 5.01 (2H, s), 2.05 (3H, s) |
| 2.20 | $^1$H-NMR (DMSO-$d_6$), δ (ppm): 10.14 (1H, bs), 7.85-7.81 (2H, m), 7.57-7.13 (6H, m), 5 (2H, s), 2.06-2.03 (3H, m) |
| 3.01 | $^1$H-NMR (DMSO-$d_6$), δ (ppm): 10.13 (1H, bs), 7.78 (1H, t, 2 Hz), 7.38 (1H, m), 7.25 (1H, d, 8 Hz), 7.14 (3H, m), 4.97 (2H, s), 2.68 (3H, s), 2.19 (3H, s), 2.04 (3H, s) |
| 3.02 | $^1$H-NMR (DMSO-$d_6$), δ (ppm): 0.14 (1H, bs), 7.8 (1H, t), 7.58-7.56 (1H, d), 7.41-7.28 (7H, m), 7.18-7.16 (1H, d), 5.03 (2H, s), 2.2 (3H, s), 2.05 (3H, s) |
| 3.03 | $^1$H-NMR (DMSO-$d_6$), δ (ppm): 10.13 (1H, s), 7.81 (1H, s), 7.60-7.10 (6H, m), 5.01 (2H, s), 2.20 (3H, s), 2.05 (3H, s) |
| 3.04 | $^1$H-NMR (DMSO-$d_6$), δ (ppm): 10.13 (1H, s), 8.27 (1H, s), 7.99 (1H, t), 7.81 (1H, s), 7.55 (1H, d), 7.37 (1H, t), 7.16 (2H, m), 5.03 (2H, s), 2.19 (3H, s), 2.04 (3H, s) |
| 3.05 | $^1$H-NMR (DMSO-$d_6$), δ (ppm): 10.1 (1H, s) 8.5-7.1 (7H, m), 5.0 (2H, s), 3.0-2.9 (1H, m), 3.2 (3H, s) 2.2 (3H, s), 2.1 (3H, s), 1.2 (6H, s) |
| 3.06 | $^1$H-NMR (DMSO-$d_6$), δ (ppm): 10.1 (1H, s) 7.8-7.0 (8H, m), 5.0 (2H, s), 4.3 (2H, t), 3.7 (2H, t), 3.4 (3H, s), 2.2 (3H, s), 2.0 (3H, s) |
| 3.07 | $^1$H-NMR (DMSO-$d_6$), δ (ppm): 9.89 (1H, bs), 8.10 (1H, m), 7.25 (6H, m), 4.98 (2H, s), 2.18 (3H, s), 2.10 (3H, s) |
| 3.08 | $^1$H-NMR (DMSO-$d_6$), δ (ppm): 10.1 (1H, s) 7.8-6.9 (8H, m), 5.0 (2H, s), 3.7 (3H, s), 2.2 (3H, s), 2.1 (3H, s) |
| 3.09 | $^1$H-NMR (DMSO-$d_6$), δ (ppm): 10.1 (1H, s) 7.8-7.1 (8H, m), 5.0 (2H, s), 3.7 (3H, s), 2.2 (3H, s), 2.1 (3H, s), 1.2 (6H, d) |
| 3.10 | $^1$H-NMR (DMSO-$d_6$), δ (ppm): 7.56-7.28 (9H, m), 5.01 (2H, s), 2.19 (3H, s) |
| 3.11 | $^1$H-NMR (DMSO-$d_6$), δ (ppm): 10.1 (1H, s) 8.0-7.2 (11H, m), 5.0 (2H, s), 2.2 (3H, s), 2.1 (3H, s) |
| 3.12 | $^1$H-NMR (DMSO-$d_6$), δ (ppm): 10.13 (1H, s), 8.50 (1H, s), 7.79 (1H, s), 7.67 (1H, d), 7.37 (1H, t), 7.23 (1H, d), 7.15 (1H, s), 4.99 (2H, s), 3.12 (1H, q), 2.19 (3H, s), 2.04 (3H, s), 2.00-1.86 (2H, m), 1.82-1.52 (6H, m) |
| 3.13 | $^1$H-NMR (DMSO-$d_6$), δ (ppm): 10.13 (1H, s), 7.81 (1H, s), 7.59-7.51 (1H, d), 7.50-7.30 (3H, m), 7.29-7.20 (1H, m), 7.19-7.12 (1H, d), 4.99 (2H, s), 2.20 (3H, s), 2.04 (3H, s) |
| 3.14 | $^1$H-NMR (DMSO-$d_6$), δ (ppm): 10.1 (1H, s), 7.8 (1H, s), 7.6-7.5 (1H, d), 7.4 (1H, t), 7.2 (1H, s), 7.0 (1H, t), 6.9 (2H, s), 5.0 (2H, s), 3.7 (6H, s), 2.2 (3H, s), 2.1 (3H, s) |
| 3.15 | $^1$H-NMR (DMSO-$d_6$), δ (ppm): 10.1 (1H, s), 7.8 (1H, s), 7.6-7.5 (1H, d), 7.5-7.4 (2H, m), 7.2-7.1 (1H, t) 7.1 (1H, d), 7.0 (1H, t), 5.0 (2H, s), 3.7 (6H, s), 2.2 (3H, s), 2.1 (3H, s) |

TABLE 7-continued

NMR-data

| Compound Nr | NMR-data |
|---|---|
| 3.16 | $^1$H-NMR (DMSO-d$_6$), δ (ppm): 10.13 (1H, s), 7.78 (1H, s), 7.56 (1H, d), 7.37 (1H, t), 7.29 (2H, d), 7.15 (1H, d), 6.85 (2H, d), 4.93 (2H, s), 4.57 (1H, q), 2.18 (3H, s), 2.04 (3H, s), 1.23 (6H, d) |
| 3.17 | $^1$H-NMR (DMSO-d$_6$), δ (ppm): 10.14 (1H, s), 8.22 (1H, d), 7.98 (1H, d), 7.91-7.80 (2H, m), 7.67-7.30 (6H, m), 7.20 (1H, d), 5.51 (2H, s), 2.24 (3H, s), 2.05 (3H, s) |
| 3.18 | $^1$H-NMR (DMSO-d$_6$), δ (ppm): 10.12 (1H, bs), 7.80 (1H, t, 2 Hz), 7.55 (1H, d, 8 Hz), 7.37 (5H, m), 7.15 (1H, dd, 1 Hz, 8 Hz), 5.00 (2H, s), 2.19 (3H, s), 2.05 (3H, s) |
| 3.19 | $^1$H-NMR (DMSO-d$_6$), δ (ppm): 9.89 (1H, bs), 8.10-8.06 (1H, m), 7.40-7.35 (1H, m), 7.27-7.24 (3H, m), 7.14-7.11 (2H, m), 4.96 (2H, s), 2.27 (3H, s), 2.18 (3H, s), 2.10 (3H, s) |
| 3.20 | $^1$H-NMR (DMSO-d$_6$), δ (ppm): 9.89 (1H, s), 8.11 (1H, s), 7.42-7.18 (3H, m), 6.98-6.89 (2H, m), 6.85 (1H, d), 4.98 (2H, s), 3.73 (3H, s), 2.19 (3H, s), 2.10 (3H, s) |
| 4.01 | $^1$H-NMR (DMSO-d$_6$), δ (ppm): 10.11 (1H, s), 7.87 (1H, s), 7.56-7.53 (1H, m), 7.43-7.34 (5H, m), 7.25-7.21 (1H, m), 5 (2H, s), 3.82 (3H, s), 2.05 (3H, s) |
| 4.02 | $^1$H-NMR (DMSO-d$_6$), δ (ppm): 10.18 (1H, bs), 8.20-8.18 (2H, d), 7.92 (1H, s), 7.68-7.64 (2H, d), 7.58-7.55 (1H, d), 7.39-7.33 (1H, t), 7.27-7.23 (1H, d), 5.12 (2H, s), 2.05 (3H, s) |
| 4.03 | $^1$H-NMR (DMSO-d$_6$), δ (ppm): 10.11 (1H, s), 7.86 (1H, s), 7.55 (1H, d), 7.37 (1H, t), 7.29-7.19 (3H, m), 7.12 (2H, d), 4.97 (2H, s), 3.81 (3H, s), 2.26 (3H, s), 2.05 (3H, s) |
| 4.04 | $^1$H-NMR (DMSO-d$_6$), δ (ppm): 10.12 (1H, s), 7.9 (1H, s), 7.73-7.53 (5H, m), 7.41-7.35 (1H, m), 7.28-7.23 (1H, m), 5.11 (2H, s), 3.84 (3H, s), 2.06 (3H, s) |
| 4.05 | $^1$H-NMR (DMSO-d$_6$), δ (ppm): 10.11 (1H, s), 7.89 (1H, s), 7.58-7.22 (6H, m), 5.01 (2H, s), 3.83 (3H, s), 2.05 (3H, s) |
| 4.06 | $^1$H-NMR (DMSO-d$_6$), δ (ppm): 7.61-7.55 (1H, m), 7.48-7.36 (3H, m), 7.22-7.17 (2H, m), 7.09-7.03 (1H, m), 5.02 (2H, s), 3.78 (3H, s), 3.74 (3H, s) |
| 4.07 | $^1$H-NMR (DMSO-d$_6$), δ (ppm): 9.96 (1H, s), 7.51-7.31 (5H, m), 7.19-7.15 (1H, m), 5 (2H, s), 3.83 (3H, s), 3.02 (3H, s) |
| 4.08 | $^1$H-NMR (DMSO-d$_6$), δ (ppm): 7.49-7.32 (6H, m), 7.19-7.16 (1H, m), 7.08-7.02 (1H, m), 5.01 (2H, s), 3.77 (3H, s), 3.73 (3H, s) |
| 4.09 | $^1$H-NMR (DMSO-d$_6$), δ (ppm): 7.60-7.67 (1H, m), 7.42-7.24 (7H, m), 7.09-7.04 (1H, m), 7.29-7.22 (2H, m), 3.81 (3H, s), 3.14-3.04 (2H, m), 1.04 (3H, t) |
| 4.10 | $^1$H-NMR (DMSO-d$_6$), δ (ppm): 10.11 (1H, s), 8.48-8.44 (1H, m), 7.88-7.84 (1H, m), 7.68-7.63 (1H, m), 7.57-7.52 (1H, m), 7.37 (1H, t), 7.25-7.18 (2H, m), 4.99 (2H, s), 3.81 (3H, s), 2.43 (3H, s), 2.05(3H, s) |
| 4.11 | $^1$H-NMR (MeOD-d$_1$), δ (ppm): 8.18-8.15 (1H, m), 7.35-7.31 (2H, m), 7.26-7.24 (2H, d, 7.9 Hz), 7.14-7.11 (2H, d, 7.9 Hz), 4.96 (2H, s), 3.8 (3H, s), 2.27 (3H, s), 2.1 (3H, s) |
| 4.12 | $^1$H-NMR (MeOD-d$_6$), δ (ppm): 8.6 (2H, bd), 8.4 (1H, s), 7.3 (2H, d), 7.1 (1H, d), 5.0 (2H, s), 3.9 (3H, s), 2.1 (3H, s) |
| 4.13 | $^1$H-NMR (DMSO-d$_6$), δ (ppm): 8.43 (1H, s), 7.90-7.83 (2H, m), 7.58-7.45 (2H, m), 7.40-7.32 (1H, m), 7.23-7.21 (1H, m), 5.02 (2H, s), 3.81 (3H, s), 2.05 (3H, s) |
| 4.14 | $^1$H-NMR (DMSO-d$_6$), δ (ppm): 8.67 (1H, s), 8.51 (1H, s), 8.38 (1H, s), 7.57-7.50 (1H, m), 7.49-7.43 (1H, m), 7.29-7.24 (1H, m), 5.02 (2H, s), 3.86 (3H, s), 2.09 (3H, s) |
| 4.15 | $^1$H-NMR (DMSO-d$_6$), δ (ppm): 7.49-7.33 (5H, m), 7.12 (1H, dd), 6.9 (1H, td), 5 (2H, s), 3.79 (3H, s), 3.73 (3H, s) |
| 4.16 | $^1$H-NMR (DMSO-d$_6$), δ (ppm): 7.54-7.28 (8H, m), 5.01 (2H, s), 4.46 (2H, s), 3.82 (3H, s), 3.31 (3H, s) |
| 4.17 | $^1$H-NMR (DMSO-d$_6$), δ (ppm): 7.53-7.38 (8H, m), 5.01 (2H, s), 4.38 (2H, s), 3.76 (3H, s), 3.18 (3H, s) |
| 4.18 | $^1$H-NMR (DMSO-d$_6$), δ (ppm): 7.45-7.36 (7H, m), 7.26-7.22 (1H, m), 5 (2H, s), 3.82 (3H, s), 3.55 (2H, t), 3.24 (3H, s), 2.85 (2H, t) |
| 4.19 | $^1$H-NMR (DMSO-d$_6$), δ (ppm): 7.70-7.52 (4H, m), 7.43-7.34 (4H, m), 5.02 (2H, s), 3.76 (3H, s) |
| 4.20 | $^1$H-NMR (DMSO-d$_6$), δ (ppm): 7.44-7.35 (4H, m), 7.19-7.15 (2H, m), 7.03-6.97 (1H, m), 5.02 (2H, s), 3.86 (3H, s), 3.75 (3H, s), 3.7 (3H, s) |
| 4.21 | $^1$H-NMR (DMSO-d$_6$), δ (ppm): 7.45-7.38 (8H, m), 5.06-4.97 (2H, m), 3.75 (3H, s), 3.46-3.36 (2H, m), 3.33-3.22 (4H, m), 2.13-1.99 (4H, m) |
| 4.22 | $^1$H-NMR (DMSO-d$_6$), δ (ppm): 7.41-7.33 (8H, m), 5 (2H, s), 3.75 (3H, s), 3.44 (2H, t), 3.14 (2H, s), 2.75 (2H, t) |
| 4.23 | $^1$H-NMR (DMSO-d$_6$), δ (ppm): 7.46-7.39 (7H, m), 7.25-7.21 (1H, m), 5.01 (2H, s), 3.85-3.75 (7H, m), 2.91 (2H, s), 1.22 (3H, s) |
| 4.24 | $^1$H-NMR (DMSO-d$_6$), δ (ppm): 7.44-7.36 (7H, m), 7.18-7.15 (1H, m), 5 (2H, s), 3.85 (2H, s), 3.83 (3H, s), 2.17 (3H, s) |
| 4.25 | $^1$H-NMR (DMSO-d$_6$), δ (ppm): 7.51-7.33 (8H, m), 5.01 (2H, s), 3.76 (3H, s), 3.33 (2H, s), 1.92 (6H, s) |
| 4.26 | $^1$H-NMR (DMSO-d$_6$), δ (ppm): 7.47-7.31 (8H, m), 5 (2H, s), 3.75 (3H, s), 3.5 (2H, bs), 2.18 (4H, bs), 1.47 (4H, bs) |
| 4.27 | $^1$H-NMR (DMSO-d$_6$), δ (ppm): 9.89 (1H, bs), 8.15 (1H, d), 7.35 (4H, m), 6.87 (2H, d), 4.95 (2H, s), 3.80 (3H, s), 3.73 (3H, s), 2.11 (3H, s) |
| 4.28 | $^1$H-NMR (CDCl$_3$), δ (ppm): 7.6 (4H, m), 7.2 (2H, t), 7.0 (2H, t), 5.1 (2H, s), 3.9 (3H, s) |
| 4.29 | $^1$H-NMR (DMSO-d$_6$), δ (ppm): 7.46-7.36 (8H, m), 5.08-4.94 (2H, m), 3.75 (3H, s), 3.33 (2H, s), 2.06-1.93 (4H, m), 1.23-1.06 (6H, m) |
| 4.30 | $^1$H-NMR (DMSO-d$_6$), δ (ppm): 7.48-7.36 (8H, m), 5 (2H, s), 3.75 (3H, s), 3.14 (2H, t), 3.08 (3H, s), 2.3 (2H, s), 1.93 (3H, s) |
| 4.31 | $^1$H-NMR (DMSO-d$_6$), δ (ppm): |
| 4.32 | $^1$H-NMR (DMSO-d$_6$), δ (ppm): 8.01 (1H, d), 7.88 (1H, t), 7.75 (1H, d), 7.65 (1H, t), 7.44-7.36 (4H, m), 5.03 (2H, s), 3.83 (3H, s) |
| 4.33 | $^1$H-NMR (DMSO-d$_6$), δ (ppm): 7.46-7.31 (6H, m), 7.24-7.16 (1H, m), 4.99 (2H, s), 4.47-4.42 (2H, m), 3.75 (3H, s) |
| 4.34 | $^1$H-NMR (DMSO-d$_6$), δ (ppm): 7.7-7.3 (8H, m), 5.0 (2H, s), 3.9 (3H, s) |
| 4.35 | $^1$H-NMR (DMSO-d$_6$), δ (ppm): 7.58 (2H, d), 7.47 (2H, t), 7.42-7.20 (6H, m), 5.03 (2H, s), 3.82 (3H, s) |
| 4.36 | $^1$H-NMR (DMSO-d$_6$), δ (ppm): 10.12 (1H, bs), 7.87 (1H, s), 7.57-7.54 (1H, m), 7.40-7.34 (1H, t), 7.30-7.18 (5H, m), 4.98 (2H, s), 3.81 (3H, s), 2.9-2.81 (1H, q), 2.05 (3H, s), 1.18-1.16 (6H, m) |
| 4.37 | $^1$H-NMR (DMSO-d$_6$), δ (ppm): 10.11 (1H, bs), 7.89-7.88 (1H, m), 7.66-7.62 (3H, m), 7.58-7.54 (2H, m), 7.50-7.34 (6H, m), 7.25-7.23 (1H, m), 5.09 (2H, s), 3.82 (3H, s), 2.05 (3H, s) |
| 4.38 | $^1$H-NMR (DMSO-d$_6$), δ (ppm): 10.11 (1H, bs), 7.89-7.88 (1H, m), 7.56-7.50 (3H, m), 7.40-7.34 (3H, m), 7.25-7.23 (1H, m), 5.04 (2H, s), 3.82 (3H, s), 2.05 (3H, s) |
| 4.39 | $^1$H-NMR (DMSO-d$_6$), δ (ppm): 10.11 (1H, bs), 7.85-7.84 (1H, s), 7.56-7.54 (1H, m), 7.39-7.33 (1H, m), 7.23-7.19 (3H, m), 6.66-6.64 (2H, m), 4.9 (2H, s), 3.8 (3H, s), 2.85 (6H, s), 2.05 (3H, s) |
| 4.40 | $^1$H-NMR (DMSO-d$_6$), δ (ppm): 10.13 (1H, bs), 7.89-7.87 (1H, m), 7.65-7.60 (4H, m), 7.57-7.54 (1H, m), 7.48-7.43 (4H, m), 7.41-7.33 (2H, m), 7.27-7.24 (1H, m), 5.07 (2H, s), 3.83 (3H, s), 2.05 (3H, s) |
| 4.41 | $^1$H-NMR (DMSO-d$_6$), δ (ppm): 10.11 (1H, s), 7.86 (1H, s), 7.55 (1H, d), 7.45-7.20 (7H, m), 5.02 (2H, s), 3.81 (3H, s), 2.05 (3H, s) |
| 4.42 | $^1$H-NMR (DMSO-d$_6$), δ (ppm): 10.1 (1H, s) 8.0-7.3 (11H, m), 5.2 (2H, s), 3.8 (3H, s), 2.0 (3H, s) |
| 4.43 | $^1$H-NMR (DMSO-d$_6$), δ (ppm): 10.11 (1H, bs), 8.51 (1H, d, 2 Hz), 7.88 (1H, t, 1 Hz), 7.7 (1H, dd, 2 Hz, 8 Hz), 7.54 (1H, d, 8 Hz), 7.37 (1H, t, 8 Hz), 7.23 (1H, d, 8 Hz), 5 (2H, s), 3.81 (3H, s), 2.99 (1H, q, 7 Hz), 2.05 (3H, s), 1.21 (3H, s), 1.19 (3H, s) |
| 4.44 | $^1$H-NMR (DMSO-d$_6$), δ (ppm): 10.11 (1H, s), 7.87 (1H, s), 7.55 (1H, d), 7.47-7.30 (3H, m), 7.23 (1H, d), 7.15 (2H, t), 5.00 (2H, s), 3.81 (3H, s), 2.05 (3H, s) |
| 4.45 | $^1$H-NMR (DMSO-d$_6$), δ (ppm): 10.1 (1H, s) 7.9-6.9 (8H, m), 5.0 (2H, s), 3.8 (3H, s), 3.7 (3H, s), 2.1 (3H, s) |
| 4.46 | $^1$H-NMR (DMSO-d$_6$), δ (ppm): 10.1 (1H, s) 8.9-7.3 (10H, m), 5.2 (2H, s), 3.8 (3H, s), 2.0 (3H, s) |
| 4.47 | $^1$H-NMR (DMSO-d$_6$), δ (ppm): 10.1 (1H, bs), 7.87 (1H, s), 7.55 (1H, d), 7.37 (1H, t), 7.27 (3H, m), 6.84 (1H, d), 4.94 (2H, s), 4.57 (1H, h), 3.81 (3H, s), 2.06 (3H, s), 1.23 (6H, d) |
| 4.48 | $^1$H-NMR (DMSO-d$_6$), δ (ppm): 10.1 (1H, s), 7.9 (1H, s), 7.6-7.5 (1H, d), 7.4 (1H, t), 7.3-7.2 (1H, s), 7.0 (1H, s), 6.9 (1H, s), 5.0 (2H, s), 3.8 (3H, s) 3.7 (6H, s), 2.1 (3H, s) |
| 4.49 | $^1$H-NMR (DMSO-d$_6$), δ (ppm): 10.1 (1H, s) 8.5-7.2 (11H, m), 5.0 (2H, s), 3.8 (3H, s), 3.2-3.1 (1H, m), 2.1 (3H, s), 2.0-1.9 (2H, m), 1.7-1.6 (6H, m) |

TABLE 7-continued

NMR-data

| Compound Nr | NMR-data |
|---|---|
| 4.50 | $^1$H-NMR (DMSO-d$_6$), δ (ppm): 7.58 (2H, d), 7.53-7.32 (7H, m), 5.01 (2H, s), 3.82 (3H, s) |
| 4.51 | $^1$H-NMR (DMSO-d$_6$), δ (ppm): 10.12 (1H, s), 8.28 (1H, s), 8.00 (1H, t), 7.89 (1H, s), 7.55 (1H, d), 7.38 (1H, t), 7.24 (1H, d), 7.17 (1H, d), 5.05 (2H, s), 3.82 (3H, s), 2.06 (3H, s) |
| 4.52 | $^1$H-NMR (DMSO-d$_6$), δ (ppm): 10.11 (1H, s), 8.35 (1H, s), 7.96 (1H, d), 7.90 (1H, s), 7.53 (1H, d), 7.37 (1H, t), 7.23 (1H, d), 5.07 (2H, s), 3.83 (3H, s), 2.05 (3H, s) |
| 4.53 | $^1$H-NMR (DMSO-d$_6$), δ (ppm): 10.11 (1H, s), 8.11 (1H, s), 7.85 (1H, s), 7.60-7.46 (2H, m), 7.36 (1H, t), 7.22 (1H, d), 6.57 (1H, d), 4.87 (2H, s), 3.80 (3H, s), 2.98 (6H, s), 2.05 (3H, s) |
| 4.54 | $^1$H-NMR (DMSO-d$_6$), δ (ppm): 10.12 (1H, bs), 7.87 (1H, t), 7.54 (1H, d), 7.37 (1H, t), 7.23 (2H, m), 7.12 (1H, d), 6.69 (1H, d), 4.93 (2H, s), 4.49 (2H, t), 3.82 (3H, s), 3.17 (2H, t), 2.06 (3H, s) |
| 4.55 | $^1$H-NMR (DMSO-d$_6$), δ (ppm): 10.4 (1H, s), 8.1 (1H, s), 7.8-7.5 (6H, m), 5.0 (2H, s), 4.1 (3H, s), 2.3 (3H, s) |
| 4.56 | $^1$H-NMR (DMSO-d$_6$), δ (ppm): 10.1 (1H, s), 7.9 (1H, s), 7.6-7.5 (1H, d), 7.5 (1H, d), 7.5-7.4 (1H, d), 7.4 (1H, t), 7.3-7.2 (1H, d), 7.0 (1H, t), 5.0 (2H, s), 3.8 (3H, s), 2.1 (3H, s) |
| 4.57 | $^1$H-NMR (DMSO-d$_6$), δ (ppm): 10.1 (1H, s), 8.2 (1H, s), 7.9 (1H, s), 7.7 (1H, dd), 7.6-7.5 (1H, s), 7.4 (1H, t), 7.2 (1H, s), 6.8 (1H, s), 5.0 (2H, s), 3.8 (3H, s) 3.8 (3H, s), 2.1 (3H, s) |
| 4.58 | $^1$H-NMR (DMSO-d$_6$), δ (ppm): 10.1 (1H, s), 8.6 (1H, d), 8.5 (1H, dd), 7.9 (1H, t), 7.8 (1H, dt), 7.6-7.5 (1H, d), 7.4 (2H, m), 7.3-7.2 (1H, d), 5.0 (2H, s), 3.8 (3H, s), 2.1 (3H, s) |
| 4.59 | $^1$H-NMR (DMSO-d$_6$), δ (ppm): 10.1 (1H, s), 8.5 (1H, d), 7.9 (1H, t), 7.8-7.7 (3H, m), 7.6-7.5 (3H, m), 7.4 (1H, t), 7.3-7.2 (1H, d), 5.0 (2H, s), 3.8 (3H, s), 2.0 (3H, s) |
| 4.60 | $^1$H-NMR (DMSO-d$_6$), δ (ppm): 10.12 (1H, bs), 7.83 (1H, dd), 7.55 (1H, d), 7.37 (1H, t), 7.19 (1H, dd), 6.69 (2H, d), 5.02 (2H, s), 3.81 (3H, s), 3.76 (3H, s), 2.05 (3H, s) |
| 4.61 | $^1$H-NMR (DMSO-d$_6$), δ (ppm): 10.1 (1H, s), 9.0-8.9 (1H, d), 8.3 (1H, d), 8.0 (2H, m), 7.9 (1H, t), 7.8-7.7 (1H, td), 7.6-7.5 (2H, m), 7.4-7.3 (1H, t), 7.3-7.2 (1H, d), 5.2 (2H, s), 3.8 (3H, s), 2.0 (3H, s) |
| 4.62 | $^1$H-NMR (DMSO-d$_6$), δ (ppm): 10.13 (1H, bs), 7.88 (1H, s), 7.56 (1H, d), 7.38 (1H, t), 7.16 (4H, m), 4.95 (2H, s), 3.82 (6H, s), 2.06 (3H, s) |
| 4.63 | $^1$H-NMR (DMSO-d$_6$), δ (ppm): 10.12 (1H, bs), 7.89 (1H, t), 7.53 (1H, d), 7.37 (1H, t), 7.22 (3H, m), 4.95 (2H, s), 3.88 (3H, s), 3.82 (3H, s), 2.05 (3H, s) |
| 4.64 | $^1$H-NMR (DMSO-d$_6$), δ (ppm): 10.12 (1H, bs), 7.88 (1H, t), 7.54 (1H, dd), 7.37 (1H, t), 7.2 (2H, m), 6.96 (1H, dt), 5.02 (2H, s), 3.85 (3H, s), 3.83 (3H, s), 2.05 (3H, s) |
| 4.65 | $^1$H-NMR (DMSO-d$_6$), δ (ppm): 10.11 (1H, s), 7.85 (1H, s), 7.56 (2H, s), 7.50-7.13 (5H, m), 6.38 (1H, s), 5.10 (2H, s), 3.81 (3H, s), 3.76 (3H, s), 2.05 (3H, s) |
| 4.66 | $^1$H-NMR (DMSO-d$_6$), δ (ppm): 10.12 (1H, bs), 7.87 (1H, t), 7.55 (1H, d), 7.33 (3H, m), 6.83 (1H, dd), 6.73 (1H, dd), 4.99 (2H, s), 3.83 (3H, s), 3.74 (3H, s), 2.05 (3H, s) |
| 4.67 | $^1$H-NMR (DMSO-d$_6$), δ (ppm): 7.2-7.6 (8H, m), 5 (2H, s), 3.8 (3H, s) |
| 4.68 | $^1$H-NMR (DMSO-d$_6$), δ (ppm): 7.6-7.1 (8H, m), 5.0 (2H, s), 3.9 (3H, s) |
| 4.69 | $^1$H-NMR (DMSO-d$_6$), δ (ppm): 7.6-7.2 (8H, m), 5 (2H, s), 3.8 (3H, s) |
| 4.80 | $^1$H-NMR (DMSO-d$_6$), δ (ppm): 10.12 (1H, bs), 7.87 (1H, s), 7.55 (1H, d), 7.39 (1H, t), 7.23 (2H, m), 6.86 (3H, m), 4.99 (2H, s), 3.82 (3H, s), 3.73 (3H, s), 2.05 (3H, s) |
| 4.90 | $^1$H-NMR (DMSO-d$_6$), δ (ppm): 7.5-7.3 (5H, m), 6.8 (4H, m), 4.5 (2H, m), 4.3 (1H, m), 4.1 (2H, m), 3.9 (3H, s) |
| 4.91 | $^1$H-NMR (DMSO-d$_6$), δ (ppm): 7.9 (2H, m), 7.5 (2H, m), 7.4-7.2 (7H, m), 5.3 (2H, s), 3.9 (3H, s) |
| 4.92 | $^1$H-NMR (DMSO-d$_6$), δ (ppm): 10.12 (1H, bs), 7.88 (1H, s), 7.56-7.54 (1H, m), 7.47-7.35 (3H, m), 7.25-7.23 (2H, m), 5.03 (2H, s), 3.84 (3H, s), 2.05 (3H, s) |
| 4.93 | $^1$H-NMR (DMSO-d$_6$), δ (ppm): 7.6-7.3 (8H, m), 5.1 (2H, s), 3.8 (3H, s) |
| 4.94 | $^1$H-NMR (DMSO-d$_6$), δ (ppm): 7.60-7.57 (2H, d, 7.42 Hz), 7.50-7.45 (2H, t), 7.38-7.12 (4H, m), 5.04 (2H, s), 3.84 (3H, s) |
| 4.95 | $^1$H-NMR (DMSO-d$_6$), δ (ppm): 7.66-7.33 (8H, m), 5.05 (2H, s), 3.83 (3H, s) |
| 4.96 | $^1$H-NMR (DMSO-d$_6$), δ (ppm): 10.1 (1H, bs), 7.9 (1H, s), 7.55 (1H, d), 7.41 (1H, t), 7.2 (1H, d), 7.1 (2H, m), 5 (2H, s), 3.9 (3H, s), 3.8 (3H, s), 2 (3H, s) |
| 4.97 | $^1$H-NMR (DMSO-d$_6$), δ (ppm): 10.1 (1H, bs), 7.9 (1H, s), 7.6 (1H, d), 7.4 (1H, t), 7.2 (2H, t), 6.6 (1H, d), 5 (2H, s), 4.6 (2H, t), 3.8 (3H, s), 3.1 (2H, t), 2.1 (3H, t) |
| 4.98 | $^1$H-NMR (DMSO-d$_6$), δ (ppm): 7.8-7.3 (8H, m), 5.1 (2H, s), 3.8 (3H, s) |
| 4.99 | $^1$H-NMR (DMSO-d$_6$), δ (ppm): 7.74-7.65 (5H, m), 7.61-7.45 (8H, m), 7.39-7.36 (1H, m) |
| 4.100 | $^1$H-NMR (DMSO-d$_6$), δ (ppm): 7.60-7.57 (2H, d, 7.42 Hz), 7.50-7.45 (2H, t), 7.38-7.12 (4H, m), 5.04 (2H, s), 3.84 (3H, s) |
| 4.101 | $^1$H-NMR (DMSO-d$_6$), δ (ppm): 10.11 (1H, bs), 8.36 (1H, d), 8.12 (2H, dd), 7.87 (1H, s), 7.54 (1H, d), 7.36 (1H, t), 7.23 (1H, d), 7.01 (1H, d), 5.14 (2H, s), 3.81 (3H, s), 2.04 (3H, s) |
| 4.102 | $^1$H-NMR (DMSO-d$_6$), δ (ppm): 10.12 (1H, bs), 8.74 (1H, s), 7.89 (1H, s), 7.78 (2H, m), 7.55 (1H, d), 7.43 (1H, m), 7.25 (1H, m), 5.17 (2H, s), 3.84 (3H, s), 2.06 (3H, s) |
| 4.103 | $^1$H-NMR (DMSO-d$_6$), δ (ppm): 10.12 (1H, bs), 7.89 (1H, d), 7.53 (1H, d), 7.37 (1H, t), 7.13 (1H, m), 6.9 (1H, m), 4.98 (2H, s), 3.82 (6H, s), 2.05 (3H, s) |
| 4.104 | $^1$H-NMR (DMSO-d$_6$), δ (ppm): 7.86 (1H, bs), 7.76-7.72 (2H, t), 7.60-7.45 (6H, m), 7.38-7.36 (1H, m), 5.07 (2H, s), 3.84 (3H, s) |
| 4.105 | $^1$H-NMR (DMSO-d$_6$), δ (ppm): 7.81-7.79 (2H, m), 7.59-7.56 (4H, m), 7.50-7.44 (2H, m), 7.38-7.33 (1H, m), 5.09 (2H, s), 3.83 (3H, s) |
| 4.106 | $^1$H-NMR (DMSO-d$_6$), δ (ppm): 10.12 (1H, bs), 7.88 (1H, s), 7.54 (1H, d), 7.37 (1H, t), 7.23 (1H, dd), 7.05 (2H, m), 4.92 (2H, s), 4.6 (2H, t), 3.81 (3H, s), 3.21 (2H, t), 2.05 (3H, s) |
| 4.107 | $^1$H-NMR (DMSO-d$_6$), δ (ppm): 7.59-7.44 (4H, m), 7.38-7.24 (5H, m), 5.17-5.13 (2H, t, 5.63 Hz), 5.01 (2H, s), 4.46-4.44 (2H, d, 5.63 Hz), 3.82 (3H, s) |
| 4.108 | $^1$H-NMR (DMSO-d$_6$), δ (ppm): 7.61-7.59 (2H, d ), 7.51-7.45 (2H, t), 7.38-7.33 (1H, t), 7.2 (1H, d), 7.09 (1H, d), 5.34 (2H, s), 4.92-4.88 (4H, d), 3.85 (3H, s) |
| 4.109 | $^1$H-NMR (DMSO-d$_6$), δ (ppm): 7.61-7.59 (2H, d ), 7.51-7.45 (2H, t), 7.38-7.33 (1H, t), 7.2 (1H, d), 7.09 (1H, d), 5.34 (2H, s), 4.92-4.88 (4H, d), 3.85 (3H, s) |
| 4.110 | $^1$H-NMR (DMSO-d$_6$), δ (ppm): 7.58-7.56 (2H, m), 7.50-7.45 (2H, m), 7.39-7.34 (1H, m), 7.05 (1H, d), 6.72 (1H, d), 5.07 (2H, bs), 3.85 (3H, s) |
| 4.111 | $^1$H-NMR (DMSO-d$_6$), δ (ppm): 10.12 (1H, bs), 7.87 (1H, s), 7.55 (1H, d), 7.39 (1H, t), 7.23 (2H, m), 6.86 (3H, m), 4.99 (2H, s), 3.82 (3H, s), 3.73 (3H, s), 2.05 (3H, s) |
| 4.112 | $^1$H-NMR (DMSO-d$_6$), δ (ppm): 10.1 (1H, s), 8.1 (1H, d), 7.9 (1H, t), 7.8 (1H, dt), 7.6-7.5 (1H, d), 7.5 (1H, dd), 7.4-7.3 (1H, t), 7.2 (1H, d), 6.5 (1H, d), 4.9 (2H, s), 3.8 (3H, s), 3.5-3.4 (4H, q), 2.1 (3H, s), 1.1-1.0 (6H, t) |
| 4.113 | $^1$H-NMR (DMSO-d$_6$), δ (ppm): 7.58-7.37 (5H, m), 7.01-6.98 (2H, d), 5.09 (2H, s), 3.81 (3H, s) |
| 4.114 | $^1$H-NMR (DMSO-d$_6$), δ (ppm): 8.17 (1H, d), 8.05-8.02 (1H, d, 8.44 Hz), 7.87 (1H, s), 7.60-7.57 (2H, d, 7.68 Hz), 7.51-7.34 (4H, m), 5.23 (2H, s), 3.83 (3H, s) |
| 4.115 | $^1$H-NMR (DMSO-d$_6$), δ (ppm): 7.0-7.6 (8H, m), 5 (2H, s), 3.8 (3H, s) |
| 4.116 | $^1$H-NMR (DMSO-d$_6$), δ (ppm): 10.12 (1H, bs), 7.91 (2H, dt), 7.61 (1H, d), 7.54 (1H, d), 7.37 (1H, t), 7.22 (1H, dt), 4.93 (2H, s), 4.54 (2H, t), 3.81 (3H, s), 3.19 (2H, t), 2.05 (3H, s) |
| 4.117 | $^1$H-NMR (DMSO-d$_6$), δ (ppm): 10.12 (1H, bs), 7.86 (1H, t), 7.54 (1H, d), 7.37 (1H, t), 7.22 (1H, dd), 7.12 (1H, dd), 6.56 (1H, d), 4.98 (2H, s), 4.59 (2H, t), 3.82 (3H, s), 3.21 (2H, t), 2.05 (3H, s) |
| 4.118 | $^1$H-NMR (DMSO-d$_6$), δ (ppm): 10.12 (1H, bs), 7.91-7.89 (1H, s), 7.82-7.75 (2H, m), 7.55-7.44 (2H, m), 7.40-7.35 (1H, t), 7.25-7.22 (1H, d), 5.06 (2H, s), 3.82 (3H, s), 2.05 (3H, s) |
| 4.119 | $^1$H-NMR (DMSO-d$_6$), δ (ppm): 10.11 (1H, s), 7.89-7.85 (1H, m), 7.69-7.67 (1H, m), 7.63-7.53 (2H, m), 7.37 (1H, t), 7.25-7.22 (1H, m), 5.13 (2H, s), 3.82 (3H, s), 2.93 (2H, q), 2.05 (3H, s), 1.32 (3H, t) |
| 4.120 | $^1$H-NMR (DMSO-d$_6$), δ (ppm): 10.12 (1H, bs), 7.89 (1H, s), 7.8 (2H, d), 7.56 (3H, m), 7.36 (1H, t), 7.22 (1H, d), 5.09 (2H, s), 3.83 (3H, s), 2.05 (3H, s) |

TABLE 7-continued

NMR-data

| Compound Nr | NMR-data |
|---|---|
| 4.121 | ¹H-NMR (DMSO-d₆), δ (ppm): 10.11 (1H, s), 7.87 (1H, s), 7.67 (1H, s), 7.61-7.52 (2H, m), 7.39-7.33 (2H, m), 7.25-7.21 (1H, m), 5.13 (2H, s), 3.82 (3H, s), 2.59 (2H, s), 2.05 (2H, s) |
| 4.122 | ¹H-NMR (DMSO-d₆), δ (ppm): 10.11 (1H, s), 7.99 (1H, s), 7.87 (1H, s), 7.55 (1H, d), 7.48-7.32 (2H, m), 7.23 (1H, d), 4.91 (2H, s), 3.81 (3H, s), 2.98 (6H, d), 2.05 (3H, s) |
| 4.123 | ¹H-NMR (DMSO-d₆), δ (ppm): 10.11 (1H, s), 7.86 (1H, t), 7.55 (1H, d), 7.37 (1H, t), 7.23 (1H, d), 7.1 (2H, m), 6.89 (1H, t), 4.92 (2H, s), 3.81 (3H, s), 2.73 (6H, s), 2.05 (3H, s) |
| 4.124 | ¹H-NMR (DMSO-d₆), δ (ppm): 10.13 (1H, s), 7.86 (1H, t), 7.55 (1H, d), 7.37 (1H, t), 7.23 (1H, d), 7.06 (2H, m), 6.42 (1H, d), 4.88 (2H, s), 3.8 (3H, s), 3.2 (2H, t), 2.82 (2H, t), 2.66 (3H, s), 2.05 (3H, s) |
| 4.125 | ¹H-NMR (DMSO-d₆), δ (ppm): 10.12 (1H, bs), 7.86 (1H, s), 7.55 (1H, d), 7.35 (1H, dd), 7.23 (1H, d), 7.07 (2H, m), 6.87 (1H, dd), 5.05 (2H, s), 3.82 (6H, s), 2.04 (3H, s) |
| 4.126 | ¹H-NMR (DMSO-d₆), δ (ppm): 10.12 (1H, bs), 7.88 (1H, t), 7.53 (1H, d), 7.37 (1H, t), 7.23 (1H, d), 7.04 (1H, dd), 6.6 (1H, t), 4.91 (2H, s), 4.64 (2H, t), 3.83 (3H, s), 3.23 (2H, t), 2.05 (3H, s) |
| 4.127 | ¹H-NMR (DMSO-d₆), δ (ppm): 10.12 (1H, bs), 7.89 (1H, t), 7.54 (1H, d), 7.39 (3H, m), 7.24 (1H, d), 5.03 (2H, s), 3.83 (3H, s), 2.06 (3H, s) |
| 4.128 | ¹H-NMR (DMSO-d₆), δ (ppm): 10.5 (1H, s), 8.9 (1H, d), 8.3 (2H, m), 7.9 (1H, d), 7.8-7.7 (1H, t), 7.6 (1H, d), 5.5 (2H, s), 4.2 (3H, s), 2.4 (3H, s) |
| 4.129 | ¹H-NMR (DMSO-d₆), δ (ppm): 10.11 (1H, s), 8.37 (1H, d), 7.89 (1H, t), 7.64 (1H, dd), 7.54 (1H, d), 7.35 (2H, dd), 7.24 (1H, d), 5.12 (2H, s), 3.85 (3H, s), 2.9 (1H, q), 2.04 (3H, s) |
| 4.130 | ¹H-NMR (DMSO-d₆), δ (ppm): 9.88 (1H, bs), 8.20-8.17 (1H, m), 7.36-7.32 (2H, m), 7.20-7.17 (2H, m), 4.95 (2H, s), 3.88 (3H, s), 3.81 (3H, s), 2.1 (3H, s) |
| 4.131 | ¹H-NMR (DMSO-d₆), δ (ppm): 9.88 (1H, bs), 8.20-8.16 (1H, m), 7.62-7.59 (1H, m), 7.48-7.46 (2H, m), 7.39-7.29 (2H, m), 5.02 (2H, s), 3.81 (3H, s), 2.1 (3H, s) |
| 4.132 | ¹H-NMR (DMSO-d₆), δ (ppm): 9.88 (1H, bs), 8.21-8.18 (1H, m), 7.59-7.51 (1H, m), 7.36-7.33 (3H, m), 5.03 (2H, s), 3.81 (3H, s), 2.1 (3H, s) |
| 4.133 | ¹H-NMR (DMSO-d₆), δ (ppm): 7.5 (8H, m), 5.01 (2H, s), 3.85 (3H, s), 3.18 (3H, s), 2.5 (3H, s) |
| 4.134 | ¹H-NMR (DMSO-d₆), δ (ppm): 8.2-7.4 (8H, m), 5.2 (2H, s), 3.9 (3H, s), 3.2 (1H, s), 1.8 (3H, s) |
| 4.135 | ¹H-NMR (DMSO-d₆), δ (ppm): 9.88 (1H, bs), 8.17-8.15 (1H, m), 7.35-7.32 (2H, m), 7.25 (1H, s), 7.13-7.10 (1H, m), 6.70-6.67 (1H, m), 4.92 (1H, s), 4.52-4.46 (2H, t, 8.71 Hz), 3.79 (3H, s), 3.16-3.10 (2H, t, 8.71 Hz), 2.10 (3H, s) |
| 4.136 | ¹H-NMR (DMSO-d₆), δ (ppm): 7.6-7.5 (3H, m), 7.3(3H, d), 6.9(2H, d), 5.0 (2H, s), 3.9 (3H, s), 3.7 (3H, s), 3.2 (3H, s), 1.8 (3H, s) |
| 4.137 | ¹H-NMR (DMSO-d₆), δ (ppm): 7.53 (3H, m), 7.33 (1H, d), 7.25 (2H, s), 7.12 (1H, d), 6.69 (1H, d), 4.94 (2H, s), 4.48 (2H, t), 3.94 (3H, s), 3.13 (5H, m), 1.83 (3H, s) |
| 4.138 | ¹H-NMR (DMSO-d₆), δ (ppm): 7.64-7.51 (3H, m), 7.38-7.31 (1H, m), 7.22-7.11 (2H, m), 7.95-7.89 (1H, m), 5 (2H, s), 3.85 (3H, s), 3.82 (3H, s), 3.18 (3H, bs), 1.83 (3H, bs) |
| 4.139 | ¹H-NMR (DMSO-d₆), δ (ppm): 7.60-7.50 (3H, m), 7.36-7.31 (1H, m), 7.17-7.04 (2H, m), 5.03 (2H, s), 3.92 (3H, s), 3.86 (3H, s), 3.18 (3H, bs), 1.83 (3H, bs) |
| 4.140 | ¹H-NMR (DMSO-d₆), δ (ppm): 7.6-7.2 (10H, m), 4.1 (2H, t), 4.1-4.0 (3H, s), 3.8 (3H, s), 2.9 (2H, t) |
| 4.141 | ¹H-NMR (CDCl₃), δ (ppm): 10.1 (1H, bs), 8.01 (1H, bs), 7.65 (1H, d), 7.4 (5H, m), 7.33 (1H, dd), 5.01 (2H, s), 4.02 (2H, s), 3.81 (3H, s), 3.38 (3H, s) |
| 4.142 | ¹H-NMR (CDCl₃), δ (ppm): 10.14 (1H, bs), 7.91 (1H, s), 7.58 (1H, d), 7.4 (5H, m), 7.25 (1H, dd), 5.01 (2H, s), 3.83 (3H, s), 3.62 (2H, t), 3.24 (3H, s), 2.54 (2H, t) |
| 4.143 | ¹H-NMR (DMSO-d₆), δ (ppm): 7.4 (4H, s), 7.30-7.23 (2H, m), 6.95-6.82 (2H, m), 5 (2H, s), 3.74 (3H, s) |
| 4.144 | ¹H-NMR (CDCl₃), δ (ppm): 10.4 (1H, s), 8.0 (1H, s), 7.6-6.9 (9H, m), 5.0 (2H, s), 3.8 (3H, s) |
| 4.145 | ¹H-NMR (CDCl₃), δ (ppm): 7.9 (1H, s), 7.6-7.3 (7H, m), 5.2 (2H, s), 3.9 (3H, s), 1.5-0.9 (6H, m) |
| 4.146 | ¹H-NMR (CDCl₃), δ (ppm): 8.27 (1H, bs), 7.98 (1H, d), 7.82-7.78 (1H, m), 7.68 (1H, t), 7.44-7.36 (4H, m), 5.03 (2H, s), 3.85 (3H, s), 2.68 (3H, s) |
| 4.147 | ¹H-NMR (DMSO-d₆), δ (ppm): 7.6-7.2 (5H, m), 7.2-7.1(2H, d), 6.9(2H, d), 4.0 (2H, t), 3.8 (3H, s), 3.7(3H, s), 2.8(2H, t) |
| 4.148 | ¹H-NMR (DMSO-d₆), δ (ppm): 7.6-7.1 (9H, m), 4.1 (2H, t), 3.8 (3H, s), 2.9 (2H, t) |
| 4.149 | ¹H-NMR (DMSO-d₆), δ (ppm): 7.6-7.3 (6H, m), 6.9-6.7 (2H, m), 4.1 (2H, t), 4.1-4.0 (3H, s), 3.8 (3H, s), 3.8 (3H, s), 2.8 (2H, t) |
| 4.150 | ¹H-NMR (DMSO-d₆), δ (ppm): 8.1- 7.7 (6H, m), 7.3 (3H, m), 4.6 (2H, t), 4.5 (3H, s), 4.3 (3H, s), 3.4 (2H, t) |
| 4.151 | ¹H-NMR (DMSO-d₆), δ (ppm): 10.12 (1H, s), 7.88 (1H, s), 7.58-7.51 (1H, m), 7.37 (1H, t), 7.24-7.13 (3H, m), 6.88 (2H, d), 3.98 (2H, t), 3.81 (3H, s), 3.72 (3H, s), 2.8 (3H, t), 2.06 (3H, s) |
| 4.152 | ¹H-NMR (DMSO-d₆), δ (ppm): 10.1 (1H, s), 7.9 (1H,s), 7.6-7.1 (7H, m), 4.0 (2H, t), 3.8 (3H, s), 2.9 (2H, t), 2.1 (3H, s) |
| 4.153 | ¹H-NMR (DMSO-d₆), δ (ppm): 10.1 (1H, s), 7.9 (1H, s), 7.6 (1H, d), 7.4 (1H, t), 7.2 (2H, m), 6.8 (3H, m), 4.1 (2H, t), 3.8 (3H, s), 3.7 (3H, s), 2.9 (2H, t), 2.1(3H, s) |
| 4.154 | ¹H-NMR (DMSO-d₆), δ (ppm): 9.88 (1H, s), 8.18-8.15 (1H, m), 7.38-7.27 (7H, m), 5.01 (2H, s), 3.81 (3H, s), 2.1 (3H, s) |
| 4.155 | ¹H-NMR (DMSO-d₆), δ (ppm): 9.88 (1H, bs), 8.17 (1H, dd), 7.31 (2H, m), 7.15 (2H, m), 6.91 (1H, m), 4.97 (2H, s), 3.81 (3H, s), 3.8 (3H, s), 2.1 (3H, s) |
| 4.156 | ¹H-NMR (DMSO-d₆), δ (ppm): 9.88 (1H, s), 8.17 (1H, dd), 7.38-7.31 (2H, m), 7.14-7.07 (2H, m), 5 (2H, s), 3.91 (3H, s), 3.81 (3H, s), 2.1 (3H, s) |
| 4.157 | ¹H-NMR (DMSO-d₆), δ (ppm): 9.88 (1H, bs), 8.22-8.18 (1H, m), 7.43-7.31 (3H, m), 7.21-7.11 (1H, m), 4.87 (2H, s), 3.83 (6H, s), 2.1 (3H, s) |
| 4.158 | ¹H-NMR (DMSO-d₆), δ (ppm): 9.9 (1H, s), 8.2-8.1 (1H, d), 7.4-7.2 (7H, m), 4.0 (2H, t), 3.8 (3H, s), 2.9-2.8 (2H, t), 2.1 (3H, s) |
| 4.159 | ¹H-NMR (DMSO-d₆), δ (ppm): 9.89 (1H, s), 8.35 (1H, s), 8.19 (1H, d), 7.96 (1H, d), 7.43-7.26 (2H, m), 5.07 (2H, s), 3.82 (3H, s), 2.10 (3H, s) |
| 4.160 | ¹H-NMR (DMSO-d₆), δ (ppm): 9.88 (1H, bs), 8.19-8.14 (1H, m), 7.38-7.31 (2H, m), 7.23 (1H, t), 6.95-6.82 (3H, m), 4.98 (2H, s), 3.81 (3H, s), 3.73 (3H, s), 2.1 (3H, s) |
| 4.161 | ¹H-NMR (DMSO-d₆), δ (ppm): 10.18 (1H, s), 7.95-7.90 (1H, m), 7.57-7.51 (1H, m), 7.32 (1H, t), 7.14-7.08 (2H, m), 5.01 (2H, s), 3.92 (3H, s), 3.78 (3H, s), 2.05 (3H, s) |
| 4.162 | ¹H-NMR (DMSO-d₆), δ (ppm): 9.88 (1H, bs), 8.14 (1H, d), 7.38-7.32 (2H, m),7.06-7.04 (2H, m), 6.41 (1H, d), 4.86 (2H, s), 3.78 (3H, s), 3.2 (2H, t), 2.81 (2H, t), 2.65 (3H, s), 2.10 (3H, s) |
| 4.163 | ¹H-NMR (DMSO-d₆), δ (ppm): 9.88 (1H, bs), 8.18 (1H, dd), 7.25 (3H, m), 6.63 (1H, dd), 4.94 (2H, s), 4.55 (2H, t), 3.81 (3H, s), 3.09 (3H, t), 2.1 (3H, s) |
| 4.164 | ¹H-NMR (DMSO-d₆), δ (ppm): 9.88 (1H, bs), 8.16 (1H, m), 7.34-7.09 (5H, m),6.89 (1H, t), 4.91 (2H, s), 3.79 (3H, s), 2.73 (6H, s), 2.1 (3H, s) |
| 4.165 | ¹H-NMR (DMSO-d₆), δ (ppm): 9.88 (1H, bs), 8.19 (1H, d), 7.35-7.08 (4H, m), 4.99 (2H, s), 3.96 (3H, s), 3.82 (3H, s), 2.1 (3H, s) |
| 4.166 | ¹H-NMR (DMSO-d₆), δ (ppm): 7.57-7.15 (10H, m), 3.88 (2H, t), 3.8 (3H, s), 2.65 (2H, t), 1.91 (2H, q) |
| 4.167 | ¹H-NMR (DMSO-d₆), δ (ppm): 7.58-7.36 (4H, m), 7.44-7.36 (4H, m), 5 (2H, s), 4.02 (2H, s), 3.8 (3H, s) |
| 4.168 | ¹H-NMR (DMSO-d₆), δ (ppm): 9.9 (1H, s), 8.2 (1H, s), 7.8 (2H, d), 7.6 (2H, d), 7.3 (2H, bs), 5.1(2H, s), 3.8 (3H, s), 2.1 (3H, s) |
| 4.169 | ¹H-NMR (DMSO-d₆), δ (ppm): 9.88 (1H, s), 8.21-8.16 (1H, s), 7.39-7.21 (4H, m), 7.09 (1H, d), 7 (1H, d), 6.86 (1H, t), 4.96 (2H, s), 3.83 (6H, s), 2.1 (3H, s) |
| 4.170 | ¹H-NMR (DMSO-d₆), δ (ppm): 9.88 (1H, bs), 8.19 (1H, dd), 7.88 (1H, t), 7.59 (1H, dd), 7.35 (3H, m), 5.08 (2H, s), 3.82 (3H, s), 2.1 (3H, s) |
| 4.171 | ¹H-NMR (DMSO-d₆), δ (ppm): 9.88 (1H, s), 8.79 (1H, s), 8.18 (1H, d), 8.12-7.97 (2H, m), 7.43-7.22 (2H, m), 5.12 (2H, s), 3.82 (3H, s), 2.10 (3H, s) |
| 4.172 | ¹H-NMR (DMSO-d₆), δ (ppm): 9.88 (1H, s), 8.5 (1H, d), 8.22 (1H, d), 7.69 (1H, dd), 7.35-7.31 (2H, m), 7.23 (1H, d), 4.98 (2H, s), 3.79 (3H, s), 2.98 (1H, m), 2.1 (3H, s), 1.19 (6H, d) |

TABLE 7-continued

NMR-data

| Compound Nr | NMR-data |
|---|---|
| 4.173 | $^1$H-NMR (DMSO-d$_6$), δ (ppm): 9.88 (1H, s), 8.5 (1H, d), 8.22 (1H, d), 7.69 (1H, dd), 7.35-7.31 (2H, m), 7.23 (1H, d), 4.98 (2H, s), 3.79 (3H, s), 2.98 (1H, m), 2.1 (3H, s) |
| 4.174 | $^1$H-NMR (DMSO-d$_6$), δ (ppm): 9.88 (1H, s), 8.88 (1H, dd), 8.34 (1H, d), 8.19 (1H, d), 8.00-7.96 (2H, m), 7.77 (1H, dd), 7.52 (1H, dd), 7.35 (2H, m), 5.21 (2H, s), 3.83 (3H, s), 2.10 (3H, s) |
| 4.175 | $^1$H-NMR (DMSO-d$_6$), δ (ppm): 9.88 (1H, bs), 8.16 (1H, d), 7.98 (1H, d), 7.67 (1H, d), 7.54 (1H, d), 7.36 (3H, m), 6.93 (1H, d), 5.1 (2H, s), 3.8 (3H, s), 2.1 (3H, s) |
| 4.176 | $^1$H-NMR (DMSO-d$_6$), δ (ppm): 9.89 (1H, s), 8.17-8.13 (1H, m), 7.39-7.25 (4H, m), 7.13 (2H, t), 4 (2H, t), 3.8 (3H, s), 2.86 (2H, t), 2.11 (3H, s) |
| 4.177 | $^1$H-NMR (DMSO-d$_6$), δ (ppm): 9.88 (1H, bs), 8.17 (1H, s), 7.45-7.44 (1H, m), 7.36-7.31 (3H, m), 7.10-7.08 (1H, m), 4.93 (2H, s), 3.83 (3H, s), 3.8 (3H, s), 2.1 (3H, s) |
| 4.178 | $^1$H-NMR (DMSO-d$_6$), δ (ppm): 10.11 (1H, bs), 7.86 (1H, s), 7.55 (1H, d), 7.37 (1H, t), 7.22 (1H, d), 7.09-7.02 (2H, m), 6.65 (1H, t), 4.89 (2H, s), 3.8 (3H, s), 3.36 (4H, s), 2.05 (3H, s), 1.87 (4H, m) |
| 4.179 | $^1$H-NMR (DMSO-d$_6$), δ (ppm): 10.11 (1H, bs), 7.87 (1H, s), 7.54 (1H, d), 7.37 (1H, t), 7.24-7.11 (2H, m), 6.97 (1H, t), 4.94 (2H, s), 3.81 (3H, s), 3.72 (4H, m), 2.96 (4H, m), 2.04 (3H, s) |
| 4.180 | $^1$H-NMR (DMSO-d$_6$), δ (ppm): 9.88 (1H, bs), 8.12 (1H, m), 7.37-7.27 (2H, m), 7.11-6.99 (2H, m), 5.09 (2H, s), 3.8 (6H, s), 2.09 (3H, s) |
| 4.181 | $^1$H-NMR (DMSO-d$_6$), δ (ppm): 9.88 (1H, bs), 8.18 (1H, m), 7.37-7.27 (2H, m), 7.69 (2H, d), 7.6 (2H, d), 7.35-7.32 (2H, m), 5.09 (2H, s), 3.81 (3H, s), 2.1 (3H, s) |
| 4.182 | $^1$H-NMR (DMSO-d$_6$), δ (ppm): 9.9 (1H, bs), 8.2 (1H, d), 7.3 (6H, m), 5.8 (2H, s), 5 (2H, s), 4.4 (2H, s), 3.8 (2H, s), 3.3 (3H, s), 2.1 (3H, s) |
| 4.183 | $^1$H-NMR (DMSO-d$_6$), δ (ppm): 9.9 (1H, bs), 8.34 (1H, d), 8.13 (3H, m), 7.31 (2H, m), 7.01 (1H, dd), 5.13 (2H, s), 3.79 (3H, s), 2.1 (3H, s) |
| 4.184 | $^1$H-NMR (DMSO-d$_6$), δ (ppm): 9.88 (1H, bs), 8.18 (1H, d), 7.37-7.32 (2H, m), 7.12 (1H, t), 6.90-6.84 (2H, m), 5 (2H, s), 3.82 (3H, s), 3.7 (3H, s), 2.1 (3H, s) |
| 4.185 | $^1$H-NMR (DMSO-d$_6$), δ (ppm): 9.88 (1H, bs), 8.16 (1H, dd), 7.38 (4H, m), 7.17 (3H, m), 4.99 (2H, s), 3.8 (3H, s), 2.1 (3H, s) |
| 4.186 | $^1$H-NMR (DMSO-d$_6$), δ (ppm): 9.88 (1H, s), 8.20-8.17 (3H, d), 7.67-7.64 (2H, d), 7.36-7.34-7.32 (2H, t), 5.13 (2H, s), 3.82 (3H, s), 2.1 (3H, s) |
| 4.187 | $^1$H-NMR (DMSO-d$_6$), δ (ppm): 9.93 (1H, s), 8.48 (1H, s), 8.21-8.13 (1H, m), 7.84-7.70 (3H, m), 7.52-7.47 (2H, m), 7.37-7.31 (2H, m), 6.53 (1H, s), 5.04 (2H, s), 3.81 (3H, s), 2.1 (3H, s) |
| 4.188 | $^1$H-NMR (DMSO-d$_6$), δ (ppm): 9.88 (1H, bs), 8.18 (1H, d), 7.35-7.32 (2H, m), 6.79-6.71 (3H, m), 4.96 (2H, s), 3.81 (3H, s), 3.75 (3H, s), 2.1 (3H, s) |
| 4.189 | $^1$H-NMR (DMSO-d$_6$), δ (ppm): 9.89 (1H, s), 8.18 (1H, s), 7.53-7.22 (2H, m), 7.10 (1H, t), 6.89-6.53 (3H, m), 4.95 (2H, s), 3.80 (3H, s), 2.87 (6H, s), 2.10 (3H, s) |
| 4.190 | $^1$H-NMR (DMSO-d$_6$), δ (ppm): 10.11 (1H, bs), 8 (1H, s), 7.89 (1H, m), 7.69 (1H, d), 7.59-7.54 (2H, m), 7.37 (1H, t), 7.25 (1H, d), 7.14 (1H, d), 5.16 (2H, s), 4.02 (3H, s), 3.84 (3H, s), 2.04 (3H, s) |
| 4.191 | $^1$H-NMR (DMSO-d$_6$), δ (ppm): 9.98 (1H, s), 8.20-8.11 (1H, m), 7.38-7.26 (2H, m), 6.90-6075 (3H, m), 4.88 (2H, s), 4.2 (4H, s), 3.79 (3H, s), 2.1 (3H, s) |
| 4.192 | $^1$H-NMR (DMSO-d$_6$), δ (ppm): 10.11 (1H, bs), 8.01 (1H, d), 7.86 (1H, t), 7.75 (1H, m), 7.60-7.53 (2H, m), 7.43 (2H, dd), 7.36 (2H, t), 7.23 (1H, m), 5.12 (2H, s), 4.01 (3H, s), 3.81 (3H, s), 2.04 (3H, s) |
| 4.193 | $^1$H-NMR (DMSO-d$_6$), δ (ppm): 10.11 (1H, bs), 8.28 (1H, s), 7.86 (1H, t), 7.67 (1H, s), 7.57-7.52 (2H, m), 7.36 (1H, t), 7.25 (2H, m), 5.06 (3H, s), 4.14 (3H, s), 3.81 (3H, s), 2.04 (3H, s) |
| 4.194 | $^1$H-NMR (DMSO-d$_6$), δ (ppm): 9.88 (1H, bs), 8.16 (1H, dd), 7.33 (2H, m), 7.14 (1H, d), 6.78 (2H, m), 4.93 (2H, s), 4.48 (2H, t), 3.79 (3H, s), 3.12 (2H, t), 2.09 (3H, s) |
| 4.195 | $^1$H-NMR (DMSO-d$_6$), δ (ppm): 9.88 (1H, bs), 8.17 (1H, dd), 7.33 (2H, m), 7.01 (1H, t), 6.74 (1H, d), 6.67 (1H, d), 4.94 (2H, s), 4.53 (2H, t), 3.81 (3H, s), 3.24 (2H, t), 2.09 (3H, s) |
| 4.196 | $^1$H-NMR (DMSO-d$_6$), δ (ppm): 10.12 (1H, bs), 8.21-8.20 (2H, m), 7.89 (1H, m), 7.56-7.53 (1H, m), 7.40-7.35 (2H, m), 7.26-7.23 (1H, m), 5.03 (2H, s), 3.82 (3H, s), 3.81 (3H, s), 2.05 (3H, s) |
| 4.197 | $^1$H-NMR (DMSO-d$_6$), δ (ppm): 10.11 (1H, bs), 7.90-7.89 (1H, s), 7.55-7.52 (1H, dm, 8.96 Hz), 7.51-7.49 (1H, d, 8.19 Hz), 7.40-7.35 (1H, t, 8.19 Hz), 7.26-7.22 (1H, dm, 7.96 Hz), 7.13-7.12 (1H, d, 1.79 Hz), 6.89-6.86 (1H, dd, 8.19 Hz, 1.79 Hz), 4.99 (2H, s), 3.83 (6H, s), 2.05 (3H, s) |
| 4.198 | $^1$H-NMR (DMSO-d$_6$), δ (ppm): 10.13 (1H, s), 7.90-7.88 (1H, m), 7.56-7.54 (1H, m), 7.41-7.20 (6H, m), 4.06-4.00 (2H, t), 3.81 (3H, s), 2.91-2.85 (2H, t), 2.06 (3H, s) |
| 4.199 | $^1$H-NMR (DMSO-d$_6$), δ (ppm): 9.88 (1H, s), 8.19 (1H, d), 7.43-7.26 (2H, m), 7.17 (1H, t), 6.93 (1H, dd), 6.68 (1H, td), 4.91 (2H, s), 3.84 (3H, s), 3.82 (3H, s), 2.10 (3H, s) |
| 4.200 | $^1$H-NMR (DMSO-d$_6$), δ (ppm): 9.88 (1H, bs), 8.20-8.17 (2H, m), 7.78 (1H, d), 7.73 (1H, t), 7.49 (1H, dd), 7.36-7.33 (3H, m), 6.55 (1H, t), 5.06 (2H, s), 3.82 (3H, s), 2.1 (3H, s) |
| 4.201 | $^1$H-NMR (DMSO-d$_6$), δ (ppm): 9.88 (1H, bs), 8.18 (1H, m), 7.45-7.24 (5H, m), 4.98 (2H, s), 3.8 (3H, s), 2.1 (3H, s) |
| 4.202 | $^1$H-NMR (DMSO-d$_6$), δ (ppm): 9.88 (1H, bs), 8.19 (1H, m), 8 (1H, s), 7.7 (1H, d), 7.59 (1H, d), 7.34 (2H, m), 7.13 (1H, d), 5.15 (2H, s), 4.02 (3H, s), 3.82 (3H, s), 2.09 (3H, s) |
| 4.203 | $^1$H-NMR (DMSO-d$_6$), δ (ppm): 9.88 (1H, s), 8.19 (1H, m), 7.63-7.35 (5H, m), 4.99 (2H, s), 3.81 (3H, s), 2.1 (3H, s) |
| 4.204 | $^1$H-NMR (DMSO-d$_6$), δ (ppm): 9.89 (1H, bs), 8.20-8.15 (1H, m), 7.36-7.33 (3H, m), 7.06-6.98 (2H, m), 6.87-6.83 (1H, m), 4.94 (2H, s), 3.8 (3H, s), 2.75 (6H, s), 2.1 (3H, s) |
| 4.205 | $^1$H-NMR (DMSO-d$_6$), δ (ppm): 9.64 (1H, bs), 8.03-8.01 (1H, m), 7.60-7.57 (1H, d, 8.72 Hz), 7.45-7.39 (1H, m), 7.18-7.12 (2H, tm, 8.71 Hz), 4.99 (2H, s), 3.82 (3H, s), 2.11 (3H, s) |
| 4.206 | $^1$H-NMR (DMSO-d$_6$), δ (ppm): 9.88 (1H, bs), 8.16 (1H, t), 7.33 (2H, m), 7.19 (1H, s), 7.10 (1H, dd), 6.61 (1H, d), 4.90 (2H, s), 3.79 (3H, s), 2.96 (1H, m), 2.10 (3H, s), 1.37 (6H, s) |
| 4.207 | $^1$H-NMR (DMSO-d$_6$), δ (ppm): 7.60-7.55 (1H, m), 7.50-7.30 (6H, m), 5 (2H, s), 4 (2H, s), 3.8 (3H, s) |
| 4.208 | $^1$H-NMR (DMSO-d$_6$), δ (ppm): 9.87 (1H, s), 9.18-9.14 (1H, m), 7.42-7.29 (7H, m), 4.99 (2H, s), 3.8 (3H, s), 2.1 (3H, s) |
| 4.209 | $^1$H-NMR (DMSO-d$_6$), δ (ppm): 11.08 (1H, s), 10.13 (1H, s), 7.9 (1H, s), 7.55 (1H, d), 7.38 (1H, t), 7.26-7.22 (1H, m), 6.99-6.92 (2H, m), 4.98 (2H, s), 3.83 (3H, s), 2.05 (3H, s) |
| 4.210 | $^1$H-NMR (DMSO-d$_6$), δ (ppm): 9.88 (1H, s), 8.19 (1H, d), 7.54 (1H, t), 7.45 (1H, dd), 7.40-7.20 (3H, m), 5.00 (2H, s), 3.81 (3H, s), 2.10 (3H, s) |
| 4.211 | $^1$H-NMR (DMSO-d$_6$), δ (ppm): 9.64 (1H, s), 8.03 (1H, d), 7.65-7.34 (4H, m), 7.26 (1H, d), 5.01 (2H, s), 3.83 (3H, s), 2.11 (3H, s) |
| 4.212 | $^1$H-NMR (DMSO-d$_6$), δ (ppm): 9.64 (1H, s), 8.04 (1H, d), 7.59 (1H, d), 7.42 (1H, dd), 7.17 (1H, t), 6.93 (1H, dd), 6.68 (1H, td), 4.91 (2H, s), 3.84 (3H, s), 2.11 (3H, s) |
| 4.213 | $^1$H-NMR (DMSO-d$_6$), δ (ppm): 9.88 (1H, s), 8.17 (1H, d), 7.47-7.24 (4H, m), 7.03 (1H, t), 5.01 (2H, s), 3.81 (3H, s), 2.1 (3H, s) |
| 4.214 | $^1$H-NMR (DMSO-d$_6$), δ (ppm): 9.88 (1H, s), 8.17 (1H, d), 7.34 (2H, m), 7.17 (1H, m), 7.09 (1H, s), 6.92 (1H, d), 4.9 (2H, s), 3.86 (3H, s), 3.82 (3H, s), 2.1 (3H, s) |
| 4.215 | $^1$H-NMR (DMSO-d$_6$), δ (ppm): 9.88 (1H, s), 8.17 (1H, d), 7.36-7.32 (3H, m), 7.15 (1H, d), 6.93 (1H, dd), 4.99 (2H, s), 3.83 (3H, s), 3.8 (3H, s), 2.1 (3H, s) |
| 4.216 | $^1$H-NMR (DMSO-d$_6$), δ (ppm): 9.89 (1H, bs), 8.14-8.11 (1H, m), 7.39-7.32 (2H, m), 7.28-7.16 (2H, m), 7.06-6.99 (1H, m), 4.06-4.01 (2H, t, 7.68 Hz), 3.79 (3H, s), 2.93-2.89 (2H, t, 7.68 Hz), 2.11 (3H, s) |
| 4.217 | $^1$H-NMR (DMSO-d$_6$), δ (ppm): 10.12 (1H, s), 8.03 (1H, d), 7.88 (1H, t), 7.66 (1H, dd), 7.54 (1H, t), 7.37 (1H, t), 7.23 (1H, d), 4.98 (2H, s), 3.92 (3H, s), 3.81 (3H, s), 2.05 (3H, s) |
| 4.218 | $^1$H-NMR (DMSO-d$_6$), δ (ppm): 9.63 (1H, bs), 8.05-8.03 (1H, m), 7.60-7.57 (1H, d, 8.7 Hz), 7.43-7.39 (1H, dd, 8.7 Hz, 2.56 Hz), 7.19-7.16 (1H, d, 8.19 Hz), 7.10-7.09 (1H, d, 1.79 Hz), 6.93-6.90 (1H, dd, 8.19 Hz, 2.56 Hz), 4.91 (2H, s), 3.86 (3H, s), 3.84 (3H, s), 2.11 (3H, s) |

TABLE 7-continued

NMR-data

| Compound Nr | NMR-data |
|---|---|
| 4.219 | $^1$H-NMR (DMSO-$d_6$), δ (ppm): 9.63 (1H, bs), 8.03 (1H, d, 2.56 Hz), 7.60-7.57 (1H, d, 8.96 Hz), 7.43-7.39 (1H, dd, 8.96 Hz, 2.56 Hz), 7.36-7.33 (1H, d, 8.19 Hz), 7.16-7.15 (1H, d, 1.79 Hz), 6.95-6.92 (1H, dd, 8.19 Hz, 1.79 Hz), 5 (2H, s), 3.84 (3H, s), 3.83 (3H, s), 2.1 (3H, s) |
| 4.220 | $^1$H-NMR (DMSO-$d_6$), δ (ppm): 9.88 (1H, bs), 8.21-8.19 (1H, m), 7.39-7.30 (2H, m), 7.05-6.98 (2H, m), 4.97 (2H, s), 3.86 (3H, s), 3.82 (3H, s), 2.1 (3H, s) |
| 4.221 | $^1$H-NMR (DMSO-$d_6$), δ (ppm): 9.64 (1H, s), 8.02 (1H, s), 7.58 (1H, d), 7.52-7.35 (3H, m), 7.24 (1H, d), 5.02 (2H, s), 3.84 (3H, s), 2.11 (3H, s) |
| 4.222 | $^1$H-NMR (DMSO-$d_6$), δ (ppm): 9.64 (1H, s), 8.02 (1H, s), 7.59 (1H, d), 7.53-7.36 (2H, m), 7.25 (1H, t), 7.04 (1H, t), 5.02 (2H, s), 3.83 (3H, s), 2.11 (3H, s) |
| 4.223 | $^1$H-NMR (DMSO-$d_6$), δ (ppm): 9.64 (1H, s), 8.03 (1H, s), 7.80-7.52 (5H, m), 7.41 (1H, dd), 5.10 (2H, s), 3.84 (3H, s), 2.11 (3H, s) |
| 4.224 | $^1$H-NMR (DMSO-$d_6$), δ (ppm): 9.87 (1H, bs), 8.18 (1H, d), 7.35-7.32 (2H, m), 7.16-7.10 (2H, m), 7 (1H, dd), 5.02 (2H, s), 3.83 (3H, s), 2.66 (6H, s), 2.09 (3H, s) |
| 4.225 | $^1$H-NMR (DMSO-$d_6$), δ (ppm): 9.63 (1H, bs), 8.03 (1H, d), 7.58 (1H, d), 7.41 (1H, dd), 7.16-7.11 (2H, m), 7 (1H, dd), 5.02 (2H, s), 3.85 (3H, s), 2.67 (6H, s), 2.1 (3H, s) |
| 4.226 | $^1$H-NMR (DMSO-$d_6$), δ (ppm): 9.63 (1H, bs), 8.03-8.01 (1H, m), 7.60-7.57 (1H, m), 7.42-7.39 (1H, m), 7.05-6.97 (2H, m), 6.87-6.82 (1H, m), 4.94 (2H, s), 3.82 (3H, s), 2.75 (6H, s), 2.11 (3H, s) |
| 4.227 | $^1$H-NMR (DMSO-$d_6$), δ (ppm): 9.64 (1H, s), 8.02 (1H, d), 7.59 (1H, d), 7.47-7.21 (6H, m), 5.02 (2H, s), 3.83 (3H, s), 2.11 (3H, s) |
| 4.228 | $^1$H-NMR (DMSO-$d_6$), δ (ppm): 9.88 (1H, bs), 8.19 (1H, t), 7.34 (2H, m), 7.11 (1H, dd), 6.95 (1H, dd), 6.77 (1H, dt), 5.02 (2H, s), 3.83 (3H, s), 2.66 (6H, s), 2.10 (3H, s) |
| 4.229 | $^1$H-NMR (DMSO-$d_6$), δ (ppm): 9.64 (1H, s), 8.05-8.02 (1H, m), 7.58 (1H, d), 7.43-7.39 (1H, m), 7.19-7.10 (2H, m), 6.95-6.88 (1H, m), 4.97 (2H, s), 3.82 (3H, s), 3.81 (3H, s), 2.11 (3H, s) |
| 4.230 | $^1$H-NMR (DMSO-$d_6$), δ (ppm): 9.88 (1H, s), 8.21 (1H, s), 7.74 (1H, t), 7.56 (1H, d), 7.49-7.26 (3H, m), 5.09 (2H, s), 3.83 (3H, s), 2.10 (3H, s) |
| 4.231 | $^1$H-NMR (DMSO-$d_6$), δ (ppm): 9.88 (1H, bs), 8.17 (1H, d), 7.36-7.29 (3H, m), 7.17 (1H, s), 6.96 (1H, dd), 4.96 (2H, s), 3.8 (3H, s), 2.71 (6H, s), 2.1 (3H, s) |
| 4.232 | $^1$H-NMR (DMSO-$d_6$), δ (ppm): 9.64 (1H, bs), 8.02 (1H, s), 7.58 (1H, d), 7.4 (1H, d), 7.3 (1H, d), 7.18 (1H, s), 6.96 (1H, d), 4.97 (2H, s), 3.82 (3H, s), 2.71 (6H, s), 2.11 (3H, s) |
| 4.233 | $^1$H-NMR (DMSO-$d_6$), δ (ppm): 9.88 (1H, s), 8.19 (1H, s), 7.88 (1H, s), 7.69 (2H, s), 7.43-7.23 (2H, m), 5.06 (2H, s), 3.81 (3H, s), 2.10 (3H, s) |
| 4.234 | $^1$H-NMR (DMSO-$d_6$), δ (ppm): 9.63 (1H, s), 8.51 (1H, d), 8.02 (1H, d), 7.70 (1H, dd), 7.58 (1H, d), 7.41 (1H, dd), 7.23 (1H, d), 4.99 (2H, s), 3.81 (3H, s), 2.98 (1H, q), 2.11 (3H, s), 1.20 (6H, d) |
| 4.235 | $^1$H-NMR (DMSO-$d_6$), δ (ppm): 9.88 (1H, s), 8.18 (1H, s), 7.73-7.55 (2H, m), 7.52-7.23 (3H, m), 5.04 (2H, s), 3.81 (3H, s), 2.11 (3H, s) |
| 4.236 | $^1$H-NMR (DMSO-$d_6$), δ (ppm): 9.64 (1H, s), 8.04-8.01 (1H, m), 7.57 (1H, d), 7.43-7.39 (1H, m), 7.23 (1H, s), 6.95-6.82 (3H, m), 4.98 (2H, s), 3.83 (3H, s), 3.73 (3H, s), 2.11 (3H, s) |
| 4.237 | $^1$H-NMR (DMSO-$d_6$), δ (ppm): 9.64 (1H, bs), 8.03-8.00 (1H, m), 7.60-7.57 (1H, m), 7.43-7.39 (1H, m), 7.25 (1H, s), 7.13-7.10 (1H, m), 6.70-6.67 (1H, m), 4.92 (2H, s), 4.52-4.46 (2H, t, 8.71 Hz), 3.81 (3H, s), 3.16-3.10 (2H, t, 8.71 Hz), 2.11 (3H, s) |
| 4.238 | $^1$H-NMR (DMSO-$d_6$), δ (ppm): 9.66 (1H, bs), 8.06-8.01 (1H, m), 7.60-7.57 (1H, m), 7.44-7.39 (1H, m), 7.12-7.05 (2H, m), 4.99 (2H, s), 3.96 (3H, s), 3.84 (3H, s), 2.11 (3H, s) |
| 4.239 | $^1$H-NMR (DMSO-$d_6$), δ (ppm): 7.69-7.53 (2H, m), 7.47-7.24 (6H, m), 5.00 (2H, s), 3.82 (3H, s) |
| 4.240 | $^1$H-NMR (DMSO-$d_6$), δ (ppm): 9.63 (1H, bs), 8.03 (1H, s), 7.88 (1H, s), 7.69 (2H, s), 7.58 (1H, d), 7.39 (1H, dd), 5.06 (2H, s), 3.82 (3H, s), 2.11 (3H, s) |
| 4.241 | $^1$H-NMR (DMSO-$d_6$), δ (ppm): 9.88 (1H, bs), 8.17 (1H, dd), 7.30 (3H, m), 7.17 (1H, dd), 7.91 (1H, dd), 4.97 (2H, s), 4.64 (1H, hex), 3.80 (3H, s), 2.10 (3H, s), 1.28 (6H, d) |
| 4.242 | $^1$H-NMR (DMSO-$d_6$), δ (ppm): 9.63 (1H, bs), 8.02 (1H, s), 7.69 (1H, d), 7.57 (2H, m), 7.42 (1H, d), 7.14 (1H, d), 5.15 (2H, s), 4.01 (3H, s), 3.84 (3H, s), 2.1 (3H, s) |
| 4.243 | $^1$H-NMR (DMSO-$d_6$), δ (ppm): 9.87 (1H, s), 8.17 (1H, d), 7.42-7.32 (4H, m), 7.17 (1H, dd), 4.99 (2H, s), 3.8 (3H, s), 3.31 (1H, m), 2.1 (3H, s), 1.19 (6H, d) |
| 4.244 | $^1$H-NMR (DMSO-$d_6$), δ (ppm): 9.88 (1H, bs), 8.16 (1H, d), 7.35-6.97 (5H, m), 7.32 (2H, s), 3.81 (3H, s), 3.72 (4H, s), 2.96 (4H, s), 2.1 (3H, s) |
| 4.245 | $^1$H-NMR (DMSO-$d_6$), δ (ppm): 10.17 (1H, bs), 9.88 (1H, bs), 8.16 (1H, dd), 7.33 (3H, m), 6.98 (1H, d), 6.81 (1H, dd), 4.90 (2H, s), 3.80 (3H, s), 2.10 (3H, s) |
| 4.246 | $^1$H-NMR (DMSO-$d_6$), δ (ppm): 9.88 (1H, bs), 8.16 (1H, dd), 7.32 (2H, m), 7.21 (1H, d), 7.10 (1H, dd), 6.69 (1H, dd), 4.93 (2H, s), 4.18 (2H, s), 3.79 (3H, s), 2.10 (3H, s), 1.25 (6H, s) |
| 4.247 | $^1$H-NMR (DMSO-$d_6$), δ (ppm): 9.88 (1H, bs), 8.17 (1H, dd), 7.34 (2H, m), 7.12 (1H, d), 6.86 (1H, dd), 6.77 (1H, s), 4.93 (2H, s), 4.18 (2H, s), 3.79 (3H, s), 2.10 (3H, s), 1.39 (3H, s), 1.25 (3H, s) |
| 4.248 | $^1$H-NMR (DMSO-$d_6$), δ (ppm): 9.88 (1H, s), 8.20-8.14 (1H, s), 7.39-7.25 (3H, m), 7.17-7.10 (2H, m), 4.97 (2H, s), 3.8 (3H, s), 3.16-3.07 (1H, m), 1.18 (6H, d) |
| 4.249 | $^1$H-NMR (DMSO-$d_6$), δ (ppm): 10.18 (1H, s), 7.95-7.90 (1H, m), 7.58-7.52 (1H, m), 7.36-7.29 (2H, m), 7.17-7.14 (1H, m), 6.97-6.93 (1H, m), 4.97 (2H, s), 3.77 (3H, s), 2.71 (6H, s), 2.05 (3H, s) |
| 4.250 | $^1$H-NMR (DMSO-$d_6$), δ (ppm): 9.88 (1H, bs), 8.19 (1H, d), 7.66 (1H, d), 7.36-7.32 (3H, m), 7.23 (1H, d), 7.06 (1H, d), 5.06 (2H, s), 3.91 (3H, s), 3.82 (3H, s), 2.1 (3H, s) |
| 4.251 | $^1$H-NMR (DMSO-$d_6$), δ (ppm): 7.68-7.58 (4H, m), 7.40-7.28 (3H, m), 5 (2H, s), 3.83 (3H, s) |
| 4.252 | $^1$H-NMR (DMSO-$d_6$), δ (ppm): 9.88 (1H, s), 8.17 (1H, dd), 7.38-7.15 (4H, m), 5.02 (2H, s), 3.88 (3H, s), 3.81 (3H, s), 2.09 (3H, s) |
| 4.253 | $^1$H-NMR (DMSO-$d_6$), δ (ppm): 7.62 (1H, d), 7.59 (1H, d), 7.32 (2H, t), 7.26 (1H, dd), 7.15 (1H, t), 5.04 (3H, s), 3.88 (3H, s), 3.83 (3H, s) |
| 4.254 | $^1$H-NMR (DMSO-$d_6$), δ (ppm): 9.89 (1H, s), 8.18 (1H, s), 7.68-7.22 (3H, m), 7.12 (1H, m), 6.88 (1H, d), 4.99 (2H, s), 3.82 (6H, d), 2.10 (3H, s) |
| 4.255 | $^1$H-NMR (DMSO-$d_6$), δ (ppm): 9.88 (1H, s), 8.17 (1H, d), 7.45-7.26 (2H, m), 7.12 (1H, d), 6.96 (1H, s), 6.88 (1H, d), 4.97 (2H, s), 3.80 (3H, s), 3.76 (3H, s), 3.19 (1H, q), 2.10 (3H, s), 1.12 (6H, d) |
| 4.256 | $^1$H-NMR (DMSO-$d_6$), δ (ppm): 7.69-7.57 (2H, m), 7.40-7.26 (2H, t), 7.12 (1H, d), 6.97 (1H, s), 6.89 (1H, d), 4.98 (2H, s), 3.82 (3H, s), 3.76 (3H, s), 3.19 (1H, q), 1.12 (6H, d) |
| 4.257 | $^1$H-NMR (DMSO-$d_6$), δ (ppm): 9.88 (1H, s), 8.20-8.14 (1H, m), 7.40-7.27 (5H, m), 7.21 (1H, d), 6.97 (1H, bs), 6.76 (2H, d), 4.94 (2H, s), 3.8 (3H, s), 3.31-3.25 (4H, m), 2.1 (3H, s), 1.89-1.83 (4H, m) |
| 4.258 | $^1$H-NMR (DMSO-$d_6$), δ (ppm): 9.88 (1H, bs), 8.18 (1H, dd), 7.76 (2H, m), 7.48 (1H, t), 7.32 (2H, m), 5.05 (2H, s), 3.81 (3H, s), 2.1 (3H, s) |
| 4.259 | $^1$H-NMR (DMSO-$d_6$), δ (ppm): 9.88 (1H, bs), 8.15 (1H, dd), 7.33 (2H, m), 7.06 (2H, m), 5.00 (2H, s), 4.35 (1H, m), 3.81 (3H, s), 2.10 (3H, s), 1.26 (6H, d) |
| 4.260 | $^1$H-NMR (DMSO-$d_6$), δ (ppm): 9.88 (1H, bs), 8.44 (1H, d), 8.20 (1H, d), 8.14 (1H, d), 7.43-7.25 (2H, m), 5.04 (2H, s), 3.82 (3H, s), 2.11 (3H, s) |
| 4.261 | $^1$H-NMR (DMSO-$d_6$), δ (ppm): 9.88 (1H, bs), 8.19 (1H, dd), 7.54 (1H, dd), 7.31 (3H, m), 5.08 (2H, s), 4.06 (3H, s), 3.83 (3H, s), 2.10 (3H, s) |
| 4.262 | $^1$H-NMR (DMSO-$d_6$), δ (ppm): 8.44 (1H, d), 8.14 (1H, d), 7.68-7.55 (2H, m), 7.32 (2H, t), 5.06 (2H, s), 3.83 (3H, s) |
| 4.263 | $^1$H-NMR (DMSO-$d_6$), δ (ppm): 9.88 (1H, bs), 8.18 (1H, dd), 7.33 (3H, m), 7.18 (1H, s), 7.02 (1H, d), 4.97 (2H, s), 3.80 (3H, s), 3.73 (4H, m), 2.96 (4H, m), 2.10 (3H, s) |
| 4.264 | $^1$H-NMR (DMSO-$d_6$), δ (ppm): 9.88 (1H, s), 8.19 (1H, dd), 7.55 (1H, d), 7.51 (1H, s), 7.39-7.31 (2H, m), 7.2 (1H, d), 5.04 (2H, s), 3.81 (3H, s), 2.66 (6H, s), 2.1 (3H, s) |
| 4.265 | $^1$H-NMR (DMSO-$d_6$), δ (ppm): 7.59 (2H, m), 7.31 (3H, m), 6.93 (1H, d), 6.91 (1H, dd), 4.99 (2H, s), 4.64 (1H, hex), 3.82 (3H, s), 1.28 (6H, d) |

TABLE 7-continued

NMR-data

| Compound Nr | NMR-data |
|---|---|
| 4.266 | $^1$H-NMR (DMSO-d$_6$), δ (ppm): 7.74-7.43 (6H, m), 5.11 (1H, s), 3.87 (1H, s), 3.12 (1H, s), 1.79 (1H, s) |
| 4.267 | $^1$H-NMR (DMSO-d$_6$), δ (ppm): 9.88 (1H, bs), 8.16 (1H, dd), 7.49 (1H, d), 7.33 (4H, m), 4.99 (2H, s), 4.45 (2H, s), 3.90 (3H, s), 3.35 (3H, s), 2.10 (3H, s) |
| 4.268 | $^1$H-NMR (DMSO-d$_6$), δ (ppm):) 9.88 (1H, bs), 8.17 (1H, dd), 7.62 (1H, m), 7.33 (2H, m), 7.06 (2H, m), 6.95 (1H, m), 4.95 (2H, s), 3.80 (4H, s), 3.72 (3H, m), 2.98 (4H, m), 2.10 (3H, s) |
| 4.269 | $^1$H-NMR (DMSO-d$_6$), δ (ppm): 9.88 (1H, s), 8.30-8.13 (2H, m), 7.84 (1H, d), 7.43-7.25 (2H, m), 5.02 (2H, s), 3.80 (3H, s), 3.20 (1H, q), 2.10 (3H, s), 1.21 (6H, d) |
| 5.01 | $^1$H-NMR (DMSO-d$_6$), δ (ppm): 10.2 (1H, bs), 7.93 (1H, s), 7.67 (1H, dt, 1 Hz, 8 Hz), 7.5 (5H, m), 7.3 (1H, dt, 1 Hz, 8 Hz), 5.11 (2H, s), 3.26 (1H, hep, 6 Hz), 2.16 (3H, s), 1.27 (6H, d, 6 Hz) |
| 5.02 | $^1$H-NMR (DMSO-d$_6$), δ (ppm): 10.13 (1H, bs), 7.83 (1H, t, 2 Hz), 7.56 (1H, dt, 1 Hz, 8 Hz), 7.38 (5H, m), 7.18 (1H, dt, 1 Hz, 8 Hz), 5 (2H, s), 2.62 (2H, q, 7 Hz), 2.05 (3H, s), 1.13 (3H, t, 7 Hz) |
| 5.03 | $^1$H-NMR (DMSO-d$_6$), δ (ppm): 10.13 (1H, bs), 7.82 (1H, s), 7.56 (1H, d, 8 Hz), 7.38 (5H, m), 7.16 (1H, d, 8 Hz), 5 (2H, s), 2.59 (2H, t, 7 Hz), 2.05 (3H, s), 1.55 (2H, m), 1.39 (2H, m), 0.89 (3H, t, 7 Hz) |
| 5.04 | $^1$H-NMR (DMSO-d$_6$), δ (ppm): 8.1 (1H, d), 8.0 (1H, m), 7.7 (2H, m), 7.5 (2H, m), 7.2 (2H, t) |
| 5.05 | $^1$H-NMR (DMSO-d$_6$), δ (ppm): 2.05 (3H, s), 2.2 (6H, s), 2.64 (2H, t, 5 Hz), 4.2 (2H, t, 5 Hz), 4.99 (1H, s), 7.22 (1H, dt, 1 Hz, 8 Hz), 7.4 (5H, m), 7.53 (1H, dt, 1 Hz, 8 Hz), 7.88 (1H, t, 2 Hz), 10.11 (1H, bs) |
| 5.06 | $^1$H-NMR (DMSO-d$_6$), δ (ppm): 8.2-7.2 (8H, m), 5.1 (2H, s), 4.3 (2H, t), 3.7 (2H, t), 3.4 (3H, s), 2.0 (3H, s) |
| 5.07 | $^1$H-NMR (DMSO-d$_6$), δ (ppm): 2.05 (3H, s), 3.67 (2H, dd, 4 Hz, 2 Hz), 4.24 (2H, dd, 4 Hz, 2 Hz), 5 (2H, s), 7.22 (1H, dt, 1 Hz, 8 Hz), 7.4 (5H, m), 7.53 (1H, dt, 1 Hz, 8 Hz), 7.85 (1H, t, 2 Hz), 10.11 (1H, bs) |
| 5.08 | $^1$H-NMR (DMSO-d$_6$), δ (ppm): 10.07 (1H, s), 7.85 (1H, s), 7.55-7.50 (1H, m), 7.41-7.22 (6H, m), 7.04-6.99 (1H, m), 5.02 (2H, s), 2.7 (3H, d) |
| 5.09 | $^1$H-NMR (DMSO-d$_6$), δ (ppm): 10.1 (1H, s), 7.87 (1H, s), 7.55-7.52 (1H, m), 7.42-7.33 (5H, m), 7.24-7.20 (1H, m), 4.98 (2H, s), 4.19 (1H, q), 2.05 (3H, s), 1.34 (3H, t) |
| 5.10 | $^1$H-NMR (DMSO-d$_6$), δ (ppm): 10.16 (1H, s), 7.81 (1H, s), 7.59-7.57 (1H, m), 7.42-7.36 (1H, m), 7.29-7.27 (2H, m), 7.17-7.11 (3H, m), 4.97 (2H, s), 2.27 (3H, s), 2.05 (3H, s) |
| 5.11 | $^1$H-NMR (DMSO-d$_6$), δ (ppm): 10.1 (1H, s), 7.87 (1H, s), 7.54-7.51 (1H, m), 7.43-7.33 (5H, m), 7.23-7.19 (1H, m), 4.98 (2H, s), 4.97-4.87 (1H, m), 2.05 (3H, s), 1.33 (3H, s), 1.31 (3H, s) |
| 5.12 | $^1$H-NMR (DMSO-d$_6$), δ (ppm): 10.17 (1H, s), 7.83 (1H, s), 7.60-7.54 (1H, s), 7.46-7.37 (5H, m), 5 (2H, s), 2.05 (3H, s) |
| 5.13 | $^1$H-NMR (DMSO-d$_6$), δ (ppm): 10.07 (1H, s), 7.87 (1H, s), 7.53-7.49 (1H, m), 7.38-7.23 (6H, m), 5 (2H, s), 2.95 (6H, s), 2.04 (3H, s) |
| 5.14 | $^1$H-NMR (DMSO-d$_6$), δ (ppm): 10.14 (1H, bs), 7.82 (1H, t), 7.56 (1H, dd), 7.4 (5H, m), 7.17 (1H, dd), 5.31 (1H, t, 6 Hz), 5 (2H, s), 4.4 (2H, d), 2.05 (3H, s) |
| 5.15 | $^1$H-NMR (DMSO-d$_6$), δ (ppm): 10.27 (1H, bs), 10.09 (1H, bs), 7.98 (1H, t), 7.47 (6H, m), 7.21 (1H, dq), 5.02 (2H, s), 4.3 (2H, s), 2.87 (6H, s), 2.06 (3H, s) |
| 5.16 | $^1$H-NMR (DMSO-d$_6$), δ (ppm): 10.15 (1H, bs), 7.82 (1H, t), 7.57 (1H, dd), 7.4 (5H, m), 7.17 (1H, dd), 5 (2H, s), 4.34 (2H, s), 2.05 (3H, s) |
| 5.17 | $^1$H-NMR (DMSO-d$_6$), δ (ppm): 7.84 (1H, bs), 7.45 (5H, m), 7.3 (3H, m), 5.15 (2H, s), 3.97 (3H, s), 2.2 (3H, s) |
| 5.18 | $^1$H-NMR (CDCl$_3$), δ (ppm): 10.22 (1H, bs), 9.26 (1H, s), 7.93 (1H, t, 2 Hz), 7.62 (1H, dt, 1 Hz, 8 Hz), 7.45 (5H, m), 7.22 (1H, dt, 1 Hz, 8 Hz), 5.07 (2H, s), 2.06 (3H, s) |
| 5.19 | $^1$H-NMR (DMSO-d$_6$), δ (ppm): 9.87 (1H, bs), 8.16-8.13 (1H, m), 7.45-7.40 (2H, m), 7.35-7.30 (2H, m), 7.18-7.12 (2H, m), 4.99 (2H, s), 4.23-4.20 (2H, m), 3.67-3.64 (2H, m), 3.31 (3H, s), 2.1 (3H, s) |

Pharmacology

The compounds provided in this invention are positive allosteric modulators of metabotropic GABA receptors; in particular they are positive allosteric modulators of GABA$_B$ receptors. The compounds of the present invention do not appear to bind to the GABA recognition site, the orthosteric ligand site, but instead to an allosteric site within the seven transmembrane region of the receptor. In the presence of GABA or an agonist of GABA$_B$ receptor, the compounds of this invention increase the GABA$_B$ response.

Hence, the present invention relates to a compound or a pharmaceutical composition for the manufacture of a medicament for treating or preventing a condition in a mammal, including a human, the treatment or prevention of which is affected or facilitated by the neuromodulatory effect of GABA$_B$ allosteric modulators, in particular positive GABA$_B$ allosteric modulators.

The pharmacological activity of positive allosteric modulators, such as the ones described in Formula I, at GABA$_B$ receptors is demonstrated in the following paragraphs.

Example A

[$^{35}$S]GTPγS Binding Assay

The [$^{35}$S]GTPγS binding is a functional membrane-based assay used to study G-protein coupled receptor (GPCR) function. This method consists of using a binding assay to assess the initial step in receptor-mediated G protein activation in membranes prepared from cells expressing recombinant GPCR or using membranes from discrete areas of the rat brain. In brief, the assay measures the activation of G proteins by catalyzing the exchange of guanosine 5'-diphosphate (GDP) by guanosine 5'-triphosphate (GTP) at the α subunit. The GTP-bound G proteins dissociate into two subunits, Gα-GTP and Gβγ, which in turn regulate intracellular enzymes and ion channels. GTP is rapidly hydrolysed by the Gα-subunit (GTPases) and the G protein is deactivated and ready for a new GTP exchange cycle (Harper, *Curr. Protoc. Pharmacol.* 1998, 2.6, 1-10, John Wiley & Sons, Inc.). [$^{35}$S]GTPγS, a non-hydrolyzed analogue of GTP, is used for this purpose.

This method is widely used to study receptor activation of G protein in membranes prepared from rat brain tissue, including GABA$_B$ receptors (Urwyler et al, *The Journal of Pharmacol. and Exp Ther.* 2003, 307, 322-330; Olianas et al, *Neurochemistry Intern.* 2005, 46, 149-158). GABA$_B$ receptors are expressed in the rat brain cortex (Odagaki and Yamauchi, Basic Clin. *Pharmacol. Toxicol.* 2004, 94, 89-98) and are coupled to Gαo/i-protein, a preferential coupling for this method.

[$^{35}$S]GTPγS binding assay using cortical rat brain membranes preparation was used and adapted from Olianas et al (*Neurochemistry Intern.* 2005, 46, 149-158) for the detection of the positive allosteric modulator properties of the compounds of this invention on native rat GABA$_B$ receptors.

Membrane Preparation.

Cortices were dissected out from brains of 200-300 g Sprague-Dawley rats (Charles River Laboratories, L'Arbresle, France). Tissues were homogenized in 6 volumes (vol/wt) of 10% sucrose at 4° C. using a glass-teflon homogenizer. The homogenate was centrifuged at 1,250 g for 10 min, and the supernatant was centrifuged at 40,000 g for 20 min (4° C.). The pellet was resuspended in 25 ml water using a Polytron disrupter (Kinematica AG, Luzern, Switzerland) and centrifuged for 10 min at 3000 g. (4° C.). The supernatant was centrifuged at 40,000 g for 20 min (4° C.). The supernatant was discarded and the pellet washed twice by resuspension in 10 volumes 5 mM HEPES-KOH, pH 7.4. The homogenate was frozen and thawed twice and centrifuged at 40,000 g for 20 min. The final pellet was resuspended in 5 mM HEPES-KOH, pH 7.4 and stored at −80° C. before its use. Protein concentration was determined by the Bradford method (Bio-Rad protein assay, Reinach, Switzerland) with bovine serum albumin as standard.

[$^{35}$S]GTPγS Binding Assay.

Measurement of GABA$_B$ receptor positive allosteric modulator properties in rat cortical membranes was performed as follows: rat cortical membrane (1.5 µg) were incubated in 96-well microplates for 15 min at 30° C. in assay buffer (50 mM HEPES pH 7.4, 100 mM NaCl, 5 mM MgCl$_2$, 10 µM GDP, 10 µg/ml saponin, 1 mM CaCl$_2$) with increasing concentrations of positive allosteric modulator (from 1 nM to 60 µM) and a minimal concentration of GABA or Baclofen, a selective GABA$_B$ receptor agonist, that has been determined in previous experiments to correspond to the EC$_{50}$, a concentration that gives 50% of the maximal response of the agonist, and is in accordance with published data (Olianas et al, *Neurochemistry Intern.* 2005, 46, 149-158). After addition of 0.1 nM [$^{35}$S]GTPγS to achieve a total reaction volume of 200 µl, microplates were shaken for 1 min and further incubated at 30° C. for 30 min. The incubation was stopped by rapid vacuum filtration over glass-fiber filter plates (Unifilter 96-well GF/C filter plates, Perkin-Elmer, Schwerzenbach, Switzerland) using a 96-well plate cell harvester (Filtermate, Perkin-Elmer, Downers Grove, USA). The Unifilter plate was washed three times with 300 µl of ice-cold wash buffer (20 mM HEPES pH 7.4, 100 mM NaCl). When filters were dry, 40 µl of liquid scintillation cocktail (Microscint 20) was added to each well. The amount of membrane-bound [$^{35}$S]GTPγS was measured using a 96-well plate reader (Top-Count, Perkin-Elmer, Downers Grove, USA). Non specific [$^{35}$S]GTPγS binding is determined in the presence of 10 µM of GTP.

Data Analysis.

The concentration-response curves of representative compounds of the present invention in the presence of EC$_{50}$ of GABA$_B$ receptor agonist were generated using the Prism Graph-Pad program (Graph Pad Software Inc, San Diego, USA). The curves were fitted to a four-parameter logistic equation (Y=Bottom+(Top−Bottom)/(1+10^((LogEC$_{50}$−X)*Hill Slope) allowing determination of EC$_{50}$ values. Each curve was performed using duplicate sample per data point and 10 concentrations. The concentration-response curves of a selective GABA$_B$ receptor agonist in the absence or in the presence of representative compounds of the present invention were also generated using Prism Graph-Pad program (Graph Pad Software Inc, San Diego, USA). The curves were fitted to a four-parameter logistic equation (Y=Bottom+(Top−Bottom)/(1+10^((LogEC$_{50}$−X)*Hill Slope) allowing determination of EC$_{50}$ values of the selective GABA$_B$ receptor agonist. Each curve was performed using duplicate sample per data point and 10 concentrations.

Data presented in FIG. A represent the ability of 10 µM of the Compound 4.02ADX48479 to increase the [GTPγ$^{35}$S] binding induced by 15 µM of Baclofen, a GABA$_B$ receptor agonist. Said example has no statistically significant agonistic activity when tested in the absence of 15 µM Baclofen (1% of maximal response, as a comparison, buffer is 0% of maximal response). Instead, when compounds are added together with a GABA$_B$ receptors agonist like Baclofen, the effect measured is significantly potentiated compared to the effect of the agonist alone at the same concentration. Each bar graph is the mean and S.E.M. of duplicate data points and is representative of at least two independent experiments.

Table 8 shows representative compounds of the present invention that were clustered into four classes according to their ability (EC$_{50}$) to potentiate an EC$_{50}$ of GABA$_B$ receptor agonist such as Baclofen. Class A: EC$_{50}$<100 nM; Class B: 100 nM<EC$_{50}$<500 nM; Class C: 500 nM<EC$_{50}$<1000 nM; Class D: EC$_{50}$>1000 nM.

TABLE 8

Summary of activity-data

| Compound Nr | EC$_{50}$ |
|---|---|
| 4.02 | B |
| 4.05 | A |
| 4.13 | D |
| 4.43 | D |
| 4.52 | D |
| 4.118 | A |
| 4.135 | B |
| 4.160 | D |
| 4.185 | B |
| 4.191 | C |
| 4.192 | B |
| 4.197 | A |
| 4.198 | B |
| 4.204 | A |
| 4.205 | B |
| 4.207 | A |
| 4.209 | A |
| 4.211 | A |
| 4.219 | D |
| 4.231 | A |
| 4.232 | A |
| 4.233 | A |
| 4.234 | A |
| 4.236 | A |
| 4.237 | D |
| 4.239 | C |
| 4.241 | A |
| 4.242 | A |
| 4.244 | A |
| 4.247 | A |
| 4.248 | A |
| 4.251 | A |
| 4.253 | A |
| 4.254 | D |
| 4.255 | A |
| 4.260 | A |
| 4.262 | B |
| 4.266 | A |
| 4.268 | A |
| 4.270 | B |

Thus, the positive allosteric modulators provided in the present invention are expected to increase the effectiveness of GABA or GABA$_B$ receptor agonists at GABA$_B$ receptors, and therefore, these positive allosteric modulators are expected to be useful for treatment of various neurological and psychiatric disorders associated with GABA dysfunction described to be treated herein and others that can be treated by such positive allosteric modulators.

Example B

Marble Burying Test, Model of Anxiety in Mice

Anxiety models in rodents are used as standard tests to demonstrate anxiolytic-like properties of novel compounds. Mice exhibit a tendency to bury harmless novel objects when encountered in a test cage. Marble burying behavior in mice is reduced by compounds which are efficacious anxiolytics in humans. Thus, marble burying in mice has been used as a model for the prediction of anxiolytic-like effects of compounds (Millan, M. J. et al., *Neuropharmacology* 2002, 42, 677-684).

Subjects:

The present studies were performed in accordance with the animal care and use policies of Addex Pharmaceuticals and the EEC directives on the protection of animals used for experimental and other scientific purposes (86/609/EEC and subsequent revisions). Male C57BL6/j mice (20-30 g), were group housed in a temperature and humidity controlled facility on a 12 hour light/dark cycle for at least 5 days before use. Mice had access to food and water ad libitum except during marble burying experiments.

Assessment of Marble Burying:

The effect of compounds on marble burying behaviour in mice was tested. On the day of the test, animals were marked on their tails and weighed in a separate preparation room, 1 hour before drug administration. Test compound or vehicle was administered p.o. 60 minutes prior to the test session. Marble burying behaviour was tested in a separate experimental room. For the test, mice were placed individually into clear plastic cages (16×22×14 cm) with 5 cm of sawdust and 10 marbles evenly spaced against the walls of the cage. The mice were left undisturbed in the cages for 30 minutes. After removal of the mice from the test cages, the number of marbles buried was counted. A marble was considered buried if it was ⅔ or more covered.

Compound Administration:

Test compounds were dissolved in a solution of 1% CMC. Test compounds were administered 60 minutes before testing by oral gavage (p.o.) in a volume of 10 mL/kg. In each assay, a vehicle and reference positive control groups were tested.

Statistical Analyses:

Statistical analyses were performed using GraphPad PRISM version 4.01 statistical software (GraphPad, San Diego, Calif., USA). Data were analyzed using a non-parametric Kruskal-Wallis test followed by a Dunn's multiple comparisons test. The significance level was set at $p<0.05$ when compared to the vehicle group.

Effect of Compounds in the Marble Burying Test in Mice:

At the doses of about 3 to 30 mg/kg, selected compounds of the invention significantly attenuate the marble burying behavior in mice.

Example C

Vogel Conflict Drinking Test, Model of Anxiety in Rats

Anxiety models in rodents are used as standard tests to demonstrate anxiolytic-like properties of novel compounds. The Vogel conflict drinking model involves the conflict between thirsts and receiving mild shocks for drinking water (punished drinking). Water-deprived rats are placed in a chamber and they receive mild electric shocks every time they drink. The shocks suppress drinking and anxiolytics reverse this shock-induced suppression of drinking. The Vogel conflict drinking model was first proposed as a screening model for anxiolytics (Vogel, J. R. et al., *Psychopharmacologia* 1971, 21:1-7) and is widely accepted as a robust model for testing the anxiolytic-like properties of compounds (Millan, M. J. and Brocco M., Eur. J. Pharm. 2003, 463:67-96).

Subjects:

The present studies were performed in accordance with the animal care and use policies of Addex Pharmaceuticals and the EEC directives on the protection of animals used for experimental and other scientific purposes (86/609/EEC and subsequent revisions). Male Sprague-Dawley rats (320-420 g) were housed in a temperature and humidity controlled facility on a 12 hours light/dark cycle for at least 5 days before use. Rats had access to food ad libitum except during Vogel conflict drinking model experiments. Rats had access to water ad libitum until 48 hours prior to the test session.

Assessment of Vogel Conflict Drinking:

The effect of compounds on drinking in the Vogel conflict drinking model in rats was tested. Test chambers are housed in sound-attenuating boxes and each chamber contains a stainless steel drinking spout and a steel grid floor (MedAssociates, Georgia, Vt., USA). Forty-eight hours prior to the test session, rats were habituated to the test chambers for 10 minutes. Water was removed from the rats immediately after the habituation session. Twenty-four hours before the test session, rats were again placed into the test chambers and allowed to drink for 4 minutes. Rats were then allowed 1 hour of access to water and then water was removed. On the test day, rats were brought to the test room at least 30 minutes before the test session. Rats were placed individually into the test chamber for a 5 minute session. Rats received a shock every $20^{th}$ lick on the drinking spout. The number of punished drinks was counted automatically by the computer interface. The number of punished drinks was compared between treatment groups. An increase in the number of punished drinks in rats treated with a compound is interpreted as an anxiolytic-like effect.

Compound Administration:

Test compounds were suspended in 1% CMC. Test compounds were administered by oral gavage (p.o.) in a volume of 3 ml/kg 1 or 2 hours before testing. In each assay, a vehicle and reference positive control groups were tested.

Statistical Analyses:

Statistical analyses were performed using GraphPad PRISM version 4.01 statistical software (GraphPad, San Diego, Calif., USA). Data were analyzed using one-way analysis of variance (ANOVA) followed by Bonferroni's multiple comparisons. The significance level was set at $p<0.05$ when compared to the vehicle group.

Effect of Compounds on the Vogel Conflict Test in Rats:

At the doses of about 0.3 to 3 mg/kg, selected compounds of the invention increase the number of punished licks in the Vogel conflict test in rats.

Example D

Elevated Plus Maze Test, Model of Anxiety in Mice or Rats

Anxiety models in rodents are used as standard tests to demonstrate anxiolytic-like properties of novel compounds. The elevated plus maze is an animal model of anxiety, which has been validated behaviourally, physiologically, and pharmacologically (Pellow et al., *J. Neurosci. Methods* 1985, 14: 149-167). Following placement on the maze, untreated animals (mice or rats) tend to avoid the open arms and spend most of their time in the closed arms. Anxiolytic drugs such as benzodiazepines increase open arm exploration. Anxiety in the elevated plus maze is measured by examining the time spent on the open arms as well as open arm entries. In addition, closed arm entries are measured and used as a general activity score.

Subjects:

The present studies were performed in accordance with the animal care and use policies of Addex Pharmaceuticals and the EEC directives on the protection of animals used for experimental and other scientific purposes (86/609/EEC and subsequent revisions). Male Sprague-Dawley rats (200-300 g) or male C57/B16J mice (20-30 g) were housed in a temperature and humidity controlled facility on a 12 hours light/ dark cycle for at least 5 days before use. Animals had access to food ad libitum excepted during elevated plus maze experiments.

Assessment of the Elevated Plus-Maze Test:

The elevated plus-maze consists of four plastic arms connected by a central square, the arms are all horizontal and at 90° angle from each other making the shape of a plus sign. The maze is raised to a height of 50 cm from the ground. Two of the opposite arms have high plastic walls whereas the other two opposite arms do not. These arms are therefore referred to as the enclosed and open arms, respectively. The central square is not enclosed and the animal is initially placed in this area facing an enclosed arm.

The animals had free access to all 4 arms for a 5 minute period. During this time, the number of entries into, and the time spent on each type of arm were recorded.

The results were presented as:

Percentage of total number of entries onto open arms.
Percentage of time spent on the open arms.
Total number of entries into all arms.

On the day of the test, animals were marked on their tails and weighed in a separate preparation room before drug administration. Test compound or vehicle was administered p.o. 60 minutes prior to the test session.

Compound Administration:

Test compounds were dissolved in a solution of 1% CMC. Test compounds were administered 60 minutes before testing by oral gavage (p.o.) in a volume of 10 mL/kg. In each assay, a vehicle and reference positive control groups were tested.

Statistical Analyses:

Statistical analyses were performed using GraphPad PRISM version 4.01 statistical software (GraphPad, San Diego, Calif., USA). Data were analyzed using one-way analysis of variance (ANOVA) followed by Bonferroni's multiple comparisons test. The significance level was set at $p<0.05$ when compared to the vehicle group.

Effect of Compounds in the Elevated Plus Maze Test:

At the doses of about 0.3 to 3 mg/kg, selected compounds of the invention increase both the number of entries and the time spent on the open arms.

Thus, the positive allosteric modulators provided in the present invention are expected to increase the effectiveness of GABA or mGABA$_B$ agonists at GABA$_B$ receptor. Therefore, these positive allosteric modulators are expected to be useful for treating, or preventing, ameliorating, controlling or reducing the risk of various central nervous system disorders as well as other disorders associated with GABA$_B$ dysfunction in a mammal, including a human, the treatment or prevention of which is affected or facilitated by the neuromodulatory effect of GABA$_B$ positive allosteric modulators.

In particular, the neurological and psychiatric disorders associated with GABA$_B$ receptor dysfunction, include one or more of the following conditions or diseases: anxiety, depression, epilepsy, schizophrenia, cognitive disorders, spasticity and skeletal muscle rigidity, spinal cord injury, multiple sclerosis, neuropathic pain and craving associated with cocaine and nicotine, amyotrophic lateral sclerosis, cerebral palsy, posttraumatic stress disorders or gastro-intestinal disorders, cerebral palsy, psychosis, panic disorder At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progress.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such a treatment, an effective amount of a compound or composition according to the invention.

Because such positive allosteric modulators of GABA$_B$ receptors, including compounds of Formula I, enhance the response of GABA$_B$ receptors to GABA, it is an advantage that the present methods utilize endogenous GABA.

Because positive allosteric modulators of GABA$_B$ receptors, including compounds of Formula I, enhance the response of GABA$_B$ receptors to agonists, it is understood that the present invention extends to the treatment of neurological and psychiatric disorders associated with GABA dysfunction by administering an effective amount of a positive allosteric modulator of GABA$_B$ receptors, including compounds of Formula I, in combination with a GABA$_B$ agonist.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

FORMULATION EXAMPLES

Typical examples of recipes for the formulation of the invention are as follows:

1) Tablets

| | |
|---|---|
| Compound 4.02 | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this example, the Compound 4.02 can be replaced by the same amount of any of the described examples.

2) Suspension

An aqueous suspension is prepared for oral administration so that each 1 milliliter contains 1 to 5 mg of one of the described example, 50 mg of sodium carboxymethyl cellulose, 1 mg of sodium benzoate, 500 mg of sorbitol and water ad 1 ml.

3) Injectable

A parenteral composition is prepared by stirring 1.5% by weight of active ingredient of the invention in 10% by volume propylene glycol and water.

4) Ointment

| | |
|---|---|
| Compound 4.02 | 5 to 1000 mg |
| Stearyl alcohol | 3 g |
| Lanoline | 5 g |
| White petroleum | 15 g |
| Water | ad 100 g |

In this example, the compound 4.02 can be replaced by the same amount of any of the described examples.

Reasonable variations are not to be regarded as a departure from the scope of the invention. It will be obvious that the thus described invention may be varied in many ways by those skilled in the art.

The invention claimed is:

1. A compound selected from the group consisting of:
N-(2-fluoro-5-(6-methoxy-3,5-dioxo-4-(4-(trifluoromethyl)benzyl)-4,5-dihydro-1,2,4-triazin-2(3H)-yl)phenyl)acetamide, N-(5-(4-(4-chlorobenzyl)-6-methoxy-3,5-dioxo-4,5-dihydro-1,2,4-triazin-2(3H)-yl)-2-fluorophenyl)acetamide, and N-(5-(4-(4-chloro-3-fluorobenzyl)-6-methoxy-3,5-dioxo-4,5-dihydro-1,2,4-triazin-2(3H)-yl)-2-fluorophenypacetamide; or a pharmaceutically acceptable salt thereof.

2. A pharmaceutical composition comprising a therapeutically effective amount of a compound according to claim 1 and a pharmaceutically acceptable carrier and/or excipient.

3. A method for treating central nervous system disorders selected from the group consisting of anxiety disorders: Agoraphobia, Generalized Anxiety Disorder (GAD), Obsessive-Compulsive Disorder (OCD), Panic Disorder, Posttraumatic Stress Disorder (PTSD), Social Phobia, Other Phobias, and Substance-Induced Anxiety Disorder, the method comprising administering to a mammalian patient in need of such treatment an effective amount of a compound according to claim 1.

4. A method for treating Attention-Deficit/Hyperactivity Disorder, the method comprising administering to a mammalian patient in need of such treatment an effective amount of a compound according to claim 1.

5. A method for treating a central nervous system disorder selected from the group consisting of psychotic disorders: Schizophrenia, Delusional Disorder, Schizoaffective Disorder, Schizophreniform Disorder, and Substance-Induced Psychotic Disorder, the method comprising administering to a mammalian patient in need of such treatment an effective amount of a compound according to claim 1.

6. A method for treating a central nervous system disorder selected from the group consisting of personality disorders: Obsessive-Compulsive Personality Disorder, Schizoid, and Schizotypal disorder, the method comprising administering to a mammalian patient in need of such treatment an effective amount of a compound according to claim 1.

7. A method for treating a central nervous system disorder selected from the group consisting of substance-related disorders: Alcohol abuse, Alcohol dependence, Alcohol withdrawal, Alcohol withdrawal delirium, Alcohol-induced psychotic disorder, Amphetamine dependence, Amphetamine withdrawal, Cocaine dependence, Cocaine withdrawal, Nicotine dependence, Nicotine withdrawal, Opioid dependence, and Opioid withdrawal, the method comprising administering to a mammalian patient in need of such treatment an effective amount of a compound according to claim 1.

8. A method for treating inflammatory or neuropathic pain, or post-operative pain, the method comprising administering to a mammalian patient in need of such treatment an effective amount of a compound according to claim 1.

9. A method for treating urge urinary incontinence, the method comprising administering to a mammal in need of such treatment, an effective amount of a compound according to claim 1.

10. A method for treating spasticity and skeletal muscle rigidity, spinal cord injury, or cerebral palsy, the method comprising administering to a mammal in need of such treatment, an effective amount of a compound according to claim 1.

11. The method of claim 3, wherein the central nervous system disorder is Generalized Anxiety Disorder (GAD).

* * * * *